US012491256B2

(12) United States Patent
Ren et al.

(10) Patent No.: US 12,491,256 B2
(45) **Date of Patent: *Dec. 9, 2025**

(54) ANTI-CUB DOMAIN-CONTAINING PROTEIN 1 (CDCP1) ANTIBODIES, ANTIBODY DRUG CONJUGATES, AND METHODS OF USE THEREOF

(71) Applicant: Bluefin BioMedicine, Inc., Beverly, MA (US)

(72) Inventors: Hong Ren, Brighton, MA (US); Scott Michael Lonning, Westford, MA (US); Nels Eric Pederson, Mansfield, MA (US); Klarisa Rikova, Reading, MA (US); Aleksandr Tkachev, Cambridge, MA (US); Tinglei Gu, Andover, MA (US)

(73) Assignee: Bluefin BioMedicine, Inc., Beverly, MA (US)

( * ) Notice: Subject to any disclaimer, the term of this patent is extended or adjusted under 35 U.S.C. 154(b) by 241 days.

This patent is subject to a terminal disclaimer.

(21) Appl. No.: 18/320,885

(22) Filed: May 19, 2023

(65) Prior Publication Data

US 2024/0084032 A1 Mar. 14, 2024

Related U.S. Application Data

(62) Division of application No. 16/469,197, filed as application No. PCT/US2017/066661 on Dec. 15, 2017, now Pat. No. 11,702,481.

(Continued)

(51) Int. Cl.
*A61K 47/68* (2017.01)
*A61K 39/00* (2006.01)
(Continued)

(52) U.S. Cl.
CPC ........ *A61K 47/68031* (2023.08); *A61K 47/65* (2017.08); *A61K 47/6803* (2017.08);
(Continued)

(58) Field of Classification Search
None
See application file for complete search history.

(56) References Cited

U.S. PATENT DOCUMENTS 6,245,989 B1 6/2001 Testa et al.
7,541,030 B2 6/2009 Buehring et al.
(Continued)

FOREIGN PATENT DOCUMENTS

EP 1597367 A1 11/2005
EP 2447719 A1 5/2012
(Continued)

OTHER PUBLICATIONS

Zugazagoitia et al. Current Challenges in Cancer Treatment. Clincal Therapeutics, 2016, vol. 38, No. 7, pp. 1551-1566 (Year: 2016).*
(Continued)

*Primary Examiner* — Daniel E Kolker
*Assistant Examiner* — Hilary Ann Petrash
(74) *Attorney, Agent, or Firm* — Morgan, Lewis & Bockius LLP

(57) ABSTRACT

This disclosure relates to anti-cancer antibodies and methods of treatment, detection, and diagnosis using the same.

18 Claims, 53 Drawing Sheets

Specification includes a Sequence Listing.

| Ab Name | VH amino acid sequence | SEQ ID NO: | VL amino acid sequence | NO: |
|---|---|---|---|---|
| 14H4 | EVQLLESGGDLVQPGGSLRLSCAASGFTFNSYAMSWVRQAPGKGLEWVSVLSGSGGDIHYADSVKGRFTVSRDNSKNMLYLQMNSLRAEDTAVYFCAQQWPQGYWGQGTLVTVSS | 1 | DIQMTQSPSSLSASVGDRVTITCRASQGISIYLAWFQQKPGKVPKLLIYAASTLQSGVPSRFSGSGSGTDFTLTISSLQPEDVATYYCQKYNSAPFTFGPGTKVEIK | 2 |
| 03B05 | QVQLVESGGGVVQPGRSLRLSCAASGFTFSSYGMHWVRQAPGKGLEWVAIIWYDGSNKYYADSVKGRFTISRDNSKNTLYLQMNSLRAEDTAVYYCAKDPSYSSGYYLFDFWGQGTLVTVSS | 11 | EIVMTQSPATLSVSPGERATLSCRASQSVSSNLAWYQQKPGQAPRLLIYGASTRATGIPARFSGSGSGTEFTLTISSLQSEDFAVYYCQQYNNWPLTFGGGTKVEIK | 12 |
| 03C05 | EVQVLESGGGLVQPGGSLRLSCAASGFTFSSYVMSWVRQAPGKGLEWVSGISGSGGSTHYADSVKGRFTISRDNSKNTLYLQMNSLRAEDTALYYCAQQWPQGYWGQGTLVTVSS | 21 | DIQMTQSPSSLSASVGDRVTITCRASQDISIYLAWFQQKPGKVPKVLIYAASTLQSGVPSRFSGSGTGTDFTLTISSLQPEDVATYFCQKYNSAPFTFGPGTKLEIK | 22 |
| 27H10 | QVQLVQSGAEVKKPGSSVKVSCKASGGTFSSYAMSWVRQAPGQGLEWMGGIIPILGTTNYAQKFQGRVTITADKSTSTAYMELSSLRSEDTAVYYCAREGLYAFDIWGQGTMVTVSS | 31 | DIQMTQSPSSLSASVGDRVTITCRASQSISSYLNWYQQKPGKAPKFLIYVASSLQSGVPSRFSGRGSGTDFTLTISSLQPEDFATYYCQQSYSTPWTFGQGTKVEIK | 32 |
| 03B11 | QVQLQQWDAGLLKPSETLSLTCAVYGGSFSSYYWSWIRQPPGKGLEWIGEINHSGSTSYNPSLKSRVTISIDTSKNQFSLKLNSMTAADTAVYFCAASPYFDYWGQGTLVTVSS | 41 | DIQLTQSPSFLSASVGDRVTITCRASQGISSYLAWYQQKPGKAPKLLIYAASTLQSGVPSRFSGSGSGTEFTLTISSLQPEDFATYYCQQLNSYPRTFGQGTKVEIK | 42 |
| 04G06 | QVQLVESGGGVVQPGRSLRLSCVVSGFTLSSYGMNWVRQAPGKGLEWVAVIWYDGSDKYYADSVKGRFTISRDNSKNTLYLQMNSLRAEDTAVYYCARDDWGFDYWGQGTLVTVSS | 51 | DIQLTQSPSFLSASVGDRVTITCRASQDISNYLAWYQQKPGKAPKLLISASTLQSGVPSRFSGSGSGTEFILTISSLQPEDFATYYCQHLNSYPFGQGTKVEIK | 52 |
| 42C5 | EVQLVESGGGLVQPGGSLRLSCAASGFTFSRYWMNWVRQAPGKGLEWVANIKQDGSEKDYVDSVKGRFTISRDNAKNSLFLQMSSLRAEDTAVYYCARVMYSSGWSFDYWGQGTLVTVSS | 61 | DIVMTQSPLSLPVTPGEPASISCRSSRSLLHSSGYNFLDWFLQKPGQSPQLLIFLGSDRASGVPDRFSGSGSGTDFTLKISRVETEDVGVYYCMQALQTPITFGQGTRLEIK | 62 |
| 47G7 | EVQLVESGGGLVQPGGSLRLSCAASGFTFSSYWMSWVRQAPGKGLEWVANIKQDGSEKDYVDSVKGRFTISRDNAKNSLYLQMNSLRVEDTAVYYCAREGGSSGWTFDYWGQGTLVTVSS | 71 | DIVMTQSPLSLPVTPGEPASISCRSSQSLLHSSGHNFLDWYLQKPGQSPQLLIYLGSNRASGVPDRFSGSGSGTDFTLKISRVEAEDVGVYYCMQALQTPPTFGQGTKLEIK | 72 |
| 18C06 | QVQLQESGPGQVKPSETLSLTCTVSGGSISSSFWSWIRQPPGKGLEWIGYIYYSESTNYNPSLKRRVTLSVDTSKNQFSLKLTSVTTADTAVYYCARNIGVAGLFDYWGQGTLVTVSS | 81 | EIVMTQSPATLSVSPGERATLSCRASQSVSSNLAWYQQKPGQAPRLLIYGASTRATGIPARFSGSGSGTEFTLTISSLQSEDFAVYYCQQYNNWPLTFGGGTKVEIK | 82 |
| 11F9 | QVQLQESGPGLVKPSETLSLTCTVSGGSISSYYWSWIRQPPGKGLEWIGYIYYSGSTNYNPSLKSRVTISVDTSKNQFSLKLSSVTAADTAVYYCARNIGVAGLFDYWGQGTLVTVSS | 91 | EIVMTQSPATLSVSPGERATLSCRASQSVSSNLAWYQQKPGQAPRLLIYGASTRATGIPARFSGSGSGTEFTLTISSLQSEDFAVYYCQQYNNWPLTFGGGTKLEIK | 92 |
| 10E2 | QVQLVESGGGVVQPGRSLRLSCAASGFTFSSYGMHWVRQAPGKGLEWVAVVWYDGTIKYYADSVKGRFTISRDNPKNTLYLQMNSLRAEDTAVYYCASQYSSGWHTDFFDVWGQGTMVTVSS | 101 | DIQMTQSPSTLSASVGDRVTITCRASQSISTWLAWYQQKPGKAPKFLIYKASSLESGVPSRFSGSGSGTEFTLTISSLQPDDFATYYCQQYSGYSLTFGGGTKVEIK | 102 |
| 01E2 | QVQLVESGGGVVQPGRSLRLSCAASGFTFSSYGMHWVRQAPGKGLEWVAVIWYAGSNKYYADSVKGRFTISRDNSKNTLYLQMNSLRAEDTAVYYCAGWDFDYWGQGTLVTVSS | 111 | EIVLTQSPATLSLSPGERATLSCRASQTVPNYLAWYQQKPGQAPRLLIYDASNRATDIPARFSGSGSGTDFTLTISSLEPEDFAVYYCQQRANWPPITFGQGTRLEIK | 112 |
| 41A9 | QVQLQQWGAGLLKPSETLSLTCAVYGGSFSDYYWSWIRQPPGKGLEWIGEINHSGSTNYNPSLKSRVTISVDTSKNQFSLKLSSVTAADTAVYYCARDYDVLTGHPYYYYGMDVWGQGTTVTVSS | 121 | EIVLTQSPATLSLSPGERATLSCRASQSVRRYLAWYQQKPGQAPRLLIYDASNRATGIPARFSGSGSGTDFTLTISSLEPEDFAVYYCQQRNNWPLTFGGGTKLEIK | 122 |
| 02F3 | QVQLVESGGGVVQPGRSLRLSCAASGFSFSDYGIHWVRQAPGKGLEWVAVIWYDGSNKYYADSVKGRFTISRDNSKNTLYLQVNSLIAEDTAVYYCARDRGYSSGWYVDYYYYGMDVWGQGTTVTVSS | 131 | DIVMTQSPLSLPVTPGEPASISCRSSQSLLHSNGYNYLDWYLQKPGQSPQILIYLGSNRASGVPDRFSGSGSGTDFTLKISRVEAEDVGVYYCMQALQTPWTFGQGTKLEIK | 132 |
| 50D6 | EVQVLESGGGLVQPGGSLRLSCAASGFTFSNYAMNWVRQAPGKGLEWVSAISGGGGSTYYADSVKGRATISRDNSENTLYLQMNSLRAEDTAVYYCAKTSSGWYDSYYDYYGLDVWGQGTTVTVSS | 141 | DIQLTQSPSFLSASVGDRVTITCRASQGISNYLAWYQQKPGKVPKLLIYAVSTLQSGVPSRFSGSGSGTEFTLTISSLQPEDFATYYCQQLNSYPFTFGGGTKLEIK | 142 |
| 38E11 | EVQLLESGGGLVQPGGSLRLSCAASGFTFSNYAMNWVRQAPGKGLEWVSAISGGGGSTYYADSVKGRFTISRDNSKNTLYLQMNSLRAEDTAVYYCAKESITMVRGVMDYYGMDVWGQGTTVTVSS | 151 | DIQLTQSPSFLSASVGDRVTITCRASQGISSYLAWYQQKPGKAPKLLIYAASTLQGGVPSRFSGSGSGTEFTLTISSLQPEDFATYYCQHLNRFPRTFGQGTKVEIK | 152 |
| 05A8 | EVQLLESGGGLVQPGGSLRLSCAASGFTFRNYAMSWVRQAPGKGLEWVSAISGRGGSTYYADSVKGRFTISRDNSKNTLYLQMNSLRAEDTAVYYCAKDIVVVPAAKGYVMDAWGQGASVTVSS | 161 | EIVMTQSPATLSVSPGERATLSCRASQSVSSNLAWYQQKPGQAPRLLIYGASTRATGIPARFSGSGSGTEFTLTFSSLQSEDFVVYYCQQYNNWPLTFGQGTRLEIK | 162 |
| 12C2 | QEQLVESGGGVVQPGRSLRLSCVTSGFTFSSYGMHWVRQAPGKGLEWVAVIWYDGTNKYYADTVKGRFTISRDNSKNTLYLQMNSLRAEDTGVYYCAREGCDTISCPYYYYGMDVWGQGTTITVSS | 171 | DILMTQSPSSLSASVGDRVTITCRASQGINYYLAWYQQKPGKVPKLLIYTASTLQSGVPSRFSGSGSGTDFTLTISSLQPEDVATYFCQKYNSAPFTFGPGTKLEIK | 172 |
| 03G11 | EVQLLESGGGLVQPGGSLRLSCAASGFTFSSYAMSWVRQAPGKGLEWVSAISGSGNSAYYADSVKGRFTISRDNSKNTLFLQMNSLRADDTAVYYCASSSGWYLVYYFDLWGRGTLVTVSS | 181 | EIVMTQSPATLSVSPGERGTLSCRASQSVSSNLAWYQQKPGQAPRLLIYGASIRATGIPARFSGSGSGTEFILTINSLQSEDFAVYYCQQYNNWPLTVGGGTKVEIK | 182 |
| 06H1 | EVQLLESGGGLVQPGGSLRLSCAASGFTFSSYAMSWVRQAPGKGLEWVSGISGSGGNTHYADSVKGRFTISRDNSKNTLYLQMNSLRAEDTALYYCAQQWPQGYWGQGTLVTVSS | 191 | DIQMTQSPSSLSASVGDRVTITCRASQGISIYLAWFQQKPGKVPKLLIYAASTLQSGVPSRFSGSGSGTDFTLTISSLQPEDFATYYCQKYNSAPFTFGPGTKLEIK | 192 |
| 07C06_D2 | EVQLLESGGGLVQPGGSLGLSCAASGFTFSNYIMSWVRQAPGKGLEWVSGISGSGGSTHYAGSVKGRFTISRDNSKNTLNLQMNSLRVEDTAVYHCVQQWPQGYWGQGTLVTVSS | 201 | DIQMTQSPSSLSASVGDRVTITCRASQGITIYLAWFQQKPGKVPKLLIYAASTLQSGVPSRFSGSGSGTDFTLTISSLQPEDVATYYCQKYNSAPFTFGPGTKLEIK | 202 |
| 09F6 | EVQLLESGGGLVQPGGSLRLSCAASGFTFSSYAMSWVRLAPGKGLEWVSGLSGSGGDTHYAGSVKGRFTISRDNSKNTLYLQMNSLRAEDTALYYCAQQWPQGYWGQGTLVTVSS | 211 | DIQMTQSPSSLSASVGDRVTITCRASQGISIYLAWFQQKPGKVPKLLIYAASTLQSGVPSRFSGSGSGTDFTLTISSLQPEDVATYYCQKYNSAPFTFGPGTKLEIK | 212 |
| 14D4 | EVQLLESGGGLVQPGESLRLSCAASGFTFSSYAMSWVRQAPGKGLEWVSGISGSGGSTHYADSVKGRFTISRDNSKNTLYLQMNSLRAEDTAAYYCAQQWPQGHWGQGILVTVSS | 221 | DIQMTQSPSSLSASVGDRVTITCRASQDISIYLAWFQQRPGKVPKLLIYAASTLQSGVPSRFSGSGSGTDFTLTISSLQPEDVATYYCQKYNSDPFTFGPGTKVEIK | 222 |
| 15H5 | EVQLLESGGGLVQPGGSLRLSCAASGFTFSSYAMSWVRQAPGKGLEWVSVLSGSGDDTHYADSVKGRFTISRDNSKNTLYLQMNSLRAEDTAVYYCAHQWPQGYWGQGTLVTVSS | 231 | DIQMTQSPSSLSASVGDRVTITCRASQDISIYLAWFHQKPGKVPKLLIYAASTLQSGVPSRFSGSGSGTDFTLTISSLQPEDVAAYYCQKYNSAPFTFGPGTKLEIK | 232 |
| 20F5 | EVQLLESGGGLVQPGGSLRLSCAASGFTFSSYVMSWVRQTPGKGLEWVSGISGSGGSTHYTDSVQGRFTISRDNSKNTLYLQMNSLRAEDTAVYYCVQQWPQGYWGQGTLVTVSS | 241 | DIQMTQSPSSLSATVGDRVTITCRASQGISIYLAWFQQKPGKVPKNLIYAASTLQSGVPSRFSGSGSGTDFTLTISSLQPEDFATYYCQKYNSAPFTFGPGTKLEIK | 242 |
| 38A6 | EVQVLESGGGLVQPGESLRLSCAASGFTFNTYAMSWVRQAPGKGLEWVSAISDNGGGTYNADSVKGRFTISRDNSKNTLYLQMNSLRAEDTAVYYCAKGEQWGAPFDYWGQGTLVTVSS | 251 | DIQMTQSPSSLSASVGDRVTITCRASQGISIYLAWYHQKPGKVPKLLIYAASTLQSGVPSRFSGSGSGTDFTLTISSLQPEDVATYYCQKYNSAPWTFGQGTKLEIK | 252 |
| 39D7 | EVQLLESGGGLVQPGGSLRLSCAASGFTFSSYAMSWVRQAPGKGLEWVSTISGSGGSTYYADSVKGRFTISRDNSKNTLYLQMNSLRAEDTAVYYCATLDTAMAADAFAIWGQGTMVTVSS | 261 | DIVMTQSPLSLPVTPGEPASISCRSSQSLLHSNGYNYLDWYLQKSGQSPQLLIYLGSNRASGVPDRFSGSGSGTDFTLKISRVEAEDVGVYYCMQALLIPLYTFGQGTKLEIK | 262 |
| 18C11 | EVQLVESGGGLVQPGGSLRLSCAASGFTFSSYWMSWVRQVPGKGLEWVANIKQDGSEKYYVDSVKGRFTISRDNAKNSLYLQMNSLRAEDTAVYYCARDWRSSGWTLDYWGQGTLVTVSS | 271 | DIVMTQSPLSLPVTPGEPASISCRSSQSLLHSSGHNFLDWYLKKPGQSPQLLIYLGSNRGSGVPDRFSGSGSGTDFTLKISRVEAEDVGVYYCMQALQTPRTFGQGTKLEIK | 272 |

Related U.S. Application Data

(60) Provisional application No. 62/588,516, filed on Nov. 20, 2017, provisional application No. 62/488,445, filed on Apr. 21, 2017, provisional application No. 62/435,509, filed on Dec. 16, 2016.

(51) Int. Cl.

| | |
|---|---|
| ***A61K 45/06*** | (2006.01) |
| ***A61K 47/65*** | (2017.01) |
| ***A61P 35/00*** | (2006.01) |
| ***C07K 16/30*** | (2006.01) |

(52) U.S. Cl.

CPC .... *A61K 47/68035* (2023.08); *A61K 47/6849* (2017.08); *A61P 35/00* (2018.01); *C07K 16/30* (2013.01); *A61K 2039/505* (2013.01); *A61K 45/06* (2013.01)

(56) References Cited

U.S. PATENT DOCUMENTS

| | | | |
|---|---|---|---|
| 7,741,114 B2 | 6/2010 | Buehring et al. | |
| 8,263,071 B2 | 9/2012 | Burgess | |
| 8,394,928 B2 | 3/2013 | Auer et al. | |
| 8,883,159 B2 | 11/2014 | Bossenmaier et al. | |
| 9,120,860 B2 | 9/2015 | Burgess | |
| 9,346,886 B2 | 5/2016 | Auer et al. | |
| 9,718,893 B2 | 8/2017 | Jung et al. | |
| 10,487,136 B2 | 11/2019 | Bilgischer et al. | |
| 10,815,469 B2 | 10/2020 | Poma et al. | |
| 10,969,391 B2 | 4/2021 | Villalba Gonzalez et al. | |
| 11,702,481 B2 | 7/2023 | Ren et al. | |
| 12,138,313 B2 | 11/2024 | Ren et al. | |
| 12,138,314 B2 | 11/2024 | Ren et al. | |
| 2003/0092059 A1 | 5/2003 | Salfeld et al. | |
| 2008/0008719 A1 | 1/2008 | Bowdish et al. | |
| 2010/0233154 A1 | 9/2010 | Elvin et al. | |
| 2011/0070246 A1* | 3/2011 | Bossenmaier | A61P 35/00 435/69.6 |
| 2011/0214205 A1 | 9/2011 | Dietrich et al. | |
| 2012/0328616 A1 | 12/2012 | Li et al. | |
| 2014/0134179 A1 | 5/2014 | St. Croix et al. | |
| 2016/0024195 A1 | 1/2016 | Economides et al. | |
| 2016/0297884 A1 | 10/2016 | Kuo et al. | |
| 2017/0362325 A1 | 12/2017 | Jung et al. | |

FOREIGN PATENT DOCUMENTS

| | | |
|---|---|---|
| JP | 2007112734 A | 5/2007 |
| WO | 2004074481 A1 | 9/2004 |
| WO | 2008/133851 A2 | 11/2008 |
| WO | 2011/023390 A1 | 3/2011 |
| WO | 2013/102825 A1 | 7/2013 |
| WO | 2015/082446 A1 | 6/2015 |

OTHER PUBLICATIONS

Zhang et al. CDCP1 regulates retinal pigmented epithelial barrier integrity for the development of experimental autoimmune uveitis. JCI Insight. 2022, 7(18): e157038 (Year: 2022).*

Lui et al. Myocardial recovery in recent onset dilated cardiomyopathy: role of CDCP1 and cardiac fibrosis. Circulation Research, 2023, 133: 810-825 (Year: 2023).*

Sharma et al. Cytotoxic autophagy in cancer therapy. Int. J. Mol. Sci. 2014, 15, 10134-10051 (Year: 2014).*

Kollmorgen et al. (2013) Antibody mediated CDCP1 degradation as a mode of action for cancer targeted therapy. Molecular Oncology 7: 1142-1151, DOI: 10.1016/j.molonc.2013.08.009 (Year: 2013).*

Murphy et al., Targeting Sema3D in pancreatic cancer: A novel therapeutic strategy. Journal of Clinical Oncology retrieved online at : https://ascopubs.org/doi/abs/10.1200/jco.2015.33.15_suppl.4129. 2015 ASCO Annual Meeting. Abstract No. 41292 2 pages, (2015).

Rudikoff et al (Proc. Natl. Acad. Sci. USA, 79(6): 1979-1983, Mar. 1982).

Paul, Fundamental Immunology, 3rd Edition, 1993, pp. 292-295.

Colman P. M. (Research in Immunology, 145:33-36, 1994).

Padlan (Advances in Protein Chemistry, 1996, 49:57-133).

Berglund (Protein Science, 2008, 17:606-613).

Murphy et al. (Journal of Immunological Methods, vol. 463, p. 127-133, 2018).

Chen (Sci Adv. Apr. 1, 2020 ;6(14):eaaz7825).

He Y, et al. Proteolysis-induced N-terminal ectodomain shedding of the integral membrane glycoprotein CUB domain-containing protein 1 (CDCP1) is accompanied by tyrosine phosphorylation of its C-terminal domain and recruitment of Src and PKCdelta. J Biol Chem. 2010;285(34):26162-26173.

Edwards et al. The remarkable flexibility of the human antibody repertoire; isolation of over one thousand different antibodies to a single protein, BLyS. J Mol Biol. Nov. 14, 2003;334(1):103-18.

Fukuchi et al., Inhibition of tumor metastasis: functional immune modulation of the CUB domain containing protein 1. Mol Pharm. Feb. 1, 2010;7(6): 1142-51.

Kollmorgen et al., Antibody mediated CDCP1 degradation as mode of action for cancer targeted therapy. Mo. Oncol. Dec. 2013; 7(6): 1142-51.

Siva e tal., Targeting CUB domain-containing protein 1 with a monoclonal antibody inhibits metastasis in a prostate cancer model. Cancer Res. May 15, 2008;68(10): 3759-66.

International Search Report and Written Opinion for Application No. PCT/US2017/066661, dated May 7, 2018, 18 pages.

International Preliminary Report of Patentability and Written Opinion for PCT/US2017/066661 dated May 7, 2018, pp. 1-11.

Chari et al., "Antibody-Drug Conjugates: An Emerging Concept in Cancer Therapy," Angew. Chem. Int. Ed., 53, 3796-3827 (Feb. 20, 2014).

Rosell et al., "Relationship between gene mutation and lung cancer metastasis," Cancer Metastasis Rev., 34, 243-248 (May 5, 2015).

* cited by examiner

* Abs compete with each other in Octet binning assay

FIG. 15

| Ab Name | HC name | VH DNA SEQ ID NO: | VH AA SEQ ID NO: | CDR1-H SEQ ID NO: | CDR2-H SEQ ID NO: | CDR3-H SEQ ID NO: | LC name | VL DNA SEQ ID NO: | VL AA SEQ ID NO: | CDR1-L SEQ ID NO: | CDR2-L SEQ ID NO: | CDR3-L SEQ ID NO: |
|---|---|---|---|---|---|---|---|---|---|---|---|---|
| 14H4 | CD1XRH2_f14H4E10hD | 3 | 1 | 5 | 6 | 7 | CD1XRH2_f14H4E10k1 | 4 | 2 | 8 | 9 | 10 |
| 03B05 | CD1XRN4_f3B5h | 13 | 11 | 15 | 16 | 17 | CD1XRN4_f3B5k | 14 | 12 | 18 | 19 | 20 |
| 03C05 | CD1XRH2_f3C5H4hA | 23 | 21 | 25 | 26 | 27 | CD1XRH2_f3C5H4k1 | 24 | 22 | 28 | 29 | 30 |
| 27H10 | CD1XRH3_f27H10hB | 33 | 31 | 35 | 36 | 37 | CD1XRH3_f27H10k8 | 34 | 32 | 38 | 39 | 40 |
| 03B11 | CD1XRH2_f3B11hCC | 43 | 41 | 45 | 46 | 47 | CD1XRH2_f3B11k1 | 44 | 42 | 48 | 49 | 50 |
| 04G06 | CD1XRH2_f4G6E5hA | 53 | 51 | 55 | 56 | 57 | CD1XRH2_f4G6E5k2 | 54 | 52 | 58 | 59 | 60 |
| 42C5 | CD1XRH3_f42C5F12h3B | 63 | 61 | 65 | 66 | 67 | CD1XRH3_f42C5F12k5A | 64 | 62 | 68 | 69 | 70 |
| 47G7 | CD1XRH3_f47G7D12hA | 73 | 71 | 75 | 76 | 77 | CD1XRH3_f47G7D12k1 | 74 | 72 | 78 | 79 | 80 |
| 18C06 | CD1XRH2_f18C6B12hE | 83 | 81 | 85 | 86 | 87 | CD1XRH2_f18C6B12k1 | 84 | 82 | 88 | 89 | 90 |
| 11F9 | CD1XRH2_f11F9A5h9H | 93 | 91 | 95 | 96 | 97 | CD1XRH2_f11F9A5k9D | 94 | 92 | 98 | 99 | 100 |
| 10E2 | CD1XRH2_f10E2h5E | 103 | 101 | 105 | 106 | 107 | CD1XRH2_f10E2k5A | 104 | 102 | 108 | 109 | 110 |
| 01E2 | CD1XRH2_f1E2F7h1A | 113 | 111 | 115 | 116 | 117 | CD1XRH2_f1E2F7k4B | 114 | 112 | 118 | 119 | 120 |
| 41A9 | CD1XRH3_f41A9B3h8E | 123 | 121 | 125 | 126 | 127 | CD1XRH3_f41A9B3k11C | 124 | 122 | 128 | 129 | 130 |
| 02F3 | CD1XRH2_f2F3H3h2A | 133 | 131 | 135 | 136 | 137 | CD1XRH2_f2F3H3k2D | 134 | 132 | 138 | 139 | 140 |
| 50D6 | CD1XRH3_f50D6B11h1B | 143 | 141 | 145 | 146 | 147 | CD1XRH3_f50D6B11k1D | 144 | 142 | 148 | 149 | 150 |
| 38E11 | CD1XRH3_f38E11E3h4C | 153 | 151 | 155 | 156 | 157 | CD1XRH3_f38E11E3k4G | 154 | 152 | 158 | 159 | 160 |
| 05A8 | CD1XRH2_f5A8G8hA | 163 | 161 | 165 | 166 | 167 | CD1XRH2_f5A8G8k1 | 164 | 162 | 168 | 169 | 170 |

FIG. 15 - Continued

| | | | | | | | | | | | | |
|---|---|---|---|---|---|---|---|---|---|---|---|---|
| 12C2 | CD1XRH2_ f12C2A1h6E | 173 | 171 | 175 | 176 | 177 | CD1XRH2_ f12C2A1k | 174 | 172 | 178 | 179 | 180 |
| 03G11 | CD1XRH2_ f3G11F3hA | 183 | 181 | 185 | 186 | 187 | CD1XRH2_ f3G11F3k1 | 184 | 182 | 188 | 189 | 190 |
| 06H1 | CD1XRH2_ f6H1G6hA | 193 | 191 | 195 | 196 | 197 | CD1XRH2_ f6H1G6k1 | 194 | 192 | 198 | 199 | 200 |
| 07C06_ D2 | CD1XRH2_ f7C6D2hA | 203 | 201 | 205 | 206 | 207 | CD1XRH2_ f7C6D2k1 | 204 | 202 | 208 | 209 | 210 |
| 09F6 | CD1XRH2_ f9F6G10hA | 213 | 211 | 215 | 216 | 217 | CD1XRH2_ f9F6G10k1 | 214 | 212 | 218 | 219 | 220 |
| 14D4 | CD1XRH2_ f14D4H11h5A | 223 | 221 | 225 | 226 | 227 | CD1XRH2_ f14D4H11k7A | 224 | 222 | 228 | 229 | 230 |
| 15H5 | CD1XRH2_ f15H5G3h6A | 233 | 231 | 235 | 236 | 237 | CD1XRH2_ f15H5G3k7E | 234 | 232 | 238 | 239 | 240 |
| 20F5 | CD1XRH2_ f20F5G6h1A | 243 | 241 | 245 | 246 | 247 | CD1XRH2_ f20F5G6k3A | 244 | 242 | 248 | 249 | 250 |
| 38A6 | CD1XRH3_ f38A6hB | 253 | 251 | 255 | 256 | 257 | CD1XRH3_ f38A6k2 | 254 | 252 | 258 | 259 | 260 |
| 39D7 | CD1XRH3_ f39D7hB | 263 | 261 | 265 | 266 | 267 | CD1XRH3_ f39D7k1 | 264 | 262 | 268 | 269 | 270 |
| 18C11 | CD1XRH2_ f18C11A3h2A | 273 | 271 | 275 | 276 | 277 | CD1XRH2_ f18C11A3k4D | 274 | 272 | 278 | 279 | 280 |
| 38G4 | CD1XRH3_ f38G4B4h3C | 283 | 281 | 285 | 286 | 287 | CD1XRH3_ f38G4B4k3C | 284 | 282 | 288 | 289 | 290 |
| 27D8 | CD1XRH3_ f27D8G3h1E | 293 | 291 | 295 | 296 | 297 | CD1XRH3_ f27D8G3k | 294 | 292 | 298 | 299 | 300 |
| 11A4 | CD1XRH2_ f11A4h6A | 303 | 301 | 305 | 306 | 307 | CD1XRH2_ f11A4k6A | 304 | 302 | 308 | 309 | 310 |
| 24H1 | CD1XRH3_ f24H1A1h7A | 313 | 311 | 315 | 316 | 317 | CD1XRH3_ f24H1A1k10A | 314 | 312 | 318 | 319 | 320 |
| 18C02 | CD1XRH2_ f18C2F6h6E | 323 | 321 | 325 | 326 | 327 | CD1XRH2_ f18C2F6k6A | 324 | 322 | 328 | 329 | 330 |
| 07C10 | CD1XRH2_ f7C10E3hA | 333 | 331 | 335 | 336 | 337 | CD1XRH2_ f7C10E3k1 | 334 | 332 | 338 | 339 | 340 |
| 12D9 | CD1XRH2_ f12D9B2h7G | 343 | 341 | 345 | 346 | 347 | CD1XRH2_ f12D9B2k7A | 344 | 342 | 348 | 349 | 350 |
| 21F2 | CD1XRH3_ f21F2D10h9D | 353 | 351 | 355 | 356 | 357 | CD1XRH3_ f21F2D10k9B | 354 | 352 | 358 | 359 | 360 |
| 25B12 | CD1XRH3_ f25B12h9A | 363 | 361 | 365 | 366 | 367 | CD1XRH3_ f25B12k11E | 364 | 362 | 368 | 369 | 370 |

FIG. 15 - Continued

| | | | | | | | | | | | | |
|---|---|---|---|---|---|---|---|---|---|---|---|---|
| 47A2 | CD1XRH3_ f47A2A6h2E | 373 | 371 | 375 | 376 | 377 | CD1XRH3_ f47A2A6k2A | 374 | 372 | 378 | 379 | 380 |
| 14F11 | CD1XRH2_ f14F11C1h | 383 | 381 | 385 | 386 | 387 | CD1XRH2_ f14F11C1k5D | 384 | 382 | 388 | 389 | 390 |
| 18B2 | CD1XRH2_ f18B2E2hA | 393 | 391 | 395 | 396 | 397 | CD1XRH2_ f18B2E2k1 | 394 | 392 | 398 | 399 | 400 |

FIG. 16

| Ab Name | VH liabilities | VL liabilities | Bin-general | Ab Name | VH liabilities | VL liabilities | Bin-general |
|---|---|---|---|---|---|---|---|
| 14H4 | √ | √ | Distal | 07C06_D2 | √ | √ | Distal |
| 03B05 | √ | √ | Distal | 09F6 | √ | √ | Distal |
| 03C05 | √ | √ | Distal | 14D4 | √ | √ | Distal |
| 27H10 | √ | √ | Distal | 15H5 | √ | . √ | Distal |
| 03B11 | NHS @ CDR2 | √ | Distal | 20F5 | √ | √ | Distal |
| 04G06 | DG @ CDR2 | √ | Distal | 38A6 | NG @ CDR2 | √ | Distal |
| 42C5 | DG @ CDR2 | √ | Distal | 39D7 | √ | √ | Distal |
| 47G7 | DG @ CDR2 | √ | Distal | 18C11 | √ | √ | Distal |
| 18C06 | √ | √ | Proximal | 38G4 | NSS @ CDR3 | √ | Distal |
| 11F9 | √ | √ | Proximal | 27D8 | √ | √ | Distal |
| 10E2 | DG @ CDR2 | √ | Proximal | 11A4 | √ | .√ | Distal |
| 01E2 | √ | √ | Proximal | 24H1 | √ | √ | Distal |
| 41A9 | NHS @ CDR2 | √ | Proximal | 18C02 | NHS @CDR2 | √ | Proximal |
| 02F3 | DG @ CDR2 | NG @ CDR1 | Proximal | 07C10 | DG @ CDR2 | √ | Proximal |
| 50D6 | √ | √ | Proximal | 12D9 | DG @ CDR2 | √ | Proximal |
| 38E11 | √ | √ | Proximal | 21F2 | √ | √ | Proximal |
| 05A8 | √ | √ | Proximal | 25B12 | √ | √ | Proximal |
| 12C2 | 2xC @CDR3 | √ | Proximal | 47A2 | NTS @ CDR2 | √ | Proximal |
| 03G11 | √ | √ | Proximal | 14F11 | √ | √ | Proximal |
| 06H1 | √ | √ | Distal | 18B2 | √ | √ | Proximal |

FIG. 17

| Ab Name | Bin-general | Bin-subclass | human CDCP1 | | | Cynomolgus monkey CDCP1 | | |
|---|---|---|---|---|---|---|---|---|
| | | | $K_d$ huCDCP1 | hu $k_{on}$ | hu $k_{off}$ | $K_d$ cyCDCP1 | cy $k_{on}$ | cy $k_{off}$ |
| **14H4** | Distal | DB1/DB2 | <1nM | 6.25E+04 | <1.0E-07 | 5 nM | 4.31E+04 | 2.06E-04 |
| **03B05** | Distal | DB1 | 17 nM | 5.90E+04 | 1.02E-03 | 75 nM | 3.37E+04 | 2.52E-03 |
| **03C05** | Distal | DB1 | 20 nM | 6.02E+04 | 1.21E-03 | 80 nM | 3.18E+04 | 3.09E-03 |
| **27H10** | Distal | DB1 | 45nM | 2.36E+05 | 1.30E-02 | 45nM | 1.86E+05 | 8.23E-03 |
| **03B11** | Distal | DB1 | 60nM | 1.99E+05 | 1.16E-02 | >500nM | 8.97E+04 | 5.13E-02 |
| **04G06** | Distal | DB1/DB2 | 4 nM | 7.21E+05 | 2.60E-03 | 27 nM | 5.94E+05 | 1.63E-02 |
| **42C5** | Distal | DB2 | 2 nM | 1.58E+05 | 2.94E-04 | 12 nM | 1.23E+05 | 1.51E-03 |
| **47G7** | Distal | DB2 | 35nM | 4.36E+05 | 1.47E-02 | 500nM | 1.42E+05 | 9.69E-01 |
| **18C06** | Proximal | CB1 - N342 clv preferred | 25nM | 3.39E+04 | 8.20E-04 | 190nM | 7.92E+03 | 1.50E-03 |
| **11F9** | Proximal | CB1 - N342 clv preferred | 470 nM | 2.49E+04 | 1.16E-02 | >500 nM | 9.32E+02 | 1.41E-02 |
| **10E2** | Proximal | PB1 - R368 clv blocker | <1nM | 2.24E+05 | <1.0E-07 | 1nM | 1.71E+05 | 1.56E-04 |
| **01E2** | Proximal | PB1 - R368 clv blocker | 20 nM | 1.43E+05 | 2.71E-03 | >500 nM | 2.78E+05 | 6.59E-01 |
| **41A9** | Proximal | PB1 - R368 clv blocker | 6nM | 1.34E+05 | 8.08E-04 | 13nM | 8.92E+04 | 1.19E-03 |
| **02F3** | Proximal | PB1 - R368 clv blocker | 8 nM | 3.24E+04 | 2.53E-04 | 83 nM | 1.06E+04 | 8.85E-04 |
| **50D6** | Proximal | PB2 | <1nM | 1.33E+05 | <1.0E-07 | <1nM | 1.17E+05 | <1.0E-07 |
| **38E11** | Proximal | PB2 | 2nM | 3.32E+05 | 8.30E-04 | 4nM | 2.38E+05 | 8.14E-04 |
| **05A8** | Proximal | PB2 | 7 nM | 1.59E+05 | 1.05E-03 | 18 nM | 1.25E+05 | 2.20E-03 |
| **12C2** | Proximal | PB3 | 1 nM | 1.83E+05 | 1.77E-04 | 8 nM | 1.66E+05 | 1.33E-03 |

FIG. 18

| Ab Name | VH amino acid sequence | SEQ ID NO: | VL amino acid sequence | NO: |
|---|---|---|---|---|
| 14H4 | EVQLLESGGDLVQPGGSLRLSCAASGFTFNSYAMSWVRQAPGK<br>GLEWVSVLSGSGGDIHYADSVKGRFTVSRDNSKNMLYLQMNSL<br>RAEDTAVYFCAQQWPQGYWGQGTLVTVSS | 1 | DIQMTQSPSSLSASVGDRVTITCRASQGISIYLAWFQQKPG<br>KVPKLLIYAASTLQSGVPSRFSGSGSGTDFTLTISSLQPED<br>VATYYCQKYNSAPFTFGPGTKVEIK | 2 |
| 03B05 | QVQLVESGGGVVQPGRSLRLSCAASGFTFSSYGMHWVRQAPGK<br>GLEWVAIIWYDGSNKYYADSVKGRFTISRDNSKNTLYLQMNSL<br>RAEDTAVYYCAKDPSYSSGYYLFDFWGQGTLVTVSS | 11 | EIVMTQSPATLSVSPGERATLSCRASQSVSSNLAWYQQKPG<br>QAPRLLIYGASTRATGIPARFSGSGSGTEFTLTISSLQSED<br>FAVYYCQQYNNWPLTFGGGTKVEIK | 12 |
| 03C05 | EVQVLESGGGLVQPGGSLRLSCAASGFTFSSYVMSWVRQAPGK<br>GLEWVSGISGSGGSTHYADSVKGRFTISRDNSKNTLYLQMNSL<br>RAEDTALYYCAQQWPQGYWGQGTLVTVSS | 21 | DIQMTQSPSSLSASVGDRVTITCRASQDISIYLAWFQQKPG<br>KVPKVLIYAASTLQSGVPSRFSGSGTGTDFTLTISSLQPED<br>VATYFCQKYNSAPFTFGPGTKLEIK | 22 |
| 27H10 | QVQLVQSGAEVKKPGSSVKVSCKASGGTFSSYAMSWVRQAPGQ<br>GLEWMGGIIPILGTTNYAQKFQGRVTITADKSTSTAYMELSSL<br>RSEDTAVYYCAREGLYAFDIWGQGTMVTVSS | 31 | DIQMTQSPSSLSASVGDRVTITCRASQSISSYLNWYQQKPG<br>KAPKFLIYVASSLQSGVPSRFSGRGSGTDFTLTISSLQPED<br>FATYYCQQSYSTPWTFGQGTKVEIK | 32 |
| 03B11 | QVQLQQWDAGLLKPSETLSLTCAVYGGSFSSYYWSWIRQPPGK<br>GLEWIGEINHSGSTSYNPSLKSRVTISIDTSKNQFSLKLNSMT<br>AADTAVYFCAASPYFDYWGQGTLVTVSS | 41 | DIQLTQSPSFLSASVGDRVTITCRASQGISSYLAWYQQKPG<br>KAPKLLIYAASTLQSGVPSRFSGSGSGTEFTLTISSLQPED<br>FATYYCQQLNSYPRTFGQGTKVEIK | 42 |
| 04G06 | QVQLVESGGGVVQPGRSLRLSCVVSGFTLSSYGMHWVRQAPGK<br>GLEWVAVIWYDGSDKYYADSVKGRFTISRDNSKNTLYLQMNSL<br>RAEDTAVYYCARDDWGFDYWGQGTLVTVSS | 51 | DIQLTQSPSFLSASVGDRVTITCRASQDISNYLAWYQQKPG<br>KAPKLLISASTLQSGVPSRFSGSGSGTEFILTISSLQPEDF<br>ATYYCQHLNSYPFGQGTKVEIK | 52 |
| 42C5 | EVQLVESGGGLVQPGGSLRLSCAASGFTFSRYWMNWVRQAPGK<br>GLEWVANIKQDGSEKDYVDSVKGRFTISRDNAKNSLFLQMSSL<br>RAEDTAVYYCARVMYSSGWSFDYWGQGTLVTVSS | 61 | DIVMTQSPLSLPVTPGEPASISCRSSRSLLHSSGYNFLDWF<br>LQKPGQSPQLLIFLGSDRASGVPDRFSGSGSGTDFTLKISR<br>VETEDVGVYYCMQALQTPITFGQGTRLEIK | 62 |
| 47G7 | EVQLVESGGGLVQPGGSLRLSCAASGFTFSSYWMSWVRQAPGK<br>GLEWVANIKQDGSEKDYVDSVKGRFTISRDNAKNSLYLQMNSL<br>RVEDTAVYYCAREGGSSGWTFDYWGQGTLVTVSS | 71 | DIVMTQSPLSLPVTPGEPASISCRSSQSLLHSSGHNFLDWY<br>LQKPGQSPQLLIYLGSNRASGVPDRFSGSGSGTDFTLKISR<br>VEAEDVGVYYCMQALQTPPTFGQGTKLEIK | 72 |
| 18C06 | QVQLQESGPGQVKPSETLSLTCTVSGGSISSSFWSWIRQPPGK<br>GLEWIGYIYYSESTNYNPSLKRRVTLSVDTSKNQFSLKLTSVT<br>TADTAVYYCARNIGVAGLFDYWGQGTLVTVSS | 81 | EIVMTQSPATLSVSPGERATLSCRASQSVSSNLAWYQQKPG<br>QAPRLLIYGASTRATGIPARFSGSGSGTEFTLTISSLQSED<br>FAVYYCQQYNNWPLTFGGGTKVEIK | 82 |
| 11F9 | QVQLQESGPGLVKPSETLSLTCTVSGGSISSYYWSWIRQPPGK<br>GLEWIGYIYYSGSTNYNPSLKSRVTISVDTSKNQFSLKLSSVT<br>AADTAVYYCARNIGVAGLFDYWGQGTLVTVSS | 91 | EIVMTQSPATLSVSPGERATLSCRASQSVSSNLAWYQQKPG<br>QAPRLLIYGASTRATGIPARFSGSGSGTEFTLTISSLQSED<br>FAVYYCQQYNNWPLTFGGGTKLEIK | 92 |
| 10E2 | QVQLVESGGGVVQPGRSLRLSCAASGFTFSSYGMHWVRQAPGK<br>GLEWVAVVWYDGTIKYYADSVKGRFTISRDNPKNTLYLQMNSL<br>RAEDTAVYYCASQYSSGWHTDFFDVWGQGTMVTVSS | 101 | DIQMTQSPSTLSASVGDRVTITCRASQSISTWLAWYQQKPG<br>KAPKFLIYKASSLESGVPSRFSGSGSGTEFTLTISSLQPDD<br>FATYYCQQYSGYSLTFGGGTKVEIK | 102 |
| 01E2 | QVQLVESGGGVVQPGRSLRLSCAASGFTFSSYGMHWVRQAPGK<br>GLEWVAVIWYAGSNKYYADSVKGRFTISRDNSKNTLYLQMNSL<br>RAEDTAVYYCAGWDFDYWGQGTLVTVSS | 111 | EIVLTQSPATLSLSPGERATLSCRASQTVPNYLAWYQQKPG<br>QAPRLLIYDASNRATDIPARFSGSGSGTDFTLTISSLEPED<br>FAVYYCQQRANWPPITFGQGTRLEIK | 112 |
| 41A9 | QVQLQQWGAGLLKPSETLSLTCAVYGGSFSDYYWSWIRQPPGK<br>GLEWIGEINHSGSTNYNPSLKSRVTISVDTSKNQFSLKLSSVT<br>AADTAVYYCARDYDVLTGHFYYYYGMDVWGQGTTVTVSS | 121 | EIVLTQSPATLSLSPGERATLSCRASQSVRRYLAWYQQKPG<br>QAPRLLIYDASNRATGIPARFSGSGSGTDFTLTISSLEPED<br>FAVYYCQQRNNWPLTFGGGTKLEIK | 122 |

FIG. 18 - Continued

| | | | | |
|---|---|---|---|---|
| 02F3 | QVQLVESGGGVVQPGRSLRLSCAASGFSFSDYGIHWVRQAPGK<br>GLEWVAVIWYDGSNKYYADSVKGRFTISRDNSKNTLYLQVNSL<br>IAEDTAVYYCARDRGYSSGWYVDYYYYGMDVWGQGTTVTVSS | 131 | DIVMTQSPLSLPVTPGEPASISCRSSQSLLHSNGYNYLDWY<br>LQKPGQSPQILIYLGSNRASGVPDRFSGSGSGTDFTLKISR<br>VEAEDVGVYYCMQALQTPWTFGQGTKLEIK | 132 |
| 50D6 | EVQVLESGGGLVQPGGSLRLSCAASGFTFSNYAMNWVRQAPGK<br>GLEWVSAISGGGGSTYYADSVKGRATISRDNSENTLYLQMNSL<br>RAEDTAVYYCAKTSSGWYDSYYDYYGLDVWGQGTTVTVSS | 141 | DIQLTQSPSFLSASVGDRVTITCRASQGISNYLAWYQQKPG<br>KVPKLLIYAVSTLQSGVPSRFSGSGSGTEFTLTISSLQPED<br>FATYYCQQLNSYPFTFGGGTKLEIK | 142 |
| 38E11 | EVQLLESGGGLVQPGGSLRLSCAASGFTFSNYAMNWVRQAPGK<br>GLEWVSAISGGGGSTYYADSVKGRFTISRDNSKNTLYLQMNSL<br>RAEDTAVYYCAKESITMVRGVMDYYGMDVWGQGTTVTVSS | 151 | DIQLTQSPSFLSASVGDRVTITCRASQGISSYLAWYQQKPG<br>KAPKLLIYAASTLQGGVPSRFSGSGSGTEFTLTISSLQPED<br>FATYYCQHLNRFPRTFGQGTKVEIK | 152 |
| 05A8 | EVQLLESGGGLVQPGGSLRLSCAASGFTFSNYAMSWVRQAPGK<br>GLEWVSAISGRGGSTYYADSVKGRFTISRDNSKNTLYLQMNSL<br>RAEDTAVYYCAKDIVVVPAAKGYVMDAWGQGASVTVSS | 161 | EIVMTQSPATLSVSPGERATLSCRASQSVSSNLAWYQQKPG<br>QAPRLLIYGASTRATGIPARFSGSGSGTEFTLTFSSLQSED<br>FVVYYCQQYNNWPLTFGQGTRLEIK | 162 |
| 12C2 | QEQLVESGGGVVQPGRSLRLSCVTSGFTFSSYGMHWVRQAPGK<br>GLEWVAVIWYDGTNKYYADTVKGRFTISRDNSKNTLYLQMNSL<br>RAEDTGVYYCAREGCDTISCPYYYYGMDVWGQGTTITVSS | 171 | DILMTQSPSSLSASVGDRVTITCRASQGINYYLAWYQQKPG<br>KVPKLLIYTASTLQSGVPSRFSGSGSGTDFTLTISSLQPED<br>VATYFCQKYNSAPFTFGPGTKLEIK | 172 |
| 03G11 | EVQLLESGGGLVQPGGSLRLSCAASGFTFSSYAMSWVRQAPGK<br>GLEWVSAISGSGNSAYYADSVKGRFTISRDNSKNTLFLQMNSL<br>RADDTAVYYCASSSGWYLVYYFDLWGRGTLVTVSS | 181 | EIVMTQSPATLSVSPGERGTLSCRASQSVSSNLAWYQQKPG<br>QAPRLLIYGASIRATGIPARFSGSGSGTEFILTINSLQSED<br>FAVYYCQQYNNWPLTVGGGTKVEIK | 182 |
| 06H1 | EVQLLESGGGLVQPGGSLRLSCAASGFTFSSYAMSWVRQAPGK<br>GLEWVSGISGSGGNTHYADSVKGRFTISRDNSKNTLYLQMNSL<br>RAEDTALYYCAQQWPQGYWGQGTLVTVSS | 191 | DIQMTQSPSSLSASVGDRVTITCRASQGISIYLAWFQQKPG<br>KVPKLLIYAASTLQSGVPSRFSGSGSGTDFTLTISSLQPED<br>FATYYCQKYNSAPFTFGPGTKLEIK | 192 |
| 07C06<br>_D2 | EVQLLESGGGLVQPGGSLGLSCAASGFTFSNYIMSWVRQAPGK<br>GLEWVSGISGSGGSTHYAGSVKGRFTISRDNSKNTLNLQMNSL<br>RVEDTAVYHCVQQWPQGYWGQGTLVTVSS | 201 | DIQMTQSPSSLSASVGDRVTITCRASQGITIYLAWFQQKPG<br>KVPKLLIYAASTLQSGVPSRFSGSGSGTDFTLTISSLQPED<br>VATYYCQKYNSAPFTFGPGTKLEIK | 202 |
| 09F6 | EVQLLESGGGLVQPGGSLRLSCAASGFTFSSYAMSWVRLAPGK<br>GLEWVSGLSGSGGDTHYAGSVKGRFTISRDNSKNTLYLQMNSL<br>RAEDTALYYCAQQWPQGYWGQGTLVTVSS | 211 | DIQMTQSPSSLSASVGDRVTITCRASQGISIYLAWFQQKPG<br>KVPKLLIYAASTLQSGVPSRFSGSGSGTDFTLTISSLQPED<br>VATYYCQKYNSAPFTFGPGTKLEIK | 212 |
| 14D4 | EVQLLESGGGLVQPGESLRLSCAASGFTFSSYAMSWVRQAPGK<br>GLEWVSGISGSGGSTHYADSVKGRFTISRDNSKNTLYLQMNSL<br>RAEDTAAYYCAQQWPQGHWGQGILVTVSS | 221 | DIQMTQSPSSLSASVGDRVTITCRASQDISIYLAWFQQRPG<br>KVPKLLIYAASTLQSGVPSRFSGSGSGTDFTLTISSLQPED<br>VATYYCQKYNSDPFTFGPGTKVEIK | 222 |
| 15H5 | EVQLLESGGGLVQPGGSLRLSCAASGFTFSSYAMSWVRQAPGK<br>GLEWVSVLSGSGDDTHYADSVKGRFTISRDNSKNTLYLQMNSL<br>RAEDTAVYYCAHQWPQGYWGQGTLVTVSS | 231 | DIQMTQSPSSLSASVGDRVTITCRASQDISIYLAWFHQKPG<br>KVPKLLIYAASTLQSGVPSRFSGSGSGTDFTLTISSLQPED<br>VAAYYCQKYNSAPFTFGPGTKLEIK | 232 |
| 20F5 | EVQLLESGGGLVQPGGSLRLSCAASGFTFSSYVMSWVRQTPGK<br>GLEWVSGISGSGGSTHYTDSVQGRFTISRDNSKNTLYLQMNSL<br>RAEDTAVYYCVQQWPQGYWGQGTLVTVSS | 241 | DIQMTQSPSSLSATVGDRVTITCRASQGISIYLAWFQQKPG<br>KVPKNLIYAASTLQSGVPSRFSGSGSGTDFTLTISSLQPED<br>FATYYCQKYNSAPFTFGPGTKLEIK | 242 |
| 38A6 | EVQVLESGGGLVQPGESLRLSCAASGFTFNTYAMSWVRQAPGK<br>GLEWVSAISDNGGGTYNADSVKGRFTISRDNSKNTLYLQMNSL<br>RAEDTAVYYCAKGEQWGAPFDYWGQGTLVTVSS | 251 | DIQMTQSPSSLSASVGDRVTITCRASQGISIYLAWYHQKPG<br>KVPKLLIYAASTLQSGVPSRFSGSGSGTDFTLTISSLQPED<br>VATYYCQKYNSAPWTFGQGTKLEIK | 252 |
| 39D7 | EVQLLESGGGLVQPGGSLRLSCAASGFTFSSYAMSWVRQAPGK<br>GLEWVSTISGSGGSTYYADSVKGRFTISRDNSKNTLYLQMNSL<br>RAEDTAVYYCATLDTAMAADAFAIWGQGTMVTVSS | 261 | DIVMTQSPLSLPVTPGEPASISCRSSQSLLHSNGYNYLDWY<br>LQKSGQSPQLLIYLGSNRASGVPDRFSGSGSGTDFTLKISR<br>VEAEDVGVYYCMQALLIPLYTFGQGTKLEIK | 262 |
| 18C11 | EVQLVESGGGLVQPGGSLRLSCAASGFTFSSYWMSWVRQVPGK<br>GLEWVANIKQDGSEKYYVDSVKGRFTISRDNAKNSLYLQMNSL<br>RAEDTAVYYCARDWRSSGWTLDYWGQGTLVTVSS | 271 | DIVMTQSPLSLPVTPGEPASISCRSSQSLLHSSGHNFLDWY<br>LKKPGQSPQLLIYLGSNRGSGVPDRFSGSGSGTDFTLKISR<br>VEAEDVGVYYCMQALQTPRTFGQGTKLEIK | 272 |

FIG. 18 - Continued

| | | | | |
|---|---|---|---|---|
| 38G4 | EVQLVESGGGLVQPGGSLRLSCAASGFTFSSYWMSWVRQAPGK<br>GLEWVANVKQDGSEKDYVDSVKGRFTISRDNAKNSLYLQMNSL<br>RAEDTAVYYCAREWNSSGWTFDYWGQGTLVTVSS | 281 | DIVMTQSPLSLPVTPGEPASISCRSSQSLLHSTGYNFLDWY<br>LQKPGQSPQLLIFLGSNRASGVPDRFSGSGSGTDFTLKISR<br>VEAEDVGIYYCMQALQTPLTFGGGTKVEIK | 282 |
| 27D8 | QVQLVESGGGVVQPGRSLRLSCAASGFTFSSYGMHWVRQAPGK<br>GLEWVAVIWYDGSNKYYADSVKGRFTISRDNSKNTLYLQMNSL<br>RAEDTAVYHCARDRVYYDGSGSYYNVGVMDVWGQGASVTVSS | 291 | EIVMTQSPATLSVSPGERATLSCRASQSVSNNLAWYQQKPG<br>QAPRLLIYGVSTRATGIPARFSGSGSGTEFTLIISSLQSED<br>FAGYYCQQYNDWPLTFGGGTKLEIK | 292 |
| 11A4 | QVQLVESGGGVVQPGGSPRLSCAASGFTFSSYAMHWVRQAPGT<br>GLEWVALIYYDGSHEYYSDSVKGRFTISRDNSKNTLYLQMSSL<br>RAEDTAVYYCARDGGSGSHYPFDAFDIWGQGTMVTVSS | 301 | DIQMTQSPSTLSASVGDRVTITCRASQSISSWLAWYQQKPG<br>KAPNLLIYKASSLESGVPSRFSGSGSGTEFTLTISSLQPDD<br>FATYYCQQYNTYYTFGQGTKVEIK | 302 |
| 24H1 | QVQLQESGPGLVKPSETLSLTCTVSGGSISSYYWSWIRQFSGK<br>GLEWIGYIYYTGRNNYNPSLKSRVTISVDTSKNQFSLKLSSVT<br>AADSAVYYCAREGGWGPHFDYWGQGTLVTVSS | 311 | DIVMTQSPLSLPVTPGEPASISCRSSQSLLHSSGYNYLDWY<br>LQKPGQSPQLLIYLGSDRASGVPDRFRGSGSGTDFTLKISR<br>VEAEDVGIYYCMQALQIPYTFGQGTKLEIK | 312 |
| 18C02 | QVQLQQWGAGLLKPSETLSLTCAVYGGSFSDYYWSWIRQPPGK<br>GLEWIGEINHSGSTNYNPSLKSRVTISVDTSKNQFSLKLSSVT<br>AADTAVYYCARDYDVLTGHFYYYYGMDVWGQGTTVTVSS | 321 | DIQMTQSPSSLSASVGDRVTITCRASQSISSYLNWFQQKPG<br>KAPKLLIYAASSLQSGVPSRFSGSGSGTDFTLTISSLQPED<br>FATYYCQQSYTMPYTFGQGTKLEIK | 322 |
| 07C10 | QVQLVESGGGVVQPGRSLRLSCAASGFTFSSYGMHWVRQAPGK<br>GLEWVALIWYDGSNKYYADSVQGRFTISRDNSKNTLYLQMNSL<br>RAEDTAVYYCAVDYDILTGHVLYVMDAWGQGVSVTVSS | 331 | EIVLTQSPATLSLSPGERATLSCRASQSVTNYLAWFQQKPG<br>QAPRLLIYDAFNRATGIPARFSGSGSGTDFTLTISSLEPED<br>FAIYYCQQRSYWPLTFGGGTKLEIK | 332 |
| 12D9 | QVQLVESGGGVVQPGRSLRLSCAASGFTFSNYGMNWVRQAPGK<br>GLEWVAVIWYDGTIKYYADSVKGRFTISRDNSKNTLYLQMISL<br>RAEDTAVYYCASEYSSGWYRGAFDIWGQGTMVTVSS | 341 | DIQLTQSPSFLSASVGDRVTITCRASQGISSYLAWYQQKPG<br>KAPKLLIYAASTLQSGVPSRFSGSGSGTEFTLTISSLQPED<br>FATYYCQQLNSYPYTFGQGTKVEIK | 342 |
| 21F2 | QVQLVESGGGVVQPGRSLRLSCAASGFTFSSYGMFWVRQTPGK<br>GLEWVANIWYDGSNKYYTDSVKGRFTISRDNSKNTLYLQMNSL<br>RAGDTAVYYCARETYYYGSGSYGGGLDVWGQGTTVTVSS | 351 | DIQMTQSPSTLSASVGDRVTITCRASQSISSWLAWYQQKPG<br>KAPKLLIYKASSLESGVPSRFSGSGSGTEFTLTISSLQPDD<br>FATYYCQQYYSYITFGQGTRLEIK | 352 |
| 25B12 | QVQLQESGPGLVKPSETLSLTCAVSGYSISSGYYWGWIRQPPG<br>KGLEWIGSIYHSGSTYYNPSLKSRVTISVDTSKNQFSLKLSSV<br>TAADTAVYYCARDKITVAAFDIWGQGTMVTVSS | 361 | DIQLTQSPSFLSASVGDRVTITCRASQGISSYLAWYQQKPG<br>KAPKLLIYAASTLQSGVPSRFSGSGSGTEFTLTISSLQPED<br>FATYYCQQLNSYPYTFGQGTKLEIK | 362 |
| 47A2 | QVQLQESGPGLVKPSETLSLTCAVSGYSISSDYYWGWIRQPPG<br>KGLEWIGSIYHSGSTYYNTSLKSRVTISLDTSKNQFSLKLTSV<br>TAADTAVYYCVREGTVGGHYYYYYGMDVWGQGTTVTVSS | 371 | EIVLTQSPATLSLSPGERATLSCRASQSVRSYLAWYQQKPG<br>QAPRLLIYDASKRATGIPARFSGSGSGTDFTLTISSLEPED<br>FAVYYCQQRNSWPTFGGGTKVEIK | 372 |
| 14F11 | EVHLLESGGGLVQPGGSLRLSCAASGFTFSSYAMSWVRQAPGK<br>GLEWVSGIDSGGDTYYADSVKGRFTISRDNSKNTLYLQMTSLR<br>AEDTAVYYCAKDLYSSGWLAFDIWGQGTMVTVSS | 381 | DIQLTQSPSFLSASVGDRVTITCRASQGISSYLAWYQQKPG<br>KAPKLLIYAASTLQSGVPSRFSGSGSGTEFTLTISSLQPED<br>FAIYYCQQLNSYPLYTFGQGTKLEIK | 382 |
| 18B2 | EVQLLESGGGSVQPGGSLRLSCAASGFTFSSYAMSWVRQAPGK<br>GLEWVSGISDNGNTYYADSVKGRFTISRDNSKNTLYLQMNSLR<br>AEDTAVYHCAKDLYSSGWLAFDIWGQGTMVTVSS | 391 | DIQLTQSPSFLSASVGDRVTITCRASQGISTYLAWYQQKPG<br>KAPKLLIYAASTLQSGVPSRFSGSGSGTEFTLTISSLQPED<br>FATYYCQQLNSYPLYTFGQGTKVEIK | 392 |

FIG. 19

| Ab Name | VH nucleotide sequence | SEQ ID NO: | VL nucleotide sequence | SEQ ID NO: |
|---|---|---|---|---|
| 14H4 | ATGGAATTGGGGCTGAGCTGTCTTTTTCTTGTGGCTATTTTAAA<br>AGGTGTCCAGTGTGAGGTGCAGCTGTTGGAGTCTGGGGGAGACT<br>TGGTACAGCCTGGGGGGTCCCTGAGACTCTCCTGTGCAGCCTCT<br>GGATTCACCTTTAACAGCTATGCCATGAGCTGGGTCCGCCAGGC<br>TCCAGGGAAGGGGCTGGAGTGGGTCTCAGTTCTCAGTGGTAGTG<br>GTGGTGACATACACTACGCAGACTCCGTGAAGGGCCGGTTCACC<br>GTCTCCAGAGACAATTCCAAGAATATGCTGTATCTGCAAATGAA<br>CAGCCTGAGAGCCGAAGACACGGCCGTTTATTTCTGTGCGCAAC<br>AGTGGCCACAGGGCTACTGGGGCCAGGGAACCCTGGTCACCGTC<br>TCCTCAGCCTCCACCAAGGGCCCATCGGTCTTCCC | 3 | ATGAGGCTCCTTGCTCAGCTCCTGGGACTCCTGCTGCCCT<br>GGCTCCCAGATACCAGATGTGACATCCAGATGACCCAGTC<br>TCCATCCTCCCTGTCTGCATCTGTAGGAGACAGAGTCACC<br>ATCACTTGCCGGGCGAGTCAGGGCATTAGCATTTATTTAG<br>CCTGGTTTCAGCAGAAACCAGGGAAAGTTCCTAAGCTCCT<br>GATCTATGCTGCATCCACTTTGCAATCAGGGGTCCCATCT<br>CGGTTCAGTGGCAGTGGATCTGGGACAGATTTCACTCTCA<br>CCATCAGCAGCCTGCAGCCTGAAGATGTTGCAACTTATTA<br>CTGTCAAAAGTATAACAGTGCCCCATTCACTTTCGGCCCT<br>GGGACCAAGGTGGAGATCAAACGAACTGTG | 4 |
| 03B05 | ATGGAGTTGGGACTGAGCTGGGTTTTCCTCGTTGCTCTTTTAAG<br>AGGTGTCCAGTGTCAGGTGCAGCTGGTGGAGTCTGGGGGAGGCG<br>TGGTCCAGCCTGGGAGGTCCCTGAGACTCTCCTGTGCAGCGTCT<br>GGATTCACCTTCAGTAGCTATGGCATGCACTGGGTCCGCCAGGC<br>TCCAGGCAAGGGGCTGGAGTGGGTGGCAATTATATGGTATGATG<br>GAAGTAATAAATACTATGCAGACTCCGTGAAGGGCCGATTCACC<br>ATCTCCAGAGACAATTCCAAGAACACGTTGTATCTGCAAATGAA<br>CAGCCTGAGAGCCGAGGACACGGCCGTTTATTACTGTGCGAAAG<br>ATCCCTCGTACAGCAGTGGCTACTACCTCTTTGACTTCTGGGGT<br>CAGGGAACCCTGGTCACCGTCTCCTCAGCCCAAACAACAGCCCC<br>ATCTGTCTATCC | 13 | GAAATAGTGATGACGCAGTCTCCAGCCACCCTGTCTGTGT<br>CTCCAGGGGAAAGAGCCACCCTCTCCTGCAGGGCCAGTCA<br>GAGTGTTAGCAGCAACTTAGCCTGGTACCAGCAGAAACCT<br>GGCCAGGCTCCCAGGCTCCTCATCTATGGTGCATCCACCA<br>GGGCCACTGGTATCCCAGCCAGGTTCAGTGGCAGTGGGTC<br>TGGGACAGAGTTCACTCTCACCATCAGCAGCCTGCAGTCT<br>GAAGATTTTGCAGTTTATTACTGTCAGCAGTATAATAACT<br>GGCCGCTCACTTTCGGCGGAGGGACCAAGGTGGAGATCAA<br>ACGGGCTGATGCTGCA | 14 |
| 03C05 | ATGGAGTTTGGGCTTAGCTGGCTTTTTCTTGTGGCTATTTTAAA<br>AGGTGTCCAGTGTGAGGTGCAGGTGTTGGAGTCTGGGGGAGGCT<br>TGGTACAGCCTGGGGGGTCCCTGAGACTCTCCTGTGCAGCCTCT<br>GGATTCACCTTTAGCAGCTATGTCATGAGCTGGGTCCGCCAGGC<br>TCCAGGGAAGGGGCTGGAGTGGGTCTCAGGTATCAGTGGTAGTG<br>GTGGTAGCACACACTACGCAGACTCCGTGAAGGGCCGGTTCACC<br>ATCTCCAGAGACAATTCCAAGAACACGCTGTATCTGCAAATGAA<br>CAGCCTGAGAGCCGAGGACACGGCCCTTTATTACTGTGCGCAGC<br>AGTGGCCACAGGGCTACTGGGGCCAGGGAACCCTGGTCACCGTC<br>TCCTCAGCCTCCACCAAGGGCCCATCGGTCTTCCC | 23 | ATGGACATGAGGGTCCTCGCTCAGCTCCTGGGACTCCTGC<br>TGCTCTGGCTCCCAGATACCAGATGTGACATCCAGATGAC<br>CCAGTCTCCATCCTCCCTGTCTGCATCTGTAGGAGACAGA<br>GTCACCATCACTTGCCGGGCGAGTCAGGACATTAGCATTT<br>ATTTAGCCTGGTTTCAGCAGAAACCAGGGAAAGTTCCTAA<br>GGTCCTGATCTATGCTGCATCCACTTTGCAATCAGGGGTC<br>CCATCTCGGTTCAGTGGCAGTGGAACTGGGACAGATTTCA<br>CTCTCACCATCAGCAGCCTGCAGCCTGAAGATGTTGCGAC<br>TTATTTCTGTCAAAAGTATAACAGTGCCCCATTCACTTTC<br>GGCCCTGGGACCAAGCTGGAGATCAAACGAACTGTG | 24 |
| 27H10 | ATGGACTGGATTTGGAGGATCCTCTTTGTGGTGGCAGCAGCTAC<br>AGGTGTCCAGTCCCAGGTGCAGCTGGTGCAGTCTGGGGCTGAGG<br>TGAAGAAGCCTGGGTCCTCGGTGAAGGTCTCCTGCAAGGCTTCT<br>GGAGGCACCTTCAGCAGTTATGCTATGAGCTGGGTGCGACAGGC<br>CCCTGGACAAGGGCTTGAGTGGATGGGAGGGATCATCCCTATCC<br>TTGGTACAACAAACTACGCACAGAAGTTCCAGGGCAGAGTCACG<br>ATTACCGCGGACAAATCCACGAGCACAGCCTACATGGAGCTGAG<br>CAGCCTGAGATCTGAGGACACGGCCGTGTATTACTGTGCGAGAG<br>AGGGGCTCTATGCTTTTGATATCTGGGGCCAAGGGACAATGGTC | 33 | ATGGACATGAGGGTGCCTGCTCAGCTCCTGGGGCTCCTGC<br>TACTCTGGCTCCGAGGTGCCAGATGTGACATCCAGATGAC<br>CCAGTCTCCATCCTCCCTGTCTGCATCTGTAGGAGACAGA<br>GTCACCATCACTTGCCGGGCAAGTCAGAGCATTAGCAGCT<br>ATTTAAATTGGTATCAGCAGAAACCAGGGAAAGCCCCTAA<br>GTTCCTGATCTATGTTGCATCCAGTTTGCAAAGTGGGGTC<br>CCATCAAGGTTCAGTGGCAGGGGATCTGGGACAGATTTCA<br>CTCTCACCATCAGCAGTCTGCAACCTGAAGATTTTGCAAC<br>TTACTACTGTCAACAGAGTTACAGTACCCCGTGGACGTTC | 34 |

FIG. 19 - Continued

| | | | | |
|---|---|---|---|---|
| | ACCGTCTCCTCA | | GGCCAAGGGACCAAGGTGGAGATCAAA | |
| 03B11 | ATGAAGCACCTGTGGTTCTTCCTCCTCCTGGTGGCAGCTCCCAG<br>ATGGGTCCTGTCCCAGGTGCAGCTACAGCAGTGGGACGCAGGAC<br>TGTTGAAGCCTTCGGAGACCCTGTCCCTCACCTGCGCTGTCTAT<br>GGTGGGTCCTTCAGTAGTTACTACTGGAGCTGGATCCGCCAGCC<br>CCCCGGGAAGGGGCTGGAGTGGATTGGGGAAATCAATCATAGTG<br>GAAGCACCAGCTACAACCCGTCCCTCAAGAGTCGAGTCACCATA<br>TCAATAGACACGTCCAAGAACCAGTTCTCCCTGAAGCTGAACTC<br>TATGACCGCCGCGGACACGGCTGTGTATTTCTGTGCGGCTTCCC<br>CATACTTTGACTACTGGGGCCAGGGAACCCTGGTCACCGTCTCC<br>TCA | 43 | ATGGACATGAGGGTGCCCGCTCAGCTCCTGGGGCTCCTGC<br>TGCTCTGGCTCCCAGGTGCCAGATGTGACATCCAGTTGAC<br>CCAGTCTCCATCCTTCCTGTCTGCATCTGTAGGAGACAGA<br>GTCACCATCACTTGCCGGGCCAGTCAGGGCATTAGCAGTT<br>ATTTAGCCTGGTATCAGCAAAAACCAGGGAAAGCCCCTAA<br>GCTCCTGATCTATGCTGCATCCACTTTGCAAAGTGGGGTC<br>CCATCAAGGTTCAGCGGCAGTGGATCTGGGACAGAATTCA<br>CTCTCACAATCAGCAGCCTGCAGCCTGAAGATTTTGCAAC<br>TTATTACTGTCAACAGCTTAATAGTTACCCTCGGACGTTC<br>GGCCAAGGGACCAAGGTGGAGATCAAA | 44 |
| 04G06 | ATGGAGTTTGGGCTGAGCTGGGTTTTCCTCGTTGCTCTTTTAAG<br>AGGTGTCCAGTGTCAGGTGCAGTTGGTGGAGTCTGGGGGAGGCG<br>TGGTCCAGCCTGGGAGGTCCCTGAGACTCTCCTGTGTAGTGTCT<br>GGATTCACCCTCAGTAGCTATGGCATGCACTGGGTCCGCCAGGC<br>TCCAGGCAAGGGGCTGGAGTGGGTGGCAGTTATTTGGTATGATG<br>GAAGTGATAAATATTATGCAGACTCCGTGAAGGGCCGATTCACC<br>ATCTCCAGAGACAATTCCAAGAACACACTATATCTGCAAATGAA<br>CAGCCTGAGAGCCGAGGACACGGCTGTGTATTACTGTGCGAGAG<br>ATGACTGGGGCTTTGACTACTGGGGCCAGGGAACCCTGGTCACC<br>GTCTCCTCAGCCTCCACCAAGGGCCCATCGGTCTTCCC | 53 | ATGAGGGTCCTCGCTCAGCTCCTGGGGCTCCTGCTGCTCT<br>GGCTCCCAGGTGCTAGATGTGACATCCAGTTGACCCAGTC<br>TCCATCCTTCCTGTCTGCATCTGTAGGAGACAGAGTCACC<br>ATCACTTGCCGGGCCAGTCAGGACATTAGCAATTATTTAG<br>CCTGGTATCAGCAAAAACCAGGGAAAGCCCCTAAGCTCCT<br>GATCTCTGCATCCACTTTGCAAAGTGGGGTCCCCTCAAGG<br>TTCAGCGGCAGTGGATCTGGGACAGAATTCATTCTCACAA<br>TCAGCAGCCTGCAGCCTGAAGATTTTGCAACTTATTACTG<br>TCAACACCTTAATAGTTATCCTTTTGGCCAGGGGACCAAG<br>GTGGAGATCAAACGAACTGTG | 54 |
| 42C5 | ATGGAGTTGGGGCTGAGCTGGGTTTTCCTTGTTGCTATTTTAGA<br>AGGTGTCCAGTGTGAGGTGCAGCTGGTGGAGTCTGGGGGAGGCT<br>TGGTCCAGCCTGGGGGGTCCCTGAGACTCTCCTGTGCAGCCTCT<br>GGATTCACCTTTAGTAGGTATTGGATGAACTGGGTCCGCCAGGC<br>TCCAGGGAAGGGGCTGGAGTGGGTGGCCAACATAAAGCAAGATG<br>GAAGTGAGAAAGACTATGTGGACTCTGTGAAGGGCCGATTCACC<br>ATCTCCAGAGACAACGCCAAGAACTCACTGTTTCTGCAAATGAG<br>CAGCCTGAGAGCCGAGGACACGGCTGTGTATTACTGTGCGAGAG<br>TAATGTATAGCAGTGGCTGGTCCTTTGACTACTGGGGCCAGGGA<br>ACCCTGGTCACCGTCTCCTCAGCCTCCACCAAGGGCCCATCGGT<br>CTTCCCTCTGGCACCCTCCTCCAAGAGCACCTCTGGGGGCACAG<br>CGGCC | 63 | ATGGAGACTGGGCTGCGCTGGCTTCTCCTGGTCGCTGTGC<br>TCAAAGGTGTCCAGGGGACCATGAGGCTCCTTGCTCAGCT<br>CCTGGGGCTGCTAATGCTCTGGGTCTCTGGATCCAGTGGG<br>GATATTGTGATGACTCAGTCTCCACTCTCCCTGCCCGTCA<br>CCCCTGGAGAGCCGGCCTCCATCTCCTGCAGGTCTAGTCG<br>GAGCCTCCTACATAGTAGTGGATACAACTTTTTGGATTGG<br>TTCCTGCAGAAGCCAGGGCAGTCTCCACAGCTCCTGATCT<br>TTTTGGGTTCTGATCGGGCCTCCGGGGTCCCTGACAGGTT<br>CAGTGGCAGTGGATCAGGCACAGATTTTACACTGAAAATC<br>AGCAGAGTGGAGACTGAGGATGTTGGAGTTTATTACTGCA<br>TGCAAGCTCTACAAACTCCTATCACCTTCGGCCAAGGGAC<br>ACGACTGGAGATTAAACGAACTGTGGCTGCACCATCTGTC<br>TTCATCTTCCCTCCATCTGATGAGCAGT | 64 |
| 47G7 | ATGGAATTGGGGCTGTGCTGGGTTTTCCTTGTTGCTATTTTAGA<br>AGGTGTCCAGTGTGAGGTGCAGCTGGTGGAGTCTGGGGGAGGCT<br>TGGTCCAGCCTGGGGGGTCCCTGAGACTCTCCTGTGCAGCCTCT<br>GGATTCACCTTTAGTAGCTATTGGATGAGCTGGGTCCGCCAGGC<br>TCCAGGGAAGGGGCTGGAGTGGGTGGCCAACATAAAGCAAGATG<br>GAAGTGAGAAAGACTATGTGGACTCTGTGAAGGGCCGATTCACC<br>ATCTCCAGAGACAACGCCAAGAACTCACTGTATCTGCAAATGAA<br>CAGCCTGAGAGTCGAGGACACGGCTGTGTATTACTGTGCGAGAG<br>AGGGGGGTAGCAGTGGCTGGACTTTTGACTACTGGGGCCAGGGA<br>ACCCTGGTCACCGTCTCCTCAGCCTCCACCAAGGGCCCATCGGT<br>CTTCCC | 73 | ATGAGGCTCCCTGCTCAGCTCCTGGGGCTGCTAATGCTCT<br>GGGTCTCTGGATCCAGTGGGGATATTGTGATGACTCAGTC<br>TCCACTCTCCCTGCCCGTCACCCCTGGAGAGCCGGCCTCC<br>ATCTCCTGCAGGTCTAGTCAGAGCCTCCTGCATAGTAGTG<br>GACACAACTTTTTGGATTGGTACCTGCAGAAGCCAGGGCA<br>GTCTCCACAGCTCCTGATCTATTTGGGTTCTAATCGGGCC<br>TCCGGGGTCCCTGACAGGTTCAGTGGCAGTGGATCAGGCA<br>CAGATTTTACACTGAAAATCAGCAGAGTGGAGGCTGAGGA<br>TGTTGGGGTTTATTACTGCATGCAAGCTCTACAAACTCCT<br>CCGACGTTCGGCCAAGGGACCAAGCTGGAGATCAAACGAA<br>CTGTG | 74 |

FIG. 19 - Continued

| | | | | |
|---|---|---|---|---|
| 18C06 | ATGAAACATCTGTGGTTCTTCCTTCTCCTGGTGGCAGCTCCCAG<br>ATGGGTCCTGTCCCAGGTGCAGCTGCAGGAGTCGGGCCCAGGAC<br>AGGTGAAGCCTTCGGAGACCCTGTCCCTCACCTGCACTGTCTCT<br>GGTGGCTCCATCAGTAGTTCCTTCTGGAGCTGGATCCGGCAGCC<br>CCCAGGGAAGGGACTGGAGTGGATTGGGTATATCTATTACAGTG<br>AGAGCACCAACTACAACCCCTCCCTCAAGAGACGAGTCACCTTA<br>TCAGTGGACACGTCCAAGAACCAGTTCTCCCTGAAGCTGACCTC<br>TGTGACCACTGCGGACACGGCCGTGTATTACTGTGCGAGAAATA<br>TAGGAGTGGCTGGTCTCTTTGACTACTGGGGCCAGGGAACCCTG<br>GTCACCGTCTCCTCAGCCTCCACCAAGGGCCCATCGGTCTTCCC | 83 | ATGGAAGCCCCAGCTCAGCTTCTCTTCCTCCTGCTACTCT<br>GGCTCCCAGATACCACTGGAGAAATAGTGATGACGCAGTC<br>TCCAGCCACCCTGTCTGTGTCTCCAGGGGAAAGAGCCACC<br>CTCTCCTGCAGGGCCAGTCAGAGTGTTAGCAGCAACTTAG<br>CCTGGTACCAGCAGAAACCTGGCCAGGCTCCCAGGCTCCT<br>CATCTATGGTGCATCCACCAGGGCCACTGGTATCCCAGCC<br>AGGTTCAGTGGCAGTGGGTCTGGGACAGAGTTCACTCTCA<br>CCATCAGCAGCCTGCAGTCTGAAGATTTTGCAGTTTATTA<br>CTGTCAGCAGTATAATAACTGGCCGCTCACTTTCGGCGGA<br>GGGACCAAGGTGGAGATCAAACGAACTGTG | 84 |
| 11F9 | ATGAAACACCTGTGGTTCTTCCTTCTCCTGGTGGCAGCTCCCAG<br>ATGGGTCCTGTCCCAGGTGCAGCTGCAGGAGTCGGGCCCAGGAC<br>TGGTGAAGCCTTCGGAGACCCTGTCCCTCACCTGCACTGTCTCT<br>GGTGGCTCCATCAGTAGTTACTACTGGAGCTGGATCCGGCAGCC<br>CCCAGGGAAGGGACTGGAGTGGATTGGGTATATCTATTACAGTG<br>GGAGCACCAACTACAACCCCTCCCTCAAGAGTCGAGTCACCATA<br>TCAGTAGACACGTCCAAGAACCAGTTCTCCCTGAAGCTGAGCTC<br>TGTGACCGCTGCGGACACGGCCGTGTATTACTGTGCGAGAAATA<br>TAGGAGTGGCTGGTCTCTTTGACTACTGGGGCCAGGGAACCCTG<br>GTCACCGTCTCCTCAGCCTCCACCAAGGGCCCATCGGTCTTCCC<br>TCTGGCACCCTCCTCCAAGAGCACCTCT | 93 | ATGGAAACCCCAGCGCAGCTTCTCTTCCTCCTGCTACTCT<br>GGCTCCCAGATACCACTGGAGAAATAGTGATGACGCAGTC<br>TCCAGCCACCCTGTCTGTGTCTCCAGGGGAAAGAGCCACC<br>CTCTCCTGCAGGGCCAGTCAGAGTGTTAGCAGCAACTTAG<br>CCTGGTACCAGCAGAAACCTGGCCAGGCTCCCAGGCTCCT<br>CATCTATGGTGCATCCACCAGGGCCACTGGTATCCCAGCC<br>AGGTTCAGTGGCAGTGGGTCTGGGACAGAGTTCACTCTCA<br>CCATCAGCAGCCTGCAGTCTGAAGATTTTGCAGTTTATTA<br>CTGTCAGCAGTATAATAACTGGCCGCTCACTTTCGGCGGA<br>GGGACCAAGCTGGAGATCAAACGAACTGTGGCTGCACCAT<br>CTGTCTTCATCTTCCC | 94 |
| 10E2 | ATGGAGTTTGGGCTGAGCTGGGTTTTCCTCGTTGCTCTTTTAAG<br>AGGTGTCCAGTGTCAGGTGCAGTTGGTGGAGTCTGGGGGAGGCG<br>TGGTCCAGCCTGGGAGGTCCCTGAGACTCTCCTGTGCAGCGTCT<br>GGATTCACCTTCAGTAGCTATGGCATGCACTGGGTCCGTCAGGC<br>TCCAGGCAAGGGGCTGGAGTGGGTGGCAGTTGTATGGTATGACG<br>GAACTATAAAATACTATGCAGACTCCGTGAAGGGCCGATTCACC<br>ATCTCCAGAGACAATCCCAAAAACACACTGTATCTCCAAATGAA<br>TAGCCTGAGAGCCGAGGACACGGCTGTGTATTACTGTGCGAGCC<br>AGTATAGCAGTGGCTGGCACACCGATTTTTTTGACGTCTGGGGC<br>CAAGGGACAATGGTCACCGTCTCCTCAGCCTCCACCAAGGGCCC<br>ATCGGTCTTCCC | 103 | ATGGACATGAGGGTCCTCGCTCAGCTCCTGGGGCTCCTGC<br>TGCTCTGGCTCCCAGGTGCCAAATGTGACATCCAGATGAC<br>CCAGTCTCCTTCCACCCTGTCTGCATCTGTAGGAGACAGA<br>GTCACCATCACTTGCCGGGCCAGTCAGAGTATTAGTACCT<br>GGTTGGCCTGGTATCAGCAGAAACCAGGGAAAGCCCCTAA<br>GTTCCTGATCTATAAGGCGTCTAGTTTAGAAAGTGGGGTC<br>CCATCAAGGTTCAGCGGCAGTGGATCTGGGACAGAATTCA<br>CTCTCACCATCAGCAGCCTGCAGCCTGATGATTTTGCAAC<br>TTATTACTGCCAACAGTATAGTGGTTATTCGCTCACTTTC<br>GGCGGAGGGACCAAGGTGGAGATCAAACGAACTGTGGCT | 104 |
| 01E2 | ATGGAGTTGGGGCTGAGCTGGGTTTTCCTCGTTGCTCTTTTAAG<br>AGGTGTCCAGTGTCAGGTGCAGCTGGTGGAGTCTGGGGGAGGCG<br>TGGTCCAGCCTGGGAGGTCCCTGAGACTCTCCTGTGCAGCGTCT<br>GGATTCACCTTCAGTAGCTATGGCATGCACTGGGTCCGCCAGGC<br>TCCAGGCAAGGGGCTGGAGTGGGTGGCAGTTATATGGTATGCTG<br>GAAGTAATAAATACTATGCAGACTCCGTGAAGGGCCGATTCACC<br>ATCTCCAGAGACAATTCCAAGAACACGCTGTATCTGCAAATGAA<br>CAGCCTGAGAGCCGAGGACACGGCTGTGTATTACTGTGCGGGTT<br>GGGACTTTGACTACTGGGGCCAGGGAACCCTGGTCACCGTCTCC<br>TCAGCCTCCACCAAGGGCCCATCGGTCTTCCCTCTGGCACCCTC<br>CTCCAAGAGCACCTCTGGGGGCACAGCGGCC | 113 | ATGGAGACTGGGCTGCGCTGGCTTCTCCTGGTCGCTGTGC<br>TCAAAGGTGTCCAGGGGACCATGGAAGCCCCAGCTCAGCT<br>TCTCTTCCTCCTGCTACTCTGGCTCCCAGATACCACCGGA<br>GAAATTGTGTTGACACAGTCTCCAGCCACCCTGTCTTTGT<br>CTCCAGGGGAAAGAGCCACCCTCTCCTGCAGGGCCAGTCA<br>GACTGTTCCCAATTACTTAGCCTGGTACCAACAGAAACCT<br>GGCCAGGCTCCCAGGCTCCTCATCTATGATGCATCGAATA<br>GGGCCACTGACATCCCAGCCAGATTCAGTGGCAGTGGGTC<br>TGGGACAGACTTCACTCTCACCATCAGCAGCCTAGAGCCT<br>GAAGATTTTGCAGTTTATTACTGTCAGCAGCGTGCCAACT<br>GGCCTCCGATCACCTTCGGCCAAGGGACACGACTGGAGAT<br>TAAACGAACTGTGGCTGCACCATCTGTCTTCATCTTCCCT<br>CCATCTGATGAGCAGT | 114 |

FIG. 19 - Continued

| | | | | |
|---|---|---|---|---|
| 41A9 | ATGAAGCACCTGTGGTTCTTCCTCCTCCTGGTGGCAGCTCCCAG<br>ATGGGTCCTGTCCCAGGTGCAGCTACAGCAGTGGGGCGCAGGAC<br>TGTTGAAGCCTTCGGAGACCCTGTCCCTCACCTGCGCTGTCTAT<br>GGTGGGTCCTTCAGTGATTACTACTGGAGCTGGATCCGCCAGCC<br>CCCAGGGAAGGGGCTGGAGTGGATTGGGGAAATCAATCATAGTG<br>GAAGCACCAATTACAACCCGTCCCTCAAGAGTCGAGTCACCATA<br>TCAGTAGACACGTCCAAGAACCAGTTCTCCCTGAAGCTGAGCTC<br>TGTGACCGCCGCGGACACGGCTGTGTATTACTGTGCGAGGGATT<br>ACGATGTTTTGACTGGTCATTTCTACTACTACTACGGTATGGAC<br>GTCTGGGGCCAAGGGACCACGGTCACCGTCTCCTCAGCCTCCAC<br>CAAGGGCCCATCGGTCTTCCCTCTGGCACCCTCCTCCAAGAGCA<br>CCTCTGGGGGCACAGCGGCC | 123 | ATGGAAACCCCAGCGCAGCTTCTCTTCCTCCTGCTACTCT<br>GGCTCCCAGATACCACCGGAGAAATTGTGTTGACACAGTC<br>TCCAGCCACCCTGTCTTTGTCTCCAGGGGAAAGAGCCACC<br>CTCTCCTGCAGGGCCAGTCAGAGTGTTAGAAGATACTTAG<br>CCTGGTACCAACAGAAACCTGGCCAGGCTCCCAGGCTCCT<br>CATCTATGATGCATCCAACAGGGCCACTGGCATCCCAGCC<br>AGGTTCAGTGGCAGTGGGTCTGGGACAGACTTCACTCTCA<br>CCATCAGCAGCCTAGAGCCTGAAGATTTTGCAGTTTATTA<br>CTGTCAGCAGCGTAACAACTGGCCGCTCACTTTCGGCGGA<br>GGGACCAAGCTGGAGATCAAACGAACTGTGGCTGCACCAT<br>CTGTCTTCATCTTCCCTCCATCTGATGAGCAGT | 124 |
| 02F3 | ATGGAACTGGGGCTCCGCTGGGTTTTCCTCGTTGCTCTTTTAAG<br>AGGTGTCCAGTGTCAGGTGCAGTTGGTGGAGTCTGGGGGAGGCG<br>TGGTCCAGCCTGGGAGGTCCCTGAGACTCTCCTGTGCAGCGTCT<br>GGATTCTCCTTCAGTGACTATGGCATACACTGGGTCCGCCAGGC<br>TCCAGGCAAGGGGCTGGAGTGGGTGGCAGTTATATGGTATGATG<br>GAAGTAATAAATACTATGCAGACTCCGTGAAGGGCCGATTCACC<br>ATCTCCAGAGACAATTCCAAGAACACGCTGTATCTGCAAGTGAA<br>CAGCCTGATAGCCGAGGACACGGCTGTGTATTACTGTGCGAGAG<br>ATCGGGGGTATAGCAGTGGCTGGTACGTAGACTACTACTACTAC<br>GGTATGGACGTCTGGGGCCAAGGGACCACGGTCACCGTCTCCTC<br>AGCCTCCACCAAGGGCCCATCGGTCTTCCCTCTGGCACCC | 133 | ATGGACATGAGGGTGCCCGTTCAGCTCCTGGGGCTGCTAA<br>TGCTCTGGGTCTCTGGATCCAGTGGGGATATTGTGATGAC<br>TCAGTCTCCACTCTCCCTGCCCGTCACCCCTGGAGAGCCG<br>GCCTCCATCTCCTGCAGGTCTAGTCAGAGCCTCCTGCATA<br>GTAATGGATACAACTATTTGGATTGGTACCTGCAGAAGCC<br>AGGGCAGTCTCCACAAATCCTGATCTATTTGGGCTCTAAT<br>CGGGCCTCCGGGGTCCCTGACAGGTTCAGTGGCAGTGGAT<br>CAGGCACAGATTTTACACTGAAAATCAGCAGAGTGGAGGC<br>TGAGGATGTTGGGGTTTATTACTGCATGCAAGCTCTACAA<br>ACTCCGTGGACGTTCGGCCAAGGGACCAAGCTGGAGATCA<br>AACGAACTGTGGCTGCACCATCTGTCTTCATCTTCCCTCC<br>ATCTGATGAGCAGT | 134 |
| 50D6 | ATGGAGTTGGGGCTGAGCTGGCTGTTTCTTGTGGCTATTTTAAA<br>AGGTGTCCACTGTGAGGTGCAGGTATTGGAGTCTGGGGGAGGCT<br>TGGTACAACCTGGGGGGTCCCTGAGACTCTCCTGTGCAGCCTCT<br>GGATTCACCTTTAGCAACTATGCCATGAACTGGGTCCGCCAGGC<br>TCCAGGGAAGGGGCTGGAATGGGTCTCAGCTATTAGTGGTGGTG<br>GTGGTAGCACATATTACGCAGACTCCGTGAAGGGCCGAGCCACC<br>ATCTCCAGAGACAATTCCGAGAACACGCTGTATCTGCAAATGAA<br>CAGCCTGAGAGCCGAGGACACGGCCGTATATTACTGTGCGAAAA<br>CCAGCAGTGGCTGGTACGACTCTTACTACGACTACTACGGTTTG<br>GACGTCTGGGGCCAAGGGACCACGGTCACCGTCTCCTCAGCCTC<br>CACCAAGGGCCCATCGGTCTTCCCTCTGGCACCCTCCTCCAAGA<br>GCACCTCT | 143 | ATGGACATGAGAGTCCTCGCTCAGCTCCTGGGGCTCCTGC<br>TGCTCTGGCTCCCAGGTGCCAGATGTGACATCCAGTTGAC<br>CCAGTCTCCATCCTTCCTGTCTGCATCTGTAGGAGACAGA<br>GTCACCATCACTTGCCGGGCCAGTCAGGGCATTAGCAATT<br>ATTTAGCCTGGTATCAGCAAAAACCAGGGAAAGTCCCTAA<br>GCTCCTGATCTATGCTGTATCCACTTTGCAAAGTGGGGTC<br>CCATCAAGGTTCAGCGGCAGTGGATCTGGGACAGAATTCA<br>CTCTCACAATCAGCAGCCTGCAGCCTGAAGATTTTGCAAC<br>TTATTACTGTCAACAGCTTAATAGTTACCCGTTCACTTTC<br>GGCGGAGGGACCAAGCTGGAGATCAAACGAACTGTGGCTG<br>CACCATCTGTCTTCATCTTCCC | 144 |
| 38E11 | ATGGAGTTTGGACTGAGCTGGCTTTTTCTTGTGGCTATTTTAAA<br>AGGTGTCCAGTGTGAGGTGCAGCTGTTGGAATCTGGGGGAGGCT<br>TGGTACAGCCTGGGGGGTCCCTGAGACTCTCCTGTGCAGCCTCT<br>GGATTCACCTTTAGCAACTATGCCATGAACTGGGTCCGCCAGGC<br>TCCAGGGAAGGGGCTGGAGTGGGTCTCAGCTATTAGTGGTGGTG<br>GTGGTAGCACATACTACGCAGACTCCGTGAAGGGCCGGTTCACC<br>ATCTCCAGAGACAATTCCAAGAACACACTGTATCTGCAGATGAA<br>CAGCCTGAGAGCCGAGGACACGGCCGTATATTACTGTGCGAAAG<br>AAAGTATTACTATGGTTCGGGGAGTTATGGACTACTACGGTATG<br>GACGTCTGGGGCCAAGGGACCACGGTCACCGTCTCCTCAGCCTC | 153 | ATGGACATGAGAGTCCTCGCTCAGCTCCTGGGGCTCCTGC<br>TGCTCTGGCTCCCAGGTGCCAGATGTGACATCCAGTTGAC<br>CCAGTCTCCATCCTTCCTGTCTGCATCTGTAGGAGACAGA<br>GTCACCATCACTTGCCGGGCCAGTCAGGGCATTAGCAGTT<br>ATTTAGCCTGGTATCAGCAAAAACCAGGGAAAGCCCCTAA<br>GCTCCTGATCTATGCTGCATCCACTTTGCAAGGTGGGGTC<br>CCATCGAGGTTCAGCGGCAGTGGATCTGGGACAGAATTCA<br>CTCTCACAATCAGCAGCCTGCAGCCTGAAGATTTTGCAAC<br>TTATTACTGTCAACACCTTAATCGTTTCCCTCGGACGTTC<br>GGCCAAGGGACCAAGGTGGAGATCAAACGAACTGTGGCTG | 154 |

FIG. 19 - Continued

| | | | | |
|---|---|---|---|---|
| | CACCAAGGGCCCATCGGTCTTCCCTCTGGCACCCTCCTCCAAGAGCACCTCT | | CACCATCTGTCTTCATCTTCCC | |
| 05A8 | ATGGAGTTGGGGCTGAGCTGGCTTTTTCTTGTGGCTATTTTAAAAGGTGTCCAGTGTGAGGTGCAACTGTTGGAGTCTGGGGGAGGCTTGGTACAGCCTGGGGGGTCCCTGAGACTCTCCTGTGCAGCCTCTGGATTCACCTTTAGCAACTATGCCATGAGCTGGGTCCGCCAGGCTCCAGGGAAGGGGCTGGAGTGGGTCTCTGCTATTAGTGGTCGTGGTGGTAGCACATACTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGAAAGATATTGTAGTAGTACCAGCTGCTAAGGGCTATGTTATGGATGCCTGGGGTCAAGGAGCTTCGGTCACCGTCTCCTCA | 163 | ATGGAAACCCCAGCGCAGCTTCTCTTCCTCCTGCTACTCTGGCTCCCAGATACCACTGGAGAAATAGTGATGACGCAGTCTCCAGCCACCCTGTCTGTGTCTCCAGGGGAAAGAGCCACCCTCTCCTGCAGGGCCAGTCAGAGTGTTAGCAGCAACTTAGCCTGGTACCAGCAGAAACCTGGCCAGGCTCCCAGGCTCCTCATCTATGGTGCTTCCACCAGGGCCACTGGTATCCCAGCCAGGTTCAGTGGCAGTGGGTCTGGGACAGAGTTCACTCTCACCTTCAGCAGCCTGCAGTCTGAAGATTTTGTAGTTTATTACTGTCAGCAGTATAATAACTGGCCTCTCACCTTCGGCCAAGGGACACGACTGGAGATTAAA | 164 |
| 12C2 | ATGGAGTTGGGGCTGAGCTGGGTTTTCCTCGTTGCTCTTTTAAGAGGTGTCCAGTGTCAGGAGCAGCTGGTGGAGTCTGGGGGAGGCGTGGTCCAGCCTGGGAGGTCCCTGAGACTCTCCTGTGTAACGTCTGGATTCACCTTCAGTAGCTATGGCATGCACTGGGTCCGCCAGGCTCCAGGCAAGGGGCTGGAGTGGGTGGCAGTTATATGGTATGATGGGACTAATAAATACTATGCAGACACCGTGAAGGGCCGATTCACCATCTCCAGAGACAATTCCAAGAACACGCTGTATCTGCAAATGAACAGCCTGAGAGCCGAGGACACGGGTGTGTATTATTGTGCGAGAGAGGGGTGTGATACTATCAGCTGCCCCTACTATTACTACGGTATGGACGTCTGGGGCCAAGGGACCACGATCACCGTCTCCTCAGCCTCCACCAAGGGCCCATCGGTCTTCCC | 173 | ATGAGGGTCCTCGCTCAGCTCCTGGGACTCCTGCTGCTCTGGCTCCCAGATACCAGATGTGACATCCTGATGACCCAGTCTCCATCCTCCCTGTCTGCATCTGTAGGAGACAGAGTCACCATCACTTGCCGGGCGAGTCAGGGCATTAACTATTATTTAGCCTGGTATCAGCAGAAACCAGGGAAAGTTCCTAAGCTCCTGATTTATACTGCATCCACTTTGCAATCAGGGGTCCCATCTCGCTTCAGTGGCAGTGGATCTGGGACAGATTTCACTCTCACCATCAGCAGCCTGCAGCCTGAAGATGTTGCAACTTATTTCTGTCAAAAGTATAACAGTGCCCCATTCACTTTCGGCCCTGGGACCAAGCTGGAGATCAAACGAACTGTG | 174 |
| 03G11 | ATGGAGTTGGGGCTGAGCTGGCTTTTTCTTGTGGCTATTTTAAAAGGTGTCCAGTGTGAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCATGAGCTGGGTCCGCCAGGCTCCAGGGAAGGGGCTGGAGTGGGTCTCAGCTATTAGTGGTAGTGGTAATAGCGCATACTACGCAGACTCCGTGAAGGGCCGGTTCACCATCTCCAGAGACAATTCCAAGAATACGCTGTTTCTCCAAATGAACAGCCTGAGAGCCGACGACACGGCCGTATATTATTGTGCGTCTAGCAGTGGCTGGTACCTAGTCTACTACTTCGATCTCTGGGGCCGTGGCACCCTGGTCACCGTCTCCTCAGCCTCCACCAAGGGCCCATCGGTCTTCCC | 183 | ATGGAAGCCCCAGCACAGCTTCTCTTCCTCCTGCTACTCTGGCTCCCAGATACCACTGGAGAAATAGTGATGACGCAGTCTCCAGCCACCCTGTCTGTGTCTCCAGGGGAAAGAGGCACCCTCTCCTGCAGGGCCAGTCAGAGTGTTAGTAGCAACTTAGCCTGGTACCAGCAGAAACCTGGCCAGGCTCCCAGGCTCCTCATCTATGGTGCATCCATCCGGGCCACTGGTATCCCAGCCAGGTTCAGTGGCAGTGGGTCTGGGACAGAGTTCATTCTCACCATCAACAGCCTGCAGTCTGAAGATTTTGCAGTTTATTACTGTCAACAGTATAATAACTGGCCGCTCACTGTCGGCGGAGGGACCAAGGTGGAGATCAAACGAACTGTGGCTGCACCATCTGTCTTCATCTTCCCTCCATCTGATGAGCAGTTGAAATCTGGAACTGCCTCTGTTGTGTGCCTGCTGAATAACTTCTATCCCAGAGAGGCCAAAGTACAGT | 184 |
| 06H1 | ATGGAGTTGGGGCTGAGCTGGCTTTTTCTTGTGGCTATTTTAAAAGGTGTCCAGTGTGAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCATGAGCTGGGTCCGCCAGGCTCCAGGGAAGGGGCTGGAGTGGGTCTCAGGTATCAGTGGTAGTGGTGGTAACACACACTACGCAGACTCCGTGAAGGGCCGGTTCACCATCTCCAGAGACAATTCCAAGAACACGCTGTATCTGCAAATGAACAGCCTGAGAGCCGAGGACACGGCCCTATATTACTGTGCGCAGCAGTGGCCACAGGGCTACTGGGGCCAGGGAACCCTGGTCACCGTCTCCTCAGCCTCCACCAAGGGCCCATCGGTCTTCCC | 193 | ATGGACATGAGGGTCCTCGCTCAGCTCCTGGGACTCCTGCTGCTCTGGCTCCCAGAAACCAGATGTGACATCCAGATGACCCAGTCTCCATCCTCCCTGTCTGCATCTGTAGGAGACAGAGTCACCATCACTTGCCGGGCGAGTCAGGGCATTAGCATTTATTTAGCCTGGTTTCAGCAGAAACCAGGGAAAGTTCCTAAGCTCCTGATCTATGCTGCATCCACTTTGCAATCAGGGGTCCCATCTCGGTTCAGTGGCAGTGGATCTGGGACAGATTTCACTCTCACCATCAGCAGCCTGCAGCCTGAAGATTTTGCAACTTATTACTGTCAAAAGTATAACAGTGCCCCATTCACTTTCGGCCCTGGGACCAAGCTGGAGATCAAACGAACTGTG | 194 |

FIG. 19 - Continued

| | | | | |
|---|---|---|---|---|
| 07C06 _D2 | ATGGAACTGGGGCTCCGCTGGCTTTTTCTTGTGGCTATTTTAAA<br>AGGTGTCCAGTGTGAGGTGCAGTTGTTGGAGTCTGGGGGAGGCT<br>TGGTACAGCCTGGGGGGTCCCTGGGACTCTCCTGTGCAGCCTCT<br>GGATTCACCTTCAGCAACTATATCATGAGCTGGGTCCGCCAGGC<br>TCCAGGGAAGGGGCTGGAGTGGGTCTCAGGTATCAGTGGTAGTG<br>GTGGTAGCACACACTACGCAGGCTCCGTGAAGGGCCGGTTCACC<br>ATCTCCAGAGACAATTCCAAGAACACGCTGAATCTGCAAATGAA<br>CAGCCTGAGAGTCGAGGACACGGCCGTCTATCACTGTGTGCAGC<br>AGTGGCCACAGGGCTACTGGGGCCAGGGAACCCTGGTCACCGTC<br>TCCTCAGCCTCCACCAAGGGCCCATCGGTCTTCCC | 203 | ATGGACATGAGGGTCCCCGCTCAGCTCCTGGGACTCCTGC<br>TGCTCTGGCTCCCAGATACCAGATGTGACATCCAGATGAC<br>CCAGTCTCCATCCTCCCTGTCTGCATCTGTAGGAGACAGA<br>GTCACCATCACTTGCCGGGCGAGTCAGGGCATTACCATTT<br>ATTTAGCCTGGTTTCAGCAGAAACCAGGGAAAGTTCCTAA<br>GCTCCTGATCTATGCTGCATCCACTTTGCAATCAGGGGTC<br>CCATCTCGGTTCAGTGGCAGTGGATCTGGGACAGATTTCA<br>CTCTCACCATCAGCAGCCTGCAGCCTGAGGATGTTGCAAC<br>TTATTACTGTCAAAAGTATAACAGTGCCCCATTCACTTTC<br>GGCCCTGGGACCAAGCTGGAGATCAAACGAACTGTG | 204 |
| 09F6 | ATGGAGTTTGGGCTGAGCTGGCTTTTTCTTGTGGCTATTTTAAA<br>AGGTGTCCAATGTGAGGTACAACTGTTGGAGTCTGGGGGAGGCT<br>TGGTACAGCCTGGGGGGTCCCTGAGACTCTCCTGTGCAGCCTCT<br>GGATTCACCTTTAGCAGCTATGCCATGAGCTGGGTCCGCCTGGC<br>TCCAGGGAAGGGACTGGAGTGGGTCTCAGGTCTCAGTGGTAGTG<br>GTGGTGACACACACTACGCAGGCTCCGTGAAGGGCCGGTTCACC<br>ATCTCCAGAGACAATTCCAAGAACACGCTGTATCTGCAAATGAA<br>CAGCCTGAGAGCCGAAGACACGGCCTTATATTACTGTGCGCAGC<br>AGTGGCCACAGGGCTACTGGGGCCAGGGAACCCTGGTCACCGTC<br>TCCTCAGCCTCCACCAAGGGCCCATCGGTCTTCCC | 213 | ATGGACATGAGGGTCCTCGCTCAGCTCCTGGGACTCCTGC<br>TGCTCTGGCTCCCAGATACCAGATGTGACATCCAGATGAC<br>CCAGTCTCCATCCTCCCTGTCTGCATCTGTAGGAGACAGA<br>GTCACCATCACTTGCCGGGCGAGTCAGGGCATTAGCATTT<br>ATTTAGCCTGGTTTCAGCAGAAACCAGGGAAAGTTCCTAA<br>GCTCCTGATCTATGCTGCATCCACTTTGCAATCAGGGGTC<br>CCATCTCGGTTCAGTGGCAGTGGATCTGGGACAGATTTCA<br>CTCTCACCATCAGCAGCCTGCAGCCTGAAGATGTTGCAAC<br>TTATTACTGTCAAAAGTATAACAGTGCCCCATTCACTTTC<br>GGCCCTGGGACCAAGCTGGAGATCAAACGAACTGTG | 214 |
| 14D4 | ATGGAGTTTGGGCTGAGCTGGCTTTTTCTTGTGGCTATTTTAAA<br>AGGTGTCCAGTGTGAGGTGCAGCTGTTGGAGTCTGGGGGAGGCT<br>TGGTACAGCCTGGGGAATCCCTGAGACTCTCCTGTGCAGCCTCT<br>GGATTCACCTTTAGCAGCTATGCCATGAGCTGGGTCCGCCAGGC<br>TCCAGGGAAGGGGCTGGAGTGGGTCTCAGGTATCAGTGGTAGTG<br>GTGGTAGCACACACTACGCAGACTCCGTGAAGGGCCGGTTCACC<br>ATCTCCAGAGACAATTCCAAGAACACGCTGTATCTGCAAATGAA<br>CAGCCTGAGAGCCGAGGACACGGCCGCATATTACTGTGCGCAGC<br>AGTGGCCACAGGGCCACTGGGGCCAGGGAATCCTGGTCACCGTC<br>TCCTCAGCCTCCACCAAGGGCCCATCGGTCTTCCC | 223 | ATGGACATGAGGGTCCTCGCTCAGCTCCTGGGACTCCTGC<br>TGCTCTGGCTCCCAGATACCAGATGTGACATCCAGATGAC<br>CCAGTCTCCATCCTCCCTGTCTGCATCTGTAGGAGACAGA<br>GTCACCATCACTTGCCGGGCGAGTCAGGACATTAGCATTT<br>ATTTAGCCTGGTTTCAGCAGAGACCAGGGAAAGTTCCTAA<br>GCTCCTGATCTATGCTGCATCCACTTTGCAATCAGGGGTC<br>CCATCTCGGTTCAGTGGCAGTGGATCTGGGACAGATTTCA<br>CTCTCACCATCAGCAGCCTGCAGCCTGAAGATGTTGCAAC<br>TTATTACTGTCAAAAGTATAACAGTGACCCATTCACTTTC<br>GGCCCTGGGACCAAGGTGGAGATCAAACGAACTGTGGCT | 224 |
| 15H5 | ATGGAACTGGGGCTCCGCTGGCTTTTTCTTGTGGCTATTTTAAA<br>AGGTGTCCAGTGTGAGGTGCAGCTGTTGGAGTCTGGGGGAGGCT<br>TAGTACAGCCTGGGGGGTCCCTGAGACTCTCCTGTGCAGCCTCT<br>GGATTCACCTTTAGCAGCTATGCCATGAGCTGGGTCCGCCAGGC<br>TCCAGGGAAGGGGCTGGAGTGGGTCTCAGTTCTCAGTGGTAGTG<br>GTGATGACACACACTACGCAGACTCCGTGAAGGGCCGGTTCACC<br>ATCTCCAGAGACAATTCCAAGAACACGCTGTATCTGCAAATGAA<br>CAGCCTGAGAGCCGAGGACACGGCCGTATATTACTGTGCGCACC<br>AGTGGCCACAGGGCTACTGGGGCCAGGGAACCCTGGTCACCGTC<br>TCCTCAGCCTCCACCAAGGGCCCATCGGTCTTCCC | 233 | ATGGACATGAGGGTCCCCGCTCAGCTCCTGGGACTCCTGC<br>TGCTCTGGCTCCCAGATACCAGATGTGACATCCAGATGAC<br>CCAGTCTCCATCCTCCCTGTCTGCATCTGTAGGAGACAGA<br>GTCACCATCACTTGCCGGGCGAGTCAGGACATTAGCATTT<br>ATTTAGCCTGGTTTCACCAGAAACCAGGGAAAGTTCCTAA<br>GCTCCTGATCTATGCTGCATCCACTTTGCAATCAGGGGTC<br>CCATCTCGGTTCAGTGGCAGTGGATCTGGGACAGATTTCA<br>CTCTCACCATCAGCAGCCTGCAGCCTGAAGATGTTGCAGC<br>TTATTACTGTCAAAAGTATAACAGTGCCCCATTCACTTTC<br>GGCCCTGGGACCAAGCTGGAGATCAAACGAACTGTGGCT | 234 |
| 20F5 | ATGGAGTTTGGGCTGAGCTGGCTTTTTCTTGTGGCTATTTTAAA<br>AGGTGTCCAGTGTGAGGTGCAGCTGTTGGAGTCTGGGGGAGGCT<br>TGGTACAGCCTGGGGGGTCCCTGAGACTCTCCTGTGCAGCCTCT<br>GGATTCACCTTTAGCAGCTATGTCATGAGCTGGGTCCGCCAGAC<br>TCCAGGGAAGGGGCTGGAGTGGGTCTCAGGTATCAGTGGTAGTG<br>GTGGTAGCACACACTACACAGACTCCGTGCAGGGCCGGTTCACC | 243 | ATGGACATGAGGGTCCTCGCTCAGCTCCTGGGACTCCTGC<br>TGCTCTGGCTCCCAGATACCAGATGTGACATCCAGATGAC<br>CCAGTCTCCATCCTCCCTGTCTGCAACTGTAGGAGACAGA<br>GTCACCATCACTTGCCGGGCGAGTCAGGGCATTAGCATTT<br>ATTTAGCCTGGTTTCAGCAGAAACCAGGGAAAGTTCCTAA<br>GAACCTGATCTATGCTGCATCCACTTTGCAATCAGGGGTC | 244 |

FIG. 19 - Continued

| | | | | |
|---|---|---|---|---|
| | ATCTCCAGAGACAATTCCAAGAACACGCTGTATCTGCAAATGAA<br>CAGCCTGAGAGCCGAGGACACGGCCGTGTATTACTGTGTGCAGC<br>AGTGGCCACAGGGCTACTGGGGCCAGGGAACCCTGGTCACCGTC<br>TCCTCAGCCTCCACCAAGGGCCCATCGGTCTTCCC | | CCATCTCGGTTCAGTGGCAGTGGATCTGGGACAGATTTCA<br>CTCTCACCATCAGCAGCCTGCAGCCTGAAGATTTTGCAAC<br>TTATTACTGTCAAAAGTATAACAGTGCCCCATTCACTTTC<br>GGCCCTGGGACCAAGCTGGAGATCAAACGAACTGTGGCT | |
| 38A6 | ATGGAGTTTGGGCTGAGCTGGCTTTTTCTTGTGGCTATTTTAAA<br>AGGTGTCCAGTGTGAGGTGCAGGTGTTGGAGTCTGGGGGAGGCT<br>TGGTACAGCCTGGGGAGTCCCTGAGACTCTCCTGTGCAGCCTCT<br>GGATTCACCTTTAACACCTATGCCATGAGCTGGGTCCGCCAGGC<br>TCCAGGGAAGGGGCTGGAGTGGGTCTCAGCTATTAGTGATAATG<br>GTGGTGGCACATACAACGCAGACTCCGTGAAGGGCCGGTTCACC<br>ATCTCCAGAGACAATTCCAAGAACACGCTGTATCTCCAAATGAA<br>CAGCCTGAGAGCCGAGGACACGGCCGTATATTACTGTGCGAAGG<br>GGGAGCAGTGGGGGGCCCCCTTTGACTACTGGGGCCAGGGAACC<br>CTGGTCACCGTCTCCTCA | 253 | ATGGACATGAGGGTGCCCGCTCAGCTCCTGGGACTCCTGC<br>TGCTCTGGCTCCCAGATACCAGATGTGACATCCAGATGAC<br>CCAGTCTCCATCCTCCCTGTCTGCATCTGTAGGAGACAGA<br>GTCACCATCACTTGCCGGGCGAGTCAGGGCATTAGCATTT<br>ATTTAGCCTGGTATCACCAGAAACCAGGGAAAGTTCCTAA<br>GCTCCTGATCTATGCTGCATCCACTTTGCAATCAGGGGTC<br>CCATCTCGGTTCAGTGGCAGTGGATCTGGGACAGATTTCA<br>CTCTCACCATCAGCAGCCTGCAGCCTGAAGATGTTGCAAC<br>TTATTACTGTCAAAAGTATAACAGTGCCCCGTGGACGTTC<br>GGCCAAGGGACCAAGCTGGAGATCAAA | 254 |
| 39D7 | ATGGAACTGGGGCTCCGCTGGCTTTTTCTTGTGGCTATTTTAAA<br>AGGTGTCCAGTGTGAGGTGCAGTTGTTGGAGTCTGGGGGAGGCT<br>TGGTACAGCCTGGGGGGTCCCTGAGACTCTCCTGTGCAGCCTCT<br>GGATTCACCTTTAGCAGCTATGCCATGAGCTGGGTCCGCCAGGC<br>TCCAGGGAAGGGGCTGGAGTGGGTCTCAACTATTAGTGGTAGTG<br>GTGGTAGCACATACTACGCAGACTCCGTGAAGGGCCGGTTCACC<br>ATCTCCAGAGACAATTCCAAGAACACGCTGTATCTGCAAATGAA<br>CAGCCTGAGAGCCGAGGACACGGCCGTATATTACTGTGCGACCT<br>TGGATACAGCTATGGCCGCTGATGCTTTTGCTATCTGGGGCCAA<br>GGGACAATGGTCACCGTCTCCTCA | 263 | ATGGACATGAGGGTCCCTGCTCAGCTCCTGGGGCTGCTAA<br>TGCTCTGGGTCTCTGGATCCAGTGGGGATATTGTGATGAC<br>TCAGTCTCCACTCTCCCTGCCCGTCACCCCTGGAGAGCCG<br>GCCTCCATCTCCTGCAGGTCTAGTCAGAGCCTCCTGCATA<br>GTAATGGATACAACTATTTGGATTGGTACCTGCAGAAGTC<br>AGGGCAGTCTCCACAGCTCCTGATCTATTTGGGTTCTAAT<br>CGGGCCTCCGGGGTCCCTGACAGGTTCAGTGGCAGTGGAT<br>CAGGCACAGATTTTACACTGAAAATCAGCAGAGTGGAGGC<br>TGAGGATGTTGGGGTTTATTACTGCATGCAAGCTCTACTA<br>ATTCCGCTGTACACTTTTGGCCAGGGGACCAAGCTGGAGA<br>TCAAA | 264 |
| 18C11 | ATGGAGTTGGGGCTGTGCTGGGTTTTCCTTGTTGCTATTTTAGA<br>AGGTGTCCAGTGTGAGGTGCAGCTGGTGGAGTCTGGGGGAGGCT<br>TGGTCCAGCCTGGGGGGTCCCTGAGACTCTCCTGTGCAGCCTCT<br>GGATTCACCTTTAGTAGCTATTGGATGAGCTGGGTCCGCCAGGT<br>TCCAGGGAAGGGGCTGGAGTGGGTGGCCAACATAAAGCAAGATG<br>GAAGTGAGAAATACTATGTGGACTCTGTGAAGGGCCGATTCACC<br>ATCTCCAGAGACAACGCCAAGAACTCACTGTATCTGCAAATGAA<br>CAGCCTGAGAGCCGAGGACACGGCTGTTTATTACTGTGCGAGAG<br>ATTGGAGGAGCAGTGGCTGGACCCTTGACTACTGGGGCCAGGGA<br>ACCCTGGTCACCGTCTCCTCAGCCTCCACCAAGGGCCCATCGGT<br>CTTCCCTCTGGCACCCTCCTCCAAGAGCACCTCTGGGGGCACAG<br>CGGCC | 273 | ATGAGGCTCCCTGCTCAGCTCCTGGGGCTGCTAATGCTCT<br>GGGTCTCTGGATCCAGTGGGGATATTGTGATGACTCAGTC<br>TCCACTCTCCCTGCCCGTCACCCCTGGAGAGCCGGCCTCC<br>ATCTCCTGCAGGTCTAGTCAGAGCCTCCTGCATAGTAGTG<br>GACACAACTTTTTGGATTGGTACCTGAAAAAGCCAGGGCA<br>GTCTCCACAACTCCTGATCTATTTGGGTTCTAATCGGGGC<br>TCCGGGGTCCCTGACAGGTTCAGTGGCAGTGGTTCAGGCA<br>CAGATTTTACACTGAAAATCAGTAGAGTGGAGGCTGAGGA<br>TGTTGGGGTTTATTACTGCATGCAAGCTCTACAAACTCCT<br>CGGACGTTCGGCCAAGGGACCAAGCTGGAGATCAAACGAA<br>CTGTGGCTGCACCATCTGTCTTCATCTTCCCTCCATCTGA<br>TGAGCAGT | 274 |
| 38G4 | ATGGAGTTTTGGCTGAGCTGGGTTTTCCTTGTTGCTATTTTAGA<br>AGGTGTCCAGTGTGAGGTGCAGCTGGTGGAGTCTGGGGGAGGCT<br>TGGTCCAGCCTGGGGGGTCCCTGAGACTCTCCTGTGCAGCCTCT<br>GGATTCACCTTTAGTAGCTATTGGATGAGCTGGGTCCGCCAGGC<br>TCCAGGGAAGGGGCTGGAGTGGGTGGCCAATGTAAAGCAAGATG<br>GAAGTGAGAAAGACTATGTGGACTCTGTGAAGGGCCGATTCACC<br>ATCTCCAGAGACAACGCCAAGAACTCACTGTATCTGCAAATGAA<br>CAGCCTGAGAGCCGAGGACACGGCTGTGTATTACTGTGCGAGAG<br>AGTGGAATAGCAGTGGCTGGACGTTTGACTACTGGGGCCAGGGA | 283 | ATGGACATGAGGGTGCCCGCTCAGCTCCTGGGGCTGCTAA<br>TGCTCTGGGTCTCTGGATCCAGTGGGGATATTGTGATGAC<br>TCAGTCTCCACTCTCCCTGCCCGTCACCCCTGGAGAGCCG<br>GCCTCCATCTCCTGCAGGTCTAGTCAGAGCCTCCTGCATA<br>GTACTGGATACAACTTTTTGGATTGGTACCTGCAGAAGCC<br>AGGGCAGTCTCCACAGCTCCTGATCTTTTTGGGTTCTAAT<br>CGGGCCTCCGGGGTCCCTGACAGGTTCAGTGGCAGTGGAT<br>CAGGCACAGATTTTACACTGAAAATCAGCAGAGTGGAGGC<br>TGAGGATGTTGGGATTTATTACTGCATGCAAGCTCTACAA | 284 |

FIG. 19 - Continued

| | | | | |
|---|---|---|---|---|
| | ACCCTGGTCACCGTCTCCTCAGCCTCCACCAAGGGCCCATCGGT<br>CTTCCCTCTGGCACCCTCCTCCAAGAGCACCTCT | | ACTCCGCTCACTTTCGGCGGAGGGACCAAGGTGGAGATCA<br>AACGAACTGTGGCTGCACCATCTGTCTTCATCTTCCC | |
| 27D8 | ATGGAACTGGGGCTCCGCTGGGTTTTCCTCGTTGCTCTTTTAAG<br>AGGTGTCCAGTGTCAGGTGCAGCTGGTGGAGTCTGGGGGAGGCG<br>TGGTCCAGCCTGGGAGGTCCCTGAGACTCTCCTGTGCAGCGTCT<br>GGATTCACCTTCAGTAGCTATGGCATGCACTGGGTCCGCCAGGC<br>TCCAGGCAAGGGGCTGGAGTGGGTGGCAGTTATATGGTATGATG<br>GAAGTAATAAATATTATGCAGACTCCGTGAAGGGCCGATTCACC<br>ATCTCCAGAGACAATTCCAAGAACACGCTGTATCTGCAAATGAA<br>CAGCCTGAGAGCCGAGGACACGGCTGTGTATCACTGTGCGAGAG<br>ATCGGGTGTATTACGATGGTTCGGGGAGTTATTATAACGTGGGT<br>GTTATGGATGTTTGGGGTCAAGGAGCTTCGGTCACCGTCTCCTC<br>AGCCTCCACCAAGGGCCCATCGGTCTTCCC | 293 | ATGGACATGAGGGTCCCTGCTCAGCTCCTCTTCCTCCTGC<br>TACTCTGGCTCCCAGATACCACTGGAGAAATAGTGATGAC<br>GCAGTCTCCAGCCACCCTGTCTGTGTCTCCAGGGGAAAGA<br>GCCACCCTCTCCTGCAGGGCCAGTCAGAGTGTTAGCAACA<br>ACTTAGCCTGGTACCAGCAGAAACCTGGCCAGGCTCCCAG<br>ACTCCTCATTTATGGTGTATCCACTAGGGCCACTGGTATT<br>CCAGCCAGGTTCAGTGGCAGTGGGTCTGGGACAGAGTTCA<br>CTCTCATCATCAGCAGCCTGCAGTCTGAAGATTTTGCAGG<br>TTATTACTGTCAGCAGTATAATGACTGGCCGCTCACTTTC<br>GGCGGAGGGACCAAGCTGGAGATCAAACGAACTGTGGCTG<br>CACCATCTGTCTTCATCTTCCCTCCATCTGATGAGCAGTT<br>GAAATCTGGAACTGC | 294 |
| 11A4 | ATGGAGTTGGGGCTGTGCTGGGTTTTCCTCGTTGCTCTTTTAAG<br>AGGTGTCCAGTGTCAGGTGCAGTTGGTGGAGTCTGGGGGAGGCG<br>TGGTCCAGCCTGGGGGGTCCCCGAGACTCTCCTGTGCAGCGTCT<br>GGATTCACCTTCAGTAGTTATGCCATGCACTGGGTCCGCCAGGC<br>TCCAGGCACGGGGCTGGAGTGGGTGGCACTTATTTACTATGATG<br>GAAGTCATGAATACTATTCAGACTCCGTGAAGGGCCGATTCACC<br>ATCTCCAGAGACAATTCCAAGAACACGCTGTATCTGCAAATGAG<br>CAGCCTGAGAGCCGAGGACACGGCTGTGTATTACTGTGCGAGAG<br>ACGGCGGTTCGGGGAGTCATTACCCCTTTGATGCTTTTGATATC<br>TGGGGCCAAGGGACAATGGTCACCGTCTCCTCAGCCTCCACCAA<br>GGGCCCATCGGTCTTCCC | 303 | ATGGACATGAGGGTCCTCGCTCAGCTCCTGGGGCTCCTGC<br>TGCTCTGGCTCCCAGGTGCCAAATGTGACATCCAGATGAC<br>CCAGTCTCCTTCCACCCTGTCTGCATCTGTAGGAGACAGA<br>GTCACCATCACTTGCCGGGCCAGTCAGAGTATTAGTAGCT<br>GGTTGGCCTGGTATCAGCAGAAACCAGGGAAAGCCCCTAA<br>CCTCCTGATCTATAAGGCGTCTAGTTTAGAAAGTGGGGTC<br>CCATCAAGGTTCAGCGGCAGTGGATCTGGGACAGAATTCA<br>CTCTCACCATCAGCAGCCTGCAGCCTGATGATTTTGCAAC<br>TTATTACTGCCAACAATATAATACTTATTACACTTTTGGC<br>CAGGGGACCAAGGTGGAGATCAAACGAACTGTGGCT | 304 |
| 24H1 | ATGAAACATCTGTGGTTCTTCCTTCTCCTGGTGGCAGCTCCCAG<br>ATGGGTCCTGTCCCAGGTGCAGCTGCAGGAGTCGGGCCCAGGCC<br>TAGTGAAGCCTTCGGAGACCCTGTCCCTCACCTGCACTGTCTCA<br>GGTGGCTCCATCAGTAGTTACTACTGGAGCTGGATCCGGCAGTT<br>CTCAGGGAAGGGACTGGAGTGGATTGGCTATATCTACTACACTG<br>GGAGGAACAACTACAACCCCTCCCTCAAGAGTCGAGTCACCATA<br>TCAGTAGACACGTCCAAGAACCAGTTCTCCCTGAAGCTGAGCTC<br>TGTGACCGCTGCGGACTCGGCCGTGTATTACTGTGCGAGAGAGG<br>GAGGGTGGGGACCCCACTTTGACTACTGGGGCCAGGGAACCCTG<br>GTCACCGTCTCCTCAGCCTCCACCAAGGGCCCATCGGTCTTCCC<br>TCTGGCACCCTCCTCCAAGAGCACCTCTGGGGGCACAGCGGCC | 313 | ATGAGGCTCCTTGCTCAGCTCCTGAGGCTGCTAATGCTCT<br>GGGTCTCTGGATCCAGTGGGGATATTGTGATGACTCAGTC<br>TCCACTCTCCCTGCCCGTCACCCCTGGAGAGCCGGCCTCC<br>ATCTCCTGTAGGTCTAGTCAGAGCCTCCTGCATAGTAGTG<br>GATACAACTATTTGGATTGGTACCTGCAGAAGCCAGGGCA<br>GTCTCCACAGCTTCTGATCTATTTGGGTTCTGATCGGGCC<br>TCCGGGGTCCCTGACAGGTTCAGGGGCAGTGGATCAGGCA<br>CAGATTTTACACTGAAAATCAGCAGAGTGGAGGCTGAGGA<br>TGTTGGGATTTATTACTGCATGCAAGCTCTACAAATTCCG<br>TACACTTTTGGCCAGGGGACCAAGCTGGAGATCAAACGAA<br>CTGTGGCTGCACCATCTGTCTTCATCTTCCCTCCATCTGA<br>TGAGCAGT | 314 |
| 18C02 | ATGAAGCACCTGTGGTTCTTCCTCCTCCTGGTGGCAGCTCCCAG<br>ATGGGTCCTGTCCCAGGTGCAGCTACAGCAGTGGGGCGCAGGAC<br>TGTTGAAGCCTTCGGAGACCCTGTCCCTCACCTGCGCTGTCTAT<br>GGTGGGTCCTTCAGTGATTACTACTGGAGCTGGATCCGCCAGCC<br>CCCAGGGAAGGGGCTGGAGTGGATTGGGGAAATCAATCATAGTG<br>GAAGCACCAATTACAACCCGTCCCTCAAGAGTCGAGTCACCATA<br>TCAGTAGACACGTCCAAGAACCAGTTCTCCCTGAAGCTGAGCTC<br>TGTGACCGCCGCGGACACGGCTGTGTATTACTGTGCGAGGGATT<br>ACGATGTTTTGACTGGTCATTTCTACTACTACTACGGTATGGAC | 323 | ATGAGGCTCCCTGCTCAGCTCCTGGGGCTCCTGCTACTCT<br>GGCTCCGAGGTGCCAGATGTGACATCCAGATGACCCAGTC<br>TCCATCCTCCCTGTCTGCATCTGTAGGAGACAGAGTCACC<br>ATCACTTGCCGGGCAAGTCAGAGCATTAGCAGCTATTTAA<br>ATTGGTTTCAGCAGAAACCAGGGAAAGCCCCTAAGCTCCT<br>GATCTATGCTGCATCCAGTTTGCAAAGTGGGGTCCCATCA<br>AGGTTCAGTGGCAGTGGATCTGGGACAGATTTCACTCTCA<br>CCATCAGCAGTCTGCAACCTGAAGATTTTGCAACTTACTA<br>CTGTCAACAGAGTTACACTATGCCGTACACTTTTGGCCAA | 324 |

FIG. 19 - Continued

| | | | | |
|---|---|---|---|---|
| | GTCTGGGGCCAAGGGACCACGGTCACCGTCTCCTCAGCCTCCAC<br>CAAGGGCCCATCGGTCTTCCCTCTGGCACCCTCCTCCAAGAGCA<br>CCTCT | | GGGACCAAGCTGGAGATCAAACGAACTGTGGCTGCACCAT<br>CTGTCTTCATCTTCCC | |
| 07C10 | ATGGAATTGGGGCTCCGCTGGGTTTTCCTCGTTGCTCTTTTAAG<br>AGGTGTCCAGTGTCAGGTGCAGCTGGTGGAGTCTGGGGGAGGCG<br>TGGTCCAGCCTGGGAGGTCCCTGAGACTCTCCTGTGCAGCGTCT<br>GGATTCACCTTCAGTAGCTATGGCATGCACTGGGTCCGCCAGGC<br>TCCAGGCAAGGGGCTGGAGTGGGTGGCACTTATATGGTATGATG<br>GAAGTAATAAATACTATGCAGACTCCGTGCAGGGCCGATTCACC<br>ATCTCCAGAGACAATTCCAAGAACACGCTGTATCTGCAAATGAA<br>CAGCCTGAGAGCCGAGGACACGGCTGTGTATTACTGTGCGGTTG<br>ATTACGATATTTTGACTGGTCATGTCCTATATGTTATGGATGCC<br>TGGGGTCAAGGAGTTTCGGTCACCGTCTCCTCA | 333 | ATGGAAACCCCAGCGCAGCTTCTCTTCCTCCTGCTACTCT<br>GGCTCCCAGATACCACCGGAGAAATTGTGTTGACACAGTC<br>TCCAGCCACCCTGTCTTTGTCTCCAGGGGAAAGAGCCACC<br>CTCTCCTGCAGGGCCAGTCAGAGTGTTACCAACTACTTGG<br>CCTGGTTCCAACAGAAACCTGGCCAGGCTCCCAGGCTCCT<br>CATCTATGATGCATTCAACAGGGCCACTGGCATCCCAGCC<br>AGGTTCAGTGGCAGTGGGTCTGGGACAGACTTCACTCTCA<br>CCATCAGCAGCCTAGAGCCTGAAGATTTTGCAATTTATTA<br>CTGTCAGCAGCGTAGCTACTGGCCGCTCACTTTCGGCGGA<br>GGGACCAAGCTGGAGATCAAA | 334 |
| 12D9 | ATGGAGTTTGGGCTGAGCTGGGTTTTCCTCGTTGCTCTTTTAAG<br>AGGTGTCCAGTGTCAGGTGCAGCTGGTGGAGTCGGGGGGAGGCG<br>TGGTCCAGCCTGGGAGGTCCCTGAGACTCTCCTGTGCAGCGTCT<br>GGATTCACCTTCAGTAACTATGGCATGAATTGGGTCCGCCAGGC<br>TCCAGGCAAGGGGCTGGAGTGGGTGGCAGTTATATGGTATGATG<br>GAACTATTAAATACTATGCAGACTCCGTGAAGGGCCGATTCACC<br>ATCTCCAGAGACAATTCCAAGAACACGCTGTATCTGCAAATGAT<br>CAGCCTGAGAGCCGAGGACACGGCTGTGTATTACTGTGCGAGCG<br>AGTATAGCAGTGGCTGGTACAGGGGTGCTTTTGATATATGGGGC<br>CAAGGGACAATGGTCACCGTCTCCTCAGCCTCCACCAAGGGCCC<br>ATCGGTCTTCCCTCTGGCACCCTCCTCCAAGAGCACCTCT | 343 | ATGGACATGAGAGTCCTCGCTCAGCTCCTGGGGCTCCTGC<br>TGCTCTGGCTCCCAGGTGCCAGATGTGACATCCAGTTGAC<br>CCAGTCTCCATCCTTCCTGTCTGCATCTGTAGGAGACAGA<br>GTCACCATCACTTGCCGGGCCAGTCAGGGCATTAGCAGTT<br>ATTTAGCCTGGTATCAGCAAAAACCAGGGAAAGCCCCTAA<br>GCTCCTGATCTATGCTGCATCCACTTTGCAAAGTGGGGTC<br>CCATCAAGGTTCAGCGGCAGTGGATCTGGGACAGAATTCA<br>CTCTCACAATCAGCAGCCTGCAGCCTGAAGATTTTGCAAC<br>TTATTACTGTCAACAGCTTAATAGTTACCCGTACACTTTT<br>GGCCAGGGGACCAAGGTGGAGATCAAACGAACTGTGGCTG<br>CACCATCTGTCTTCATCTTCCC | 344 |
| 21F2 | ATGGAATTGGGGCTGTGCTGGGTTTTCCTCGTTGCTCTTTTAAG<br>AGGTGTCCAGTGTCAGGTGCAGCTGGTGGAGTCTGGGGGAGGCG<br>TGGTCCAGCCTGGGAGGTCCCTGAGACTCTCCTGTGCAGCGTCT<br>GGATTCACCTTCAGTAGTTATGGCATGTTCTGGGTCCGCCAGAC<br>TCCAGGCAAGGGGCTGGAGTGGGTGGCAAATATATGGTATGATG<br>GAAGCAATAAATATTATACAGACTCCGTGAAGGGCCGATTCACC<br>ATCTCCAGAGACAATTCCAAGAACACGCTGTATCTGCAAATGAA<br>CAGCCTGAGAGCCGGGGACACGGCTGTATATTACTGTGCGAGAG<br>AGACATATTACTATGGTTCGGGGAGTTATGGGGGGGGTTTGGAC<br>GTCTGGGGCCAAGGGACCACGGTCACCGTCTCCTCAGCCTCCAC<br>CAAGGGCCCATCGGTCTTCCCTCTGGCACCCTCCTCCAAGAGCA<br>CCTCTGGGGGCACAGCGGCC | 353 | ATGGACATGAGGGTCCTCGCTCAGCTCCTGGGGCTCCTGC<br>TGCTCTGGCTCCCAGGTGCCAAATGTGACATCCAGATGAC<br>CCAGTCTCCTTCCACCCTGTCTGCTTCTGTAGGAGACAGA<br>GTCACCATCACTTGCCGGGCCAGTCAGAGTATTAGTAGCT<br>GGTTGGCCTGGTATCAGCAGAAACCAGGGAAAGCCCCTAA<br>GCTCCTGATCTATAAGGCGTCTAGTTTAGAAAGTGGGGTC<br>CCATCAAGGTTCAGCGGCAGTGGATCTGGGACAGAATTCA<br>CTCTCACCATCAGCAGCCTGCAGCCTGATGATTTTGCAAC<br>TTATTACTGCCAACAGTATTATAGTTATATCACCTTCGGC<br>CAAGGGACACGACTGGAGATTAAACGAACTGTGGCTGCAC<br>CATCTGTCTTCATCTTCCCTCCATCTGATGAGCAGT | 354 |
| 25B12 | ATGAAGCATCTGTGGTTCTTCCTCCTGCTGGTGGCAGCTCCCAG<br>ATGGGTCCTGCCCCAGGTGCAGCTGCAGGAGTCGGGCCCAGGAC<br>TGGTGAAGCCTTCGGAGACCCTGTCCCTCACCTGCGCTGTCTCT<br>GGTTACTCCATCAGCAGTGGTTACTACTGGGGCTGGATCCGGCA<br>GCCCCCAGGGAAGGGGCTGGAGTGGATTGGGAGTATCTATCATA<br>GTGGGAGCACCTACTACAACCCGTCCCTCAAGAGTCGAGTCACC<br>ATATCAGTAGACACGTCCAAGAACCAGTTCTCCCTGAAGCTGAG<br>CTCTGTGACCGCCGCAGACACGGCCGTGTATTACTGTGCGAGAG<br>ATAAGATAACAGTGGCTGCTTTTGATATCTGGGGCCAAGGGACA<br>ATGGTCACCGTCTCCTCAGCCTCCACCAAGGGCCCATCGGTCTT | 363 | ATGGACATGAGGGTCCCCGCTCAGCTCCTGGGGCTCCTGC<br>TGCTCTGGCTCCCAGGTGCCAGATGTGACATCCAGTTGAC<br>CCAGTCTCCATCCTTCCTGTCTGCATCTGTAGGAGACAGA<br>GTCACCATCACTTGCCGGGCCAGTCAGGGCATTAGCAGTT<br>ATTTAGCCTGGTATCAGCAAAAACCAGGGAAAGCCCCTAA<br>GCTCCTGATCTATGCTGCATCCACTTTGCAAAGTGGGGTC<br>CCATCAAGGTTCAGCGGCAGTGGATCTGGGACAGAATTCA<br>CTCTCACAATCAGCAGCCTGCAGCCTGAAGATTTTGCAAC<br>TTATTACTGTCAACAGCTTAATAGTTACCCGTACACTTTT<br>GGCCAGGGGACCAAGCTGGAGATCAAACGAACTGTGGCT | 364 |

FIG. 19 - Continued

| | | | | |
|---|---|---|---|---|
| | CCC | | | |
| 47A2 | ATGAAGCATCTGTGGTTCTTCCTCCTGCTGGTGGCAGCTCCCAG<br>ATGGGTCCTGCCCCAGGTGCAGCTGCAGGAGTCGGGCCCAGGAC<br>TGGTGAAGCCTTCGGAGACCCTGTCCCTCACCTGCGCTGTCTCT<br>GGTTACTCCATCAGCAGTGATTACTACTGGGGCTGGATCCGGCA<br>GCCCCCAGGGAAGGGGCTGGAGTGGATTGGGAGTATCTATCATA<br>GTGGGAGCACCTACTACAATACGTCCCTCAAGAGTCGAGTCACC<br>ATATCACTGGACACGTCCAAGAACCAGTTCTCCCTGAAACTGAC<br>CTCTGTGACCGCCGCAGACACGGCCGTGTATTATTGTGTGAGAG<br>AGGGAACAGTGGGTGGCCATTACTACTACTACTACGGTATGGAC<br>GTCTGGGGCCAAGGGACCACGGTCACCGTCTCCTCAGCCTCCAC<br>CAAGGGCCCATCGGTCTTCCCTCTGGCACCCTCCTCCAAGAGCA<br>CCTCT | 373 | ATGGAAACCCCAGCGCAGCTTCTCTTCCTCCTGCTACTCT<br>GGCTCCCAGATACCACCGGAGAAATTGTGTTGACACAGTC<br>TCCAGCCACCCTGTCTTTGTCTCCAGGGGAAAGAGCCACC<br>CTCTCCTGCAGGGCCAGTCAGAGTGTTAGAAGCTACTTAG<br>CCTGGTACCAACAGAAACCTGGCCAGGCTCCCAGGCTCCT<br>CATCTATGATGCATCCAAGAGGGCCACTGGCATCCCAGCC<br>AGGTTCAGTGGCAGTGGGTCTGGGACAGACTTCACTCTCA<br>CCATCAGCAGCCTAGAGCCTGAAGATTTTGCAGTTTATTA<br>CTGTCAGCAACGTAACAGCTGGCCCACTTTCGGCGGAGGG<br>ACCAAGGTGGAGATCAAACGAACTGTGGCTGCACCATCTG<br>TCTTCATCTTCCC | 374 |
| 14F11 | ATGGAGTTTGGGCTGAGCTGGCTTTTTCTTGTGGCTATTTTAAA<br>AGGTGTCCAGTGTGAGGTGCACCTGTTGGAGTCTGGGGGAGGCT<br>TGGTACAGCCTGGGGGGTCCCTGAGACTCTCCTGTGCAGCCTCT<br>GGATTCACCTTTAGCAGCTATGCCATGAGTTGGGTCCGCCAGGC<br>TCCAGGGAAGGGGCTGGAGTGGGTCTCAGGTATTGATAGTGGTG<br>GTGACACATACTACGCAGACTCCGTGAAGGGCCGGTTCACCATC<br>TCCAGAGACAATTCCAAGAACACTCTGTATCTGCAAATGACCAG<br>CCTGAGAGCCGAGGACACGGCCGTATATTACTGTGCGAAAGATC<br>TATATAGCAGTGGCTGGTTGGCTTTTGATATCTGGGGCCAAGGG<br>ACAATGGTCACCGTCTCCTCAGCCTCCACCAAGGGCCCATCGGT<br>CTTCCC | 383 | ATGGACATGAGGGTCCTCGCTCAGCTCCTGGGGCTCCTGC<br>TGCTCTGGCTCCCAGGTGCCAGATGTGACATCCAGTTGAC<br>CCAGTCTCCATCCTTCCTGTCTGCATCTGTAGGAGACAGA<br>GTCACCATCACTTGCCGGGCCAGTCAGGGCATTAGCAGTT<br>ATTTAGCCTGGTATCAGCAAAAACCAGGGAAAGCCCCTAA<br>GCTCCTGATCTATGCTGCATCCACTTTGCAAAGTGGGGTC<br>CCATCAAGGTTCAGCGGCAGTGGATCTGGGACAGAATTCA<br>CTCTCACAATCAGCAGCCTGCAGCCTGAAGATTTTGCAAT<br>TTATTACTGTCAACAGCTTAATAGTTATCCGCTGTACACT<br>TTTGGCCAGGGGACCAAGCTGGAGATCAAACGAACTGTG | 384 |
| 18B2 | ATGGAGTTGGGGCTGTGCTGGCTTTTTCTTGTGGCTATTTTAAA<br>AGGTGTCCAGTGTGAGGTGCAGTTGTTGGAGTCTGGGGGAGGCT<br>CGGTACAGCCTGGGGGGTCCCTGAGACTCTCCTGTGCAGCCTCT<br>GGATTCACCTTTAGCAGCTATGCCATGAGCTGGGTCCGCCAGGC<br>TCCAGGGAAGGGGCTGGAGTGGGTCTCAGGTATTAGTGATAATG<br>GTAACACATACTACGCAGACTCCGTGAAGGGCCGGTTCACCATC<br>TCCAGAGACAATTCCAAGAATACGCTGTATCTGCAAATGAACAG<br>CCTGAGAGCCGAGGACACGGCCGTATATCACTGTGCGAAAGATC<br>TGTATAGCAGTGGCTGGTTGGCTTTTGATATCTGGGGCCAAGGG<br>ACAATGGTCACCGTCTCCTCAGCCTCCACCAAGGGCCCATCGGT<br>CTTCCC | 393 | ATGGACATGAGGGTCCTCGCTCAGCTCCTGGGGCTCCTGC<br>TGCTCTGGCTCCCAGGTGCCAGATGTGACATCCAGTTGAC<br>CCAGTCTCCATCCTTCCTGTCTGCATCTGTAGGAGACAGA<br>GTCACCATCACTTGCCGGGCCAGTCAGGGCATTAGCACTT<br>ATTTAGCCTGGTATCAGCAAAAACCAGGGAAAGCCCCTAA<br>GCTCCTGATCTATGCTGCATCCACTTTGCAAAGTGGGGTC<br>CCATCAAGGTTCAGCGGCAGTGGATCTGGGACAGAATTCA<br>CTCTCACAATCAGCAGCCTGCAGCCTGAAGATTTTGCAAC<br>TTATTACTGTCAACAGCTTAATAGTTACCCTCTGTACACT<br>TTTGGCCAGGGGACCAAGGTGGAGATCAAACGAACTGTG | 394 |

FIG. 20

| Ab Name | VH CDI | SEQ ID: | VH | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 14H4 | GFTFNSYAMS | 5 | VLSGSGGDIHYADSV | 6 | AQQWPQGY | 7 | RASQGISIYLA | 8 | AASTLQS | 9 | QKYNSAPFT | 10 |
| 03B05 | GFTFSSYGMH | 15 | IIWYDGSN | 16 | AKDPSYSSGYYLFDF | 17 | RASQSVSSNLA | 18 | GASTRAT | 19 | QQYNNWPLT | 20 |
| 03C05 | GFTFSSYVMS | 25 | GISGSGGSTHYADSV | 26 | AQQWPQGY | 27 | RASQDISIYLA | 28 | AASTLQS | 29 | QKYNSAPFT | 30 |
| 27H10 | GGTFSSYAMS | 35 | GIIPILGTTNYAQ | 36 | AREGLYAFDI | 37 | RASQSISSYLN | 38 | VASSLQS | 39 | QQSYSTPWT | 40 |
| 03B11 | GGSFSSYYWS | 45 | EINHSGSTSYNPSL | 46 | AASPYFDY | 47 | RASQGISSYLA | 48 | AASTLQS | 49 | QQLNSYPRT | 50 |
| 04G06 | GFTLSSYGMH | 55 | VIWYDGSD | 56 | ARDDWGFDY | 57 | RASQDISNYLA | 58 | SASTLQS | 59 | QHLNSYP | 60 |
| 42C5 | GFTFSRYWMN | 65 | NIKQDGSE | 66 | ARVMYSSGWSFDY | 67 | RSSRSLLHSSGYNFLD | 68 | LGSDRAS | 69 | MQALQTPIT | 70 |
| 47G7 | GFTFSSYWMS | 75 | NIKQDGSE | 76 | AREGGSSGWTFDY | 77 | RSSQSLLHSSGHNFLD | 78 | LGSNRAS | 79 | MQALQTPPT | 80 |
| 18C06 | GGSISSSFWS | 85 | YIYYSESTNYNPSL | 86 | ARNIGVAGLFDY | 87 | RASQSVSSNLA | 88 | GASTRAT | 89 | QQYNNWPLT | 90 |
| 11F9 | GGSISSYYWS | 95 | YIYYSGSTNYNPSL | 96 | ARNIGVAGLFDY | 97 | RASQSVSSNLA | 98 | GASTRAT | 99 | QQYNNWPLT | 100 |
| 10E2 | GFTFSSYGMH | 105 | VVWYDGTI | 106 | ASQYSSGWHTDFFDV | 107 | RASQSISTWLA | 108 | KASSLES | 109 | QQYSGYSLT | 110 |
| 01E2 | GFTFSSYGMH | 115 | VIWYAGSN | 116 | AGWDFDY | 117 | RASQTVPNYLA | 118 | DASNRAT | 119 | QQRANWPPIT | 120 |
| 41A9 | GGSFSDYYWS | 125 | EINHSGSTNYNPSL | 126 | ARDYDVLTGHFYYYYGMDV | 127 | RASQSVRRYLA | 128 | DASNRAT | 129 | QQRNNWPLT | 130 |
| 02F3 | GFSFSDYGIH | 135 | VIWYDGSN | 136 | ARDRGYSSGWYVDYYYYGMDV | 137 | RSSQSLLHSNGYNYLD | 138 | LGSNRAS | 139 | MQALQTPWT | 140 |
| 50D6 | GFTFSNYAMN | 145 | AISGGGGSTYYADSV | 146 | AKTSSGWYDSYYDYYGLDV | 147 | RASQGISNYLA | 148 | AVSTLQS | 149 | QQLNSYPFT | 150 |
| 38E11 | GFTFSNYAMN | 155 | AISGGGGSTYYADSV | 156 | AKESITMVRGVMDYYGMDV | 157 | RASQGISSYLA | 158 | AASTLQG | 159 | QHLNRFPRT | 160 |
| 05A8 | GFTFSNYAMS | 165 | AISGRGGSTYYADSV | 166 | AKDIVVVPAAKGYVMDA | 167 | RASQSVSSNLA | 168 | GASTRAT | 169 | QQYNNWPLT | 170 |
| 12C2 | GFTFSSYGMH | 175 | VIWYDGTNKYYADTV | 176 | AREGCDTISCPYYYYGMDV | 177 | RASQGINYYLA | 178 | TASTLQS | 179 | QKYNSAPFT | 180 |
| 03G11 | GFTFSSYAMS | 185 | AISGSGNSAYYADSVKG | 186 | SSGWYLVYYFDL | 187 | RASQSVSSNLA | 188 | GASIRAT | 189 | QQYNNWPLT | 190 |

FIG. 20 - Continued

| | | | | | | | | | | | |
|---|---|---|---|---|---|---|---|---|---|---|---|
| 06H1 | GFTFSSYAMS | 195 | GISGSGGNTHYADSVKG | 196 | QWPQGY | 197 | RASQGISIYLA | 198 | AASTLQS | 199 | QKYNSAPFT | 200 |
| 07C06D2 | GFTFSNYIMS | 205 | GISGSGGSTHYAGSVKG | 206 | QWPQGY | 207 | RASQGITIYLA | 208 | AASTLQS | 209 | QKYNSAPFT | 210 |
| 09F6 | GFTFSSYAMS | 215 | GLSGSGGDTHYAGSVKG | 216 | QWPQGY | 217 | RASQGISIYLA | 218 | AASTLQS | 219 | QKYNSAPFT | 220 |
| 14D4 | GFTFSSYAMS | 225 | GISGSGGSTHYADSVKG | 226 | QWPQGH | 227 | RASQDISIYLA | 228 | AASTLQS | 229 | QKYNSDPFT | 230 |
| 15H5 | GFTFSSYAMS | 235 | VLSGSGDDTHYADSVKG | 236 | QWPQGY | 237 | RASQDISIYLA | 238 | AASTLQS | 239 | QKYNSAPFT | 240 |
| 20F5 | GFTFSSYVMS | 245 | GISGSGGSTHYTDSVQG | 246 | QWPQGY | 247 | RASQGISIYLA | 248 | AASTLQS | 249 | QKYNSAPFT | 250 |
| 38A6 | GFTFNTYAMS | 255 | AISDNGGGTYNADSVKG | 256 | GEQWGAPFDY | 257 | RASQGISIYLA | 258 | AASTLQS | 259 | QKYNSAPWT | 260 |
| 39D7 | GFTFSSYAMS | 265 | TISGSGGSTYYADSVKG | 266 | LDTAMAADAFAI | 267 | RSSQSLLHSNGYNYLD | 268 | LGSNRAS | 269 | MQALLIPLY | 270 |
| 18C11 | GFTFSSYWMS | 275 | NIKQDGSEKYYVDSVKG | 276 | DWRSSGWTLDY | 277 | RSSQSLLHSSGHNFLD | 278 | LGSNRGS | 279 | MQALQTPRT | 280 |
| 38G4 | GFTFSSYWMS | 285 | NVKQDGSEKDYVDSVKG | 286 | EWNSSGWTFDY | 287 | RSSQSLLHSTGYNFLD | 288 | LGSNRAS | 289 | MQALQTPLT | 290 |
| 27D8 | GFTFSSYGMH | 295 | VIWYDGSNKYYADSVKG | 296 | DRVYYDGSGSYYNVGVMDV | 297 | RASQSVSNNLA | 298 | GVSTRAT | 299 | QQYNDWPLT | 300 |
| 11A4 | GFTFSSYAMH | 305 | LIYYDGSHEYYSDSVKG | 306 | DGGSGSHYPFDAFDI | 307 | RASQSISSWLA | 308 | KASSLES | 309 | QQYNTYYT | 310 |
| 24H1 | GGSISSYYWS | 315 | YIYYTGRNNYNPSLKS | 316 | EGGWGPHFDY | 317 | RSSQSLLHSSGYNYLD | 318 | LGSDRAS | 319 | MQALQIPYT | 320 |
| 18C02 | GGSFSDYYWS | 325 | EINHSGSTNYNPSLKS | 326 | DYDVLTGHFYYYYGMDV | 327 | RASQSISSYLN | 328 | AASSLQS | 329 | QQSYTMPYT | 330 |
| 07C10 | GFTFSSYGMH | 335 | LIWYDGSNKYYADSVQG | 336 | DYDILTGHVLYVMDA | 337 | RASQSVTNYLA | 338 | DAFNRAT | 339 | QQRSYWPLT | 340 |
| 12D9 | GFTFSNYGMN | 345 | VIWYDGTIKYYADSVKG | 346 | EYSSGWYRGAFDI | 347 | RASQGISSYLA | 348 | AASTLQS | 349 | QQLNSYPYT | 350 |
| 21F2 | GFTFSSYGMF | 355 | NIWYDGSNKYYTDSVKG | 356 | ETYYYGSGSYGGGLDV | 357 | RASQSISSWLA | 358 | KASSLES | 359 | QQYYSYIT | 360 |
| 25B12 | GYSISSGYYWG | 365 | SIYHSGSTYYNPSLKS | 366 | DKITVAAFDI | 367 | RASQGISSYLA | 368 | AASTLQS | 369 | QQLNSYPYT | 370 |
| 47A2 | GYSISSDYYWG | 375 | SIYHSGSTYYNTSLKS | 376 | EGTVGGHYYYYYGMDV | 377 | RASQSVRSYLA | 378 | DASKRAT | 379 | QQRNSWPT | 380 |
| 14F11 | GFTFSSYAMS | 385 | GIDSGGDTYYADSVKG | 386 | DLYSSGWLAFDI | 387 | RASQGISSYLA | 388 | AASTLQS | 389 | QQLNSYPLYT | 390 |
| 18B2 | GFTFSSYAMS | 395 | GISDNGNTYYADSVKG | 396 | DLYSSGWLAFDI | 397 | RASQGISTYLA | 398 | AASTLQS | 399 | QQLNSYPLYT | 400 |

ANTI-CUB DOMAIN-CONTAINING PROTEIN 1 (CDCP1) ANTIBODIES, ANTIBODY DRUG CONJUGATES, AND METHODS OF USE THEREOF

RELATED APPLICATIONS

This application is a divisional of U.S. patent application Ser. No. 16/469,197 filed on Jun. 13, 2019, which in turn is a 35 U.S.C. § 371 national stage filing of International Application No. PCT/US2017/066661, filed on Dec. 15, 2017, which in turn claims the benefit of priority to U.S. Provisional Patent Application No. 62/435,509, filed on Dec. 16, 2016. U.S. Provisional Patent Application No. 62/488,445, filed on Apr. 21, 2017, and U.S. Provisional Patent Application No. 62/588,516, filed on Nov. 20, 2017. The entire contents of each of the foregoing applications are incorporated herein by reference.

SEQUENCE LISTING

The instant application contains a Sequence Listing which has been submitted electronically in XML format and is hereby incorporated by reference in its entirety. Said XML copy, created on May 19, 2023, is named "Sequence Listing 133186-5004-US01_" and is 569,344 bytes in size.

BACKGROUND

CDCP1, also known as "CUB domain-containing protein 1," "CD318," "Transmembrane and associated with src kinases" ("TRASK"), and "SIMA135," is an 836 amino acid, type I transmembrane protein that consists of a signal peptide of 29 amino acids, a larger extracellular domain of 636 amino acids, heavily glycosylated with three regions that have a low homology to C1r/C1s, urchin embryonic growth factor, and bone mor-phogenetic protein 1 (CUB) domains, a transmembrane and a cytoplasmic domain of 21 and 150 amino acids, respectively. The cytoplasmic domain of CDCP1 includes five conserved tyrosine residues that act as a substrate of Src Family Kinases (SFK) such as Src. Fyn and Yes for subsequent phosphorylation.

CDCP1 is widely expressed in human epithelial tissues. CDCP1 functions in the tyrosine phosphorylation-dependent regulation of cellular events that are involved in tumor invasion and metastasis, but its phosphorylation is only observed in mitotically detached or shedding cells, consistent with its role in the negative regulation of cell adhesion. The phosphorylation of CDCP1 is seen in many cancers, including some pre-invasive cancers as well as in invasive tumors and in tumor metastases Recent clinical and commercial success of anticancer antibodies has created great interest in antibody-based therapeutics. As antibodies can target specific antigens on the cancer cells, antibody-based therapeutics are likely to be more effective for treating cancers and have lower toxic effects as compared to commonly-used chemotherapies. Thus, there is a need to develop anti-cancer antibodies for use in various antibody-based therapeutics to treat cancers.

Antibody drug conjugates (ADC) represent a new class of therapeutics comprising an antibody conjugated to a cytotoxic drug via a chemical linker. The therapeutic concept of ADCs is to combine binding capabilities of an antibody with a drug, where the antibody is used to deliver the drug to a tumor cell by means of binding to a target surface antigen.

Accordingly, there remains a need in the art for anti-CDCP1 antibodies and ADCs that can be used for therapeutic purposes in the treatment of cancer.

SUMMARY

In certain aspects, the present invention provides for anti-CDCP1 antibodies and antibody drug conjugates (ADCs). In certain embodiments of the invention, the antibodies, or antigen binding portions thereof, bind to CDCP1 (e.g., the amino acid sequence provided in GenBank Accession No. NP_073753.3 and/or the amino acid sequence provided in NP_835488.1, the entire contents of each of which are incorporated herein by reference), or the extracellular domain of CDCP1. In one embodiment, the antibodies, or antigen binding portions thereof, of the invention, bind to CDCP1 with a $K_d$ of about 2.000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, or about 0.01 nM or less, or about 0.001 nM or less.

In yet other embodiments of the invention, anti-CDCP1 antibody drug conjugates (ADCs) of the invention (e.g., the CDCP1 antibodies of the invention conjugated to a toxin) capable of being internalized. In another embodiment, the anti-CDCP1 antibody drug conjugates (ADCs) of the invention are capable of inducing cell death of cells endogenously expressing CDCP1.

In one aspect of the invention, the present disclosure provides an isolated antibody, or antigen binding portion thereof, that binds to human CDCP1, wherein the antibody, or antigen binding portion thereof, comprises a heavy chain variable region comprising a CDR3 having the amino acid sequence of SEQ ID NO: 157 and a light chain variable region comprising a CDR3 having the amino acid sequence of SEQ ID NO: 160. In some embodiments, the antibody, or antigen binding portion thereof, further comprises a heavy chain variable region comprising a CDR2 having the amino acid sequence of SEQ ID NO: 156 and a light chain variable region comprising a CDR2 having the amino acid sequence of SEQ ID NO: 159. In other embodiments, the antibody, or antigen binding portion thereof, comprises a heavy chain variable region comprising a CDR1 having the amino acid sequence of SEQ ID NO: 155 and a light chain variable region comprising a CDR1 having the amino acid sequence of either SEQ ID NO: 158.

In one aspect of the invention, the present disclosure provides an isolated antibody, or antigen binding portion thereof, that binds to human CDCP1, wherein the antibody, or antigen binding portion thereof, comprises a heavy chain variable region comprising a CDR3 having the amino acid sequence of SEQ ID NO: 37 and a light chain variable region comprising a CDR3 having the amino acid sequence of SEQ ID NO: 40. In some embodiments, the antibody, or antigen binding portion thereof, further comprises a heavy chain variable region comprising a CDR2 having the amino acid sequence of SEQ ID NO: 36 and a light chain variable region comprising a CDR2 having the amino acid sequence of SEQ ID NO: 39. In other embodiments, the antibody, or antigen binding portion thereof, comprises a heavy chain variable region comprising a CDR1 having the amino acid sequence of SEQ ID NO: 35 and a light chain variable region comprising a CDR1 having the amino acid sequence of either SEQ ID NO: 38.

In one aspect of the invention, the present disclosure provides an isolated antibody, or antigen binding portion thereof, that binds to human CDCP1, wherein the antibody, or antigen binding portion thereof, comprises a heavy chain variable region comprising a CDR3 having the amino acid sequence of SEQ ID NO: 87 and a light chain variable region comprising a CDR3 having the amino acid sequence of SEQ ID NO: 90. In some embodiments, the antibody, or antigen binding portion thereof, comprises a heavy chain variable region comprising a CDR2 having the amino acid sequence of SEQ ID NO: 86 and a light chain variable region comprising a CDR2 having the amino acid sequence of SEQ ID NO: 89. In other embodiments, the antibody, or antigen binding portion thereof, comprises a heavy chain variable region comprising a CDR1 having the amino acid sequence of SEQ ID NO: 85 and a light chain variable region comprising a CDR1 having the amino acid sequence of either SEQ ID NO: 88.

In yet another aspect of the invention, the present disclosure provides an isolated antibody, or antigen binding portion thereof, that binds to human CDCP1, wherein the antibody, or antigen binding portion thereof, comprises a heavy chain variable region comprising a CDR3 having the amino acid sequence of SEQ ID NO: 107 and a light chain variable region comprising a CDR3 having the amino acid sequence of SEQ ID NO: 110. In some embodiments, the antibody, or antigen binding portion thereof, comprises a heavy chain variable region comprising a CDR2 having the amino acid sequence of SEQ ID NO: 106 and a light chain variable region comprising a CDR2 having the amino acid sequence of SEQ ID NO: 109. In other embodiments, the antibody, or antigen binding portion thereof, comprises a heavy chain variable region comprising a CDR1 having the amino acid sequence of SEQ ID NO: 105 and a light chain variable region comprising a CDR1 having the amino acid sequence of either SEQ ID NO: 108.

In another aspect of the invention, the present disclosure provides an isolated antibody, or antigen binding portion thereof, that binds to human CDCP1, wherein the antibody, or antigen binding portion thereof, comprises a heavy chain variable region comprising a CDR3 having the amino acid sequence of SEQ ID NO: 127 and a light chain variable region comprising a CDR3 having the amino acid sequence of SEQ ID NO: 130. In some embodiments, the antibody, or antigen binding portion thereof, comprises a heavy chain variable region comprising a CDR2 having the amino acid sequence of SEQ ID NO: 126 and a light chain variable region comprising a CDR2 having the amino acid sequence of SEQ ID NO: 129. In other embodiments, the antibody, or antigen binding portion thereof, comprises a heavy chain variable region comprising a CDR1 having the amino acid sequence of SEQ ID NO: 125 and a light chain variable region comprising a CDR1 having the amino acid sequence of either SEQ ID NO: 128.

In one aspect of the invention, the present disclosure provides an isolated antibody, or antigen binding portion thereof, that binds to human CDCP1, wherein the antibody, or antigen binding portion thereof, comprises a heavy chain variable region comprising a CDR3 having the amino acid sequence of SEQ ID NO: 47 and a light chain variable region comprising a CDR3 having the amino acid sequence of SEQ ID NO: 50. In some embodiments, the antibody, or antigen binding portion thereof, comprises a heavy chain variable region comprising a CDR2 having the amino acid sequence of SEQ ID NO: 46 and a light chain variable region comprising a CDR2 having the amino acid sequence of SEQ ID NO: 49. In other embodiments, the antibody, or antigen binding portion thereof, comprises a heavy chain variable region comprising a CDR1 having the amino acid sequence of SEQ ID NO: 45 and a light chain variable region comprising a CDR1 having the amino acid sequence of either SEQ ID NO: 48.

In another aspect of the invention, the present disclosure provides an isolated antibody, or antigen binding portion thereof, that binds to human CDCP1, wherein the antibody, or antigen binding portion thereof, comprises a heavy chain variable region comprising a CDR3 having the amino acid sequence of SEQ ID NO: 77 and a light chain variable region comprising a CDR3 having the amino acid sequence of SEQ ID NO: 80. In some embodiments, the antibody, or antigen binding portion thereof, comprises a heavy chain variable region comprising a CDR2 having the amino acid sequence of SEQ ID NO: 76 and a light chain variable region comprising a CDR2 having the amino acid sequence of SEQ ID NO: 79. In other embodiments, the antibody, or antigen binding portion thereof, comprises a heavy chain variable region comprising a CDR1 having the amino acid sequence of SEQ ID NO: 75 and a light chain variable region comprising a CDR1 having the amino acid sequence of either SEQ ID NO: 78.

In some aspects, the antibody, or antigen binding portion thereof, is an IgG isotype.

In some aspects, the antibody, or antigen binding portion thereof, has a $K_D$ of 200 nM or less.

In another aspect of the invention, the present disclosure provides an anti-CDCP1 antibody, or antigen-binding portion thereof, comprising a heavy chain variable region comprising a CDR3 domain comprising the amino acid sequence of SEQ ID NO: 157, a CDR2 domain comprising the amino acid sequence of SEQ ID NO: 156, and a CDR1 domain comprising the amino acid sequence of SEQ ID NO: 155, and a light chain variable region comprising a CDR3 domain comprising the amino acid sequence of SEQ ID NO: 160, a CDR2 domain comprising the amino acid sequence of SEQ ID NO: 159, and a CDR1 domain comprising the amino acid sequence of SEQ ID NO: 158.

In another aspect of the invention, the present disclosure provides an anti-CDCP1 antibody, or antigen-binding portion thereof, comprising a heavy chain variable region comprising a CDR3 domain comprising the amino acid sequence of SEQ ID NO: 37, a CDR2 domain comprising the amino acid sequence of SEQ ID NO: 36, and a CDR1 domain comprising the amino acid sequence of SEQ ID NO: 35, and a light chain variable region comprising a CDR3 domain comprising the amino acid sequence of SEQ ID NO: 40, a CDR2 domain comprising the amino acid sequence of SEQ ID NO: 39, and a CDR1 domain comprising the amino acid sequence of SEQ ID NO: 38.

In another aspect of the invention, the present disclosure provides an anti-CDCP1 antibody, or antigen-binding portion thereof, comprising a heavy chain variable region comprising a CDR3 domain comprising the amino acid sequence of SEQ ID NO: 87, a CDR2 domain comprising the amino acid sequence of SEQ ID NO: 86, and a CDR1 domain comprising the amino acid sequence of SEQ ID NO: 85, and a light chain variable region comprising a CDR3 domain comprising the amino acid sequence of SEQ ID NO: 90, a CDR2 domain comprising the amino acid sequence of SEQ ID NO: 89, and a CDR1 domain comprising the amino acid sequence of SEQ ID NO: 88.

In another aspect of the invention, the present disclosure provides an anti-CDCP1 antibody, or antigen-binding portion thereof, comprising a heavy chain variable region comprising a CDR3 domain comprising the amino acid sequence of SEQ ID NO: 107, a CDR2 domain comprising the amino acid sequence of SEQ ID NO: 106, and a CDR1 domain comprising the amino acid sequence of SEQ ID NO: 105, and a light chain variable region comprising a CDR3 domain comprising the amino acid sequence of SEQ ID NO: 110, a CDR2 domain comprising the amino acid sequence of SEQ ID NO: 109, and a CDR1 domain comprising the amino acid sequence of SEQ ID NO: 108.

In another aspect of the invention, the present disclosure provides an anti-CDCP1 antibody, or antigen-binding portion thereof, comprising a heavy chain variable region comprising a CDR3 domain comprising the amino acid sequence of SEQ ID NO: 127, a CDR2 domain comprising the amino acid sequence of SEQ ID NO: 126, and a CDR1 domain comprising the amino acid sequence of SEQ ID NO: 125, and a light chain variable region comprising a CDR3 domain comprising the amino acid sequence of SEQ ID NO: 130, a CDR2 domain comprising the amino acid sequence of SEQ ID NO: 129, and a CDR1 domain comprising the amino acid sequence of SEQ ID NO: 128.

In one aspect of the invention, the present disclosure provides an anti-CDCP1 antibody, or antigen-binding portion thereof, comprising a heavy chain variable region comprising a CDR3 domain comprising the amino acid sequence of SEQ ID NO: 47, a CDR2 domain comprising the amino acid sequence of SEQ ID NO: 46, and a CDR1 domain comprising the amino acid sequence of SEQ ID NO: 45, and a light chain variable region comprising a CDR3 domain comprising the amino acid sequence of SEQ ID NO: 50, a CDR2 domain comprising the amino acid sequence of SEQ ID NO: 49, and a CDR1 domain comprising the amino acid sequence of SEQ ID NO: 48.

In another aspect of the invention, the present disclosure provides an anti-CDCP1 antibody, or antigen-binding portion thereof, comprising a heavy chain variable region comprising a CDR3 domain comprising the amino acid sequence of SEQ ID NO: 77, a CDR2 domain comprising the amino acid sequence of SEQ ID NO: 76, and a CDR1 domain comprising the amino acid sequence of SEQ ID NO: 75, and a light chain variable region comprising a CDR3 domain comprising the amino acid sequence of SEQ ID NO: 80, a CDR2 domain comprising the amino acid sequence of SEQ ID NO: 79, and a CDR1 domain comprising the amino acid sequence of SEQ ID NO: 78.

In some aspects, the antibody, or antigen binding portion thereof, is an IgG isotype.

In some aspects, the antibody, or antigen binding portion thereof, has a $K_D$ of 200 nM or less.

In another aspect of the invention, the present disclosure provides an anti-CDCP1 antibody, or antigen-binding portion thereof, comprising a heavy chain variable domain comprising an amino acid sequence set forth in SEQ ID NO: 151 and a light chain variable domain comprising an amino acid sequence set forth in SEQ ID NO: 152.

In another aspect of the invention, the present disclosure provides an anti-CDCP1 antibody, or antigen-binding portion thereof, comprising a heavy chain comprising an amino acid sequence set forth in SEQ ID NO: 151, or a sequence having at least 90%, 95%, 96%, 97%, 98%, or 99% identity to SEQ ID NO: 151, and/or a light chain comprising an amino acid sequence set forth in SEQ ID NO: 152, or a sequence having at least 90%, 95%, 96%, 97%, 98%, or 99% identity to SEQ ID NO: 152.

In another aspect of the invention, the present disclosure provides an anti-CDCP1 antibody, or antigen-binding portion thereof, comprising a heavy chain variable region comprising the amino acid sequence of SEQ ID NO: 31 and a light chain variable region comprising the amino acid sequence of SEQ ID NO: 32.

In another aspect of the invention, the present disclosure provides an anti-CDCP1 antibody, or antigen-binding portion thereof, comprising a heavy chain comprising an amino acid sequence set forth in SEQ ID NO: 31, or a sequence having at least 90%, 95%, 9%%, 97%, 98%, or 99% identity to SEQ ID NO: 31, and/or a light chain comprising an amino acid sequence set forth in SEQ ID NO: 32, or a sequence having at least 90%, 95%, 96%, 97%, 98%, or 99% identity to SEQ ID NO: 32.

In another aspect of the invention, the present disclosure provides an anti-CDCP1 antibody, or antigen-binding portion thereof, comprising a heavy chain variable region comprising the amino acid sequence of SEQ ID NO: 81 and a light chain variable region comprising the amino acid sequence of SEQ ID NO: 82.

In another aspect of the invention, the present disclosure provides an anti-CDCP1 antibody, or antigen-binding portion thereof, comprising a heavy chain comprising an amino acid sequence set forth in SEQ ID NO: 81, or a sequence having at least 90%, 95%, 96%, 97%, 98%, or 99% identity to SEQ ID NO: 81, and/or a light chain comprising an amino acid sequence set forth in SEQ ID NO: 82, or a sequence having at least 90%, 95%, 96%, 97%, 98%, or 99% identity to SEQ ID NO: 82.

In another aspect of the invention, the present disclosure provides an anti-CDCP1 antibody, or antigen-binding portion thereof, comprising a heavy chain variable region comprising the amino acid sequence of SEQ ID NO: 101 and a light chain variable region comprising the amino acid sequence of SEQ ID NO: 102.

In another aspect of the invention, the present disclosure provides an anti-CDCP1 antibody, or antigen-binding portion thereof, comprising a heavy chain comprising an amino acid sequence set forth in SEQ ID NO: 101, or a sequence having at least 90%, 95%, 96%, 97%, 98%, or 99% identity to SEQ ID NO: 101, and/or a light chain comprising an amino acid sequence set forth in SEQ ID NO: 102, or a sequence having at least 90%, 95%, 96%, 97%, 98%, or 99% identity to SEQ ID NO: 102.

In another aspect of the invention, the present disclosure provides an anti-CDCP1 antibody, or antigen-binding portion thereof, comprising a heavy chain variable region comprising the amino acid sequence of SEQ ID NO: 121 and a light chain variable region comprising the amino acid sequence of SEQ ID NO: 122.

In another aspect of the invention, the present disclosure provides an anti-CDCP1 antibody, or antigen-binding portion thereof, comprising a heavy chain comprising an amino acid sequence set forth in SEQ ID NO: 121, or a sequence having at least 90%, 95%, 96%, 97%, 98%, or 99% identity to SEQ ID NO: 121, and/or a light chain comprising an amino acid sequence set forth in SEQ ID NO: 12, or a sequence having at least 90%, 95%, 96%, 97%, 98%, or 99% identity to SEQ ID NO: 122.

In another aspect of the invention, the present disclosure provides an anti-CDCP1 antibody, or antigen-binding portion thereof, comprising a heavy chain variable region comprising the amino acid sequence of SEQ ID NO: 41 and a light chain variable region comprising the amino acid sequence of SEQ ID NO: 42.

In another aspect of the invention, the present disclosure provides an anti-CDCP1 antibody, or antigen-binding portion thereof, comprising a heavy chain comprising an amino acid sequence set forth in SEQ ID NO: 41, or a sequence having at least 90%, 95%, 96%, 97%, 98%, or 99% identity to SEQ ID NO: 41, and/or a light chain comprising an amino acid sequence set forth in SEQ ID NO: 42, or a sequence having at least 90%, 95%, 96%, 97%, 98%, or 99% identity to SEQ ID NO: 42.

In another aspect of the invention, the present disclosure provides an anti-CDCP1 antibody, or antigen-binding portion thereof, comprising a heavy chain variable region comprising the amino acid sequence of SEQ ID NO: 71 and a light chain variable region comprising the amino acid sequence of SEQ ID NO: 72.

In another aspect of the invention, the present disclosure provides an anti-CDCP1 antibody, or antigen-binding portion thereof, comprising a heavy chain comprising an amino acid sequence set forth in SEQ ID NO: 71, or a sequence having at least 90%, 95%, 96%/o, 97%, 98%, or 99% identity to SEQ ID NO: 71, and/or a light chain comprising an amino acid sequence set forth in SEQ ID NO: 72, or a sequence having at least 90%, 95%, 96%, 97%, 98%, or 99% identity to SEQ ID NO: 72.

In one aspect of the invention, the present disclosure provides an anti-CUB domain-containing protein 1 (-CDCP1) antibody, or antigen-binding portion thereof, wherein the antibody, or antigen binding portion thereof, comprises a heavy chain variable region comprising a CDR3 having an amino acid sequence selected from the group consisting of any one of the amino acid sequences in FIG. 15, 18, or 20, and a light chain variable region comprising a CDR3 having an amino acid sequence selected from the group consisting of any one of the amino acid sequences in FIG. 15, 18, or 20.

In one embodiment, the heavy chain variable region further comprises a CDR2 having an amino acid sequence selected from the group consisting of any one of the amino acid sequences in FIG. 15, 18, or 20, and the light chain variable region further comprises a CDR2 having an amino acid sequence selected from the group consisting of any one of the amino acid sequences in FIG. 15, 18, or 20.

In another embodiment, the heavy chain variable region further comprises a CDR1 having an amino acid sequence selected from the group consisting of any one of the amino acid sequences in FIG. 15, 18, or 20, and the light chain variable region further comprises a CDR1 having an amino acid sequence selected from the group consisting of any one of the amino acid sequences in FIG. 15, 18, or 20.

In another aspect of the invention, the present disclosure provides an antibody, or antigen-binding portion thereof, that binds to the same epitope as an antibody, or antigen-binding portion thereof, as described herein.

In another aspect of the invention, the present disclosure provides an isolated nucleic acid encoding an antibody, or antigen binding portion thereof, as described herein.

In another aspect of the invention, the present disclosure provides a pharmaceutical composition comprising the antibody, or antigen binding portion thereof, as described herein, and a pharmaceutically acceptable carrier.

In another aspect of the invention, the present disclosure provides an antibody, or antigen binding portion thereof, as described herein, conjugated to at least one drug.

In some aspects, the at least one drug is selected from the group consisting of an anti-apoptotic agent, a mitotic inhibitor, an anti-tumor antibiotic, an immunomodulating agent, a nucleic acid for gene therapy, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In other embodiments, the at least one drug is conjugated to the antibody, or antigen-binding portion thereof, via a linker. In another embodiment, the linker is a cleavable linker. In yet other embodiments, the linker is a non-cleavable linker.

In one embodiment, the anti-CUB domain-containing protein 1 (-CDCP1) antibodies, or antigen-binding portions thereof, of the present invention are bispecific antibodies. In one embodiment, the anti-CUB domain-containing protein 1 (-CDCP1) antibodies, or antigen-binding portions thereof, of the present invention are multispecific antibodies.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 157, a CDR2 domain comprising the amino acid sequence of SEQ ID NO: 156, and a CDR1 domain comprising the amino acid sequence of SEQ ID NO: 155, and a light chain variable region comprising a CDR3 domain comprising the amino acid sequence of SEQ ID NO: 160, a CDR2 domain comprising the amino acid sequence of SEQ ID NO: 159, and a CDR1 domain comprising the amino acid sequence of SEQ ID NO: 158.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 37, a CDR2 domain comprising the amino acid sequence of SEQ ID NO: 36, and a CDR1 domain comprising the amino acid sequence of SEQ ID NO: 35, and a light chain variable region comprising a CDR3 domain comprising the amino acid sequence of SEQ ID NO: 40, a CDR2 domain comprising the amino acid sequence of SEQ ID NO: 39, and a CDR1 domain comprising the amino acid sequence of SEQ ID NO: 38.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 87, a CDR2 domain comprising the amino acid sequence of SEQ ID NO: 86, and a CDR1 domain comprising the amino acid sequence of SEQ ID NO: 85, and a light chain variable region comprising a CDR3 domain comprising the amino acid sequence of SEQ ID NO: 90, a CDR2 domain comprising the amino acid sequence of SEQ ID NO: 89, and a CDR1 domain comprising the amino acid sequence of SEQ ID NO: 88.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 107, a CDR2 domain comprising the amino acid sequence of SEQ ID NO: 106, and a CDR1 domain comprising the amino acid sequence of SEQ ID NO: 105, and a light chain variable region comprising a CDR3 domain comprising the amino acid sequence of SEQ ID NO: 110, a CDR2 domain comprising the amino acid sequence of SEQ ID NO: 109, and a CDR1 domain comprising the amino acid sequence of SEQ ID NO: 108.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 127, a CDR2 domain comprising the amino acid sequence of SEQ ID NO: 126, and a CDR1 domain comprising the amino acid sequence of SEQ ID NO: 125, and a light chain variable region comprising a CDR3 domain comprising the amino acid sequence of SEQ ID NO: 130, a CDR2 domain comprising the amino acid sequence of SEQ ID NO: 129, and a CDR1 domain comprising the amino acid sequence of SEQ ID NO: 128.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 47, a CDR2 domain comprising the amino acid sequence of SEQ ID NO: 46, and a CDR1 domain comprising the amino acid sequence of SEQ ID NO: 45, and a light chain variable region comprising a CDR3 domain comprising the amino acid sequence of SEQ ID NO: 50, a CDR2 domain comprising the amino acid sequence of SEQ ID NO: 49, and a CDR1 domain comprising the amino acid sequence of SEQ ID NO: 48.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 77, a CDR2 domain comprising the amino acid sequence of SEQ ID NO: 76, and a CDR1 domain comprising the amino acid sequence of SEQ ID NO: 75, and a light chain variable region comprising a CDR3 domain comprising the amino acid sequence of SEQ ID NO: 80, a CDR2 domain comprising the amino acid sequence of SEQ ID NO: 79, and a CDR1 domain comprising the amino acid sequence of SEQ ID NO: 78.

In another aspect of the invention, the present disclosure provides an antibody, or antigen binding portion thereof, as described herein, conjugated to at least one drug.

In some embodiments, the at least one drug is selected from the group consisting of an anti-apoptotic agent, a mitotic inhibitor, an anti-tumor antibiotic, an immunomodulating agent, a nucleic acid for gene therapy, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In other embodiments, the at least one drug is conjugated to the antibody, or antigen-binding portion thereof, via a linker. In yet other embodiments, the linker is a cleavable linker. In another embodiment, the linker is a non-cleavable linker.

In some embodiments, the at least one drug is conjugated via a linker. In other embodiments, the linker is a cleavable linker. In yet other embodiments, the linker is a non-cleavable linker.

In some embodiments, the antibody, or antigen binding portion thereof, is an IgG1 isotype.

In another aspect of the invention, the present disclosure provides a pharmaceutical composition comprising an ADC mixture comprising a plurality of the ADC as described herein, and a pharmaceutically acceptable carrier.

In some embodiments, the ADC mixture has an average drug to antibody ratio (DAR) of 0 to 8.

In another aspect of the invention, the present disclosure provides a method for treating cancer, comprising administering a therapeutically effective amount of an antibody or antigen binding portion thereof, as described herein, or a bispecific antibody as described herein, or an ADC as described herein, to a subject in need thereof.

In some embodiments, the cancer is selected from the group consisting of breast cancer, lung cancer, small cell lung cancer, liver cancer, pancreatic cancer, ovarian cancer, kidney cancer, and colon cancer. In one embodiment, the cancer is breast cancer, e.g., triple negative breast cancer. In one embodiment, the cancer is colon cancer. In one embodiment, the cancer is lung cancer, e.g., non-small cell lung cancer (NSCLC).

In another aspect, the present invention provides a method for inhibiting or decreasing solid tumor growth in a subject having a solid tumor. The method includes administering a therapeutically effective amount of an antibody or antigen binding portion thereof, as described herein, or a bispecific antibody as described herein, or an ADC as described herein to the subject having the solid tumor, such that the solid tumor growth is inhibited or decreased.

In some embodiments, the cancer is selected from the group consisting of breast cancer, lung cancer, small cell lung cancer, liver cancer, pancreatic cancer, ovarian cancer, kidney cancer, and colon cancer. In one embodiment, the cancer is breast cancer, e.g., triple negative breast cancer. In one embodiment, the cancer is colon cancer. In one embodiment, the cancer is lung cancer, e.g., non-small cell lung cancer (NSCLC).

In one embodiment, the antibody or antigen binding portion thereof, or a bispecific antibody as described herein, or the ADC is administered in combination with an additional agent or an additional therapy. In one embodiment, the additional agent is an immune checkpoint inhibitor, e.g., an antibody, such as an antibody selected from the group consisting of an anti-PD1 antibody, an anti-PD-L1 antibody and an anti-CTLA-4 antibody. In one embodiment, the additional therapy is radiation. In one embodiment, the additional agent is a chemotherapeutic agent.

In one embodiment, the cancer or tumor is characterized as having CDCP1 expression or overexpression.

In another aspect of the invention, the present disclosure provides a method for treating cancer. The method includes administering a therapeutically effective amount of an antibody or antigen binding portion thereof, as described herein, or a bispecific antibody as described herein, or an ADC as described herein, and an anti-PD-L1 antibody to a subject in need thereof.

In some embodiments, the cancer is selected from the group consisting of breast cancer, lung cancer, small cell lung cancer, liver cancer, pancreatic cancer, ovarian cancer, kidney cancer, and colon cancer. In one embodiment, the cancer is breast cancer, e.g., triple negative breast cancer. In one embodiment, the cancer is colon cancer. In one embodiment, the cancer is lung cancer, e.g., non-small cell lung cancer (NSCLC).

In another aspect, the present invention provides a method for inhibiting or decreasing solid tumor growth in a subject having a solid tumor. The method includes administering a therapeutically effective amount of an antibody or antigen binding portion thereof, as described herein, or a bispecific antibody as described herein, or an ADC as described herein, and an anti-PD-L1 antibody to the subject having the solid tumor, such that the solid tumor growth is inhibited or decreased.

In some embodiments, the cancer is selected from the group consisting of breast cancer, lung cancer, small cell lung cancer, liver cancer, pancreatic cancer, ovarian cancer, kidney cancer, and colon cancer. In one embodiment, the cancer is breast cancer, e.g., triple negative breast cancer. In one embodiment, the cancer is colon cancer. In one embodiment, the cancer is lung cancer, e.g., non-small cell lung cancer (NSCLC).

In one embodiment, the antibody or antigen binding portion thereof or a bispecific antibody as described herein, or the ADC is administered in combination with an additional agent or an additional therapy. In one embodiment, the additional agent is an immune checkpoint inhibitor, e.g., an antibody, such as an antibody that is selected from the group consisting of an anti-PD1 antibody and an anti-CTLA-4 antibody. In one embodiment, the additional therapy is radiation. In one embodiment, the additional agent is a chemotherapeutic agent.

In one embodiment, the cancer or tumor is characterized as having CDCP1 expression or overexpression.

In some embodiments, the present disclosure provides a method for inhibiting or decreasing solid tumor growth in a subject having a solid tumor, said method comprising administering an effective amount of the antibody or antigen binding portion thereof, as described herein, or the ADC, as described herein, to the subject having the solid tumor, such that the solid tumor growth is inhibited or decreased.

In some embodiments, the antibody or antigen binding portion thereof or the ADC is administered in combination with an additional agent or an additional therapy. In other embodiments, the additional agent is an immune checkpoint inhibitor. In yet another embodiment, the immune checkpoint inhibitor is an antibody. In another embodiment, the antibody is selected from the group consisting of an anti-PD1 antibody, an anti-PD-L1 antibody or an anti-CTLA-4 antibody. In other embodiments, the additional therapy is radiation. In yet another embodiment, the additional agent is a chemotherapeutic agent. In some embodiments, the cancer or tumor is characterized as having CDCP1 expression or overexpression.

In another aspect, the disclosure relates to a polynucleotide linked to a heterologous nucleic acid, wherein the polynucleotide is selected from the group consisting of (a) a polynucleotide encoding an immunoglobulin heavy chain or a fragment thereof comprising a heavy chain variable region (VH) comprising complementarity determining regions (CDRs) 1, 2, and 3 with the amino acid sequences set forth in FIG. 20, and wherein the VH when paired with the corresponding light chain variable region (VL) as shown in FIG. 15 binds to CDCP1 protein; (b) a polynucleotide encoding an immunoglobulin light chain or a fragment thereof comprising a VL comprising CDRs 1, 2, and 3 with the amino acid sequences set forth in FIG. 20, and wherein the VL when paired with the corresponding VH as shown in FIG. 15 binds to CDCP1; (c) a polynucleotide encoding (i) an immunoglobulin heavy chain or a fragment thereof comprising a VH comprising CDRs 1, 2, and 3 with the amino acid sequences set forth in FIG. 20; and (ii) an immunoglobulin light chain or a fragment thereof comprising a VL comprising CDRs 1, 2, and 3 with the amino acid sequences set forth in FIG. 20; and (d) a polynucleotide encoding an immunoglobulin heavy chain or a fragment thereof comprising a VH comprising the amino acid sequence set forth in FIG. 18, wherein the VH when paired with the corresponding VL as shown in FIG. 15 binds to CDCP1.

In one aspect, the disclosure features an expression vector comprising a heterologous promoter operably linked to a polynucleotide encoding a polypeptide disclosed herein.

In another aspect, the disclosure provides an expression vector comprising: a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in FIG. 20; and a second polynucleotide encoding a second polypeptide comprising an immunoglobulin light chain or a fragment thereof comprising a light chain variable region (VL) comprising VL CDRs 1, 2, and 3 with the amino acid sequences set forth in FIG. 20, wherein the immunoglobulin heavy chain or fragment thereof when paired with the immunoglobulin light chain or fragment thereof forms an anti-CDCP1 antibody or CDCP1-binding fragment thereof, and wherein the expression vector is, for example, a plasmid, phage, or virus.

In some embodiments, the complementarity determining region (CDR) sequences in the heavy chain variable region and the light chain variable region comprise or consist of the CDR sequences as set forth in FIG. 20. In some embodiments, the CDR sequences in the heavy chain variable region and the light chain variable region are at least 80%, 90%, 92%, 95%, 97%, 98%, 99%, or 100% identical to the CDR sequences as set forth in FIG. 20. In some embodiments, the CDR sequences in the heavy chain variable region and the light chain variable region differ from the CDR sequences in FIG. 20 by one, two, three, four, or five amino acids. In some embodiments, the CDRs in FIG. 20 are substituted by one, two, three, four, or five conservative amino acids.

In another aspect, the present disclosure features compositions that include at least one antibody disclosed herein conjugated to a therapeutic agent, e.g., a cytotoxic drug or radioisotope, and/or to a reporter group. In some embodiments, an antibody that is conjugated to a therapeutic agent is administered to a subject to induce cell death of a cancer cell, e.g., a cancer cell that expresses or overexpresses CDCP1 protein, or has CDCP1 protein on the cell surface.

In some embodiments, the antibodies are conjugated to a detectable marker. The conjugates are administered to a subject to detect a cancer cell that expresses CDCP1 protein and/or has a detectable and/or elevated level of a CDCP1 protein.

In some embodiments, an antibody is linked (e.g., covalently bonded, hydrogen bonded, or ionically bonded) to a surface (e.g., a microfluidic device, a chromatography resin, an array, polymer, or a bead).

In a further aspect, the disclosure features compositions that include at least one of the antibodies disclosed herein and a pharmaceutically acceptable excipient. In some embodiments, the disclosure features dry (e.g., lyophilized) compositions that include one or more antibodies disclosed herein and, optionally, one or more pharmaceutically acceptable excipients.

In another aspect, the disclosure features polynucleotides, e.g., DNA, that encode a polypeptide chain, e.g., an antibody heavy or light chain, of any of the antibodies disclosed herein. For example, the poly nucleotide may include a sequence disclosed herein. In some embodiments, the polynucleotides, e.g., DNA, do not include introns. The disclosure also features vectors, e.g., recombinant vectors and expression vectors that include the above polynucleotides, and a cell, e.g., an isolated cell, e.g., recombinant cells or hybridomas, that include the above polynucleotides and/or vectors. In some embodiments, the vector is stably integrated into a chromosome of the cell, e.g., a mammalian cell, bacterial cell, or yeast cell. In some embodiments, the disclosure features methods of producing antibodies that include culturing the cells, e.g., isolated cells, under conditions where the antibodies are expressed, and methods of collecting the antibodies.

The disclosure features the antibodies, nucleic acids, compositions, and cells disclosed herein and the use thereof for treatment, prophylaxis, imaging, and/or diagnosis of a cancer. In some embodiments, the composition is formulated for intravenous administration. In some embodiments, the cancer expresses (e.g., overexpresses) CDCP1 or has CDCP1 on the cell surface. In some embodiments, the cancer is characterized by the presence of a CDCP1 and/or an elevated level of a CDCP1 protein (e.g., as compared to a reference level, e.g., a level of a CDCP1 protein in a CDCP1 protein produced by a healthy subject) produced by the cancer cells. In a further aspect, the disclosure features methods for treatment of a cancer (e.g., a cancer characterized by overexpression of CDCP1 in cancer cells, or a cancer characterized by having CDCP1 on the surface of the cancer cells) (e.g., breast cancer, triple-negative breast cancer, carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, gastric cancer, testicular cancer, thyroid cancer, bladder cancer, urethral cancer, colorectal cancer, or hematologic malignancy), that include administering an antibody, nucleic acid, composition, or cell disclosed herein to a subject with a cancer in a therapeutically effective amount.

In another aspect, the disclosure features methods that include administering an antibody or composition, e.g., a cell composition, antibody-drug conjugate, or antibody-radioisotope conjugate disclosed herein to a subject in need thereof, e.g., a subject having, or identified or diagnosed as having a cancer characterized by overexpression of CDCP1 in cancer cells, or a cancer characterized by having CDCP1 on the surface of the cancer cells, e.g., breast cancer, triple-negative breast cancer, carcinoid cancer, cervical cancer, endometrial cancer, glioma, head and neck cancer, liver cancer, lung cancer, small cell lung cancer, non-small cell lung cancer, lymphoma, melanoma, ovarian cancer, pancreatic cancer, prostate cancer, renal cancer, gastric cancer, testicular cancer, thyroid cancer, bladder cancer, urethral cancer, colorectal cancer, colon cancer, or hematologic malignancy cells.

In some embodiments, the subject is identified as being a subject who expresses CDCP1, e.g., using any of the methods described herein, or has an elevated level of a CDCP1 protein, e.g., as compared to a reference level, e.g., a level of a CDCP1 protein in a CDCP1 protein produced by a healthy subject, a level of a CDCP1 protein in CDCP1 protein produced by a non-cancerous, e.g., primary cell, or a threshold level of a CDCP1 protein, in which a determined level of a CDCP1 protein that is above this value indicates that the subject should be administered an antibody described herein.

In yet another aspect, the disclosure features methods for cancer prophylaxis (or reducing a subject's risk of developing a cancer characterized by expression, e.g., overexpression, of CDCP1 protein in cancer cells or a cancer characterized by having CDCP1 on the surface of the cancer cells, e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, gastric cancer, testicular cancer, thyroid cancer, bladder cancer, urethral cancer, colorectal cancer, or hematologic malignancy cells (e.g., as compared to a subject at risk for developing cancer but receiving no treatment or receiving a different treatment). The methods include administering an antibody, nucleic acid, composition, or cell disclosed herein to a subject in need thereof in a prophylactically effective amount. In some embodiments, the cancer expresses CDCP1 protein. In some embodiments, the cancer cells have CDCP1 on the cell surface. In some embodiments of any of these methods, the subject is identified as having an elevated risk of developing cancer.

In another aspect, the disclosure features methods of detecting a CDCP1 protein (e.g., a CDCP1 protein) in a sample (e.g., a biopsy sample). The methods include contacting a sample with an antibody disclosed herein and detecting binding of the agent to the sample, thereby detecting CDCP1 protein in the sample. Some embodiments further include recording the detection or non-detection of CDCP1 protein in the clinical records of a subject from whom the sample was obtained. In some embodiments, the clinical record is stored on a tangible computer readable medium, e.g., a disc, magnetic tape, or computer memory.

In some embodiments of any of the methods described herein, the antibodies described herein are contacted with a sample and/or a cell, and the antibody to CDCP1 can be used in an immunoassay (e.g., an enzyme-linked immunosorbent assay), fluorescence-assisted cell sorting, microfluidics, and chromatography.

In one aspect, the present invention provides an antibody or antigen-binding fragment thereof that binds to CUB domain-containing protein 1 (CDCP1). The antibody or antigen-binding fragment thereof comprises a heavy chain variable region (VH) comprising complementarity determining regions (CDRs) 1, 2, 3, wherein the CDR1 region comprises an amino acid sequence that is at least 80% identical to a selected VH CDR1 amino acid sequence, the CDR2 region comprises an amino acid sequence that is at least 80% identical to a selected VH CDR2 amino acid sequence, and the CDR3 region comprises an amino acid sequence that is at least 80% identical to a selected VH CDR3 amino acid sequence, and a light chain variable region (VL) comprising CDRs 1, 2, 3, wherein the CDR1 region comprises an amino acid sequence that is at least 80% identical to a selected VL CDR1 amino acid sequence, the CDR2 region comprises an amino acid sequence that is at least 80% identical to a selected VL CDR2 amino acid sequence, and the CDR3 region comprises an amino acid sequence that is at least 80% identical to a selected VL CDR3 amino acid sequence, wherein the selected VH CDRs 1, 2, 3 amino acid sequences and the selected VL CDRs, 1, 2, 3 amino acid sequences are one of the following: (1) the selected VH CDRs 1, 2, 3 amino acid sequences are set forth in SEQ ID NOs: 5, 6, 7, respectively, and the selected VL CDRs 1, 2, 3 amino acid sequences are set forth in SEQ ID NOs: 8, 9, 10, respectively; (2) the selected VH CDRs 1, 2, 3 amino acid sequences are set forth in SEQ ID NOs: 15, 16, 17, respectively, and the selected VL CDRs 1, 2, 3 amino acid sequences are set forth in SEQ ID NOs: 18, 19, 20, respectively; (3) the selected VH CDRs 1, 2, 3 amino acid sequences are set forth in SEQ ID NOs: 25, 26, 27, respectively, and the selected VL CDRs 1, 2, 3 amino acid sequences are set forth in SEQ ID NOs: 28, 29, 30, respectively; (4) the selected VH CDRs 1, 2, 3 amino acid sequences are set forth in SEQ ID NOs: 35, 36, 37, respectively, and the selected VL CDRs 1, 2, 3 amino acid sequences are set forth in SEQ ID NOs: 38, 39, 40, respectively; (5) the selected VH CDRs 1, 2, 3 amino acid sequences are set forth in SEQ ID NOs: 45, 46, 47, respectively, and the selected VL CDRs 1, 2, 3 amino acid sequences are set forth in SEQ ID NOs: 48, 49, 50, respectively; (6) the selected VH CDRs 1, 2, 3 amino acid sequences are set forth in SEQ ID NOs: 55, 56, 57, respectively, and the selected VL CDRs 1, 2, 3 amino acid sequences are set forth in SEQ ID NOs: 58, 59, 60, respectively; (7) the selected VH CDRs 1, 2, 3 amino acid sequences are set forth in SEQ ID NOs: 65, 66, 67, respectively, and the selected VL CDRs 1, 2, 3 amino acid sequences are set forth in SEQ ID NOs: 68, 69, 70, respectively; (8) the selected VH CDRs 1, 2, 3 amino acid sequences are set forth in SEQ ID NOs: 75, 76, 77, respectively, and the selected VL CDRs 1, 2, 3 amino acid sequences are set forth in SEQ ID NOs: 78, 79, 80, respectively; (9) the selected VH CDRs 1, 2, 3 amino acid sequences are set forth in SEQ ID NOs: 85, 86, 87, respectively, and the selected VL CDRs 1, 2, 3 amino acid sequences are set forth in SEQ ID NOs: 88, 89, 90, respectively; (10) the selected VH CDRs 1, 2, 3 amino acid sequences are set forth in SEQ ID NOs: 95, 96, 97, respectively, and the selected VL CDRs 1, 2, 3 amino acid sequences are set forth in SEQ ID NOs: 98, 99, 100, respectively; (11) the selected VH CDRs 1, 2, 3 amino acid sequences are set forth in SEQ ID NOs: 105, 106, 107, respectively, and the selected VL CDRs 1, 2, 3 amino acid sequences are set forth in SEQ ID NOs: 108, 109, 110, respectively; (12) the selected VH CDRs 1, 2, 3 amino acid sequences are set forth in SEQ ID NOs: 115, 116, 117, respectively, and the selected VL CDRs 1, 2, 3 amino acid sequences are set forth in SEQ ID NOs: 118, 119, 120, respectively; (13) the selected VH CDRs 1, 2, 3 amino acid sequences are set forth in SEQ ID NOs: 125, 126, 127, respectively, and the selected VL CDRs 1, 2, 3 amino acid sequences are set forth in SEQ ID NOs: 128, 129, 130, respectively; (14) the selected VH CDRs 1, 2, 3 amino acid sequences are set forth in SEQ ID NOs: 135, 136, 137, respectively, and the selected VL CDRs 1, 2, 3 amino acid sequences are set forth in SEQ ID NOs: 138, 139, 140, respectively; (15) the selected VH CDRs 1, 2, 3 amino acid sequences are set forth in SEQ ID NOs: 145, 146, 147, respectively, and the selected VL CDRs 1, 2, 3 amino acid sequences are set forth in SEQ ID NOs: 148, 149, 150, respectively; (16) the selected VH CDRs 1, 2, 3 amino acid sequences are set forth in SEQ ID NOs: 155, 156, 157, respectively, and the selected VL CDRs 1, 2, 3 amino acid sequences are set forth in SEQ ID NOs: 158, 159, 160, respectively; (17) the selected VH CDRs 1, 2, 3 amino acid sequences are set forth in SEQ ID NOs: 165, 166, 167, respectively, and the selected VL CDRs 1, 2, 3 amino acid sequences are set forth in SEQ ID NOs: 168, 169, 170, respectively; (18) the selected VH CDRs 1, 2, 3 amino acid sequences are set forth in SEQ ID NOs: 175, 176, 177, respectively, and the selected VL CDRs 1, 2, 3 amino acid sequences are set forth in SEQ ID NOs: 178, 179, 180, respectively; (19) the selected VH CDRs 1, 2, 3 amino acid sequences are set forth in SEQ ID NOs: 185, 186, 187, respectively, and the selected VL CDRs 1, 2, 3 amino acid sequences are set forth in SEQ ID NOs: 188, 189, 190, respectively; (20) the selected VH CDRs 1, 2, 3 amino acid sequences are set forth in SEQ ID NOs: 195, 1%, 197, respectively, and the selected VL CDRs 1, 2, 3 amino acid sequences are set forth in SEQ ID NOs: 198, 199, 200, respectively; (21) the selected VH CDRs 1, 2, 3 amino acid sequences are set forth in SEQ ID NOs: 205, 206, 207, respectively, and the selected VL CDRs 1, 2, 3 amino acid sequences are set forth in SEQ ID NOs: 208, 209, 210, respectively; (22) the selected VH CDRs 1, 2, 3 amino acid sequences are set forth in SEQ ID NOs: 215, 216, 217, respectively, and the selected VL CDRs 1, 2, 3 amino acid sequences are set forth in SEQ ID NOs: 218, 219, 220, respectively; (23) the selected VH CDRs 1, 2, 3 amino acid sequences are set forth in SEQ ID NOs: 225, 226, 227, respectively, and the selected VL CDRs 1, 2, 3 amino acid sequences are set forth in SEQ ID NOs: 228, 229, 230, respectively; (24) the selected VH CDRs 1, 2, 3 amino acid sequences are set forth in SEQ ID NOs: 235, 236, 237, respectively, and the selected VL CDRs 1, 2, 3 amino acid sequences are set forth in SEQ ID NOs: 238, 239, 240, respectively; (25) the selected VH CDRs 1, 2, 3 amino acid sequences are set forth in SEQ ID NOs: 245, 246, 247, respectively, and the selected VL CDRs 1, 2, 3 amino acid sequences are set forth in SEQ ID NOs: 248, 249, 250, respectively; (26) the selected VH CDRs 1, 2, 3 amino acid sequences are set forth in SEQ ID NOs: 255, 256, 257, respectively, and the selected VL CDRs 1, 2, 3 amino acid sequences are set forth in SEQ ID NOs: 258, 259, 260, respectively; (27) the selected VH CDRs 1, 2, 3 amino acid sequences are set forth in SEQ ID NOs: 265, 266, 267, respectively, and the selected VL CDRs 1, 2, 3 amino acid sequences are set forth in SEQ ID NOs: 268, 269, 270, respectively; (28) the selected VH CDRs 1, 2, 3 amino acid sequences are set forth in SEQ ID NOs: 275, 276, 277, respectively, and the selected VL CDRs 1, 2, 3 amino acid sequences are set forth in SEQ ID NOs: 278, 279, 280, respectively; (29) the selected VH CDRs 1, 2, 3 amino acid sequences are set forth in SEQ ID NOs: 285, 286, 287, respectively, and the selected VL CDRs 1, 2, 3 amino acid sequences are set forth in SEQ ID NOs: 288, 289, 290, respectively; (30) the selected VH CDRs 1, 2, 3 amino acid sequences are set forth in SEQ ID NOs: 295, 296, 297, respectively, and the selected VL CDRs 1, 2, 3 amino acid sequences are set forth in SEQ ID NOs: 298, 299, 300, respectively; (31) the selected VH CDRs 1, 2, 3 amino acid sequences are set forth in SEQ ID NOs: 305, 306, 307, respectively, and the selected VL CDRs 1, 2, 3 amino acid sequences are set forth in SEQ ID NOs: 308, 309.310, respectively; (32) the selected VH CDRs 1, 2, 3 amino acid sequences are set forth in SEQ ID NOs: 315, 316, 317, respectively, and the selected VL CDRs 1, 2, 3 amino acid sequences are set forth in SEQ ID NOs: 318, 319, 320, respectively; (33) the selected VH CDRs 1, 2, 3 amino acid sequences are set forth in SEQ ID NOs: 325, 326, 327, respectively, and the selected VL CDRs 1, 2, 3 amino acid sequences are set forth in SEQ ID NOs: 328, 329, 330, respectively; (34) the selected VH CDRs 1, 2, 3 amino acid sequences are set forth in SEQ ID NOs: 335, 336, 337, respectively, and the selected VL CDRs 1, 2, 3 amino acid sequences are set forth in SEQ ID NOs: 338, 339, 340, respectively; (35) the selected VH CDRs 1, 2, 3 amino acid sequences are set forth in SEQ ID NOs: 345, 346, 347, respectively, and the selected VL CDRs 1, 2, 3 amino acid sequences are set forth in SEQ ID NOs: 348, 349, 350, respectively; (36) the selected VH CDRs 1, 2, 3 amino acid sequences are set forth in SEQ ID NOs: 355, 356, 357, respectively, and the selected VL CDRs 1, 2, 3 amino acid sequences are set forth in SEQ ID NOs: 358, 359, 360, respectively; (37) the selected VH CDRs 1, 2, 3 amino acid sequences are set forth in SEQ ID NOs: 365, 366, 367, respectively, and the selected VL CDRs 1, 2, 3 amino acid sequences are set forth in SEQ ID NOs: 368, 369, 370, respectively; (38) the selected VH CDRs 1, 2, 3 amino acid sequences are set forth in SEQ ID NOs: 375, 376, 377, respectively, and the selected VL CDRs 1, 2, 3 amino acid sequences are set forth in SEQ ID NOs: 378, 379, 380, respectively; (39) the selected VH CDRs 1, 2, 3 amino acid sequences are set forth in SEQ ID NOs: 385, 386, 387, respectively, and the selected VL CDRs 1, 2, 3 amino acid sequences are set forth in SEQ ID NOs: 388, 389, 390, respectively; and (40) the selected VH CDRs 1, 2, 3 amino acid sequences are set forth in SEQ ID NOs: 395, 396, 397, respectively, and the selected VL CDRs 1, 2, 3 amino acid sequences are set forth in SEQ ID NOs: 398, 399, 400, respectively, wherein the antibody or antigen-binding fragment thereof specifically binds to CUB domain-containing protein 1 (CDCP1).

In one embodiment, the antibody or antigen-binding fragment thereof specifically binds to human CDCP1 and/or Cynomolgus CDCP1. In one embodiment, the antibody or antigen-binding fragment thereof has a dissociation constant ($K_d$) for human CDCP1 that is less than 10 nM, and/or a $K_d$ for Cynomolgus CDCP1 that is less than 10 nM. In one embodiment, the antibody or antigen-binding fragment thereof is a humanized antibody or antigen-binding fragment thereof.

In one embodiment, the VH of the antibody or antigen-binding fragment thereof comprises CDRs 1, 2, 3 with the amino acid sequences set forth in SEQ ID NOs: 5, 6, and 7 respectively, and the VL comprises CDRs 1, 2, 3 with the amino acid sequences set forth in SEQ ID NOs: 8, 9, and 10, respectively.

In one embodiment, the VH of the antibody or antigen-binding fragment thereof comprises CDRs 1, 2, 3 with the amino acid sequences set forth in SEQ ID NOs: 15, 16, and 17 respectively, and the VL comprises CDRs 1, 2, 3 with the amino acid sequences set forth in SEQ ID NOs: 18, 19, and 20, respectively.

In one embodiment, the VH of the antibody or antigen-binding fragment thereof comprises CDRs 1, 2, 3 with the amino acid sequences set forth in SEQ ID NOs: 25, 26, and 27 respectively, and the VL comprises CDRs 1, 2, 3 with the amino acid sequences set forth in SEQ ID NOs: 28, 29, and 30, respectively.

In one embodiment, the VH of the antibody or antigen-binding fragment thereof comprises CDRs 1, 2, 3 with the amino acid sequences set forth in SEQ ID NOs: 35, 36, and 37 respectively, and the VL comprises CDRs 1, 2, 3 with the amino acid sequences set forth in SEQ ID NOs: 38, 39, and 40, respectively.

In one embodiment, the VH of the antibody or antigen-binding fragment thereof comprises CDRs 1, 2, 3 with the amino acid sequences set forth in SEQ ID NOs: 45, 46, and 47 respectively, and the VL comprises CDRs 1, 2, 3 with the amino acid sequences set forth in SEQ ID NOs: 48, 49, and 50, respectively.

In one embodiment, the VH of the antibody or antigen-binding fragment thereof comprises CDRs 1, 2, 3 with the amino acid sequences set forth in SEQ ID NOs: 55, 56, and 57 respectively, and the VL comprises CDRs 1, 2, 3 with the amino acid sequences set forth in SEQ ID NOs: 58, 59, and 60, respectively.

In one embodiment, the VH of the antibody or antigen-binding fragment thereof comprises CDRs 1, 2, 3 with the amino acid sequences set forth in SEQ ID NOs: 65, 66, and 67 respectively, and the VL comprises CDRs 1, 2, 3 with the amino acid sequences set forth in SEQ ID NOs: 68, 69, and 70, respectively.

In one embodiment, the VH of the antibody or antigen-binding fragment thereof comprises CDRs 1, 2, 3 with the amino acid sequences set forth in SEQ ID NOs: 75, 76, and 77 respectively, and the VL comprises CDRs 1, 2, 3 with the amino acid sequences set forth in SEQ ID NOs: 78, 79, and 80, respectively.

In one embodiment, the VH of the antibody or antigen-binding fragment thereof comprises CDRs 1, 2, 3 with the amino acid sequences set forth in SEQ ID NOs: 85, 86, and 87 respectively, and the VL comprises CDRs 1, 2, 3 with the amino acid sequences set forth in SEQ ID NOs: 88, 89, and 90, respectively.

In one embodiment, the VH of the antibody or antigen-binding fragment thereof comprises CDRs 1, 2, 3 with the amino acid sequences set forth in SEQ ID NOs: 95, 96, and 97 respectively, and the VL comprises CDRs 1, 2, 3 with the amino acid sequences set forth in SEQ ID NOs: 98, 99, and 100, respectively.

In one embodiment, the VH of the antibody or antigen-binding fragment thereof comprises CDRs 1, 2, 3 with the amino acid sequences set forth in SEQ ID NOs: 105, 106, and 107 respectively, and the VL comprises CDRs 1, 2, 3 with the amino acid sequences set forth in SEQ ID NOs: 108, 109, and 110, respectively.

In one embodiment, the VH of the antibody or antigen-binding fragment thereof comprises CDRs 1, 2, 3 with the amino acid sequences set forth in SEQ ID NOs: 115, 116, and 117 respectively, and the VL comprises CDRs 1, 2, 3 with the amino acid sequences set forth in SEQ ID NOs: 118, 119, and 120, respectively.

In one embodiment, the VH of the antibody or antigen-binding fragment thereof comprises CDRs 1, 2, 3 with the amino acid sequences set forth in SEQ ID NOs: 125, 126, and 127 respectively, and the VL comprises CDRs 1, 2, 3 with the amino acid sequences set forth in SEQ ID NOs: 128, 129, and 130, respectively.

In one embodiment, the VH of the antibody or antigen-binding fragment thereof comprises CDRs 1, 2, 3 with the amino acid sequences set forth in SEQ ID NOs: 135, 136, and 137 respectively, and the VL comprises CDRs 1, 2, 3 with the amino acid sequences set forth in SEQ ID NOs: 138, 139, and 140, respectively.

In one embodiment, the VH of the antibody or antigen-binding fragment thereof comprises CDRs 1, 2, 3 with the amino acid sequences set forth in SEQ ID NOs: 145, 146, and 147 respectively, and the VL comprises CDRs 1, 2, 3 with the amino acid sequences set forth in SEQ ID NOs: 148, 149, and 150, respectively.

In one embodiment, the VH of the antibody or antigen-binding fragment thereof comprises CDRs 1, 2, 3 with the amino acid sequences set forth in SEQ ID NOs: 155, 156, and 157 respectively, and the VL comprises CDRs 1, 2, 3 with the amino acid sequences set forth in SEQ ID NOs: 158, 159, and 160, respectively.

In one embodiment, the VH of the antibody or antigen-binding fragment thereof comprises CDRs 1, 2, 3 with the amino acid sequences set forth in SEQ ID NOs: 165, 166, and 167 respectively, and the VL comprises CDRs 1, 2, 3 with the amino acid sequences set forth in SEQ ID NOs: 168, 169, and 170, respectively.

In one embodiment, the VH of the antibody or antigen-binding fragment thereof comprises CDRs 1, 2, 3 with the amino acid sequences set forth in SEQ ID NOs: 175, 176, and 177 respectively, and the VL comprises CDRs 1, 2, 3 with the amino acid sequences set forth in SEQ ID NOs: 178, 179, and 180, respectively.

In one embodiment, the VH of the antibody or antigen-binding fragment thereof comprises CDRs 1, 2, 3 with the amino acid sequences set forth in SEQ ID NOs: 185, 186, and 187 respectively, and the VL comprises CDRs 1, 2, 3 with the amino acid sequences set forth in SEQ ID NOs: 188, 189, and 190, respectively.

In one embodiment, the VH of the antibody or antigen-binding fragment thereof comprises CDRs 1, 2, 3 with the amino acid sequences set forth in SEQ ID NOs: 195, 196, and 197 respectively, and the VL comprises CDRs 1, 2, 3 with the amino acid sequences set forth in SEQ ID NOs: 198, 199, and 200, respectively.

In one embodiment, the VH of the antibody or antigen-binding fragment thereof comprises CDRs 1, 2, 3 with the amino acid sequences set forth in SEQ ID NOs: 205, 206, and 207 respectively, and the VL comprises CDRs 1, 2, 3 with the amino acid sequences set forth in SEQ ID NOs: 208, 209, and 210, respectively.

In one embodiment, the VH of the antibody or antigen-binding fragment thereof comprises CDRs 1, 2, 3 with the amino acid sequences set forth in SEQ ID NOs: 215, 216, and 217 respectively, and the VL comprises CDRs 1, 2, 3 with the amino acid sequences set forth in SEQ ID NOs: 218, 219, and 220, respectively.

In one embodiment, the VH of the antibody or antigen-binding fragment thereof comprises CDRs 1, 2, 3 with the amino acid sequences set forth in SEQ ID NOs: 225, 226, and 227 respectively, and the VL comprises CDRs 1, 2, 3 with the amino acid sequences set forth in SEQ ID NOs: 228, 229, and 230, respectively.

In one embodiment, the VH of the antibody or antigen-binding fragment thereof comprises CDRs 1, 2, 3 with the amino acid sequences set forth in SEQ ID NOs: 235, 236, and 237 respectively, and the VL comprises CDRs 1, 2, 3 with the amino acid sequences set forth in SEQ ID NOs: 238, 239, and 240, respectively.

In one embodiment, the VH of the antibody or antigen-binding fragment thereof comprises CDRs 1, 2, 3 with the amino acid sequences set forth in SEQ ID NOs: 245, 246, and 247 respectively, and the VL comprises CDRs 1, 2, 3 with the amino acid sequences set forth in SEQ ID NOs: 248, 249, and 250, respectively.

In one embodiment, the VH of the antibody or antigen-binding fragment thereof comprises CDRs 1, 2, 3 with the amino acid sequences set forth in SEQ ID NOs: 255, 256, and 257 respectively, and the VL comprises CDRs 1, 2, 3 with the amino acid sequences set forth in SEQ ID NOs: 258, 259, and 260, respectively.

In one embodiment, the VH of the antibody or antigen-binding fragment thereof comprises CDRs 1, 2, 3 with the amino acid sequences set forth in SEQ ID NOs: 265, 266, and 267 respectively, and the VL comprises CDRs 1, 2, 3 with the amino acid sequences set forth in SEQ ID NOs: 268, 269, and 270, respectively.

In one embodiment, the VH of the antibody or antigen-binding fragment thereof comprises CDRs 1, 2, 3 with the amino acid sequences set forth in SEQ ID NOs: 275, 276, and 277 respectively, and the VL comprises CDRs 1, 2, 3 with the amino acid sequences set forth in SEQ ID NOs: 278, 279, and 280, respectively.

In one embodiment, the VH of the antibody or antigen-binding fragment thereof comprises CDRs 1, 2, 3 with the amino acid sequences set forth in SEQ ID NOs: 285, 286, and 287 respectively, and the VL comprises CDRs 1, 2, 3 with the amino acid sequences set forth in SEQ ID NOs: 288, 289, and 290, respectively.

In one embodiment, the VH of the antibody or antigen-binding fragment thereof comprises CDRs 1, 2, 3 with the amino acid sequences set forth in SEQ ID NOs: 295, 2%, and 297 respectively, and the VL comprises CDRs 1, 2, 3 with the amino acid sequences set forth in SEQ ID NOs: 298, 299, and 300, respectively.

In one embodiment, the VH of the antibody or antigen-binding fragment thereof comprises CDRs 1, 2, 3 with the amino acid sequences set forth in SEQ ID NOs: 305, 306, and 307 respectively, and the VL comprises CDRs 1, 2, 3 with the amino acid sequences set forth in SEQ ID NOs: 308, 309, and 310, respectively.

In one embodiment, the VH of the antibody or antigen-binding fragment thereof comprises CDRs 1, 2, 3 with the amino acid sequences set forth in SEQ ID NOs: 315, 316, and 317 respectively, and the VL comprises CDRs 1, 2, 3 with the amino acid sequences set forth in SEQ ID NOs: 318, 319, and 320, respectively.

In one embodiment, the VH of the antibody or antigen-binding fragment thereof comprises CDRs 1, 2, 3 with the amino acid sequences set forth in SEQ ID NOs: 325, 326, and 327 respectively, and the VL comprises CDRs 1, 2, 3 with the amino acid sequences set forth in SEQ ID NOs: 328, 329, and 330, respectively.

In one embodiment, the VH of the antibody or antigen-binding fragment thereof comprises CDRs 1, 2, 3 with the amino acid sequences set forth in SEQ ID NOs: 335, 336, and 337 respectively, and the VL comprises CDRs 1, 2, 3 with the amino acid sequences set forth in SEQ ID NOs: 338, 339, and 340, respectively.

In one embodiment, the VH of the antibody or antigen-binding fragment thereof comprises CDRs 1, 2, 3 with the amino acid sequences set forth in SEQ ID NOs: 345, 346, and 347 respectively, and the VL comprises CDRs 1, 2, 3 with the amino acid sequences set forth in SEQ ID NOs: 348, 349, and 350, respectively.

In one embodiment, the VH of the antibody or antigen-binding fragment thereof comprises CDRs 1, 2, 3 with the amino acid sequences set forth in SEQ ID NOs: 355, 356, and 357 respectively, and the VL comprises CDRs 1, 2, 3 with the amino acid sequences set forth in SEQ ID NOs: 358, 359, and 360, respectively.

In one embodiment, the VH of the antibody or antigen-binding fragment thereof comprises CDRs 1, 2, 3 with the amino acid sequences set forth in SEQ ID NOs: 365, 366, and 367 respectively, and the VL comprises CDRs 1, 2, 3 with the amino acid sequences set forth in SEQ ID NOs: 368, 369, and 370, respectively.

In one embodiment, the VH of the antibody or antigen-binding fragment thereof comprises CDRs 1, 2, 3 with the amino acid sequences set forth in SEQ ID NOs: 375, 376, and 377 respectively, and the VL comprises CDRs 1, 2, 3 with the amino acid sequences set forth in SEQ ID NOs: 378, 379, and 380, respectively.

In one embodiment, the VH of the antibody or antigen-binding fragment thereof comprises CDRs 1, 2, 3 with the amino acid sequences set forth in SEQ ID NOs: 385, 386, and 387 respectively, and the VL comprises CDRs 1, 2, 3 with the amino acid sequences set forth in SEQ ID NOs: 388, 389, and 390, respectively.

In one embodiment, the VH of the antibody or antigen-binding fragment thereof comprises CDRs 1, 2, 3 with the amino acid sequences set forth in SEQ ID NOs: 395, 396, and 397 respectively, and the VL comprises CDRs 1, 2, 3 with the amino acid sequences set forth in SEQ ID NOs: 398, 399, and 400, respectively.

In another aspect, the present invention provides a cDNA comprising a polynucleotide encoding a polypeptide comprises (1) an immunoglobulin heavy chain or a fragment thereof comprising a heavy chain variable region (VH) comprising complementarity determining regions (CDRs) 1, 2, and 3 with the amino acid sequences set forth in SEQ ID NOs: 5, 6, and 7, respectively, and wherein the VH when paired with a light chain variable region (VL) comprising the amino acid sequence set forth in SEQ ID NO: 2 binds to CDCP1; (2) an immunoglobulin light chain or a fragment thereof comprising a VL comprising CDRs 1, 2, and 3 with the amino acid sequences set forth in SEQ ID NOs: 8, 9, and 10, respectively, and wherein the VL when paired with a VH comprising the amino acid sequence set forth in SEQ ID NO:1 binds to CDCP1; (3) an immunoglobulin heavy chain or a fragment thereof comprising a VH comprising CDRs 1, 2, and 3 with the amino acid sequences set forth in SEQ ID NOs: 15, 16, and 17, respectively, and wherein the VH when paired with a VL comprising the amino acid sequence set forth in SEQ ID NO: 12 binds to CDCP1; (4) an immunoglobulin light chain or a fragment thereof comprising a VL comprising CDRs 1, 2, and 3 with the amino acid sequences set forth in SEQ ID NOs: 18, 19, and 20, respectively, and wherein the VL when paired with a VH comprising the amino acid sequence set forth in SEQ ID NO: 11 binds to CDCP1; (5) an immunoglobulin heavy chain or a fragment thereof comprising a VH comprising CDRs 1, 2, and 3 with the amino acid sequences set forth in SEQ ID NOs: 25, 26, and 27, respectively, and wherein the VH when paired with a VL comprising the amino acid sequence set forth in SEQ ID NO: 22 binds to CDCP1; (6) an immunoglobulin light chain or a fragment thereof comprising a VL comprising CDRs 1, 2, and 3 with the amino acid sequences set forth in SEQ ID NOs: 28, 29, and 30, respectively, and wherein the VL when paired with a VH comprising the amino acid sequence set forth in SEQ ID NO: 21 binds to CDCP1; (7) an immunoglobulin heavy chain or a fragment thereof comprising a VH comprising CDRs 1, 2, and 3 with the amino acid sequences set forth in SEQ ID NOs: 35, 36, and 37, respectively, and wherein the VH when paired with a VL comprising the amino acid sequence set forth in SEQ ID NO: 32 binds to CDCP1; (8) an immunoglobulin light chain or a fragment thereof comprising a VL comprising CDRs 1, 2, and 3 with the amino acid sequences set forth in SEQ ID NOs: 38, 39, and 40, respectively, and wherein the VL when paired with a VH comprising the amino acid sequence set forth in SEQ ID NO: 31 binds to CDCP1; (9) an immunoglobulin heavy chain or a fragment thereof comprising a VH comprising CDRs 1, 2, and 3 with the amino acid sequences set forth in SEQ ID NOs: 45, 46, and 47, respectively, and wherein the VH when paired with a VL comprising the amino acid sequence set forth in SEQ ID NO: 42 binds to CDCP1; (10) an immunoglobulin light chain or a fragment thereof comprising a VL comprising CDRs 1, 2, and 3 with the amino acid sequences set forth in SEQ ID NOs: 48, 49, and 50, respectively, and wherein the VL when paired with a VH comprising the amino acid sequence set forth in SEQ ID NO: 41 binds to CDCP1; (11) an immunoglobulin heavy chain or a fragment thereof comprising a VH comprising CDRs 1, 2, and 3 with the amino acid sequences set forth in SEQ ID NOs: 55, 56, and 57, respectively, and wherein the VH when paired with a VL comprising the amino acid sequence set forth in SEQ ID NO: 52 binds to CDCP1; (12) an immunoglobulin light chain or a fragment thereof comprising a VL comprising CDRs 1, 2, and 3 with the amino acid sequences set forth in SEQ ID NOs: 58, 59, and 60, respectively, and wherein the VL when paired with a VH comprising the amino acid sequence set forth in SEQ ID NO: 51 binds to CDCP1; (13) an immunoglobulin heavy chain or a fragment thereof comprising a VH comprising CDRs 1, 2, and 3 with the amino acid sequences set forth in SEQ ID NOs: 65, 66, and 67, respectively, and wherein the VH when paired with a VL comprising the amino acid sequence set forth in SEQ ID NO: 62 binds to CDCP1; (14) an immunoglobulin light chain or a fragment thereof comprising a VL comprising CDRs 1, 2, and 3 with the amino acid sequences set forth in SEQ ID NOs: 68, 69, and 70, respectively, and wherein the VL when paired with a VH comprising the amino acid sequence set forth in SEQ ID NO: 61 binds to CDCP1; (15) an immunoglobulin heavy chain or a fragment thereof comprising a VH comprising CDRs 1, 2, and 3 with the amino acid sequences set forth in SEQ ID NOs: 75, 76, and 77, respectively, and wherein the VH when paired with a VL comprising the amino acid sequence set forth in SEQ ID NO: 72 binds to CDCP1; (16) an immunoglobulin light chain or a fragment thereof comprising a VL comprising CDRs 1, 2, and 3 with the amino acid sequences set forth in SEQ ID NOs: 78, 79, and 80, respectively, and wherein the VL when paired with a VH comprising the amino acid sequence set forth in SEQ ID NO: 71 binds to CDCP1; (17) an immunoglobulin heavy chain or a fragment thereof comprising a VH comprising CDRs 1, 2, and 3 with the amino acid sequences set forth in SEQ ID NOs: 85, 86, and 87, respectively, and wherein the VH when paired with a VL comprising the amino acid sequence set forth in SEQ ID NO: 82 binds to CDCP1; (18) an immunoglobulin light chain or a fragment thereof comprising a VL comprising CDRs 1, 2, and 3 with the amino acid sequences set forth in SEQ ID NOs: 88, 89, and 90, respectively, and wherein the VL when paired with a VH comprising the amino acid sequence set forth in SEQ ID NO: 81 binds to CDCP1; (19) an immunoglobulin heavy chain or a fragment thereof comprising a VH comprising CDRs 1, 2, and 3 with the amino acid sequences set forth in SEQ ID NOs: 95, 96, and 97, respectively, and wherein the VH when paired with a VL comprising the amino acid sequence set forth in SEQ ID NO: 92 binds to CDCP1; (20) an immunoglobulin light chain or a fragment thereof comprising a VL comprising CDRs 1, 2, and 3 with the amino acid sequences set forth in SEQ ID NOs: 98.99, and 100, respectively, and wherein the VL when paired with a VH comprising the amino acid sequence set forth in SEQ ID NO: 91 binds to CDCP1; (21) an immunoglobulin heavy chain or a fragment thereof comprising a VH comprising CDRs 1, 2, and 3 with the amino acid sequences set forth in SEQ ID NOs: 105, 106, and 107, respectively, and wherein the VH when paired with a VL comprising the amino acid sequence set forth in SEQ ID NO: 102 binds to CDCP1; (22) an immunoglobulin light chain or a fragment thereof comprising a VL comprising CDRs 1, 2, and 3 with the amino acid sequences set forth in SEQ ID NOs: 108, 109, and 110, respectively, and wherein the VL when paired with a VH comprising the amino acid sequence set forth in SEQ ID NO: 101 binds to CDCP1; (23) an immunoglobulin heavy chain or a fragment thereof comprising a VH comprising CDRs 1, 2, and 3 with the amino acid sequences set forth in SEQ ID NOs: 115, 116, and 117, respectively, and wherein the VH when paired with a VL comprising the amino acid sequence set forth in SEQ ID NO: 112 binds to CDCP1; (24) an immunoglobulin light chain or a fragment thereof comprising a VL comprising CDRs 1, 2, and 3 with the amino acid sequences set forth in SEQ ID NOs: 118, 119, and 120, respectively, and wherein the VL when paired with a VH comprising the amino acid sequence set forth in SEQ ID NO: 111 binds to CDCP1; (25) an immunoglobulin heavy chain or a fragment thereof comprising a VH comprising CDRs 1, 2, and 3 with the amino acid sequences set forth in SEQ ID NOs: 125, 126, and 127, respectively, and wherein the VH when paired with a VL comprising the amino acid sequence set forth in SEQ ID NO: 122 binds to CDCP1; (26) an immunoglobulin light chain or a fragment thereof comprising a VL comprising CDRs 1, 2, and 3 with the amino acid sequences set forth in SEQ ID NOs: 128, 129, and 130, respectively, and wherein the VL when paired with a VH comprising the amino acid sequence set forth in SEQ ID NO: 121 binds to CDCP1; (27) an immunoglobulin heavy chain or a fragment thereof comprising a VH comprising CDRs 1, 2, and 3 with the amino acid sequences set forth in SEQ ID NOs: 135, 136, and 137, respectively, and wherein the VH when paired with a VL comprising the amino acid sequence set forth in SEQ ID NO: 132 binds to CDCP1; (28) an immunoglobulin light chain or a fragment thereof comprising a VL comprising CDRs 1, 2, and 3 with the amino acid sequences set forth in SEQ ID NOs: 138, 139, and 140, respectively, and wherein the VL when paired with a VH comprising the amino acid sequence set forth in SEQ ID NO: 131 binds to CDCP1; (29) an immunoglobulin heavy chain or a fragment thereof comprising a VH comprising CDRs 1, 2, and 3 with the amino acid sequences set forth in SEQ ID NOs: 145, 146, and 147, respectively, and wherein the VH when paired with a VL comprising the amino acid sequence set forth in SEQ ID NO: 142 binds to CDCP1; (30) an immunoglobulin light chain or a fragment thereof comprising a VL comprising CDRs 1, 2, and 3 with the amino acid sequences set forth in SEQ ID NOs: 148, 149, and 150, respectively, and wherein the VL when paired with a VH comprising the amino acid sequence set forth in SEQ ID NO: 141 binds to CDCP1; (31) an immunoglobulin heavy chain or a fragment thereof comprising a VH comprising CDRs 1, 2, and 3 with the amino acid sequences set forth in SEQ ID NOs: 155, 156, and 157, respectively, and wherein the VH when paired with a VL comprising the amino acid sequence set forth in SEQ ID NO: 152 binds to CDCP1; (32) an immunoglobulin light chain or a fragment thereof comprising a VL comprising CDRs 1, 2, and 3 with the amino acid sequences set forth in SEQ ID NOs: 158, 159, and 160, respectively, and wherein the VL when paired with a VH comprising the amino acid sequence set forth in SEQ ID NO: 151 binds to CDCP1; (33) an immunoglobulin heavy chain or a fragment thereof comprising a VH comprising CDRs 1, 2, and 3 with the amino acid sequences set forth in SEQ ID NOs: 165, 166, and 167, respectively, and wherein the VH when paired with a VL comprising the amino acid sequence set forth in SEQ ID NO: 162 binds to CDCP1; (34) an immunoglobulin light chain or a fragment thereof comprising a VL comprising CDRs 1, 2, and 3 with the amino acid sequences set forth in SEQ ID NOs: 168, 169, and 170, respectively, and wherein the VL when paired with a VH comprising the amino acid sequence set forth in SEQ ID NO: 161 binds to CDCP1; (35) an immunoglobulin heavy chain or a fragment thereof comprising a VH comprising CDRs 1, 2, and 3 with the amino acid sequences set forth in SEQ ID NOs: 175, 176, and 177, respectively, and wherein the VH when paired with a VL comprising the amino acid sequence set forth in SEQ ID NO: 172 binds to CDCP1; (36) an immunoglobulin light chain or a fragment thereof comprising a VL comprising CDRs 1, 2, and 3 with the amino acid sequences set forth in SEQ ID NOs: 178, 179, and 180, respectively, and wherein the VL when paired with a VH comprising the amino acid sequence set forth in SEQ ID NO: 171 binds to CDCP1; (37) an immunoglobulin heavy chain or a fragment thereof comprising a VH comprising CDRs 1, 2, and 3 with the amino acid sequences set forth in SEQ ID NOs: 185, 186, and 187, respectively, and wherein the VH when paired with a VL comprising the amino acid sequence set forth in SEQ ID NO: 182 binds to CDCP1; (38) an immunoglobulin light chain or a fragment thereof comprising a VL comprising CDRs 1, 2, and 3 with the amino acid sequences set forth in SEQ ID NOs: 188, 189, and 190, respectively, and wherein the VL when paired with a VH comprising the amino acid sequence set forth in SEQ ID NO: 181 binds to CDCP1. (39) an immunoglobulin heavy chain or a fragment thereof comprising a VH comprising CDRs 1, 2, and 3 with the amino acid sequences set forth in SEQ ID NOs: 195, 196, and 197, respectively, and wherein the VH when paired with a VL comprising the amino acid sequence set forth in SEQ ID NO: 192 binds to CDCP1; (40) an immunoglobulin light chain or a fragment thereof comprising a VL comprising CDRs 1, 2, and 3 with the amino acid sequences set forth in SEQ ID NOs: 198, 199, and 200, respectively, and wherein the VL when paired with a VH comprising the amino acid sequence set forth in SEQ ID NO: 191 binds to CDCP1; (41) an immunoglobulin heavy chain or a fragment thereof comprising a VH comprising CDRs 1, 2, and 3 with the amino acid sequences set forth in SEQ ID NOs: 205, 206, and 207, respectively, and wherein the VH when paired with a VL comprising the amino acid sequence set forth in SEQ ID NO: 202 binds to CDCP1; (42) an immunoglobulin light chain or a fragment thereof comprising a VL comprising CDRs 1, 2, and 3 with the amino acid sequences set forth in SEQ ID NOs: 208, 209, and 210, respectively, and wherein the VL when paired with a VH comprising the amino acid sequence set forth in SEQ ID NO: 201 binds to CDCP1; (43) an immunoglobulin heavy chain or a fragment thereof comprising a VH comprising CDRs 1, 2, and 3 with the amino acid sequences set forth in SEQ ID NOs: 215, 216, and 217, respectively, and wherein the VH when paired with a VL comprising the amino acid sequence set forth in SEQ ID NO: 212 binds to CDCP1; (44) an immunoglobulin light chain or a fragment thereof comprising a VL comprising CDRs 1, 2, and 3 with the amino acid sequences set forth in SEQ ID NOs: 218, 219, and 220, respectively, and wherein the VL when paired with a VH comprising the amino acid sequence set forth in SEQ ID NO: 211 binds to CDCP1; (45) an immunoglobulin heavy chain or a fragment thereof comprising a VH comprising CDRs 1, 2, and 3 with the amino acid sequences set forth in SEQ ID NOs: 225, 226, and 227, respectively, and wherein the VH when paired with a VL comprising the amino acid sequence set forth in SEQ ID NO: 222 binds to CDCP1; (46) an immunoglobulin light chain or a fragment thereof comprising a VL comprising CDRs 1, 2, and 3 with the amino acid sequences set forth in SEQ ID NOs: 228, 229, and 230, respectively, and wherein the VL when paired with a VH comprising the amino acid sequence set forth in SEQ ID NO: 221 binds to CDCP1; (47) an immunoglobulin heavy chain or a fragment thereof comprising a VH comprising CDRs 1, 2, and 3 with the amino acid sequences set forth in SEQ ID NOs: 235, 236, and 237, respectively, and wherein the VH when paired with a VL comprising the amino acid sequence set forth in SEQ ID NO: 232 binds to CDCP1; (48) an immunoglobulin light chain or a fragment thereof comprising a VL comprising CDRs 1, 2, and 3 with the amino acid sequences set forth in SEQ ID NOs: 238, 239, and 240, respectively, and wherein the VL when paired with a VH comprising the amino acid sequence set forth in SEQ ID NO: 231 binds to CDCP1; (49) an immunoglobulin heavy chain or a fragment thereof comprising a VH comprising CDRs 1, 2, and 3 with the amino acid sequences set forth in SEQ ID NOs: 245, 246, and 247, respectively, and wherein the VH when paired with a VL comprising the amino acid sequence set forth in SEQ ID NO: 242 binds to CDCP1; (50) an immunoglobulin light chain or a fragment thereof comprising a VL comprising CDRs 1, 2, and 3 with the amino acid sequences set forth in SEQ ID NOs: 248, 249, and 250, respectively, and wherein the VL when paired with a VH comprising the amino acid sequence set forth in SEQ ID NO: 241 binds to CDCP1; (51) an immunoglobulin heavy chain or a fragment thereof comprising a VH comprising CDRs 1, 2, and 3 with the amino acid sequences set forth in SEQ ID NOs: 255, 256, and 257, respectively, and wherein the VH when paired with a VL comprising the amino acid sequence set forth in SEQ ID NO: 252 binds to CDCP1; (52) an immunoglobulin light chain or a fragment thereof comprising a VL comprising CDRs 1, 2, and 3 with the amino acid sequences set forth in SEQ ID NOs: 258, 259, and 260, respectively, and wherein the VL when paired with a VH comprising the amino acid sequence set forth in SEQ ID NO: 251 binds to CDCP1; (53) an immunoglobulin heavy chain or a fragment thereof comprising a VH comprising CDRs 1, 2, and 3 with the amino acid sequences set forth in SEQ ID NOs: 265, 266, and 267, respectively, and wherein the VH when paired with a VL comprising the amino acid sequence set forth in SEQ ID NO: 262 binds to CDCP1; (54) an immunoglobulin light chain or a fragment thereof comprising a VL comprising CDRs 1, 2, and 3 with the amino acid sequences set forth in SEQ ID NOs: 268, 269, and 270, respectively, and wherein the VL when paired with a VH comprising the amino acid sequence set forth in SEQ ID NO: 261 binds to CDCP1; (55) an immunoglobulin heavy chain or a fragment thereof comprising a VH comprising CDRs 1, 2, and 3 with the amino acid sequences set forth in SEQ ID NOs: 275, 276, and 277, respectively, and wherein the VH when paired with a VL comprising the amino acid sequence set forth in SEQ ID NO: 272 binds to CDCP1; (56) an immunoglobulin light chain or a fragment thereof comprising a VL comprising CDRs 1, 2, and 3 with the amino acid sequences set forth in SEQ ID NOs: 278, 279, and 280, respectively, and wherein the VL when paired with a VH comprising the amino acid sequence set forth in SEQ ID NO: 271 binds to CDCP1; (57) an immunoglobulin heavy chain or a fragment thereof comprising a VH comprising CDRs 1, 2, and 3 with the amino acid sequences set forth in SEQ ID NOs: 285, 286, and 287, respectively, and wherein the VH when paired with a VL comprising the amino acid sequence set forth in SEQ ID NO: 282 binds to CDCP1; (58) an immunoglobulin light chain or a fragment thereof comprising a VL comprising CDRs 1, 2, and 3 with the amino acid sequences set forth in SEQ ID NOs: 288, 289, and 290, respectively, and wherein the VL when paired with a VH comprising the amino acid sequence set forth in SEQ ID NO: 281 binds to CDCP1; (59) an immunoglobulin heavy chain or a fragment thereof comprising a VH comprising CDRs 1, 2, and 3 with the amino acid sequences set forth in SEQ ID NOs: 295, 296, and 297, respectively, and wherein the VH when paired with a VL comprising the amino acid sequence set forth in SEQ ID NO: 292 binds to CDCP1; (60) an immunoglobulin light chain or a fragment thereof comprising a VL comprising CDRs 1, 2, and 3 with the amino acid sequences set forth in SEQ ID NOs: 298, 299, and 300, respectively, and wherein the VL when paired with a VH comprising the amino acid sequence set forth in SEQ ID NO: 291 binds to CDCP1; (61) an immunoglobulin heavy chain or a fragment thereof comprising a VH comprising CDRs 1, 2, and 3 with the amino acid sequences set forth in SEQ ID NOs: 305, 306, and 307, respectively, and wherein the VH when paired with a VL comprising the amino acid sequence set forth in SEQ ID NO: 302 binds to CDCP1; (62) an immunoglobulin light chain or a fragment thereof comprising a VL comprising CDRs 1, 2, and 3 with the amino acid sequences set forth in SEQ ID NOs: 308, 309, and 310, respectively, and wherein the VL when paired with a VH comprising the amino acid sequence set forth in SEQ ID NO: 301 binds to CDCP1; (63) an immunoglobulin heavy chain or a fragment thereof comprising a VH comprising CDRs 1, 2, and 3 with the amino acid sequences set forth in SEQ ID NOs: 315, 316, and 317, respectively, and wherein the VH when paired with a VL comprising the amino acid sequence set forth in SEQ ID NO: 312 binds to CDCP1; (64) an immunoglobulin light chain or a fragment thereof comprising a VL comprising CDRs 1, 2, and 3 with the amino acid sequences set forth in SEQ ID NOs: 318, 319, and 320, respectively, and wherein the VL when paired with a VH comprising the amino acid sequence set forth in SEQ ID NO: 311 binds to CDCP1; (65) an immunoglobulin heavy chain or a fragment thereof comprising a VH comprising CDRs 1, 2, and 3 with the amino acid sequences set forth in SEQ ID NOs: 325, 326, and 327, respectively, and wherein the VH when paired with a VL comprising the amino acid sequence set forth in SEQ ID NO: 322 binds to CDCP1; (66) an immunoglobulin light chain or a fragment thereof comprising a VL comprising CDRs 1, 2, and 3 with the amino acid sequences set forth in SEQ ID NOs: 328, 329, and 330, respectively, and wherein the VL when paired with a VH comprising the amino acid sequence set forth in SEQ ID NO: 321 binds to CDCP1; (67) an immunoglobulin heavy chain or a fragment thereof comprising a VH comprising CDRs 1, 2, and 3 with the amino acid sequences set forth in SEQ ID NOs: 335, 336, and 337, respectively, and wherein the VH when paired with a VL comprising the amino acid sequence set forth in SEQ ID NO: 332 binds to CDCP1; (68) an immunoglobulin light chain or a fragment thereof comprising a VL comprising CDRs 1, 2, and 3 with the amino acid sequences set forth in SEQ ID NOs: 338, 339, and 340, respectively, and wherein the VL when paired with a VH comprising the amino acid sequence set forth in SEQ ID NO: 331 binds to CDCP1; (69) an immunoglobulin heavy chain or a fragment thereof comprising a VH comprising CDRs 1, 2, and 3 with the amino acid sequences set forth in SEQ ID NOs: 345, 346, and 347, respectively, and wherein the VH when paired with a VL comprising the amino acid sequence set forth in SEQ ID NO: 342 binds to CDCP1; (70) an immunoglobulin light chain or a fragment thereof comprising a VL comprising CDRs 1, 2, and 3 with the amino acid sequences set forth in SEQ ID NOs: 348, 349, and 350, respectively, and wherein the VL when paired with a VH comprising the amino acid sequence set forth in SEQ ID NO: 341 binds to CDCP1. (71) an immunoglobulin heavy chain or a fragment thereof comprising a VH comprising CDRs 1, 2, and 3 with the amino acid sequences set forth in SEQ ID NOs: 355, 356, and 357, respectively, and wherein the VH when paired with a VL comprising the amino acid sequence set forth in SEQ ID NO: 352 binds to CDCP1; (72) an immunoglobulin light chain or a fragment thereof comprising a VL comprising CDRs 1, 2, and 3 with the amino acid sequences set forth in SEQ ID NOs: 358, 359, and 360, respectively, and wherein the VL when paired with a VH comprising the amino acid sequence set forth in SEQ ID NO: 351 binds to CDCP1; (73) an immunoglobulin heavy chain or a fragment thereof comprising a VH comprising CDRs 1, 2, and 3 with the amino acid sequences set forth in SEQ ID NOs: 365, 366, and 367, respectively, and wherein the VH when paired with a VL comprising the amino acid sequence set forth in SEQ ID NO: 362 binds to CDCP1; (74) an immunoglobulin light chain or a fragment thereof comprising a VL comprising CDRs 1, 2, and 3 with the amino acid sequences set forth in SEQ ID NOs: 368, 369, and 370, respectively, and wherein the VL when paired with a VH comprising the amino acid sequence set forth in SEQ ID NO: 361 binds to CDCP1; (75) an immunoglobulin heavy chain or a fragment thereof comprising a VH comprising CDRs 1, 2, and 3 with the amino acid sequences set forth in SEQ ID NOs: 375, 376, and 377, respectively, and wherein the VH when paired with a VL comprising the amino acid sequence set forth in SEQ ID NO: 372 binds to CDCP1; (76) an immunoglobulin light chain or a fragment thereof comprising a VL comprising CDRs 1, 2, and 3 with the amino acid sequences set forth in SEQ ID NOs: 378, 379, and 380, respectively, and wherein the VL when paired with a VH comprising the amino acid sequence set forth in SEQ ID NO: 371 binds to CDCP1; (77) an immunoglobulin heavy chain or a fragment thereof comprising a VH comprising CDRs 1, 2, and 3 with the amino acid sequences set forth in SEQ ID NOs: 385, 386, and 387, respectively, and wherein the VH when paired with a VL comprising the amino acid sequence set forth in SEQ ID NO: 382 binds to CDCP1; (78) an immunoglobulin light chain or a fragment thereof comprising a VL comprising CDRs 1, 2, and 3 with the amino acid sequences set forth in SEQ ID NOs: 388, 389, and 390, respectively, and wherein the VL when paired with a VH comprising the amino acid sequence set forth in SEQ ID NO: 381 binds to CDCP1; (79) an immunoglobulin heavy chain or a fragment thereof comprising a VH comprising CDRs 1, 2, and 3 with the amino acid sequences set forth in SEQ ID NOs: 395, 396, and 397, respectively, and wherein the VH when paired with a VL comprising the amino acid sequence set forth in SEQ ID NO: 392 binds to CDCP1; or (80) an immunoglobulin light chain or a fragment thereof comprising a VL comprising CDRs 1, 2, and 3 with the amino acid sequences set forth in SEQ ID NOs: 398, 399, and 400, respectively, and wherein the VL when paired with a VH comprising the amino acid sequence set forth in SEQ ID NO: 391 binds to CDCP1.

In one embodiment, the VH when paired with a VL specifically binds to human CDCP1 and/or Cynomolgus CDCP1, and the VL when paired with a VH specifically binds to human CDCP1 and/or Cynomolgus CDCP1.

In one embodiment, the immunoglobulin heavy chain or the fragment thereof is a humanized immunoglobulin heavy chain or a fragment thereof, and the immunoglobulin light chain or the fragment thereof is a humanized immunoglobulin light chain or a fragment thereof.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 5, 6, and 7, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 8, 9, and 10, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 15, 16, and 17, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 18, 19, and 20, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 25, 26, and 27, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 28, 29, and 30, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 35, 36, and 37, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 38, 39, and 40, respectively.

In one embodiment, the cDNA comprises a polynucleotide encoding a poly peptide comprising an immunoglobulin heavy chain or a fragment thereof comprising a VH comprising CDRs 1, 2, and 3 with the amino acid sequences set forth in SEQ ID NOs: 45, 46, and 47, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 48, 49, and 50, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 55, 56, and 57, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 58, 59, and 60, respectively. In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 65, 66, and 67, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 68, 69, and 70, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 75, 76, and 77, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 78, 79, and 80, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 85, 86, and 87, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 88, 89, and 90, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 95, 96, and 97, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 98, 99, and 100, respectively.

In one embodiment, the cDNA comprises a polynucleotide encoding a poly peptide comprising an immunoglobulin heavy chain or a fragment thereof comprising a VH comprising CDRs 1, 2, and 3 with the amino acid sequences set forth in SEQ ID NOs: 105, 106, and 107, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 108, 109, and 110, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 115, 116, and 117, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 118, 119, and 120, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 125, 126, and 127, respectively.

In one embodiment, the cDNA comprises a polynucleotide encoding a poly peptide comprising an immunoglobulin light chain or a fragment thereof comprising a VL comprising CDRs 1, 2, and 3 with the amino acid sequences set forth in SEQ ID NOs: 128, 129, and 130, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 135, 136, and 137, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 138, 139, and 140, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 145, 146, and 147, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 148, 149, and 150, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 155, 156, and 157, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 158, 159, and 160, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 165, 166, and 167, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 168, 169, and 170, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 175, 176, and 177, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 178, 179, and 180, respectively.

In one embodiment, the cDNA comprises a polynucleotide encoding a poly peptide comprising an immunoglobulin heavy chain or a fragment thereof comprising a VH comprising CDRs 1, 2, and 3 with the amino acid sequences set forth in SEQ ID NOs: 185, 186, and 187, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 188, 189, and 190, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 195, 1%, and 197, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 198, 199, and 200, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 205, 206, and 207, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 208, 209, and 210, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 215, 216, and 217, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 218, 219, and 220, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 225, 226, and 227, respectively.

In one embodiment, the cDNA comprises a polynucleotide encoding a poly peptide comprising an immunoglobulin light chain or a fragment thereof comprising a VL comprising CDRs 1, 2, and 3 with the amino acid sequences set forth in SEQ ID NOs: 228, 229, and 230, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 235, 236, and 237, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 238, 239, and 240, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 245, 246, and 247, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 248, 249, and 250, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 255, 256, and 257, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 258, 259, and 260, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 265, 266, and 267, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 268, 269, and 270, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 275, 276, and 277, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 278, 279, and 280, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 285, 286, and 287, respectively.

In one embodiment, the cDNA comprises a polynucleotide encoding a poly peptide comprising an immunoglobulin light chain or a fragment thereof comprising a VL comprising CDRs 1, 2, and 3 with the amino acid sequences set forth in SEQ ID NOs: 288, 289, and 290, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 295, 296, and 297, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 298, 299, and 300, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 305, 306, and 307, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 308, 309, and 310, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 315, 316, and 317, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 318, 319, and 320, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 325, 326, and 327, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 328, 329, and 330, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 335, 336, and 337, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 338, 339, and 340, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 345, 346, and 347, respectively.

In one embodiment, the cDNA comprises a polynucleotide encoding a poly peptide comprising an immunoglobulin light chain or a fragment thereof comprising a VL comprising CDRs 1, 2, and 3 with the amino acid sequences set forth in SEQ ID NOs: 348, 349, and 350, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 355, 356, and 357, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 358, 359, and 360, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 365, 366, and 367, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 368, 369, and 370, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 375, 376, and 377, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 378, 379, and 380, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 385, 386, and 387, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 388, 389, and 390, respectively.

In one embodiment, the cDNA comprises a polynucleotide encoding a polypeptide comprising an immunoglobulin heavy chain or a fragment thereof comprising a VH comprising CDRs 1, 2, and 3 with the amino acid sequences set forth in SEQ ID NOs: 395, 396, and 397, respectively.

In one embodiment, the cDNA comprises a polynucleotide encoding a polypeptide comprising an immunoglobulin light chain or a fragment thereof comprising a VL comprising CDRs 1, 2, and 3 with the amino acid sequences set forth in SEQ ID NOs: 398, 399, and 400, respectively.

In one aspect, the present invention provides an antibody or antigen-binding fragment thereof binds to CDCP1 comprising a heavy chain variable region (VH) comprising an amino acid sequence that is at least 90% identical to a selected VH sequence, and a light chain variable region (VL) comprising an amino acid sequence that is at least 90% identical to a selected VL sequence, wherein the selected VH sequence and the selected VL sequence are one of the following: (1) the selected VH sequence is SEQ ID NO: 1, and the selected VL sequence is SEQ ID NO: 2; (2) the selected VH sequence is SEQ ID NO: 11, and the selected VL sequence is SEQ ID NO: 12; (3) the selected VH sequence is SEQ ID NO: 21, and the selected VL sequence is SEQ ID NO: 22; (4) the selected VH sequence is SEQ ID NO: 31, and the selected VL sequence is SEQ ID NO: 32; (5) the selected VH sequence is SEQ ID NO: 41, and the selected VL sequence is SEQ ID NO: 42; (6) the selected VH sequence is SEQ ID NO: 51, and the selected VL sequence is SEQ ID NO: 52; (7) the selected VH sequence is SEQ ID NO: 61, and the selected VL sequence is SEQ ID NO: 62; (8) the selected VH sequence is SEQ ID NO: 71, and the selected VL sequence is SEQ ID NO: 72; (9) the selected VH sequence is SEQ ID NO: 81, and the selected VL sequence is SEQ ID NO: 82; (10) the selected VH sequence is SEQ ID NO: 91, and the selected VL sequence is SEQ ID NO: 92; (11) the selected VH sequence is SEQ ID NO: 101, and the selected VL sequence is SEQ ID NO: 102; (12) the selected VH sequence is SEQ ID NO: 111, and the selected VL sequence is SEQ ID NO: 112; (13) the selected VH sequence is SEQ ID NO: 121, and the selected VL sequence is SEQ ID NO: 122; (14) the selected VH sequence is SEQ ID NO: 131, and the selected VL sequence is SEQ ID NO: 132; (15) the selected VH sequence is SEQ ID NO: 141, and the selected VL sequence is SEQ ID NO: 142; (16) the selected VH sequence is SEQ ID NO: 151, and the selected VL sequence is SEQ ID NO: 152; (17) the selected VH sequence is SEQ ID NO: 161, and the selected VL sequence is SEQ ID NO: 162; and (18) the selected VH sequence is SEQ ID NO: 171, and the selected VL sequence is SEQ ID NO: 172; (19) the selected VH sequence is SEQ ID NO: 181, and the selected VL sequence is SEQ ID NO: 182; (20) the selected VH sequence is SEQ ID NO: 191, and the selected VL sequence is SEQ ID NO: 192; (21) the selected VH sequence is SEQ ID NO: 201, and the selected VL sequence is SEQ ID NO: 202; (22) the selected VH sequence is SEQ ID NO: 211, and the selected VL sequence is SEQ ID NO: 212; (23) the selected VH sequence is SEQ ID NO: 221, and the selected VL sequence is SEQ ID NO: 222; (24) the selected VH sequence is SEQ ID NO: 231, and the selected VL sequence is SEQ ID NO: 232; (25) the selected VH sequence is SEQ ID NO: 241, and the selected VL sequence is SEQ ID NO: 242; (26) the selected VH sequence is SEQ ID NO: 251, and the selected VL sequence is SEQ ID NO: 252; (27) the selected VH sequence is SEQ ID NO: 261, and the selected VL sequence is SEQ ID NO: 262; (28) the selected VH sequence is SEQ ID NO: 271, and the selected VL sequence is SEQ ID NO: 272; (29) the selected VH sequence is SEQ ID NO: 281, and the selected VL sequence is SEQ ID NO: 282; (30) the selected VH sequence is SEQ ID NO: 291, and the selected VL sequence is SEQ ID NO: 292; (31) the selected VH sequence is SEQ ID NO: 301, and the selected VL sequence is SEQ ID NO: 302; (32) the selected VH sequence is SEQ ID NO: 311, and the selected VL sequence is SEQ ID NO: 312; (33) the selected VH sequence is SEQ ID NO: 321, and the selected VL sequence is SEQ ID NO: 322; (34) the selected VH sequence is SEQ ID NO: 331, and the selected VL sequence is SEQ ID NO: 332; (35) the selected VH sequence is SEQ ID NO: 341, and the selected VL sequence is SEQ ID NO: 342; (36) the selected VH sequence is SEQ ID NO: 351, and the selected VL sequence is SEQ ID NO: 352; (37) the selected VH sequence is SEQ ID NO: 361, and the selected VL sequence is SEQ ID NO: 362; (38) the selected VH sequence is SEQ ID NO: 371, and the selected VL sequence is SEQ ID NO: 372; (39) the selected VH sequence is SEQ ID NO: 381, and the selected VL sequence is SEQ ID NO: 382; and (40) the selected VH sequence is SEQ ID NO: 391, and the selected VL sequence is SEQ ID NO: 392, wherein the antibody or antigen-binding fragment thereof specifically binds to CUB domain-containing protein 1 (CDCP1).

In one embodiment the antibody or antigen-binding fragment specifically binds to human CDCP1 and/or Cynomolgus CDCP1.

In one embodiment the antibody or antigen-binding fragment has a dissociation constant ($K_d$) for human CDCP1 that is less than 10 nM, and/or a dissociation constant ($K_d$) for Cynomolgus CDCP1 that is less than 10 nM.

In one embodiment the antibody or antigen-binding fragment is a humanized antibody or antigen-binding fragment thereof.

In one embodiment the VH of the antibody or antigen-binding fragment thereof comprises the sequence of SEQ ID NO: 1 and the VL comprises the sequence of SEQ ID NO: 2.

In one embodiment the VH of the antibody or antigen-binding fragment thereof comprises the sequence of SEQ ID NO: 11 and the VL comprises the sequence of SEQ ID NO: 12.

In one embodiment the VH of the antibody or antigen-binding fragment thereof comprises the sequence of SEQ ID NO: 21 and the VL comprises the sequence of SEQ ID NO: 22.

In one embodiment the VH of the antibody or antigen-binding fragment thereof comprises the sequence of SEQ ID NO: 31 and the VL comprises the sequence of SEQ ID NO: 32.

In one embodiment the VH of the antibody or antigen-binding fragment thereof comprises the sequence of SEQ ID NO: 41 and the VL comprises the sequence of SEQ ID NO: 42.

In one embodiment the VH of the antibody or antigen-binding fragment thereof comprises the sequence of SEQ ID NO: 51 and the VL comprises the sequence of SEQ ID NO: 52.

In one embodiment the VH of the antibody or antigen-binding fragment thereof comprises the sequence of SEQ ID NO: 61 and the VL comprises the sequence of SEQ ID NO: 62.

In one embodiment the VH of the antibody or antigen-binding fragment thereof comprises the sequence of SEQ ID NO: 71 and the VL comprises the sequence of SEQ ID NO: 72.

In one embodiment the VH of the antibody or antigen-binding fragment thereof comprises the sequence of SEQ ID NO: 81 and the VL comprises the sequence of SEQ ID NO: 82.

In one embodiment the VH of the antibody or antigen-binding fragment thereof comprises the sequence of SEQ ID NO: 91 and the VL comprises the sequence of SEQ ID NO: 92.

In one embodiment the VH of the antibody or antigen-binding fragment thereof comprises the sequence of SEQ ID NO: 101 and the VL comprises the sequence of SEQ ID NO: 102.

In one embodiment the VH of the antibody or antigen-binding fragment thereof comprises the sequence of SEQ ID NO: 111 and the VL comprises the sequence of SEQ ID NO: 112.

In one embodiment the VH of the antibody or antigen-binding fragment thereof comprises the sequence of SEQ ID NO: 121 and the VL comprises the sequence of SEQ ID NO: 122.

In one embodiment the VH of the antibody or antigen-binding fragment thereof comprises the sequence of SEQ ID NO: 131 and the VL comprises the sequence of SEQ ID NO: 132.

In one embodiment the VH of the antibody or antigen-binding fragment thereof comprises the sequence of SEQ ID NO: 141 and the VL comprises the sequence of SEQ ID NO: 142.

In one embodiment the VH of the antibody or antigen-binding fragment thereof comprises the sequence of SEQ ID NO: 151 and the VL comprises the sequence of SEQ ID NO:152.

In one embodiment the VH of the antibody or antigen-binding fragment thereof comprises the sequence of SEQ ID NO: 161 and the VL comprises the sequence of SEQ ID NO: 162.

In one embodiment the VH of the antibody or antigen-binding fragment thereof comprises the sequence of SEQ ID NO: 171 and the VL comprises the sequence of SEQ ID NO: 172.

In one embodiment the VH of the antibody or antigen-binding fragment thereof comprises the sequence of SEQ ID NO:181 1 and the VL comprises the sequence of SEQ ID NO: 182.

In one embodiment the VH of the antibody or antigen-binding fragment thereof comprises the sequence of SEQ ID NO: 191 and the VL comprises the sequence of SEQ ID NO: 192.

In one embodiment the VH of the antibody or antigen-binding fragment thereof comprises the sequence of SEQ ID NO: 201 and the VL comprises the sequence of SEQ ID NO: 202.

In one embodiment the VH of the antibody or antigen-binding fragment thereof comprises the sequence of SEQ ID NO: 211 and the VL comprises the sequence of SEQ ID NO: 212.

In one embodiment the VH of the antibody or antigen-binding fragment thereof comprises the sequence of SEQ ID NO: 221 and the VL comprises the sequence of SEQ ID NO: 222.

In one embodiment the VH of the antibody or antigen-binding fragment thereof comprises the sequence of SEQ ID NO: 231 and the VL comprises the sequence of SEQ ID NO: 232.

In one embodiment the VH of the antibody or antigen-binding fragment thereof comprises the sequence of SEQ ID NO: 241 and the VL comprises the sequence of SEQ ID NO: 242.

In one embodiment the VH of the antibody or antigen-binding fragment thereof comprises the sequence of SEQ ID NO: 251 and the VL comprises the sequence of SEQ ID NO: 252.

In one embodiment the VH of the antibody or antigen-binding fragment thereof comprises the sequence of SEQ ID NO: 261 and the VL comprises the sequence of SEQ ID NO: 262.

In one embodiment the VH of the antibody or antigen-binding fragment thereof comprises the sequence of SEQ ID NO: 271 and the VL comprises the sequence of SEQ ID NO: 272.

In one embodiment the VH of the antibody or antigen-binding fragment thereof comprises the sequence of SEQ ID NO: 281 and the VL comprises the sequence of SEQ ID NO: 282.

In one embodiment the VH of the antibody or antigen-binding fragment thereof comprises the sequence of SEQ ID NO: 291 and the VL comprises the sequence of SEQ ID NO: 292.

In one embodiment the VH of the antibody or antigen-binding fragment thereof comprises the sequence of SEQ ID NO: 301 and the VL comprises the sequence of SEQ ID NO: 302.

In one embodiment the VH of the antibody or antigen-binding fragment thereof comprises the sequence of SEQ ID NO: 311 and the VL comprises the sequence of SEQ ID NO: 312.

In one embodiment the VH of the antibody or antigen-binding fragment thereof comprises the sequence of SEQ ID NO: 321 and the VL comprises the sequence of SEQ ID NO: 322.

In one embodiment the VH of the antibody or antigen-binding fragment thereof comprises the sequence of SEQ ID NO: 331 and the VL comprises the sequence of SEQ ID NO: 332.

In one embodiment the VH of the antibody or antigen-binding fragment thereof comprises the sequence of SEQ ID NO: 341 and the VL comprises the sequence of SEQ ID NO: 342.

In one embodiment the VH of the antibody or antigen-binding fragment thereof comprises the sequence of SEQ ID NO: 351 and the VL comprises the sequence of SEQ ID NO: 352.

In one embodiment the VH of the antibody or antigen-binding fragment thereof comprises the sequence of SEQ ID NO: 361 and the VL comprises the sequence of SEQ ID NO: 362.

In one embodiment the VH of the antibody or antigen-binding fragment thereof comprises the sequence of SEQ ID NO: 371 and the VL comprises the sequence of SEQ ID NO: 372.

In one embodiment the VH of the antibody or antigen-binding fragment thereof comprises the sequence of SEQ ID NO: 381 and the VL comprises the sequence of SEQ ID NO: 382.

In one embodiment the VH of the antibody or antigen-binding fragment thereof comprises the sequence of SEQ ID NO: 391 and the VL comprises the sequence of SEQ ID NO: 392, wherein the antibody or antigen-binding fragment thereof specifically binds to CUB domain-containing protein 1 (CDCP1).

In one embodiment, the antibody or antigen-binding fragment thereof binds to human CDCP1, and blocks cleavage of human CDCP1 at residue 342. In one embodiment, the antibody or antigen-binding fragment thereof comprises a VH comprising CDRs 1, 2, 3 with amino acid sequences set forth in SEQ ID NOs: 85, 86, and 87, and a VL comprising CDRs 1, 2, 3 with amino acid sequences set forth in SEQ ID NOs: 88, 89, and 90. In one embodiment, the antibody or antigen-binding fragment thereof comprises a VH comprising CDRs 1, 2, 3 with amino acid sequences set forth in SEQ ID NOs: 95, 96, and 97, and a VL comprising CDRs 1, 2, 3 with amino acid sequences set forth in SEQ ID NOs: 98, 99, and 100.

In another aspect, the disclosure relates to antibody drug conjugates having an antibody or antigen-binding fragment thereof disclosed herein, and a therapeutic agent.

In one embodiment, the an antibody drug conjugate comprises the antibody or antigen-binding fragment thereof and a therapeutic agent. In one embodiment, the therapeutic agent of the antibody drug conjugate is a cytotoxic or cytostatic agent. In one embodiment, the cytotoxic or cytostatic agent in the antibody drug conjugate is a microtubule inhibitor or a DNA alkylator. In one embodiment, the cytotoxic or cytostatic agent in the antibody drug conjugate is selected from the group consisting of DM4, MMAE, PDX, PDB, and IGN. In one embodiment, the agent is DM4. In another embodiment, the agent is MMAE. In one embodiment, the agent is PDX. In one embodiment, the agent is PDB. In one embodiment, the agent is IGN. In one embodiment, the antibody or antigen-binding fragment in the antibody drug conjugate is linked to the therapeutic agent by a linker.

In one embodiment, the linker in the antibody drug conjugate is selected from the group consisting of a cleavable peptide, a charged hindered disulfide, and maleimidocaproyl-valine-citrulline.

In one embodiment, the therapeutic agent in the antibody drug conjugate is DM4, and the linker is D-Ala-L-Ala dpa.

In one embodiment, the therapeutic agent in the antibody drug conjugate is DM4, and the linker is N-succinimidyl 4-(2-pyridyldithio)-2-sulfobutanoate (sSPDB).

In one embodiment, the therapeutic agent in the antibody drug conjugate is MMAE, and the linker is maleimidocaproyl-valine-citrulline (MC-VC).

In one embodiment, therapeutic agent in the antibody drug conjugate is IGN, and the linker is D-Ala-L-Ala dpa.

In one aspect the present invention provides a an antibody drug conjugate has the formula Ab-[L-D]n, wherein Ab comprises the antibody or antigen-binding fragment thereof wherein L comprises an optional linker; D is a therapeutic agent; and n is an integer from about 1 to about 20.

In one embodiment, a method of treating cancer in a subject is provided, comprising: identifying a subject having cancer; and administering to the subject a pharmaceutical composition comprising a therapeutically effective amount of the antibody drug conjugate.

In one embodiment, the cancer is breast cancer, lung cancer, small cell lung cancer, liver cancer, pancreatic cancer, ovarian cancer, kidney cancer or colon cancer.

In one embodiment, the cancer is triple negative breast cancer. In one embodiment, the therapeutic agent in the antibody drug conjugate is DM4, and the linker is D-Ala-L-Ala dpa or sSPDB. In one embodiment, the therapeutic agent in the antibody drug conjugate is MMAE, and the linker is MC-VC.

In one embodiment, the cancer is colon cancer. In one embodiment, the therapeutic agent in the antibody drug conjugate is IGN, and the linker is D-Ala-L-Ala dpa. In one embodiment, the therapeutic agent in the antibody drug conjugate is DM4, and the linker is D-Ala-L-Ala dpa or sSPDB. In one embodiment, the therapeutic agent in the antibody drug conjugate is MMAE, and the linker is MC-VC.

In one embodiment, the cancer is small cell lung cancer. In one embodiment, the therapeutic agent in the antibody drug conjugate is IGN, and the linker is D-Ala-L-Ala dpa.

In another aspect, the present invention provides a method of treating cancer in a subject is provided, comprising identifying a subject having cancer; and administering to the subject a pharmaceutical composition comprising a therapeutically effective amount of the antibody or antigen-binding fragment thereof, or a therapeutically effective amount of the antibody drug conjugate.

In one embodiment, the cancer is breast cancer, triple negative breast cancer, lung cancer, small cell lung cancer, liver cancer, pancreatic cancer, ovarian cancer, kidney cancer or colon cancer.

In another aspect, the disclosure relates to a polynucleotide linked to a heterologous nucleic acid, wherein the polynucleotide is selected from the group consisting of (a) a polynucleotide encoding an immunoglobulin heavy chain or a fragment thereof comprising a heavy chain variable region (VH) comprising complementarity determining regions (CDRs) 1, 2, and 3 with the amino acid sequences set forth in FIG. 20, and wherein the VH when paired with the corresponding light chain variable region (VL) as shown in FIG. 15 binds to CDCP1 protein; (b) a polynucleotide encoding an immunoglobulin light chain or a fragment thereof comprising a VL comprising CDRs 1, 2, and 3 with the amino acid sequences set forth in FIG. 20, and wherein the VL when paired with the corresponding VH as shown in FIG. 15 binds to CDCP1; (c) a polynucleotide encoding (i) an immunoglobulin heavy chain or a fragment thereof comprising a VH comprising CDRs 1, 2, and 3 with the amino acid sequences set forth in FIG. 20; and (ii) an immunoglobulin light chain or a fragment thereof comprising a VL comprising CDRs 1, 2, and 3 with the amino acid sequences set forth in FIG. 20; and (d) a polynucleotide encoding an immunoglobulin heavy chain or a fragment thereof comprising a VH comprising the amino acid sequence set forth in FIG. 18, wherein the VH when paired with the corresponding VL as shown in FIG. 15 binds to CDCP1.

In one aspect, the present invention an expression vector comprising a heterologous promoter operably linked to a polynucleotide encoding a polypeptide disclosed herein.

In another aspect, the disclosure provides an expression vector comprising: a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in FIG. 20; and a second polynucleotide encoding a second polypeptide comprising an immunoglobulin light chain or a fragment thereof comprising a light chain variable region (VL) comprising VL CDRs 1, 2, and 3 with the amino acid sequences set forth in FIG. 20, wherein the immunoglobulin heavy chain or fragment thereof when paired with the immunoglobulin light chain or fragment thereof forms an anti-CDCP1 antibody or CDCP1-binding fragment thereof, and wherein the expression vector is, for example, a plasmid, phage, or virus.

In some embodiments, the complementarity determining region (CDR) sequences in the heavy chain variable region and the light chain variable region comprise or consist of the CDR sequences as set forth in FIG. 20. In some embodiments, the CDR sequences in the heavy chain variable region and the light chain variable region are at least 80%, 90%, 92%, 95%, 97%, 98%, 99%, or 100% identical to the CDR sequences as set forth in FIG. 20. In some embodiments, the CDR sequences in the heavy chain variable region and the light chain variable region differ from the CDR sequences in FIG. 20 by one, two, three, four, or five amino acids. In some embodiments, the CDRs in FIG. 20 are substituted by one, two, three, four, or five conservative amino acids.

In another aspect, the present invention provides compositions that include at least one antibody disclosed herein conjugated to a therapeutic agent, e.g., a cytotoxic drug or radioisotope, and/or to a reporter group. In some implementations, an antibody that is conjugated to a therapeutic agent is administered to a subject to induce cell death of a cancer cell, e.g., a cancer cell that expresses or overexpresses CDCP1 protein, or has CDCP1 protein on the cell surface.

In some embodiments, the antibodies are conjugated to a detectable marker. The conjugates are administered to a subject to detect a cancer cell that expresses CDCP1 protein and/or has a detectable and/or elevated level of a CDCP1 protein.

In some embodiments, an antibody is linked (e.g., covalently bonded, hydrogen bonded, or ionically bonded) to a surface (e.g., a microfluidic device, a chromatography resin, an array, polymer, or a bead).

In a further aspect, the present invention provides compositions that include at least one of the antibodies disclosed herein and a pharmaceutically acceptable excipient. In some embodiments, the disclosure features dry (e.g., lyophilized) compositions that include one or more antibodies disclosed herein and, optionally, one or more pharmaceutically acceptable excipients.

In another aspect, the present invention provides polynucleotides, e.g., DNA, that encode a polypeptide chain, e.g., an antibody heavy or light chain, of any of the antibodies disclosed herein. For example, the poly nucleotide may include a sequence disclosed herein. In some implementations, the polynucleotides, e.g., DNA, do not include introns. The disclosure also features vectors, e.g., recombinant vectors and expression vectors that include the above polynucleotides, and a cell, e.g., an isolated cell, e.g., recombinant cells or hybridomas, that include the above polynucleotides and/or vectors. In some implementations, the vector is stably integrated into a chromosome of the cell, e.g., a mammalian cell, bacterial cell, or yeast cell. In some implementations, the disclosure features methods of producing antibodies that include culturing the cells, e.g., isolated cells, under conditions where the antibodies are expressed, and methods of collecting the antibodies.

The present invention also provides the antibodies, nucleic acids, compositions, and cells disclosed herein and the use thereof for treatment, prophylaxis, imaging, and/or diagnosis of a cancer.

In some embodiments, the composition is formulated for intravenous administration. In some implementations, the cancer expresses (e.g., overexpresses) CDCP1 or has CDCP1 on the cell surface. In some implementations, the cancer is characterized by the presence of a CDCP1 and/or an elevated level of a CDCP1 protein (e.g., as compared to a reference level, e.g., a level of a CDCP1 protein in a CDCP1 protein produced by a healthy subject) produced by the cancer cells.

In a further aspect, the present invention provides methods for treatment of a cancer (e.g., a cancer characterized by overexpression of CDCP1 in cancer cells, or a cancer characterized by having CDCP1 on the surface of the cancer cells) (e.g., breast cancer, triple-negative breast cancer, carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, gastric cancer, testicular cancer, thyroid cancer, bladder cancer, urethral cancer, colorectal cancer, or hematologic malignancy), that include administering an antibody, nucleic acid, composition, or cell disclosed herein to a subject with a cancer in a therapeutically effective amount.

In another aspect, the present invention provides methods that include administering an antibody or composition, e.g., a cell composition, antibody-drug conjugate, or antibody-radioisotope conjugate disclosed herein to a subject in need thereof, e.g., a subject having, or identified or diagnosed as having a cancer characterized by overexpression of CDCP1 in cancer cells, or a cancer characterized by having CDCP1 on the surface of the cancer cells, e.g., breast cancer, triple-negative breast cancer, carcinoid cancer, cervical cancer, endometrial cancer, glioma, head and neck cancer, liver cancer, lung cancer, small cell lung cancer, non-small cell lung cancer, lymphoma, melanoma, ovarian cancer, pancreatic cancer, prostate cancer, renal cancer, gastric cancer, testicular cancer, thyroid cancer, bladder cancer, urethral cancer, colorectal cancer, colon cancer, or hematologic malignancy cells.

In some embodiments, the subject is identified as being a subject who expresses CDCP1, e.g., using any of the methods described herein, or has an elevated level of a CDCP1 protein, e.g., as compared to a reference level, e.g., a level of a CDCP1 protein in a CDCP1 protein produced by a healthy subject, a level of a CDCP1 protein in CDCP1 protein produced by a non-cancerous, e.g., primary cell, or a threshold level of a CDCP1 protein, in which a determined level of a CDCP1 protein that is above this value indicates that the subject should be administered an antibody described herein.

In yet another aspect, the present invention provides methods for cancer prophylaxis (or reducing a subject's risk of developing a cancer characterized by expression, e.g., overexpression, of CDCP1 protein in cancer cells or a cancer characterized by having CDCP1 on the surface of the cancer cells, e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, gastric cancer, testicular cancer, thyroid cancer, bladder cancer, urethral cancer, colorectal cancer, or hematologic malignancy cells (e.g., as compared to a subject at risk for developing cancer but receiving no treatment or receiving a different treatment). The methods include administering an antibody, nucleic acid, composition, or cell disclosed herein to a subject in need thereof in a prophylactically effective amount.

In some embodiments, the cancer expresses CDCP1 protein. In some embodiments, the cancer cells have CDCP1 on the cell surface. In some implementations of any of these methods, the subject is identified as having an elevated risk of developing cancer.

In another aspect, the present invention provides methods of detecting a CDCP1 protein (e.g., a CDCP1 protein) in a sample (e.g., a biopsy sample). The methods include contacting a sample with an antibody disclosed herein and detecting binding of the agent to the sample, thereby detecting CDCP1 protein in the sample. Some implementations further include recording the detection or non-detection of CDCP1 protein in the clinical records of a subject from whom the sample was obtained. In some implementations, the clinical record is stored on a tangible computer readable medium, e.g., a disc, magnetic tape, or computer memory.

In some embodiments of any of the methods described herein, the antibodies described herein are contacted with a sample and/or a cell, and the antibody to CDCP1 can be used in an immunoassay (e.g., an enzyme-linked immunosorbent assay), fluorescence-assisted cell sorting, microfluidics, and chromatography.

BRIEF DESCRIPTION OF THE DRAWINGS

FIG. 15 lists the SEQ ID numbers for the nucleic acid sequences of the variable regions of the heavy chain and the light chain, and the amino acid sequences of the variable regions and complementarity determining regions (CDRs) of the heavy chain and the light chain of 40 anti-CDCP1 antibodies.

FIG. 16 shows the properties of 40 anti-CDCP1 antibodies.

FIG. 17 shows the properties of 18 anti-CDCP1 antibodies, which are a subset of the 40 anti-CDCP1 antibodies in FIG. 16.

FIG. 18 lists the amino acid sequence of the heavy chain variable region (VH) and the light chain variable region (VL) of the 40 anti-CDCP1 antibodies in FIG. 15.

FIG. 19 lists the nucleotide sequence of the heavy chain variable region and the light chain variable region of the 40 anti-CDCP1 antibodies in FIG. 15.

FIG. 20 lists the amino acid sequence of the complementary determining regions in the heavy chain variable region (VH CDR1, VH CDR2, VH CDR3) and complementary determining regions in the light chain variable region (VL CDR1, VL CDR2. VL CDR3)) of the 40 anti-CDCP1 antibodies in FIG. 15.

DETAILED DESCRIPTION

Figures 1A, 1B, 1C:
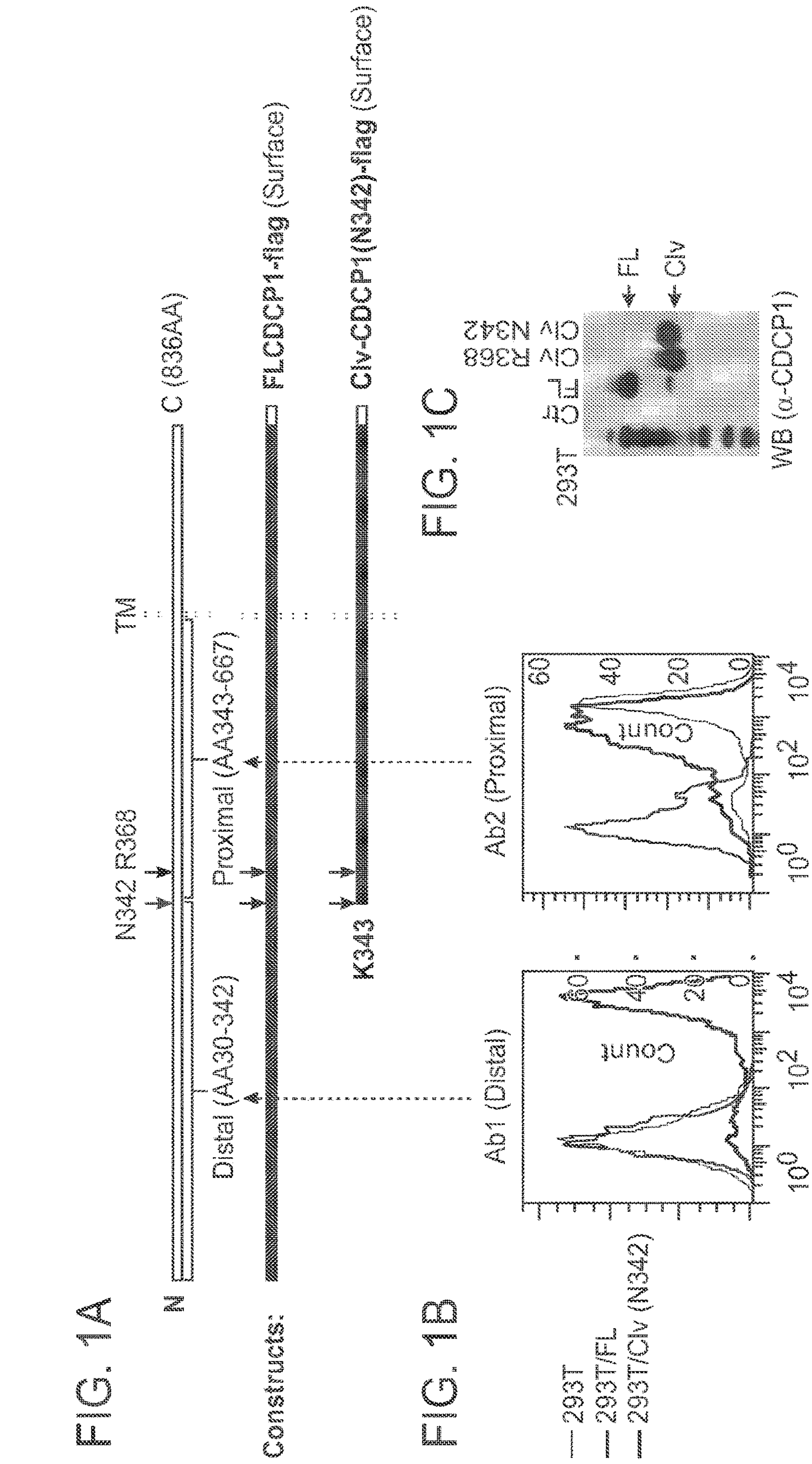
FIG. 1A is a schematic diagram showing CDCP1 constructs expressing full length CDCP1 (FL-CDCP1) or cleaved CDCP1 (Clv-CDCP1(N342)) (having amino acids 343-836).
FIG. 1B are graphs showing flow cytometry analysis of two CDCP1 antibodies on live 293T, 293T/FL-CDCP1, and 293T/Clv N342 cells.
FIG. 1C is an image of a Western blot of lysates of 293T cells stably transfected with FL or two forms of Clv-CDCP1: R368 (AA369-836), and N342: (AA343-836).

Various aspects of the disclosure relate to anti-CUB domain-containing protein 1 (anti-CDCP1) antibodies and antibody fragments, anti-CDCP1 ADCs, and pharmaceutical compositions thereof, as well as nucleic acids, recombinant expression vectors and host cells for making such antibodies and fragments. Methods of using the antibodies and ADCs described herein to detect human CDCP1, to bind to and inhibit human CDCP1 on CDCP1 expressing cells, to inhibit CDCP1 signaling, in vivo, and/or to treat CDCP1-associated disorders, e.g., cancer, including, but not limited to, breast cancer, e.g., triple negative breast cancer, lung cancer, e.g., non-small cell lung cancer (NSCLC), liver cancer, pancreatic cancer, ovarian cancer, kidney cancer, and colon cancer.

In one embodiment, the anti-CDCP1 antibodies or ADCs of the invention are administered in combination with one or more immune checkpoint inhibitors (e.g., antibody or small molecule immune checkpoint inhibitors) for the treatment of a cancer. In another embodiment of the invention, anti-CDCP1 antibody drug conjugates (ADCs) of the invention (e.g., the CDCP1 antibodies of the invention conjugated to a toxin) are internalized and induce cell death of cells endogenously expressing CDCP1.

In one embodiment, the anti-CDCP1 antibodies, bispecific antibodies, or ADCs disclosed herein are administered in combination with a PARP (poly ADP ribose polymerase) inhibitor. PARP inhibitors are well known to those of ordinary skill in the art and include, but are not limited to, Niraparib, Olaparib, Rucaparib. Iniparib, Talazoparib, Veliparib, CEP 9722. E7016. BGB-290, and 3-aminobenazamine.

I. Definitions

In order that the invention may be more readily understood, certain terms are first defined. In addition, it should be noted that whenever a value or range of values of a parameter are recited, it is intended that values and ranges intermediate to the recited values are also intended to be part of this invention.

The terms "CUB domain-containing protein 1 antibody" or "anti-CDCP1 antibody", used interchangeably herein, refer to an antibody that specifically binds to CDCP1, e.g., human CDCP1. An antibody "which binds" an antigen of interest, i.e., CDCP1, is one capable of binding that antigen with sufficient affinity such that the antibody is useful in targeting a cell expressing the antigen. In a preferred embodiment, the antibody specifically binds to human CDCP1 (hCDCP1). Examples of anti-CDCP1 antibodies are disclosed in the Examples, below. Unless otherwise indicated, the term "anti-CDCP1 antibody" is meant to refer to an antibody which binds to wild type CDCP1, a variant, or an isoform of CDCP1.

Alternative splicing results in at least two transcript variants of hCDCP1. CDCP1 nucleotide and polypeptide sequences are reported as Accession Nos. NM_022842.4 (transcript variant 1 mRNA), NP_073753.3 (isoform 1 polypeptide) and NM_178181.2 (transcript variant 2 mRNA), NP_835488.1 (isoform 2 polypeptide). CDCP1 contains a CUB domain at positions 225-297 of NP_073753.3. The extracellular domain of the protein described in NP_073753.3 includes amino acid residues 30-667.

The terms "specific binding" or "specifically binding", as used herein, in reference to the interaction of a CDCP1 antibody or an ADC with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC.

In one embodiment, the phrase "specifically binds to hCDCP1" or "specific binding to hCDCP1", as used herein, refers to the ability of an anti-CDCP1 antibody or ADC to interact with CDCP1 (human or cynomolgus monkey CDCP1) with a dissociation constant ($K_D$) of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, about 0.01 nM or less, or about 0.001 nM or less. In another embodiment, the phrase "specifically binds to hCDCP1" or "specific binding to hCDCP1", as used herein, refers to the ability of an anti-DCP1 antibody or ADC to interact with hCDCP1 with a dissociation constant ($K_L$) of between about 1 pM (0.001 nM) to 2.000 nM, between about 500 pM (0.5 nM) to 1,000 nM, between about 500 pM (0.5 nM) to 500 nM, between about 1 nM) to 200 nM, between about 1 nM to 100 nM, between about 1 nM to 50 nM, between about 1 nM to 20 nM, or between about 1 nM to 5 nM. In one embodiment, K) is determined by surface plasmon resonance or Bio-Layer Interferometry, or by any other method known in the art. Bio-Layer Interferometry refers to an optical phenomenon that allows for the analysis of real-time biospecific interactions by measuring the interference patterns of reflected white light, for example using the Octet™ system (ForteBio. Pall Corp. Fremont. CA). For further description of the Octet™ system, see Li, B et al. (2011) J. Pharm. Biomed Anal. 54(2):286-294 and Abdiche, Y. N., et al. (2009) *Anal. Biochem.* 386(2):172-180, the contents of which are incorporated herein by reference.

The term "antibody" broadly refers to an immunoglobulin (Ig) molecule, generally comprised of four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1. CDR1, FR2, CDR2, FR3, CDR3, FR4. Immunoglobulin molecules can be of any type (e.g., IgG, IgE, IgM, IgD, IgA and IgY) and class (e.g., IgG1, IgG2, IgG3, IgG4, IgA1 and IgA2) or subclass.

The term "antigen binding portion" of an antibody (or simply "antibody portion"), as used herein, refers to one or more fragments of an antibody that retain the ability to specifically bind to an antigen (e.g., hCDCP1). It has been shown that the antigen binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen binding portion" of an antibody include (i) a Fab fragment, a monovalent fragment consisting of the VL. VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains: (iv) a Fv fragment consisting of the VL and VH domains of a single arm of an antibody. (v) a dAb fragment (Ward et al., (1989) Nature 341:544-546. Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad Sci. USA 85:5879-5883). Such single chain antibodies are also intended to be encompassed within the term "antigen binding portion" of an antibody. In certain embodiments, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak. R. J., et al. (1994) *Structure* 2:1121-1123). Such antibody binding portions are known in the art (Kontennann and Dubel eds., Antibody Engineering (2001) Springer-Verlag. New York. 790 pp. (ISBN 3-540-41354-5).

The term "antibody construct" as used herein refers to a polypeptide comprising one or more the antigen binding portions disclosed herein linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger. P., el al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds CDCP1 is substantially free of antibodies that specifically bind antigens other than CDCP1). An isolated antibody that specifically binds CDCP1 may, however, have cross-reactivity to other antigens, such as CDCP1 molecules from other species. Moreover, an isolated antibody may be substantially free of other cellular material and/or chemicals.

The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. In particular, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab'. F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge. CH2, CH3, and CH4 regions of the heavy chain. In some embodiments, a humanized antibody only contains a humanized light chain. In other embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The terms "Kabat numbering," "Kabat definitions," and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad Sci. 190:382-391 and Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain (HC) and the light chain (LC), which are designated CDR1. CDR2 and CDR3 (or specifically HC CDR1. HC CDR2, HC CDR3, LC CDR1, LC CDR2, and LC CDR3), for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda. Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1. FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker. From Genes to Clones (Verlagsgesellschaft. Weinheim, Germany 1987). In a family of immunoglobulins, each position in the consensus sequence is occupied by the amino acid occurring most frequently at that position in the family. If two amino acids occur equally frequently, either can be included in the consensus sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST. BLAST-2. ALIGN or Megalign (DNASTAR) software. Those skilled in the art can determine appropriate parameters for measuring alignment, including any algorithms needed to achieve maximal alignment over the full length of the sequences being compared. In one embodiment, the disclosure includes an amino acid sequence having at least 80%, at least 85%, at least 90%, at least 95%, at least 96%, at least 97%$_0$, at least 98%, or at least 99% identity to an amino acid sequence set forth in any one of SEQ ID NOs: 1 to 400 and 402-505.

The term "multivalent antibody" is used herein to denote an antibody comprising two or more antigen binding sites. In certain embodiments, the multivalent antibody may be engineered to have the three or more antigen binding sites, and is generally not a naturally occurring antibody.

The term "multispecific antibody" refers to an antibody capable of binding two or more unrelated antigens.

The term "dual variable domain" or "DVD," as used interchangeably herein, are antigen binding proteins that comprise two or more antigen binding sites and are tetravalent or multivalent binding proteins. Such DVDs may be monospecific, i.e., capable of binding one antigen or multispecific, i.e, capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. In one embodiment, the CDRs described herein are used in an anti-CDCP1 DVD.

The term "activity" includes activities such as the binding specificity/affinity of an antibody or ADC for an antigen, for example, an anti-hCDCP1 antibody or ADC that binds to a CDCP1 antigen. In one embodiment, an anti-CDCP1 antibody or anti-CDCP1 ADC activity includes, but it not limited to, binding to CDCP1 in vitro; binding to CDCP1 on cells expressing CDCP1 in vivo; modulating (e.g., inhibiting) src and/or EGFR signaling: inducing cell death in cells expressing CDCP1, including breast cancer cells, e.g., triple negative breast cancer cells, colon cancer cells, lung cancer cells, e.g., non-small cell lung carcinoma (NSCLC) cells, liver cancer cells, pancreatic cancer cells, ovarian cancer cells, kidney cancer cells; inhibiting cancer cell invasion and metastasis; decreasing or inhibiting cancer, e.g., breast cancer, e.g., triple negative breast cancer, colon cancer, lung cancer, e.g., non-small cell lung carcinoma (NSCLC), liver cancer, pancreatic cancer, ovarian cancer, kidney cancer; and decreasing or inhibiting tumor cellular proliferation or tumor growth in vivo. In one embodiment, an anti-CDCP1 antibody or ADC is capable of being internalized into a cell expressing CDCP1 and/or inducing cytotoxicity.

The term "epitope" refers to a region of an antigen that is bound by an antibody, antibody fragment, or ADC. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BiAcore system (Pharmacia Biosensor AB. Uppsala, Sweden and Piscataway, NJ). For further descriptions, see Jönsson, U., el al. (1993) *Ann. Biol. Chm.* 51:19-26; Jönsson, U., et al. (1991) *Biotechniques* 11:620-627; Johnsson, B., et al. (1995) *J. Mol. Recognit.* 8:125-131; and Johnnson. B., et al. (1991) *Anal. Biochem.* 198:268-277.

The term "$k_{on}$" or "$k_a$", as used herein, is intended to refer to the on rate constant for association of an antibody to the antigen to form the antibody/antigen complex.

The term "$k_{off}$" or "$k_d$", as used herein, is intended to refer to the off rate constant for dissociation of an antibody from the antibody/antigen complex.

The term "$K_D$", as used herein, is intended to refer to the equilibrium dissociation constant of a particular antibody-antigen interaction. $K_D$ is calculated by $k_a/k_d$. In one embodiment, the antibodies of the invention have a $K_D$ of about 2,000 nM or less, about 1.000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, about 0.01 nM or less, or about 0.001 nM or less.

The term "competitive binding", as used herein, refers to a situation in which a first antibody competes with a second antibody, for a binding site on a third molecule, e.g., an antigen. In one embodiment, competitive binding between two antibodies is determined using FACS analysis.

The term "competitive binding assay" is an assay used to determine whether two or more antibodies bind to the same epitope. In one embodiment, a competitive binding assay is a competition fluorescent activated cell sorting (FACS) assay which is used to determine whether two or more antibodies bind to the same epitope by determining whether the fluorescent signal of a labeled antibody is reduced due to the introduction of a non-labeled antibody, where competition for the same epitope will lower the level of fluorescence.

The term "labeled antibody" as used herein, refers to an antibody, or an antigen binding portion thereof, with a label incorporated that provides for the identification of the binding protein, e.g., an antibody. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}H$, $^{14}C$, $^{35}S$, $^{90}Y$, $^{99}Tc$, $^{111}In$, $^{125}I$, $^{131}I$, $^{177}Lu$, $^{199}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody-drug-conjugate" or "ADC" refers to a binding protein, such as an antibody or antigen binding fragment thereof, chemically linked to one or more chemical drug(s) (also referred to herein as agent(s)) that may optionally be therapeutic or cytotoxic agents. In a preferred embodiment, an ADC includes an antibody, a cytotoxic or therapeutic drug, and a linker that enables attachment or conjugation of the drug to the antibody. An ADC typically has anywhere from 1 to 8 drugs conjugated to the antibody, including drug loaded species of 2, 4, 6, or 8. Non-limiting examples of drugs that may be included in the ADCs are mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

The term "antibody drug conjugate" refers to an ADC comprising an antibody, or antigen-binding portion thereof, that specifically binds to CDCP1, whereby the antibody is conjugated to one or more chemical agent(s) or payloads. In one embodiment, the chemical agent is linked to the antibody via a linker.

The term "drug-to-antibody ratio" or "DAR" refers to the number of drugs, e.g., IGN, auristatin, or maytansinoid, attached to the antibody of the ADC. The DAR of an ADC can range from 1 to 8, although higher loads, e.g., 10, are also possible depending on the number of linkage site on an antibody. The term DAR may be used in reference to the number of drugs loaded onto an individual antibody, or, alternatively, may be used in reference to the average or mean DAR of a group of ADCs.

The term "CDCP1 associated disorder." as used herein, includes any disorder or disease (including proliferative disorders, e.g., cancer) that is marked, diagnosed, detected or identified by a phenotypic or genotypic aberration of CDCP1 genetic components or expression during the course or etiology of the disease or disorder. In this regard a CDCP1 phenotypic aberration or determinant may, for example, comprise increased or decreased levels of CDCP1 protein expression on one cell population, e.g., a cancer cell population, as compared to another cell population, e.g., a normal cell population, or increased or decreased CDCP1 protein expression on certain definable cell populations, or increased or decreased CDCP1 protein expression at an inappropriate phase or stage of a cell lifecycle. It will be appreciated that similar expression patterns of genotypic determinants (e.g., mRNA transcription levels) of CDCP1 may also be used to classify or detect CDCP1 associated disorders. In one embodiment, an CDCP1 associated disorder is breast cancer, e.g., triple negative breast cancer. In another embodiment, an CDCP1 associated disorder is colon cancer. In another embodiment, a CDCP1 associated disorder is lung cancer, e.g., non-small cell lung cancer (NSCLC). In another embodiment, an CDCP1 associated disorder is liver cancer. In another embodiment, an CDCP1 associated disorder is pancreatic cancer. In another embodiment, an CDCP1 associated disorder is ovarian cancer. In another embodiment, an CDCP1 associated disorder is kidney cancer.

The term "cancer." as used herein, is meant to refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include, but are not limited to, breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, lung cancer, small cell lung cancer, non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, environmentally induced cancers including those induced by asbestos, hematologic malignancies including, for example, multiple myeloma. B-cell lymphoma, Hodgkin lymphoma/primary mediastinal B-cell lymphoma, non-Hodgkin's lymphomas, acute myeloid leukemia (AML), myelodysplastic syndrome (MDS), acute lymphoblastic leukemia (ALL), chronic myelogenous leukemia (CML), myeloproliferative disorders (MPD), chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma. T-cell lymphoma, and precursor T-lymphoblastic lymphoma, PVNS, acute myeloid leukemia, adrenocortico carcinoma, ladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma, and any combinations of said cancers. The present invention is also applicable to treatment of metastatic cancers In one embodiment, the antibodies or ADCs of the invention are administered to a patient having a solid tumor, including an advanced solid tumor. In one embodiment, the antibodies or ADCs of the invention are administered to a patient having a leukemia. In another embodiment, administration of antibodies or ADCs of the invention induce cell death of CDCP1 expressing cells.

The term "CDCP1 expressing tumor," as used herein, refers to a tumor which expresses CDCP1 protein (including a tumor comprising tumor infiltrating cells that express CDCP1 protein). In one embodiment, CDCP1 expression in a tumor is determined using immunohistochemical staining of tumor cell membranes, where any immunohistochemical staining above background level in a tumor sample indicates that the tumor is a CDCP1 expressing tumor. In another embodiment, a CDCP1 expressing tumor is identified in a patient when greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a tumor sample are positive for CDCP1 expression. In another embodiment, CDCP1 positive expression is determined based on membrane staining as determined by, e.g., immunohistochemistry (IHC) analysis.

A CDCP1 expressing tumor is identified as having an "elevated level of CDCP1" or "expressing CDCP1 at an elevated level" when the level of CDCP1 is higher than in tissue surrounding the cancer. In some embodiments, an "elevated level of CDCP1" is one in which 5% or more of the cells in a tumor sample have membrane staining. In some embodiments a "high level" in regard to CDCP1 is 5% or more staining, for example, 5, 10, 20, 30, 40, 50, 60, 70, 80, 90, or 100% of the cells in the tumor sample are stained. In some embodiments, the protein expression levels can be measured by IHC analysis.

A CDCP1 expressing tumor is identified as having a "low level of CDCP1" or "expressing CDCP1 at a low level" is one in which 5% or less of the cells in a tumor sample have membrane staining. In some embodiments a "low level" in regard to CDCP1 is 5% or less staining, for example, 4.9, 4.5, 4, 3, 2, 1, 0.9, 0.8, 0.7, 0.6, 0.5, 0.4, 0.3, 0.2, 0.1% or less of the cells in the tumor sample are stained. In some embodiments, the protein expression levels can be measured by IHC analysis.

A cell that expresses no CDCP1 can also be described as expressing a "low level of CDCP1". Thus, the phrase "expresses a low level of CDCP1" encompasses no CDCP1 expression. In some embodiments, a low level of CDCP1 is within the background staining levels. In some embodiments, a sample that is CDCP1 "negative" has no CDCP1 expression or a low level of CDCP1. In some embodiments. CDCP1 staining is negative when no or less than 5%, 4%, 3%, 2%, or 1% of the cells have membrane staining for CDCP1.

As used herein, the term "tumor sample" refers to a tumor tissue or cell sample obtained from a solid tumor. The sample can include both tumor cells and tumor infiltrating cells, e.g., tumor infiltrating immune cells.

As used herein, the term "non-cancer sample" or "normal sample" refers to a sample from a normal tissue (e.g., a lung or ovarian tissue sample or a normal cell sample). In some embodiments, the non-cancer sample comes from the same subject, but is from a different part of the subject than that being tested. In some embodiments, the non-cancer sample is from a tissue area surrounding or adjacent to the cancer. In some embodiments, the non-cancer sample is not from the subject being tested, but is a sample from a subject known to have, or not to have, a disorder in question (for example, a particular cancer such a CDCP1 related disorder). In some embodiments, the non-cancer sample is from the same subject, but from a point in time before the subject developed cancer. In some embodiments, the reference sample is from a benign cancer sample (for example, benign ovarian cancer sample), from the same or a different subject.

Methods for detecting expression of CDCP1 in a tumor are known in the art.

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Thus, overexpression refers to either protein or RNA levels. Overexpression can also be by 5%, 10%, 20%, 30%, 40%, 50%, 60%, 70%, 80%, 90% or more in comparison to a normal cell or comparison cell. In certain embodiments, the anti-CDCP1 antibodies or ADCs are used to treat solid tumors likely to overexpress CDCP1.

The term "administering" as used herein is meant to refer to the delivery of a substance (e.g., an anti-CDCP1 antibody or ADC) to achieve a therapeutic objective (e.g., the treatment of an CDCP1-associated disorder or the inhibition or reduction of a tumor). Modes of administration may be parenteral, enteral and topical. Parenteral administration is usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "combination therapy", as used herein, refers to the administration of two or more therapeutic substances, e.g., an anti-CDCP1 antibody or ADC and an additional therapeutic agent. The additional therapeutic agent may be administered concomitant with, prior to, or following the administration of the anti-CDCP1 antibody or ADC. In one embodiment, the anti-CDCP1 antibodies or ADCs of the invention are administered in combination with one or more immune checkpoint inhibitors or (e.g., one or more antibody or small molecule immune checkpoint inhibitors) for the treatment of a cancer. In one embodiment, the anti-CDCP1 antibodies, bispecific antibodies, or ADCs disclosed herein are administered in combination with a PARP (poly ADP ribose polymerase) inhibitor. PARP inhibitors are well known to those of ordinary skill in the art and include, but are not limited to. Niraparib, Olaparib. Rucaparib, Iniparib, Talazoparib. Veliparib, CEP 9722, E7016, BGB-290, and 3-aminobenazamine.

As used herein, the term "effective amount" or "therapeutically effective amount" refers to the amount of a drug, e.g., an antibody or ADC, which is sufficient to reduce or ameliorate the severity and/or duration of a disorder, e.g., cancer, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of an antibody or ADC may, for example, inhibit tumor growth (e.g., inhibit an increase in tumor volume), decrease tumor growth (e.g., decrease tumor volume), reduce the number of cancer cells, and/or relieve to some extent one or more of the symptoms associated with the cancer. The effective amount may, for example, improve disease free survival (DFS), improve overall survival (OS), or decrease likelihood of recurrence.

Various aspects of the invention are described in further detail in the following subsections.

II. Anti-CDCP1 Antibodies

One aspect disclosed herein provides humanized anti-CDCP1 antibodies, or antigen binding portions thereof. Another aspect disclosed herein provides human anti-CDCP1 antibodies, or antigen binding portions thereof. In one embodiment, the antibodies disclosed herein bind human CDCP1. In another embodiment, the antibodies disclosed herein bind cynomolgus monkey CDCP1. In another embodiment, the antibodies disclosed herein bind human CDCP1 expressed on tumor cells.

Another aspect disclosed herein features antibody drug conjugates (ADCs) comprising an anti-CDCP1 antibody described herein and at least one drug(s). The antibodies or ADCs disclosed herein have characteristics including, but not limited to, binding to human CDCP1 in vitro, modulating, e.g., inhibiting IL-1 signaling, inducing cell death in cells expressing CDCP1, including, but not limited to, leukemia cells, and decreasing or inhibiting cancer, tumor cellular proliferation or tumor growth, or tumor invasion and metastasis. ADCs disclosed herein, in particular, have characteristics including, but not limited to, inducing cell death in cells expressing CDCP1, e.g., leukemia cells expressing CDCP1. In one embodiment, an anti-CDCP1 antibody or ADC disclosed herein is capable of being internalized into a cell expressing CDCP1.

In one embodiment, anti-CDCP1 antibodies are disclosed which have the ability to bind to CDCP1, as described in the Examples below. Collectively, the novel antibodies are referred to herein as "CDCP1 antibodies." The anti-CDCP1 antibodies, ADCs, or antigen binding fragments thereof, are able to inhibit or decrease tumor growth in vivo. The tumor can be a CDCP1 negative tumor or an CDCP1 expressing tumor. In various embodiments, anti-CDCP1 antibodies, ADCs, or antigen binding fragments thereof, are capable of modulating a biological function of CDCP1. In other embodiments of the foregoing aspects, the anti-CDCP1 antibodies. ADCs, or antigen binding fragments thereof, bind CDCP1 on cells expressing CDCP1. Thus, the disclosure includes anti-CDCP1 antibodies. ADCs, or antigen binding fragments thereof, that are effective at inhibiting or decreasing tumor growth.

In addition, the present inventors have shown that CDCP1 is expressed by numerous solid tumors, including breast cancer tumors, e.g., triple negative breast cancer tumors, lung cancer tumors, e.g., non-small cell lung cancer tumors, liver cancer tumors, pancreatic cancer tumors, ovarian cancer tumors, kidney cancer tumors, and colon cancer tumors (see, e.g., Examples 3-7). Accordingly, the anti-CDCP1 antibodies. ADCs, and antigen-binding portions thereof, can be used for the treatment of breast cancer, e.g., triple negative breast cancer, lung cancer, e.g., non-small cell lung cancer, liver cancer, pancreatic cancer, ovarian cancer, kidney cancer, and colon cancer in a subject. In one embodiment, greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a tumor sample, e.g., breast cancer tumor, e.g., triple negative breast cancer tumor, lung cancer tumor, e.g., non-small cell lung cancer tumor, liver cancer tumor, pancreatic cancer tumor, ovarian cancer tumor, kidney cancer tumor, and colon cancer tumor, are positive for CDCP1 expression. In another embodiment, a tumor sample has a high level of CDCP1 expression. For example, in one embodiment, at least 5% or more of the cells in a tumor sample, e.g., breast cancer tumor, e.g., triple negative breast cancer tumor, lung cancer tumor, e.g., non-small cell lung cancer tumor, liver cancer tumor, pancreatic cancer tumor, ovarian cancer tumor, kidney cancer tumor, and colon cancer tumor, have membrane staining. In another embodiment, a tumor sample obtained from the subject displays a low level of expression of CDCP1. The expression level of CDCP1 can be determined by any method known in the art. For example, the expression level of CDCP1 can be determined via immunohistochemical analysis. In another embodiment, the cancer has been previously treated with another anti-cancer agent or anti-cancer therapy, e.g., a chemotherapy. In one embodiment, the cancer is resistant to chemotherapy.

Antibodies having combinations of any of the aforementioned characteristics are contemplated as aspects of the disclosure. ADCs, described in more detail below, may also have any of the foregoing characteristics.

One aspect of the disclosure features an anti-human CDCP1 (anti-hCDCP1) Antibody Drug Conjugate (ADC) comprising an anti-hCDCP1 antibody conjugated to a drug via a linker. Exemplary anti-CDCP1 antibodies (and sequences thereof) that can be used in the ADCs are described herein.

The anti-CDCP1 antibodies described herein provide the ADCs with the ability to bind to CDCP1 such that the cytotoxic molecule attached to the antibody may be delivered to the CDCP1-expressing cell, particularly a CDCP1 expressing cancer cell.

While the term "antibody" is used throughout, it should be noted that antibody fragments (i.e., antigen-binding portions of an anti-CDCP1 antibody) are also included in the disclosure and may be included in the embodiments (methods and compositions) described throughout. For example, an anti-CDCP1 antibody fragment may be conjugated to the drugs, as described herein. In certain embodiments, an anti-CDCP1 antibody binding portion is a Fab, a Fab', a F(ab')2, a Fv, a disulfide linked Fv, an scFv, a single domain antibody, or a diabody.

Example 2 describes the generation of fully human CDCP1 antibodies against the extracellular domain of human CDCP1. The heavy and light chain variable region CDR amino acid sequences and the heavy and light chain variable region amino acid sequences for these human antibodies are set forth in FIGS. 15, 18, and 20, and the nucleotide sequence encoding the heavy and light chain variable region amino acid sequences for these human antibodies are set forth in FIG. 19.

Thus, in one embodiment, the disclosure includes human anti-CDCP1 antibodies, or antigen binding portions thereof, comprising a heavy chain variable region comprising an amino acid sequence selected from the group consisting of SEQ ID NOs:1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, and 391; and a light chain variable region comprising an amino acid sequence selected from the group consisting of 2, 12, 22, 32, 42, 52, 62, 72, 82, 92, 102, 112, 122, 132, 142, 152, 162, 172, 182, 192, 202, 222, 222, 232, 242, 252, 262, 272, 282, 292, 302, 322,322, 332, 342, 352, 362, 372, 382, and 392.

In one embodiment, the disclosure includes a human anti-CDCP1 antibody, or antigen binding portion thereof, comprising an HC CDR set (CDR1, CDR2, and CDR3) selected from those set forth in FIG. 15 or 20; and an LC CDR set (CDR1, CDR2, and CDR3) selected from those set forth in FIG. 15 or 20.

In one embodiment, an anti-CDCP1 antibody, or antigen binding portion thereof, is the human antibody 38E11. The 38E11 antibody comprises a heavy chain variable region comprising a CDR3 domain comprising the amino acid sequence of SEQ ID NO: 157, a CDR2 domain comprising the amino acid sequence of SEQ ID NO: 156, and a CDR1 domain comprising the amino acid sequence of SEQ ID NO: 155, and a light chain variable region comprising a CDR3 domain comprising the amino acid sequence of SEQ ID NO: 160, a CDR2 domain comprising the amino acid sequence of SEQ ID NO: 159, and a CDR1 domain comprising the amino acid sequence of SEQ ID NO: 158. In further embodiments, disclosed herein is an antibody having a heavy chain variable region comprising the amino acid sequence of SEQ ID NO: 151 and a light chain variable region comprising the amino acid sequence of SEQ ID NO: 152.

In some embodiments, an anti-CDCP1 antibody, or antigen-binding portion thereof, comprises a heavy chain comprising an amino acid sequence set forth in SEQ ID NO: 151, or a sequence having at least 90%, 95%, 96%, 97%, 98%, or 99% identity to SEQ ID NO: 151, and/or a light chain comprising an amino acid sequence set forth in SEQ ID NO: 152, or a sequence having at least 90%, 95%, 96%, 97%, 98%, or 99% identity to SEQ ID NO: 152.

In one embodiment, an anti-CDCP1 antibody, or antigen binding portion thereof, is the human antibody 27H10. The 27H10 antibody comprises a heavy chain variable region comprising a CDR3 domain comprising the amino acid sequence of SEQ ID NO: 37, a CDR2 domain comprising the amino acid sequence of SEQ ID NO: 36, and a CDR1 domain comprising the amino acid sequence of SEQ ID NO: 35, and a light chain variable region comprising a CDR3 domain comprising the amino acid sequence of SEQ ID NO: 40, a CDR2 domain comprising the amino acid sequence of SEQ ID NO: 39, and a CDR1 domain comprising the amino acid sequence of SEQ ID NO: 38. In further embodiments, disclosed herein is an antibody having a heavy chain variable region comprising the amino acid sequence of SEQ ID NO: 31 and a light chain variable region comprising the amino acid sequence of SEQ ID NO: 32.

In some embodiments, an anti-CDCP1 antibody, or antigen-binding portion thereof, comprises a heavy chain comprising an amino acid sequence set forth in SEQ ID NO: 31, or a sequence having at least 90%, 95%, 96%, 97%, 98%, or 99% identity to SEQ ID NO: 31, and/or a light chain comprising an amino acid sequence set forth in SEQ ID NO: 32, or a sequence having at least 90%, 95%, 96%, 97%, 98%, or 99% identity to SEQ ID NO: 32.

In one embodiment, an anti-CDCP1 antibody, or antigen binding portion thereof, is the human antibody 18C6. The 18C6 antibody comprises a heavy chain variable region comprising a CDR3 domain comprising the amino acid sequence of SEQ ID NO: 87, a CDR2 domain comprising the amino acid sequence of SEQ ID NO: 86, and a CDR1 domain comprising the amino acid sequence of SEQ ID NO: 85, and a light chain variable region comprising a CDR3 domain comprising the amino acid sequence of SEQ ID NO: 90, a CDR2 domain comprising the amino acid sequence of SEQ ID NO: 89, and a CDR1 domain comprising the amino acid sequence of SEQ ID NO: 88. In further embodiments, disclosed herein is an antibody having a heavy chain variable region comprising the amino acid sequence of SEQ ID NO: 81 and a light chain variable region comprising the amino acid sequence of SEQ ID NO: 82.

In some embodiments, an anti-CDCP1 antibody, or antigen-binding portion thereof, comprises a heavy chain comprising an amino acid sequence set forth in SEQ ID NO: 81, or a sequence having at least 90%, 95%, 96%, 97%, 98%, or 99% identity to SEQ ID NO: 81, and/or a light chain comprising an amino acid sequence set forth in SEQ ID NO: 82, or a sequence having at least 90%, 95%, 96%, 97%, 98%, or 99% identity to SEQ ID NO: 82.

In one embodiment, an anti-CDCP1 antibody, or antigen binding portion thereof, is the human antibody 10E2. The 10E2 antibody comprises a heavy chain variable region comprising a CDR3 domain comprising the amino acid sequence of SEQ ID NO: 107, a CDR2 domain comprising the amino acid sequence of SEQ ID NO: 106, and a CDR1 domain comprising the amino acid sequence of SEQ ID NO: 105, and a light chain variable region comprising a CDR3 domain comprising the amino acid sequence of SEQ ID NO: 110, a CDR2 domain comprising the amino acid sequence of SEQ ID NO: 109, and a CDR1 domain comprising the amino acid sequence of SEQ ID NO: 108. In further embodiments, disclosed herein is an antibody having a heavy chain variable region comprising the amino acid sequence of SEQ ID NO: 101 and a light chain variable region comprising the amino acid sequence of SEQ ID NO: 102.

In some embodiments, an anti-CDCP1 antibody, or antigen-binding portion thereof, comprises a heavy chain comprising an amino acid sequence set forth in SEQ ID NO: 101, or a sequence having at least 90%, 95%, 96%, 97%, 98%, or 99% identity to SEQ ID NO: 101, and/or a light chain comprising an amino acid sequence set forth in SEQ ID NO: 102, or a sequence having at least 90%, 95%, 96%, 97%, 98%, or 99% identity to SEQ ID NO: 102.

In one embodiment, an anti-CDCP1 antibody, or antigen binding portion thereof, is the human antibody 41A9. The 41A9 antibody comprises a heavy chain variable region comprising a CDR3 domain comprising the amino acid sequence of SEQ ID NO: 127, a CDR2 domain comprising the amino acid sequence of SEQ ID NO: 126, and a CDR1 domain comprising the amino acid sequence of SEQ ID NO: 125, and a light chain variable region comprising a CDR3 domain comprising the amino acid sequence of SEQ ID NO: 130, a CDR2 domain comprising the amino acid sequence of SEQ ID NO: 129, and a CDR1 domain comprising the amino acid sequence of SEQ ID NO: 128. In further embodiments, disclosed herein is an antibody having a heavy chain variable region comprising the amino acid sequence of SEQ ID NO: 121 and a light chain variable region comprising the amino acid sequence of SEQ ID NO: 122.

In some embodiments, an anti-CDCP1 antibody, or antigen-binding portion thereof, comprises a heavy chain comprising an amino acid sequence set forth in SEQ ID NO: 121, or a sequence having at least 90%, 95%, 96%, 97%, 98%, or 99% identity to SEQ ID NO: 121, and/or a light chain comprising an amino acid sequence set forth in SEQ ID NO: 122, or a sequence having at least 90%, 95%, %%, 97%, 98%, or 99% identity to SEQ ID NO: 122.

In one embodiment, an anti-CDCP1 antibody, or antigen binding portion thereof, is the human antibody 3B111. The 3B11 antibody comprises a heavy chain variable region comprising a CDR3 domain comprising the amino acid sequence of SEQ ID NO: 47, a CDR2 domain comprising the amino acid sequence of SEQ ID NO: 46, and a CDR1 domain comprising the amino acid sequence of SEQ ID NO: 45, and a light chain variable region comprising a CDR3 domain comprising the amino acid sequence of SEQ ID NO: 50, a CDR2 domain comprising the amino acid sequence of SEQ ID NO: 49, and a CDR1 domain comprising the amino acid sequence of SEQ ID NO: 48. In further embodiments, disclosed herein is an antibody having a heavy chain variable region comprising the amino acid sequence of SEQ ID NO: 41 and a light chain variable region comprising the amino acid sequence of SEQ ID NO: 42.

In some embodiments, an anti-CDCP1 antibody, or antigen-binding portion thereof, comprises a heavy chain comprising an amino acid sequence set forth in SEQ ID NO: 41, or a sequence having at least 90%, 95%, 96%, 97%, 98%, or 99% identity to SEQ ID NO: 41, and/or a light chain comprising an amino acid sequence set forth in SEQ ID NO: 42, or a sequence having at least 90%, 95%, 96%, 97%, 98%, or 99% identity to SEQ ID NO: 42.

In one embodiment, an anti-CDCP1 antibody, or antigen binding portion thereof, is the human antibody 47G7. The 47G7 antibody comprises a heavy chain variable region comprising a CDR3 domain comprising the amino acid sequence of SEQ ID NO: 77, a CDR2 domain comprising the amino acid sequence of SEQ ID NO: 76, and a CDR1 domain comprising the amino acid sequence of SEQ ID NO: 75, and a light chain variable region comprising a CDR3 domain comprising the amino acid sequence of SEQ ID NO: 80, a CDR2 domain comprising the amino acid sequence of SEQ ID NO: 79, and a CDR1 domain comprising the amino acid sequence of SEQ ID NO: 78. In further embodiments, disclosed herein is an antibody having a heavy chain variable region comprising the amino acid sequence of SEQ ID NO: 71 and a light chain variable region comprising the amino acid sequence of SEQ ID NO: 72.

In some embodiments, an anti-CDCP1 antibody, or antigen-binding portion thereof, comprises a heavy chain comprising an amino acid sequence set forth in SEQ ID NO: 71, or a sequence having at least 90%, 95%, 96%, 97%, 98%, or 99% identity to SEQ ID NO: 71, and/or a light chain comprising an amino acid sequence set forth in SEQ ID NO: 72, or a sequence having at least 90%, 95%, 96%, 97%, 98%, or 99% identity to SEQ ID NO: 72.

The foregoing anti-CDCP1 antibody CDR sequences establish a novel family of CDCP1 binding proteins, isolated in accordance with this disclosure, and comprising antigen binding polypeptides that include the CDR sequences listed in FIGS. 15, 18, and 20, as well as the Sequence Summary.

In some embodiments, the anti-CDCP1 antibodies of the present invention are human or humanized. In some embodiments, the anti-CDCP1 antibodies specifically bind to the same epitope as the specific antibodies disclosed herein.

The disclosure also provides antibodies that specifically bind to specific epitopes on a target CDCP1 molecule. Likewise, the disclosure provides epitopes useful for identifying the antibodies that specifically bind to a target CDCP1 molecule comprising the epitope.

Epitope mapping can be done using standard methods. For example, phage display is an in vitro selection technique in which a peptide is genetically fused to a coat protein of a bacteriophage resulting in display of a fused protein on the exterior of the virion. Biopanning of these virions by incubating the pool of phage displayed variants with a specific antibody of interest, which has been immobilized on a plate. The unbound phage is then washed away and the specifically bound phage is then eluted. The eluted phage is then amplified in *E. coli* and the process is repeated, resulting in enrichment of the phage pool in favor of the tightest binding sequences.

An advantage of this technology is that it allows for the screening of greater than $10^9$ sequences in an unbiased way. Phage display is especially useful if the immunogen is unknown or a large protein fragment. One of the limitations of phage display includes cross-contamination between phage particles that can enrich sequences that do not specifically bind to the antibody. Additionally, sequences that are not found in nature will be present in the phage displayed peptide library. These sequences may not resemble the immunizing peptide at all and may bind tightly to the antibody of interest. Retrieving sequences that do not resemble the immunizing peptide can be very confounding and it is difficult to decipher whether these peptides are contamination or unnatural peptides with high binding affinity to the antibody of interest.

In another aspect, the present disclosure features polynucleotide sequences that comprise or consist of the sequences as shown in FIG. 19, and/or amino acid sequences that comprise or consist of the sequences as shown in FIG. 18 and FIG. 20.

In one aspect, the disclosure relates to an antibody or antigen-binding fragment thereof that binds to CUB domain-containing protein 1 (CDCP1) having a heavy chain variable region (VH) including complementarity determining regions (CDRs) 1, 2, 3, wherein the CDR1 region includes an amino acid sequence that is at least 80%, 90%, 92%, 95%, 97%, 98%, 99%, or 100% identical to a selected VH CDR1 amino acid sequence, the CDR2 region includes an amino acid sequence that is at least 80%, 90%, 92%, 95%, 97%, 98%, 99%, or 100% identical to a selected VH CDR2 amino acid sequence, and the CDR3 region includes an amino acid sequence that is at least 8(0%, 90%, 92%, 95%, 97%, 98%, 99%, or 1(00% identical to a selected VH CDR3 amino acid sequence, and a light chain variable region (VL) comprising CDRs 1, 2, 3, wherein the CDR1 region comprises an amino acid sequence that is at least 80%, 90%, 92%, 95%, 97%, 98%, 99%, or 100% identical to a selected VL CDR1 amino acid sequence, the CDR2 region comprises an amino acid sequence that is at least 80%, 90%, 92%, 95%, 97%, 98%, 99%, or 100% identical to a selected VL CDR2 amino acid sequence, and the CDR3 region comprises an amino acid sequence that is at least 80%, 90%, 92%, 95%, 97%, 98%, 99%, or 1(00% identical to a selected VL CDR3 amino acid sequence, wherein the selected VH CDRs 1, 2, 3 amino acid sequences and the selected VL CDRs, 1, 2, 3 amino acid sequences are one of the following:

(1) the selected VH CDRs 1, 2, 3 amino acid sequences are set forth in SEQ ID NOs: 5, 6, 7, respectively, and the selected VL CDRs 1, 2, 3 amino acid sequences are set forth in SEQ ID NOs: 8, 9, 10, respectively;
(2) the selected VH CDRs 1, 2, 3 amino acid sequences are set forth in SEQ ID NOs: 15, 16, 17, respectively, and the selected VL CDRs 1, 2, 3 amino acid sequences are set forth in SEQ ID NOs: 18, 19, 20, respectively;
(3) the selected VH CDRs 1, 2, 3 amino acid sequences are set forth in SEQ ID NOs: 25, 26, 27, respectively, and the selected VL CDRs 1, 2, 3 amino acid sequences are set forth in SEQ ID NOs: 28, 29, 30, respectively;
(4) the selected VH CDRs 1, 2, 3 amino acid sequences are set forth in SEQ ID NOs: 35, 36, 37, respectively, and the selected VL CDRs 1, 2, 3 amino acid sequences are set forth in SEQ ID NOs: 38, 39, 40, respectively;

(5) the selected VH CDRs 1, 2, 3 amino acid sequences are set forth in SEQ ID NOs: 45, 46, 47, respectively, and the selected VL CDRs 1, 2, 3 amino acid sequences are set forth in SEQ ID NOs: 48, 49, 50, respectively;

(6) the selected VH CDRs 1, 2, 3 amino acid sequences are set forth in SEQ ID NOs: 55, 56, 57, respectively, and the selected VL CDRs 1, 2, 3 amino acid sequences are set forth in SEQ ID NOs: 58, 59, 60, respectively;

(7) the selected VH CDRs 1, 2, 3 amino acid sequences are set forth in SEQ ID NOs: 65, 66, 67, respectively, and the selected VL CDRs 1, 2, 3 amino acid sequences are set forth in SEQ ID NOs: 68, 69, 70, respectively;

(8) the selected VH CDRs 1, 2, 3 amino acid sequences are set forth in SEQ ID NOs: 75, 76, 77, respectively, and the selected VL CDRs 1, 2, 3 amino acid sequences are set forth in SEQ ID NOs: 78, 79, 80, respectively;

(9) the selected VH CDRs 1, 2, 3 amino acid sequences are set forth in SEQ ID NOs: 85, 86, 87, respectively, and the selected VL CDRs 1, 2, 3 amino acid sequences are set forth in SEQ ID NOs: 88, 89, 90, respectively;

(10) the selected VH CDRs 1, 2, 3 amino acid sequences are set forth in SEQ ID NOs: 95, 96, 97, respectively, and the selected VL CDRs 1, 2, 3 amino acid sequences are set forth in SEQ ID NOs: 98, 99, 100, respectively;

(11) the selected VH CDRs 1, 2, 3 amino acid sequences are set forth in SEQ ID NOs: 105, 106, 107, respectively, and the selected VL CDRs 1, 2, 3 amino acid sequences are set forth in SEQ ID NOs: 108, 109, 110, respectively;

(12) the selected VH CDRs 1, 2, 3 amino acid sequences are set forth in SEQ ID NOs: 115, 116, 117, respectively, and the selected VL CDRs 1, 2, 3 amino acid sequences are set forth in SEQ ID NOs: 118, 119, 120, respectively;

(13) the selected VH CDRs 1, 2, 3 amino acid sequences are set forth in SEQ ID NOs: 125, 126, 127, respectively, and the selected VL CDRs 1, 2, 3 amino acid sequences are set forth in SEQ ID NOs: 128, 129, 130, respectively;

(14) the selected VH CDRs 1, 2, 3 amino acid sequences are set forth in SEQ ID NOs: 135, 136, 137, respectively, and the selected VL CDRs 1, 2, 3 amino acid sequences are set forth in SEQ ID NOs: 138, 139, 140, respectively;

(15) the selected VH CDRs 1, 2, 3 amino acid sequences are set forth in SEQ ID NOs: 145, 146, 147, respectively, and the selected VL CDRs 1, 2, 3 amino acid sequences are set forth in SEQ ID NOs: 148, 149, 150, respectively;

(16) the selected VH CDRs 1, 2, 3 amino acid sequences are set forth in SEQ ID NOs: 155, 156, 157, respectively, and the selected VL CDRs 1, 2, 3 amino acid sequences are set forth in SEQ ID NOs: 158, 159, 160, respectively;

(17) the selected VH CDRs 1, 2, 3 amino acid sequences are set forth in SEQ ID NOs: 165, 166, 167, respectively, and the selected VL CDRs 1, 2, 3 amino acid sequences are set forth in SEQ ID NOs: 168, 169, 170, respectively;

(18) the selected VH CDRs 1, 2, 3 amino acid sequences are set forth in SEQ ID NOs: 175, 176, 177, respectively, and the selected VL CDRs 1, 2, 3 amino acid sequences are set forth in SEQ ID NOs: 178, 179, 180, respectively;

(19) the selected VH CDRs 1, 2, 3 amino acid sequences are set forth in SEQ ID NOs: 185, 186, 187, respectively, and the selected VL CDRs 1, 2, 3 amino acid sequences are set forth in SEQ ID NOs: 188, 189, 190, respectively;

(20) the selected VH CDRs 1, 2, 3 amino acid sequences are set forth in SEQ ID NOs: 195, 196, 197, respectively, and the selected VL CDRs 1, 2, 3 amino acid sequences are set forth in SEQ ID NOs: 198, 199, 200, respectively;

(21) the selected VH CDRs 1, 2, 3 amino acid sequences are set forth in SEQ ID NOs: 205, 206, 207, respectively, and the selected VL CDRs 1, 2, 3 amino acid sequences are set forth in SEQ ID NOs: 208, 209, 210, respectively;

(22) the selected VH CDRs 1, 2, 3 amino acid sequences are set forth in SEQ ID NOs: 215, 216, 217, respectively, and the selected VL CDRs 1, 2, 3 amino acid sequences are set forth in SEQ ID NOs: 218, 219, 220, respectively;

(23) the selected VH CDRs 1, 2, 3 amino acid sequences are set forth in SEQ ID NOs: 225, 226, 227, respectively, and the selected VL CDRs 1, 2, 3 amino acid sequences are set forth in SEQ ID NOs: 228, 229, 230, respectively;

(24) the selected VH CDRs 1, 2, 3 amino acid sequences are set forth in SEQ ID NOs: 235, 236, 237, respectively, and the selected VL CDRs 1, 2, 3 amino acid sequences are set forth in SEQ ID NOs: 238, 239, 240, respectively;

(25) the selected VH CDRs 1, 2, 3 amino acid sequences are set forth in SEQ ID NOs: 245, 246, 247, respectively, and the selected VL CDRs 1, 2, 3 amino acid sequences are set forth in SEQ ID NOs: 248, 249, 250, respectively;

(26) the selected VH CDRs 1, 2, 3 amino acid sequences are set forth in SEQ ID NOs: 255, 256, 257, respectively, and the selected VL CDRs 1, 2, 3 amino acid sequences are set forth in SEQ ID NOs: 258, 259, 260, respectively;

(27) the selected VH CDRs 1, 2, 3 amino acid sequences are set forth in SEQ ID NOs: 265, 266, 267, respectively, and the selected VL CDRs 1, 2, 3 amino acid sequences are set forth in SEQ ID NOs: 268, 269, 270, respectively;

(28) the selected VH CDRs 1, 2, 3 amino acid sequences are set forth in SEQ ID NOs: 275, 276, 277, respectively, and the selected VL CDRs 1, 2, 3 amino acid sequences are set forth in SEQ ID NOs: 278, 279, 280, respectively;

(29) the selected VH CDRs 1, 2, 3 amino acid sequences are set forth in SEQ ID NOs: 285, 286, 287, respectively, and the selected VL CDRs 1, 2, 3 amino acid sequences are set forth in SEQ ID NOs: 288, 289, 290, respectively;

(30) the selected VH CDRs 1, 2, 3 amino acid sequences are set forth in SEQ ID NOs: 295, 296, 297, respectively, and the selected VL CDRs 1, 2, 3 amino acid sequences are set forth in SEQ ID NOs: 298, 299, 300, respectively;

(31) the selected VH CDRs 1, 2, 3 amino acid sequences are set forth in SEQ ID NOs: 305, 306, 307, respectively, and the selected VL CDRs 1, 2, 3 amino acid sequences are set forth in SEQ ID NOs: 308, 309, 310, respectively;

(32) the selected VH CDRs 1, 2, 3 amino acid sequences are set forth in SEQ ID NOs: 315, 316, 317, respectively, and the selected VL CDRs 1, 2, 3 amino acid sequences are set forth in SEQ ID NOs: 318, 319, 320, respectively;

(33) the selected VH CDRs 1, 2, 3 amino acid sequences are set forth in SEQ ID NOs: 325, 326, 327, respectively, and the selected VL CDRs 1, 2, 3 amino acid sequences are set forth in SEQ ID NOs: 328, 329, 330, respectively;

(34) the selected VH CDRs 1, 2, 3 amino acid sequences are set forth in SEQ ID NOs: 335, 336, 337, respectively, and the selected VL CDRs 1, 2, 3 amino acid sequences are set forth in SEQ ID NOs: 338, 339, 340, respectively;

(35) the selected VH CDRs 1, 2, 3 amino acid sequences are set forth in SEQ ID NOs: 345, 346, 347, respectively, and the selected VL CDRs 1, 2, 3 amino acid sequences are set forth in SEQ ID NOs: 348, 349, 350, respectively;

(36) the selected VH CDRs 1, 2, 3 amino acid sequences are set forth in SEQ ID NOs: 355, 356, 357, respectively, and the selected VL CDRs 1, 2, 3 amino acid sequences are set forth in SEQ ID NOs: 358, 359, 360, respectively;

(37) the selected VH CDRs 1, 2, 3 amino acid sequences are set forth in SEQ ID NOs: 365, 366, 367, respectively, and the selected VL CDRs 1, 2, 3 amino acid sequences are set forth in SEQ ID NOs: 368, 369, 370, respectively;

(38) the selected VH CDRs 1, 2, 3 amino acid sequences are set forth in SEQ ID NOs: 375, 376, 377, respectively, and the selected VL CDRs 1, 2, 3 amino acid sequences are set forth in SEQ ID NOs: 378, 379, 380, respectively;

(39) the selected VH CDRs 1, 2, 3 amino acid sequences are set forth in SEQ ID NOs: 385, 386, 387, respectively, and the selected VL CDRs 1, 2, 3 amino acid sequences are set forth in SEQ ID NOs: 388, 389, 390, respectively; and

(40) the selected VH CDRs 1, 2, 3 amino acid sequences are set forth in SEQ ID NOs: 395, 396, 397, respectively, and the selected VL CDRs 1, 2, 3 amino acid sequences are set forth in SEQ ID NOs: 398, 399, 400, respectively, wherein the antibody or antigen-binding fragment thereof specifically binds to CUB domain-containing protein 1 (CDCP1).

In some embodiments, the antibody or antigen-binding fragment specifically binds to human CDCP1 and/or Cynomolgus CDCP1.

In some embodiments, the antibody or antigen-binding fragment has a dissociation constant ($K_d$) for human CDCP1 that is less than 10 nM, and/or a $K_d$ for Cynomolgus CDCP1 that is less than 10 nM.

In some embodiments, the antibody or antigen-binding fragment is a humanized antibody or antigen-binding fragment thereof.

The disclosure also provides a cDNA including a polynucleotide encoding a polypeptide comprising:

(1) an immunoglobulin heavy chain or a fragment thereof comprising a heavy chain variable region (VH) comprising complementarity determining regions (CDRs) 1, 2, and 3 with the amino acid sequences set forth in SEQ ID NOs: 5, 6, and 7, respectively, and wherein the VH when paired with a light chain variable region (VL) comprising the amino acid sequence set forth in SEQ ID NO: 2 binds to CDCP1;

(2) an immunoglobulin light chain or a fragment thereof comprising a VL comprising CDRs 1, 2, and 3 with the amino acid sequences set forth in SEQ ID NOs: 8, 9, and 10, respectively, and wherein the VL when paired with a VH comprising the amino acid sequence set forth in SEQ ID NO:1 binds to CDCP1;

(3) an immunoglobulin heavy chain or a fragment thereof comprising a VH comprising CDRs 1, 2, and 3 with the amino acid sequences set forth in SEQ ID NOs: 15, 16, and 17, respectively, and wherein the VH when paired with a VL comprising the amino acid sequence set forth in SEQ ID NO: 12 binds to CDCP1;

(4) an immunoglobulin light chain or a fragment thereof comprising a VL comprising CDRs 1, 2, and 3 with the amino acid sequences set forth in SEQ ID NOs: 18, 19, and 20, respectively, and wherein the VL when paired with a VH comprising the amino acid sequence set forth in SEQ ID NO: 11 binds to CDCP1;

(5) an immunoglobulin heavy chain or a fragment thereof comprising a VH comprising CDRs 1, 2, and 3 with the amino acid sequences set forth in SEQ ID NOs: 25, 26, and 27, respectively, and wherein the VH when paired with a VL comprising the amino acid sequence set forth in SEQ ID NO: 22 binds to CDCP1;

(6) an immunoglobulin light chain or a fragment thereof comprising a VL comprising CDRs 1, 2, and 3 with the amino acid sequences set forth in SEQ ID NOs: 28, 29, and 30, respectively, and wherein the VL when paired with a VH comprising the amino acid sequence set forth in SEQ ID NO: 21 binds to CDCP1;

(7) an immunoglobulin heavy chain or a fragment thereof comprising a VH comprising CDRs 1, 2, and 3 with the amino acid sequences set forth in SEQ ID NOs: 35, 36, and 37, respectively, and wherein the VH when paired with a VL comprising the amino acid sequence set forth in SEQ ID NO: 32 binds to CDCP1;

(8) an immunoglobulin light chain or a fragment thereof comprising a VL comprising CDRs 1, 2, and 3 with the amino acid sequences set forth in SEQ ID NOs: 38, 39, and 40, respectively, and wherein the VL when paired with a VH comprising the amino acid sequence set forth in SEQ ID NO: 31 binds to CDCP1;

(9) an immunoglobulin heavy chain or a fragment thereof comprising a VH comprising CDRs 1, 2, and 3 with the amino acid sequences set forth in SEQ ID NOs: 45, 46, and 47, respectively, and wherein the VH when paired with a VL comprising the amino acid sequence set forth in SEQ ID NO: 42 binds to CDCP1;

(10) an immunoglobulin light chain or a fragment thereof comprising a VL comprising CDRs 1, 2, and 3 with the amino acid sequences set forth in SEQ ID NOs: 48, 49, and 50, respectively, and wherein the VL when paired with a VH comprising the amino acid sequence set forth in SEQ ID NO: 41 binds to CDCP1;

(11) an immunoglobulin heavy chain or a fragment thereof comprising a VH comprising CDRs 1, 2, and 3 with the amino acid sequences set forth in SEQ ID NOs: 55, 56, and 57, respectively, and wherein the VH when paired with a VL comprising the amino acid sequence set forth in SEQ ID NO: 52 binds to CDCP1;

(12) an immunoglobulin light chain or a fragment thereof comprising a VL comprising CDRs 1, 2, and 3 with the amino acid sequences set forth in SEQ ID NOs: 58, 59, and 60, respectively, and wherein the VL when paired with a VH comprising the amino acid sequence set forth in SEQ ID NO: 51 binds to CDCP1;

(13) an immunoglobulin heavy chain or a fragment thereof comprising a VH comprising CDRs 1, 2, and 3 with the amino acid sequences set forth in SEQ ID NOs: 65, 66, and 67, respectively, and wherein the VH when paired with a VL comprising the amino acid sequence set forth in SEQ ID NO: 62 binds to CDCP1;

(14) an immunoglobulin light chain or a fragment thereof comprising a VL comprising CDRs 1, 2, and 3 with the amino acid sequences set forth in SEQ ID NOs: 68, 69, and 70, respectively, and wherein the VL when paired with a VH comprising the amino acid sequence set forth in SEQ ID NO: 61 binds to CDCP1;

(15) an immunoglobulin heavy chain or a fragment thereof comprising a VH comprising CDRs 1, 2, and 3 with the amino acid sequences set forth in SEQ ID NOs: 75, 76, and 77, respectively, and wherein the VH when paired with a VL comprising the amino acid sequence set forth in SEQ ID NO: 72 binds to CDCP1;

(16) an immunoglobulin light chain or a fragment thereof comprising a VL comprising CDRs 1, 2, and 3 with the amino acid sequences set forth in SEQ ID NOs: 78, 79, and 80, respectively, and wherein the VL when paired with a VH comprising the amino acid sequence set forth in SEQ ID NO: 71 binds to CDCP1;

(17) an immunoglobulin heavy chain or a fragment thereof comprising a VH comprising CDRs 1, 2, and 3 with the amino acid sequences set forth in SEQ ID NOs: 85, 86, and 87, respectively, and wherein the VH when paired with a VL comprising the amino acid sequence set forth in SEQ ID NO: 82 binds to CDCP1;

(18) an immunoglobulin light chain or a fragment thereof comprising a VL comprising CDRs 1, 2, and 3 with the amino acid sequences set forth in SEQ ID NOs: 88, 89, and 90, respectively, and wherein the VL when paired with a VH comprising the amino acid sequence set forth in SEQ ID NO: 81 binds to CDCP1;

(19) an immunoglobulin heavy chain or a fragment thereof comprising a VH comprising CDRs 1, 2, and 3 with the amino acid sequences set forth in SEQ ID NOs: 95, 96, and 97, respectively, and wherein the VH when paired with a VL comprising the amino acid sequence set forth in SEQ ID NO: 92 binds to CDCP1;

(20) an immunoglobulin light chain or a fragment thereof comprising a VL comprising CDRs 1, 2, and 3 with the amino acid sequences set forth in SEQ ID NOs: 98, 99, and 100, respectively, and wherein the VL when paired with a VH comprising the amino acid sequence set forth in SEQ ID NO: 91 binds to CDCP1;

(21) an immunoglobulin heavy chain or a fragment thereof comprising a VH comprising CDRs 1, 2, and 3 with the amino acid sequences set forth in SEQ ID NOs: 105, 106, and 107, respectively, and wherein the VH when paired with a VL comprising the amino acid sequence set forth in SEQ ID NO: 102 binds to CDCP1;

(22) an immunoglobulin light chain or a fragment thereof comprising a VL comprising CDRs 1, 2, and 3 with the amino acid sequences set forth in SEQ ID NOs: 108, 10), and 110, respectively, and wherein the VL when paired with a VH comprising the amino acid sequence set forth in SEQ ID NO: 101 binds to CDCP1;

(23) an immunoglobulin heavy chain or a fragment thereof comprising a VH comprising CDRs 1, 2, and 3 with the amino acid sequences set forth in SEQ ID NOs: 115, 116, and 117, respectively, and wherein the VH when paired with a VL comprising the amino acid sequence set forth in SEQ ID NO: 112 binds to CDCP1;

(24) an immunoglobulin light chain or a fragment thereof comprising a VL comprising CDRs 1, 2, and 3 with the amino acid sequences set forth in SEQ ID NOs: 118, 119, and 120, respectively, and wherein the VL when paired with a VH comprising the amino acid sequence set forth in SEQ ID NO: 111 binds to CDCP1;

(25) an immunoglobulin heavy chain or a fragment thereof comprising a VH comprising CDRs 1, 2, and 3 with the amino acid sequences set forth in SEQ ID NOs: 125, 126, and 127, respectively, and wherein the VH when paired with a VL comprising the amino acid sequence set forth in SEQ ID NO: 122 binds to CDCP1;

(26) an immunoglobulin light chain or a fragment thereof comprising a VL comprising CDRs 1, 2, and 3 with the amino acid sequences set forth in SEQ ID NOs: 128, 129, and 130, respectively, and wherein the VL when paired with a VH comprising the amino acid sequence set forth in SEQ ID NO: 121 binds to CDCP1;

(27) an immunoglobulin heavy chain or a fragment thereof comprising a VH comprising CDRs 1, 2, and 3 with the amino acid sequences set forth in SEQ ID NOs: 135, 136, and 137, respectively, and wherein the VH when paired with a VL comprising the amino acid sequence set forth in SEQ ID NO: 132 binds to CDCP1;

(28) an immunoglobulin light chain or a fragment thereof comprising a VL comprising CDRs 1, 2, and 3 with the amino acid sequences set forth in SEQ ID NOs: 138, 139, and 140, respectively, and wherein the VL when paired with a VH comprising the amino acid sequence set forth in SEQ ID NO: 131 binds to CDCP1;

(29) an immunoglobulin heavy chain or a fragment thereof comprising a VH comprising CDRs 1, 2, and 3 with the amino acid sequences set forth in SEQ ID NOs: 145, 146, and 147, respectively, and wherein the VH when paired with a VL comprising the amino acid sequence set forth in SEQ ID NO: 142 binds to CDCP1;

(30) an immunoglobulin light chain or a fragment thereof comprising a VL comprising CDRs 1, 2, and 3 with the amino acid sequences set forth in SEQ ID NOs: 148, 149, and 150, respectively, and wherein the VL when paired with a VH comprising the amino acid sequence set forth in SEQ ID NO: 141 binds to CDCP1;

(31) an immunoglobulin heavy chain or a fragment thereof comprising a VH comprising CDRs 1, 2, and 3 with the amino acid sequences set forth in SEQ ID NOs: 155, 156, and 157, respectively, and wherein the VH when paired with a VL comprising the amino acid sequence set forth in SEQ ID NO: 152 binds to CDCP1;

(32) an immunoglobulin light chain or a fragment thereof comprising a VL comprising CDRs 1, 2, and 3 with the amino acid sequences set forth in SEQ ID NOs: 158, 159, and 160, respectively, and wherein the VL when paired with a VH comprising the amino acid sequence set forth in SEQ ID NO: 151 binds to CDCP1;

(33) an immunoglobulin heavy chain or a fragment thereof comprising a VH comprising CDRs 1, 2, and 3 with the amino acid sequences set forth in SEQ ID NOs: 165, 166, and 167, respectively, and wherein the VH when paired with a VL comprising the amino acid sequence set forth in SEQ ID NO: 162 binds to CDCP1;

(34) an immunoglobulin light chain or a fragment thereof comprising a VL comprising CDRs 1, 2, and 3 with the amino acid sequences set forth in SEQ ID NOs: 168, 169, and 170, respectively, and wherein the VL when paired with a VH comprising the amino acid sequence set forth in SEQ ID NO: 161 binds to CDCP1;

(35) an immunoglobulin heavy chain or a fragment thereof comprising a VH comprising CDRs 1, 2, and 3 with the amino acid sequences set forth in SEQ ID NOs: 175, 176, and 177, respectively, and wherein the VH when paired with a VL comprising the amino acid sequence set forth in SEQ ID NO: 172 binds to CDCP1,

(36) an immunoglobulin light chain or a fragment thereof comprising a VL comprising CDRs 1, 2, and 3 with the amino acid sequences set forth in SEQ ID NOs: 178, 179, and 180, respectively, and wherein the VL when paired with a VH comprising the amino acid sequence set forth in SEQ ID NO: 171 binds to CDCP1;

(37) an immunoglobulin heavy chain or a fragment thereof comprising a VH comprising CDRs 1, 2, and 3 with the amino acid sequences set forth in SEQ ID NOs: 185, 186, and 187, respectively, and wherein the VH when paired with a VL comprising the amino acid sequence set forth in SEQ ID NO: 182 binds to CDCP1;

(38) an immunoglobulin light chain or a fragment thereof comprising a VL comprising CDRs 1, 2, and 3 with the amino acid sequences set forth in SEQ ID NOs: 188, 189, and 190, respectively, and wherein the VL when paired with a VH comprising the amino acid sequence set forth in SEQ ID NO: 181 binds to CDCP1;

(39) an immunoglobulin heavy chain or a fragment thereof comprising a VH comprising CDRs 1, 2, and 3 with the amino acid sequences set forth in SEQ ID NOs: 195, 196, and 197, respectively, and wherein the VH when paired with a VL comprising the amino acid sequence set forth in SEQ ID NO: 192 binds to CDCP1;

(40) an immunoglobulin light chain or a fragment thereof comprising a VL comprising CDRs 1, 2, and 3 with the amino acid sequences set forth in SEQ ID NOs: 198, 199, and 200, respectively, and wherein the VL when paired with a VH comprising the amino acid sequence set forth in SEQ ID NO: 191 binds to CDCP1;

(41) an immunoglobulin heavy chain or a fragment thereof comprising a VH comprising CDRs 1, 2, and 3 with the amino acid sequences set forth in SEQ ID NOs: 205, 206, and 207, respectively, and wherein the VH when paired with a VL comprising the amino acid sequence set forth in SEQ ID NO: 202 binds to CDCP1;

(42) an immunoglobulin light chain or a fragment thereof comprising a VL comprising CDRs 1, 2, and 3 with the amino acid sequences set forth in SEQ ID NOs: 208, 209, and 210, respectively, and wherein the VL when paired with a VH comprising the amino acid sequence set forth in SEQ ID NO: 201 binds to CDCP1;

(43) an immunoglobulin heavy chain or a fragment thereof comprising a VH comprising CDRs 1, 2, and 3 with the amino acid sequences set forth in SEQ ID NOs: 215, 216, and 217, respectively, and wherein the VH when paired with a VL comprising the amino acid sequence set forth in SEQ ID NO: 212 binds to CDCP1;

(44) an immunoglobulin light chain or a fragment thereof comprising a VL comprising CDRs 1, 2, and 3 with the amino acid sequences set forth in SEQ ID NOs: 218, 219, and 220, respectively, and wherein the VL when paired with a VH comprising the amino acid sequence set forth in SEQ ID NO: 211 binds to CDCP1;

(45) an immunoglobulin heavy chain or a fragment thereof comprising a VH comprising CDRs 1, 2, and 3 with the amino acid sequences set forth in SEQ ID NOs: 225, 226, and 227, respectively, and wherein the VH when paired with a VL comprising the amino acid sequence set forth in SEQ ID NO: 222 binds to CDCP1;

(46) an immunoglobulin light chain or a fragment thereof comprising a VL comprising CDRs 1, 2, and 3 with the amino acid sequences set forth in SEQ ID NOs: 228, 229, and 230, respectively, and wherein the VL when paired with a VH comprising the amino acid sequence set forth in SEQ ID NO: 221 binds to CDCP1;

(47) an immunoglobulin heavy chain or a fragment thereof comprising a VH comprising CDRs 1, 2, and 3 with the amino acid sequences set forth in SEQ ID NOs: 235, 236, and 237, respectively, and wherein the VH when paired with a VL comprising the amino acid sequence set forth in SEQ ID NO: 232 binds to CDCP1;

(48) an immunoglobulin light chain or a fragment thereof comprising a VL comprising CDRs 1, 2, and 3 with the amino acid sequences set forth in SEQ ID NOs: 238, 239, and 240, respectively, and wherein the VL when paired with a VH comprising the amino acid sequence set forth in SEQ ID NO: 231 binds to CDCP1;

(49) an immunoglobulin heavy chain or a fragment thereof comprising a VH comprising CDRs 1, 2, and 3 with the amino acid sequences set forth in SEQ ID NOs: 245, 246, and 247, respectively, and wherein the VH when paired with a VL comprising the amino acid sequence set forth in SEQ ID NO: 242 binds to CDCP1;

(50) an immunoglobulin light chain or a fragment thereof comprising a VL comprising CDRs 1, 2, and 3 with the amino acid sequences set forth in SEQ ID NOs: 248, 249, and 250, respectively, and wherein the VL when paired with a VH comprising the amino acid sequence set forth in SEQ ID NO: 241 binds to CDCP1,

(51) an immunoglobulin heavy chain or a fragment thereof comprising a VH comprising CDRs 1, 2, and 3 with the amino acid sequences set forth in SEQ ID NOs: 255, 256, and 257, respectively, and wherein the VH when paired with a VL comprising the amino acid sequence set forth in SEQ ID NO: 252 binds to CDCP1;

(52) an immunoglobulin light chain or a fragment thereof comprising a VL comprising CDRs 1, 2, and 3 with the amino acid sequences set forth in SEQ ID NOs: 258, 259, and 260, respectively, and wherein the VL when paired with a VH comprising the amino acid sequence set forth in SEQ ID NO: 251 binds to CDCP1;

(53) an immunoglobulin heavy chain or a fragment thereof comprising a VH comprising CDRs 1, 2, and 3 with the amino acid sequences set forth in SEQ ID NOs: 265, 266, and 267, respectively, and wherein the VH when paired with a VL comprising the amino acid sequence set forth in SEQ ID NO: 262 binds to CDCP1;

(54) an immunoglobulin light chain or a fragment thereof comprising a VL comprising CDRs 1, 2, and 3 with the amino acid sequences set forth in SEQ ID NOs: 268, 269, and 270, respectively, and wherein the VL when paired with a VH comprising the amino acid sequence set forth in SEQ ID NO: 261 binds to CDCP1,

(55) an immunoglobulin heavy chain or a fragment thereof comprising a VH comprising CDRs 1, 2, and 3 with the amino acid sequences set forth in SEQ ID NOs: 275, 276, and 277, respectively, and wherein the VH when paired with a VL comprising the amino acid sequence set forth in SEQ ID NO: 272 binds to CDCP1;

(56) an immunoglobulin light chain or a fragment thereof comprising a VL comprising CDRs 1, 2, and 3 with the amino acid sequences set forth in SEQ ID NOs: 278, 279, and 280, respectively, and wherein the VL when paired with a VH comprising the amino acid sequence set forth in SEQ ID NO: 271 binds to CDCP1;

(57) an immunoglobulin heavy chain or a fragment thereof comprising a VH comprising CDRs 1, 2, and 3 with the amino acid sequences set forth in SEQ ID NOs: 285, 286, and 287, respectively, and wherein the VH when paired with a VL comprising the amino acid sequence set forth in SEQ ID NO: 282 binds to CDCP1;

(58) an immunoglobulin light chain or a fragment thereof comprising a VL comprising CDRs 1, 2, and 3 with the amino acid sequences set forth in SEQ ID NOs: 288, 289, and 290, respectively, and wherein the VL when paired with a VH comprising the amino acid sequence set forth in SEQ ID NO: 281 binds to CDCP1;

(59) an immunoglobulin heavy chain or a fragment thereof comprising a VH comprising CDRs 1, 2, and 3 with the amino acid sequences set forth in SEQ ID NOs: 295, 296, and 297, respectively, and wherein the VH when paired with a VL comprising the amino acid sequence set forth in SEQ ID NO: 292 binds to CDCP1;

(60) an immunoglobulin light chain or a fragment thereof comprising a VL comprising CDRs 1, 2, and 3 with the amino acid sequences set forth in SEQ ID NOs: 298, 299, and 300, respectively, and wherein the VL when paired with a VH comprising the amino acid sequence set forth in SEQ ID NO: 291 binds to CDCP1;

(61) an immunoglobulin heavy chain or a fragment thereof comprising a VH comprising CDRs 1, 2, and 3 with the amino acid sequences set forth in SEQ ID NOs: 305, 306, and 307, respectively, and wherein the VH when paired with a VL comprising the amino acid sequence set forth in SEQ ID NO: 302 binds to CDCP1;

(62) an immunoglobulin light chain or a fragment thereof comprising a VL comprising CDRs 1, 2, and 3 with the amino acid sequences set forth in SEQ ID NOs: 308, 309, and 310, respectively, and wherein the VL when paired with a VH comprising the amino acid sequence set forth in SEQ ID NO: 301 binds to CDCP1;

(63) an immunoglobulin heavy chain or a fragment thereof comprising a VH comprising CDRs 1, 2, and 3 with the amino acid sequences set forth in SEQ ID NOs: 315, 316, and 317, respectively, and wherein the VH when paired with a VL comprising the amino acid sequence set forth in SEQ ID NO: 312 binds to CDCP1;

(64) an immunoglobulin light chain or a fragment thereof comprising a VL comprising CDRs 1, 2, and 3 with the amino acid sequences set forth in SEQ ID NOs: 318, 319, and 320, respectively, and wherein the VL when paired with a VH comprising the amino acid sequence set forth in SEQ ID NO: 311 binds to CDCP1;

(65) an immunoglobulin heavy chain or a fragment thereof comprising a VH comprising CDRs 1, 2, and 3 with the amino acid sequences set forth in SEQ ID NOs: 325, 326, and 327, respectively, and wherein the VH when paired with a VL comprising the amino acid sequence set forth in SEQ ID NO: 322 binds to CDCP1;

(66) an immunoglobulin light chain or a fragment thereof comprising a VL comprising CDRs 1, 2, and 3 with the amino acid sequences set forth in SEQ ID NOs: 328, 329, and 330, respectively, and wherein the VL when paired with a VH comprising the amino acid sequence set forth in SEQ ID NO: 321 binds to CDCP1;

(67) an immunoglobulin heavy chain or a fragment thereof comprising a VH comprising CDRs 1, 2, and 3 with the amino acid sequences set forth in SEQ ID NOs: 335, 336, and 337, respectively, and wherein the VH when paired with a VL comprising the amino acid sequence set forth in SEQ ID NO: 332 binds to CDCP1;

(68) an immunoglobulin light chain or a fragment thereof comprising a VL comprising CDRs 1, 2, and 3 with the amino acid sequences set forth in SEQ ID NOs: 338, 339, and 340, respectively, and wherein the VL when paired with a VH comprising the amino acid sequence set forth in SEQ ID NO: 331 binds to CDCP1;

(69) an immunoglobulin heavy chain or a fragment thereof comprising a VH comprising CDRs 1, 2, and 3 with the amino acid sequences set forth in SEQ ID NOs: 345, 346, and 347, respectively, and wherein the VH when paired with a VL comprising the amino acid sequence set forth in SEQ ID NO: 342 binds to CDCP1;

(70) an immunoglobulin light chain or a fragment thereof comprising a VL comprising CDRs 1, 2, and 3 with the amino acid sequences set forth in SEQ ID NOs: 348, 349, and 350, respectively, and wherein the VL when paired with a VH comprising the amino acid sequence set forth in SEQ ID NO: 341 binds to CDCP1;

(71) an immunoglobulin heavy chain or a fragment thereof comprising a VH comprising CDRs 1, 2, and 3 with the amino acid sequences set forth in SEQ ID NOs: 355, 356, and 357, respectively, and wherein the VH when paired with a VL comprising the amino acid sequence set forth in SEQ ID NO: 352 binds to CDCP1;

(72) an immunoglobulin light chain or a fragment thereof comprising a VL comprising CDRs 1, 2, and 3 with the amino acid sequences set forth in SEQ ID NOs: 358, 359, and 360, respectively, and wherein the VL when paired with a VH comprising the amino acid sequence set forth in SEQ ID NO: 351 binds to CDCP1;

(73) an immunoglobulin heavy chain or a fragment thereof comprising a VH comprising CDRs 1, 2, and 3 with the amino acid sequences set forth in SEQ ID NOs: 365, 366, and 367, respectively, and wherein the VH when paired with a VL comprising the amino acid sequence set forth in SEQ ID NO: 362 binds to CDCP1;

(74) an immunoglobulin light chain or a fragment thereof comprising a VL comprising CDRs 1, 2, and 3 with the amino acid sequences set forth in SEQ ID NOs: 368, 369, and 370, respectively, and wherein the VL when paired with a VH comprising the amino acid sequence set forth in SEQ ID NO: 361 binds to CDCP1;

(75) an immunoglobulin heavy chain or a fragment thereof comprising a VH comprising CDRs 1, 2, and 3 with the amino acid sequences set forth in SEQ ID NOs: 375, 376, and 377, respectively, and wherein the VH when paired with a VL comprising the amino acid sequence set forth in SEQ ID NO: 372 binds to CDCP1;

(76) an immunoglobulin light chain or a fragment thereof comprising a VL comprising CDRs 1, 2, and 3 with the amino acid sequences set forth in SEQ ID NOs: 378, 379, and 380, respectively, and wherein the VL when paired with a VH comprising the amino acid sequence set forth in SEQ ID NO: 371 binds to CDCP1;

(77) an immunoglobulin heavy chain or a fragment thereof comprising a VH comprising CDRs 1, 2, and 3 with the amino acid sequences set forth in SEQ ID NOs: 385, 386, and 387, respectively, and wherein the VH when paired with a VL comprising the amino acid sequence set forth in SEQ ID NO: 382 binds to CDCP1;

(78) an immunoglobulin light chain or a fragment thereof comprising a VL comprising CDRs 1, 2, and 3 with the amino acid sequences set forth in SEQ ID NOs: 388, 389, and 390, respectively, and wherein the VL when paired with a VH comprising the amino acid sequence set forth in SEQ ID NO: 381 binds to CDCP1;

(79) an immunoglobulin heavy chain or a fragment thereof comprising a VH comprising CDRs 1, 2, and 3 with the amino acid sequences set forth in SEQ ID NOs: 395, 396, and 397, respectively, and wherein the VH when paired with a VL comprising the amino acid sequence set forth in SEQ ID NO: 392 binds to CDCP1; or

(80) an immunoglobulin light chain or a fragment thereof comprising a VL comprising CDRs 1, 2, and 3 with the amino acid sequences set forth in SEQ ID NOs: 398, 399, and 400, respectively, and wherein the VL when paired with a VH comprising the amino acid sequence set forth in SEQ ID NO: 391 binds to CDCP1.

In some embodiments, the VH when paired with a VL specifically binds to human CDCP1 and/or Cynomolgus CDCP1, and the VL when paired with a VH specifically binds to human CDCP1 and/or Cynomolgus CDCP1.

In some embodiments, the immunoglobulin heavy chain or the fragment thereof is a humanized immunoglobulin heavy chain or a fragment thereof, and the immunoglobulin light chain or the fragment thereof is a humanized immunoglobulin light chain or a fragment thereof.

In another aspect, the disclosure provides an antibody or antigen-binding fragment thereof that binds to CDCP1 having a heavy chain variable region (VH) comprising an amino acid sequence that is at least 80%, 90%, 92%, 95%, 97%, 98%, 99%, or 100% identical to a selected VH sequence, and a light chain variable region (VL) comprising an amino acid sequence that is at least 80%, 90%, 92%, 95%, 97%, 98%, 99%, or 100% identical to a selected VL sequence, wherein the selected VH sequence and the selected VL sequence are one of the following:

(1) the selected VH sequence is SEQ ID NO: 1, and the selected VL sequence is SEQ ID NO: 2;

(2) the selected VH sequence is SEQ ID NO: 11, and the selected VL sequence is SEQ ID NO: 12;

(3) the selected VH sequence is SEQ ID NO: 21, and the selected VL sequence is SEQ ID NO: 22;

(4) the selected VH sequence is SEQ ID NO: 31, and the selected VL sequence is SEQ ID NO: 32;

(5) the selected VH sequence is SEQ ID NO: 41, and the selected VL sequence is SEQ ID NO: 42;

(6) the selected VH sequence is SEQ ID NO: 51, and the selected VL sequence is SEQ ID NO: 52;

(7) the selected VH sequence is SEQ ID NO: 61, and the selected VL sequence is SEQ ID NO: 62;

(8) the selected VH sequence is SEQ ID NO: 71, and the selected VL sequence is SEQ ID NO: 72;

(9) the selected VH sequence is SEQ ID NO: 81, and the selected VL sequence is SEQ ID NO:82;

(10) the selected VH sequence is SEQ ID NO: 91, and the selected VL sequence is SEQ ID NO: 92;

(11) the selected VH sequence is SEQ ID NO: 101, and the selected VL sequence is SEQ ID NO: 102;

(12) the selected VH sequence is SEQ ID NO: 111, and the selected VL sequence is SEQ ID NO: 112;

(13) the selected VH sequence is SEQ ID NO: 121, and the selected VL sequence is SEQ ID NO: 122;

(14) the selected VH sequence is SEQ ID NO: 131, and the selected VL sequence is SEQ ID NO: 132;

(15) the selected VH sequence is SEQ ID NO: 141, and the selected VL sequence is SEQ ID NO: 142;

(16) the selected VH sequence is SEQ ID NO: 151, and the selected VL sequence is SEQ ID NO: 152;

(17) the selected VH sequence is SEQ ID NO: 161, and the selected VL sequence is SEQ ID NO: 162; and

(18) the selected VH sequence is SEQ ID NO: 171, and the selected VL sequence is SEQ ID NO: 172;

(19) the selected VH sequence is SEQ ID NO: 181, and the selected VL sequence is SEQ ID NO: 182;

(20) the selected VH sequence is SEQ ID NO: 191, and the selected VL sequence is SEQ ID NO: 192;

(21) the selected VH sequence is SEQ ID NO: 201, and the selected VL sequence is SEQ ID NO: 202;

(22) the selected VH sequence is SEQ ID NO: 211, and the selected VL sequence is SEQ ID NO: 212;

(23) the selected VH sequence is SEQ ID NO: 221, and the selected VL sequence is SEQ ID NO: 222;

(24) the selected VH sequence is SEQ ID NO: 231, and the selected VL sequence is SEQ ID NO: 232;

(25) the selected VH sequence is SEQ ID NO: 241, and the selected VL sequence is SEQ ID NO: 242;

(26) the selected VH sequence is SEQ ID NO: 251, and the selected VL sequence is SEQ ID NO: 252;

(27) the selected VH sequence is SEQ ID NO: 261, and the selected VL sequence is SEQ ID NO: 262;

(28) the selected VH sequence is SEQ ID NO: 271, and the selected VL sequence is SEQ ID NO: 272;

(29) the selected VH sequence is SEQ ID NO: 281, and the selected VL sequence is SEQ ID NO: 282;

(30) the selected VH sequence is SEQ ID NO: 291, and the selected VL sequence is SEQ ID NO: 292;

(31) the selected VH sequence is SEQ ID NO: 301, and the selected VL sequence is SEQ ID NO: 302;

(32) the selected VH sequence is SEQ ID NO: 311, and the selected VL sequence is SEQ ID NO: 312;

(33) the selected VH sequence is SEQ ID NO: 321, and the selected VL sequence is SEQ ID NO: 322;

(34) the selected VH sequence is SEQ ID NO: 331, and the selected VL sequence is SEQ ID NO: 332;

(35) the selected VH sequence is SEQ ID NO: 341, and the selected VL sequence is SEQ ID NO: 342;

(36) the selected VH sequence is SEQ ID NO: 351, and the selected VL sequence is SEQ ID NO: 352;

(37) the selected VH sequence is SEQ ID NO: 361, and the selected VL sequence is SEQ ID NO: 362;

(38) the selected VH sequence is SEQ ID NO: 371, and the selected VL sequence is SEQ ID NO: 372;

(39) the selected VH sequence is SEQ ID NO: 381, and the selected VL sequence is SEQ ID NO: 382; and

(40) the selected VH sequence is SEQ ID NO: 391, and the selected VL sequence is SEQ ID NO: 392, wherein the antibody or antigen-binding fragment thereof specifically binds to CUB domain-containing protein 1 (CDCP1).

In some embodiments, the antibody or antigen-binding fragment specifically binds to human CDCP1 and/or Cynomolgus CDCP1. In some embodiments, the antibody or antigen-binding fragment has a dissociation constant ($K_d$) for human CDCP1 that is less than 10 nM, and/or a dissociation constant ($K_d$) for Cynomolgus CDCP1 that is less than 10 nM. In some embodiments, the antibody or antigen-binding fragment is a humanized antibody or antigen-binding fragment thereof.

In another aspect, the disclosure relates to an antibody or antigen-binding fragment thereof, wherein the antibody or antigen-binding fragment thereof binds to human CDCP1, and blocks cleavage of human CDCP1 at residue 342. In some embodiments, the antibody or antigen-binding fragment thereof comprises a VH having CDRs 1, 2, 3 with amino acid sequences set forth in SEQ ID NOs: 85, 86, and 87, and a VL having CDRs 1, 2, 3 with amino acid sequences set forth in SEQ ID NOs: 88, 89, and 90. In some embodiments, the antibody or antigen-binding fragment thereof comprises a VH having CDRs 1, 2, 3 with amino acid sequences set forth in SEQ ID NOs: 95, 96, and 97, and a VL having CDRs 1, 2, 3 with amino acid sequences set forth in SEQ ID NOs: 98, 99, and 100.

In some embodiments, the complementarity determining region (CDR) sequences in the heavy chain variable region and the light chain variable region comprise or consist of the CDR sequences as set forth in FIG. 20. In some embodiments, the CDR sequences in the heavy chain variable region and the light chain variable region are at least 80%, 90%, 92%, 95%, 97%, 98%, 99%, or 100% identical to the CDR sequences as set forth in FIG. 20. In some embodiments, the CDR sequences in the heavy chain variable region and the light chain variable region differ from the CDR sequences in FIG. 20 by one, two, three, four, or five amino acids. In some embodiments, the CDRs in FIG. 20 are substituted by one, two, three, four, or five conservative amino acids.

To generate and to select CDRs having preferred CDCP1 binding and/or neutralizing activity with respect to hCDCP1, standard methods known in the art for generating antibodies, or antigen binding portions thereof, and assessing the CDCP1 binding and/or neutralizing characteristics of those antibodies, or antigen binding portions thereof, may be used, including but not limited to those specifically described herein.

In certain embodiments, the antibody comprises a heavy chain constant region, such as an IgG1, IgG2, IgG3, IgG4, IgA, IgE, IgM, or IgD constant region. In certain embodiments, the anti-CDCP1 antibody, or antigen binding portion thereof, comprises a heavy chain immunoglobulin constant domain selected from the group consisting of a human IgG constant domain, a human IgM constant domain, a human IgE constant domain, and a human IgA constant domain. In further embodiments, the antibody, or antigen binding portion thereof, has an IgG1 heavy chain constant region, an IgG2 heavy chain constant region, an IgG3 constant region, or an IgG4 heavy chain constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In certain embodiments, the anti-CDCP1 antibody binding portion is a Fab, a Fab', a F(ab')2, a Fv, a disulfide linked Fv, an scFv, a single domain antibody, or a diabody.

In certain embodiments, the anti-CDCP1 antibody, or antigen binding portion thereof, is a multispecific antibody, e.g., a bispecific antibody.

Replacements of amino acid residues in the Fc portion to alter antibody effector function are have been described (Winter, et al. U.S. Pat. Nos. 5,648,260 and 5,624,821, incorporated by reference herein). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc□Rs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment includes a labeled anti-CDCP1 antibody, or antibody portion thereof, where the antibody is derivatized or linked to one or more functional molecule(s) (e.g., another peptide or protein). For example, a labeled antibody can be derived by functionally linking an antibody or antibody portion of the disclosure (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion thereof, may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present the addition of hydrogen peroxide and diaminobenzidine leads to a colored reaction product, which is detectable. An antibody may also be derivatized with biotin, and detected through indirect measurement of avidin or streptavidin binding.

In one embodiment, the antibody is conjugated to an imaging agent. Examples of imaging agents that may be used in the compositions and methods described herein include, but are not limited to, a radiolabel (e.g., indium), an enzyme, a fluorescent label, a luminescent label, a bioluminescent label, a magnetic label, and biotin.

In one embodiment, the antibodies or ADCs are linked to a radiolabel, such as, but not limited to, indium ($^{111}$In). $^{111}$Indium may be used to label the antibodies and ADCs described herein for use in identifying CDCP1 positive tumors. In a certain embodiment, anti-CDCP1 antibodies (or ADCs) described herein are labeled with $^{111}$I via a bifunctional chelator which is a bifunctional cyclohexyl diethylenetriaminepentaacetic acid (DTPA) chelate (see U.S. Pat. Nos. 5,124,471; 5,434,287; and 5,286,850, each of which is incorporated herein by reference).

Another embodiment of the disclosure provides a glycosylated binding protein wherein the anti-CDCP1 antibody or antigen binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, Biotechnol. Prog. 21 (2005). pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick. S. C., et al., *Exp. Med.* (1988) 168:1099-1109; Wright, A., et al., *EMBO J.* (1991) 10:2717-2723).

One aspect of the disclosure is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the disclosure.

In still another embodiment, the glycosylation of the anti-CDCP1 antibody or antigen binding portion is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified anti-CDCP1 antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example. Shields, R. L. et al. (2002) J. Biol. Chem. 277:26733-26740; Umana et al. (1999) Nat. Biotech. 17:176-1, as well as, European Patent No: EP 1,176.195; PCT Publications WO 03/035835: WO 99/5434280, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful may include, but are not limited to, glucose, galactose, mannose, fucose, n-acetylglucosamine and sialic acid. Preferably the glycosylated binding protein comprises glycosyl residues such that the glycosylation pattern is human.

Differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using recombinant techniques, a practitioner may generate antibodies or antigen binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

Antibodies may be produced by any of a number of techniques. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation. DEAE-dextran transfection and the like. Although it is possible to express antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies disclosed herein include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) Mol. Biol. 159:601-621), NS0 myeloma cells. COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the disclosure. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the disclosure. In addition, bifunctional antibodies may be produced in which one heavy and one light chain are an antibody of the disclosure and the other heavy and light chain are specific for an antigen other than the antigens of interest by crosslinking an antibody of the disclosure to a second antibody by standard chemical crosslinking methods.

In a preferred system for recombinant expression of an antibody, or antigen binding portion thereof, a recombinant expression vector encoding both the antibody heavy chain and the antibody light chain is introduced into CHO cells comprising a glutamine synthase expression system, commercially available from Lonza (hereafter GS-CHO) (Bebbington, C. R. et al. (1992), Biotechnology, 10, pages 169-175).

In another system for recombinant expression of an antibody, or antigen binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the disclosure provides a method of synthesizing a recombinant antibody by culturing a host cell in a suitable culture medium until a recombinant antibody is synthesized. Recombinant antibodies may be produced using nucleic acid molecules corresponding to the amino acid sequences disclosed herein. In one embodiment, the nucleic acid molecules set forth in SEQ ID NOs: 82-101 are used in the production of a recombinant antibody. The method can further comprise isolating the recombinant antibody from the culture medium.

III. Anti-CDCP1 Antibody Drug Conjugates (ADCs)

Anti-CDCP1 antibodies described herein may be conjugated to a drug moiety to form an anti-CDCP1 Antibody Drug Conjugate (ADC). Antibody-drug conjugates (ADCs) may increase the therapeutic efficacy of antibodies in treating disease, e.g., cancer, due to the ability of the ADC to selectively deliver one or more drug moiety(s) to target tissues or cells, e.g., CDCP1 expressing tumors or CDCP1 expressing cells. Thus, in certain embodiments, the disclosure provides anti-CDCP1 ADCs for therapeutic use, e.g., treatment of cancer.

Anti-CDCP1 ADCs comprise an anti-CDCP1 antibody. i.e., an antibody that specifically binds to CDCP1, linked to one or more drug moieties. The specificity of the ADC is defined by the specificity of the antibody. i.e., anti-CDCP1. In one embodiment, an anti-CDCP1 antibody is linked to one or more cytotoxic drug(s) which is delivered internally to a cancer cell expressing CDCP1.

Examples of drugs that may be used in the anti-CDCP1 ADCs are provided below, as are linkers that may be used to conjugate the antibody and the one or more drug(s). The terms "drug." "agent." and "drug moiety" are used interchangeably herein. The terms "linked" and "conjugated" are also used interchangeably herein and indicate that the antibody and moiety are covalently linked.

In some embodiments, the ADC has the following formula (formula I):

$$Ab\text{-}(L\text{-}D)_n \quad (1)$$

wherein Ab an anti-CDCP1 antibody described herein, and (L-D) is a Linker-Drug moiety. The Linker-Drug moiety is made of L—which is a Linker, and -D, which is a drug moiety having, for example, cytostatic, cytotoxic, or otherwise therapeutic activity against a target cell, e.g., a cell expressing CDCP1; and n is an integer from 1 to 20. In some embodiments, n ranges from 1 to 8, 1 to 7, 1 to 6, 1 to 5, 1 to 4, 1 to 3, 1 to 2, or is 1. The DAR of an ADC is equivalent to the "n" referred to in Formula I.

Additional details regarding drugs (D of Formula I) and linkers (L of Formula I) that may be used in the ADCs, as well as alternative ADC structures, are described below.

A. Anti-CDCP1 ADCs: Exemplary Drugs for Conjugation

Anti-CDCP1 antibodies may be used in ADCs to target one or more drug(s) to a cell of interest, e.g., a cell expressing CDCP1. The anti-CDCP1 ADCs disclosed herein provide a targeted therapy that may, for example, reduce the side effects often seen with anti-cancer therapies, as the one or more drug(s) is delivered to a specific cell. In one embodiment, the drug used in an ADC is saporin. In another embodiment, the drug used in an ADC is dacarbazine. In another embodiment, the drug used in an ADC is carboplatin.

Examples of drugs that may be used in ADCs, i.e., drugs that may be conjugated to the anti-CDCP1 antibodies, are provided below, and include mitotic inhibitors, antitumor antibiotics, immunomodulating agents, gene therapy vectors, alkylating agents, antiangiogenic agents, antimetabolites, boron-containing agents, chemoprotective agents, hormone agents, glucocorticoids, photoactive therapeutic agents, oligonucleotides, radioactive isotopes, radiosensitizers, topoisomerase inhibitors, tyrosine kinase inhibitors, and combinations thereof.

1. Milotic Inhibitors

In one aspect, anti-CDCP1 antibodies may be conjugated to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by effecting microtubule polymerization (e.g., inhibiting microtubule polymerization) or microtubule depolymerization (e.g., stabilizing the microtubule cytoskeleton against depolymerization). Thus, in one embodiment, an anti-CDCP1 antibody of the invention is conjugated to one or more mitotic inhibitor(s) that disrupts microtubule formation by inhibiting tubulin polymerization. In another embodiment, an anti-CDCP1 antibody of the invention is conjugated to one or more mitotic inhibitor(s) that stabilizes the microtubule cytoskeleton from depolymerization. In one embodiment, the mitotic inhibitor used in the ADCs of the invention is Ixempra (ixabepilone). Examples of mitotic inhibitors that may be used in the anti-CDCP1 ADCs of the invention are provided below. Included in the genus of mitotic inhibitors are auristatins, described below.

a. Dolastatins

The anti-CDCP1 antibodies of the invention may be conjugated to at least one dolastatin to form an ADC. Dolastatins are short peptidic compounds isolated from the Indian Ocean sea hare *Dolabella auricularia* (see Pettit et al., J. Am. Chem. Soc., 1976, 98, 4677). Examples of dolastatins include dolastatin 10 and dolatstin 15. Dolastatin 15, a seven-subunit depsipeptide derived from *Dolabella auricularia*, and is a potent antimitotic agent structurally related to the antitubulin agent dolastatin 10, a five-subunit peptide obtained from the same organism. Thus, in one embodiment, the anti-CDCP1 ADC of the invention comprises an anti-CDCP1 antibody, as described herein, and at least one dolastatin. Auristatins are synthetic derivatives of dolastatin 10.

b. Auristatins

Anti-CDCP1 antibodies may be conjugated to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit. Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No, WO 04/010957, International Patent Publication No, WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein.

In one embodiment, anti-CDCP1 antibodies are conjugated to at least one MMAE (monomethyl auristatin E). Monomethyl auristatin E (MMAE, vedotin) inhibits cell division by blocking the polymerization of tubulin. Because of its super toxicity, it also cannot be used as a drug itself. In recent cancer therapy developments, it is linked to a monoclonal antibody (mAb) that recognizes a specific marker expression in cancer cells and directs MMAE to the cancer cells. In one embodiment, the linker linking MMAE to the anti-CDCP1 antibody is stable in extracellular fluid (i.e., the medium or environment that is external to cells), but is cleaved by cathepsin once the ADC has bound to the specific cancer cell antigen and entered the cancer cell, thus releasing the toxic MMAE and activating the potent anti-mitotic mechanism.

The structure of MMAE is provided below.

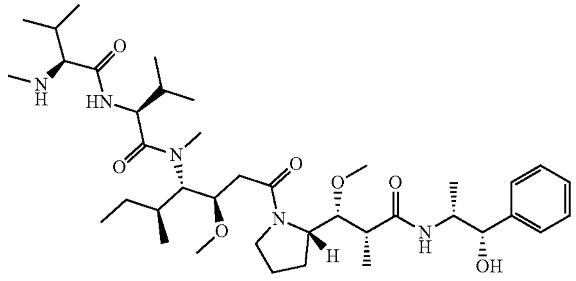

Monomethyl Auristatin E (MMAE)

In one embodiment, the antibody is coupled to a single drug and, therefore, has a DAR of 1. In certain embodiments, the ADC will have a DAR of 2 to 8, or, alternatively, 2 to 4.

c. Maytansinoids

The anti-CDCP1 antibodies of the invention may be conjugated to at least one maytansinoid to form an ADC. Maytansinoids are potent antitumor agents that were originally isolated from members of the higher plant families Celastraceae, Rhamnaceae, and Euphorbiaceae, as well as some species of mosses (Kupchan et al. J. Am. Chem. Soc. 94:1354-1356 [1972]; Wani et al. J. Chem. Soc. Chem. Commun. 390: 119731; Powell et al, J. Nat. Prod. 46:660-666 [1983]; Sakai et al. J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1.000-fold greater than conventional chemotherapeutic agents, such as, for example, methotrexate, daunorubicin, and vincristine (see, e.g., U.S. Pat. No. 5,208,020).

Maytansinoids to include maytansine, maytansinol, C-3 esters of maytansinol, and other maytansinol analogues and derivatives (see, e.g., U.S. Pat. Nos. 5,208,020 and 6,441,163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., J. Med. Chem., 21, 31-37 (1978).

Suitable maytansinoids for use in ADCs of the invention can be isolated from natural sources, synthetically produced, or semi-synthetically produced. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate, and is described in more detail in the linker section below. The structure of an exemplary maytansinoid, mertansine (DM1), is provided below.

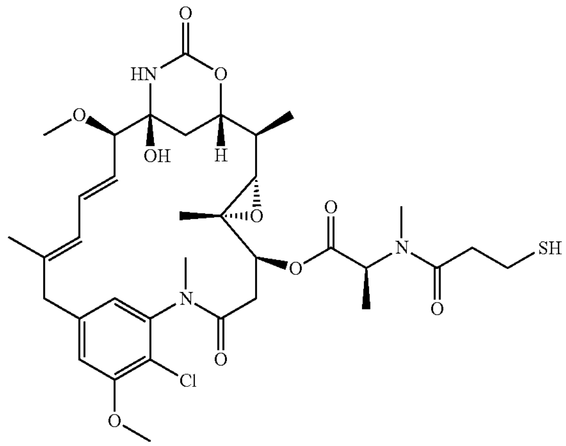

Mertansine (DM1)

Representative examples of maytansinoids include, but are not limited, to DM1 ($N^{2'}$-deacetyl-$N^{2'}$-(3-mercapto-1-oxopropyl)-maytansine; also referred to as mertansine, drug maytansinoid 1; ImmunoGen, Inc.; see also Chari et al. (1992) Cancer Res 52:127), DM2. DM3 ($N^{2'}$-deacetyl-$N^{2'}$-(4-mercapto-1-oxopentyl)-maytansine). DM4 (4-methyl-4-mercapto-1-oxopentyl)-maytansine), and maytansinol (a synthetic may tansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin PI, ansamitocin P2, ansamitocin P3, and ansamitocin P4.

In one embodiment of the invention, an anti-CDCPlantibody is conjugated to at least one DM1. In one embodiment, an anti-CDCP1 antibody is conjugated to at least one DM2. In one embodiment, an anti-CDCP1 antibody is conjugated to at least one DM3. In one embodiment, an anti-CDCP1 antibody is conjugated to at least one DM4.

2. Antitumor Antibiotics

Anti-CDCP1 antibodies may be conjugated to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the anti-CDCP1 ADCs include, but are not limited to, actinomycines (e.g., pyrrolo[2.1-c][1,4]benzodiazepines), anthracyclines, calicheamicins, and duocarmycins. In addition to the foregoing, additional antitumor antibiotics that may be used in the anti-CDCP1 ADCs include bleomycin (Blenoxane, Bristol-Myers Squibb), mitomycin, and plicamycin (also known as mithramycin).

3. Immunomodulating Agents

In one aspect, anti-CDCP1 antibodies may be conjugated to at least one immunomodulating agent. As used herein, the term "immunomodulating agent" refers to an agent that can stimulate or modify an immune response. In one embodiment, an immunomodulating agent is an immunostimulator which enhances a subject's immune response. In another embodiment, an immunomodulating agent is an immunosuppressant which prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, bacillus calmette-guerin (BCG) and levamisole (Ergamisol). Other examples of immunomodulating agents that may be used in the ADCs include, but are not limited to, cancer vaccines, and cytokines.

As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant disclosure, administering an ADC comprising an anti-CDCP1 antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the anti-CDCP1 ADCs include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil. Merck & Company), and sipuleucel-T (Provenge. Dendreon). Thus, in one embodiment, the anti-CDCP1 antibody is conjugated to at least one cancer vaccine that is either an immunostimulator or is an immunosuppressant.

The anti-CDCP1 antibodies may be conjugated to at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) Cancers 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12. IL-15. IL-18 and IL-21, enter clinical trials for patients with advanced cancer (Lee and Margoli, supra).

Examples of cytokines that may be used in the ADCs include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β and γ, colony stimulating factors (CSFs); granulocyte-macrophage-C-SF (GM-CSF); and granulocyte-CSF (G-CSF); interleukins (ILs) such as IL-1, IL-la, IL-2, IL-3. IL-4. IL-5, IL-6, IL-7. IL-8. IL-9, IL-11, IL-12; tumor necrosis factor, and other polypeptide factors including LIF and kit ligand (KL). As used herein, the term cytokine includes proteins from natural sources or from recombinant cell culture and biologically active equivalents of the native sequence cytokines. Thus, in one embodiment, the disclosure provides an ADC comprising an anti-CDCP1 antibody described herein and a cytokine.

The anti-CDCP1 antibodies may be conjugated to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in the anti-CDCP1 ADCs include, but are not limited to erythropoietin (Epoetin), filgrastim (Neopogen (also known as granulocyte colony-stimulating factor (G-CSF); Amgen. Inc.), sargramostim (leukine (granulocyte-macrophage colony-stimulating factor and GM-CSF); Genzyme Corporation), promegapoietin, and Oprelvekin (recombinant IL-11; Pfizer, Inc.). Thus, in one embodiment, an ADC may comprise an ani-CDCP1 antibody described herein and a CSF.

4. Alkylating Agents

The anti-CDCP1 antibodies may be conjugated to one or more alkylating agent(s). Alkylating agents are a class of antineoplastic compounds that attaches an alkyl group to DNA. Examples of alkylating agents that may be used in the ADCs include, but are not limited to, alkyl sulfonates, ethylenimimes, methylamine derivatives, epoxides, nitrogen mustards, nitrosoureas, triazines and hydrazines.

DNA Alkylating Agents

The term "DNA alkylating agent", as used herein, includes a family of DNA alkylating agents including indolino-benzodiazepines (IGNs). IGNs represent a chemical class of cytotoxic molecules with high in vitro potency ($IC_{50}$ values in the low pmol/L range) toward cancer cells. Examples of IGN DNA alkylating agents that can be used as a cytotoxic payload in an ADC are described in Miller el al. (2016) *Molecular Cancer Therapeutics,* 15(8)). The IGN compounds described in Miller et al. bind to the minor groove of DNA followed by covalent reaction of guanine residues with the two imine functionalities in the molecule resulting in cross-linking of DNA. The structure of an exemplary IGN is provided below.

2

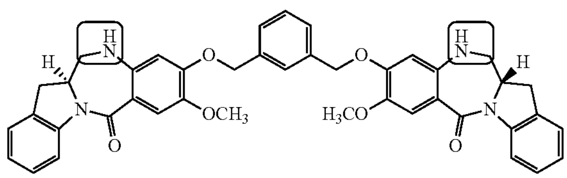

5. Antiangiogenic Agents

In one aspect, the anti-CDCP1 antibodies described herein are conjugated to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs include, but are not limited to, angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SUS416, with paclitaxel, with gemcitabine and cisplatin, and with irinotecan and cisplatin and with radiation, tecogalan, temozolomide and PEG interferon α2b, tetrathiomolybdate. TNP470, thalidomide, CC-5013 and with taxotere, tumstatin, 2-methoxyestradiol. VEGF trap, mTOR inhibitors (deforolimus, everolimus (Afinitor, Novartis Pharmaceutical Corporation), and temsirolimus (Torisel. Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb. GlaxoSmithKline Pharmaceuticals), sorafenib (Nexavar. Bayer and Onyx), phosphoinositide 3-kinases (PI3K).

6. Antimetabolites

The anti-CDCP1 antibodies may be conjugated to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolites that may be used in the ADCs include, but are not limited to, a folic acid antagonist (e.g., methotrexate), a pyrimidine antagonist (e.g., 5-Fluorouracil. Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

7 Boron-Containing Agents

The anti-CDCP1 antibody may be conjugated to at least one boron containing agent. Boron-containing agents comprise a class of cancer therapeutic compounds which interfere with cell proliferation. Representative examples of boron containing agents include, but are not limited, to borophycin and bortezomib (Velcade, Millenium Pharmaceuticals). 8. Chemoprotective Agents The anti-CDCP1 antibodies may be conjugated to at least one chemoprotective agent.

Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune. Inc.), which is used to reduce renal toxicity associated with cumulative doses of cisplatin, dexrazoxane (Totect. Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

9. Photoactive Therapeutic Agents

The anti-CDCP1 antibodies may be conjugated to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

10. Radionuclide Agents (Radioactive Isotopes)

The anti-CDCP1 antibodies may be conjugated to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{7}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-11111, Sb-119, I-125, Ho-161, Os-189m and Ir-192, Decay energies of useful beta-particle-emitting nuclides are preferably Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$0, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

11. Radiosensitizers

The anti-CDCP1 antibodies may be conjugated to at least one radiosensitizer. The term "radiosensitizer." as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethyhnisonidazole, pimonidazole, etanidazole, nimorazole, mitomycin C, RSU 1069. SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives. Photofrin®, benzoporphyrin derivatives. NPe6, tin etioporphyrin (SnET2), pheoborbide a, bacteriochlorophyll a, naphthalocyanines, phthalocyanines, zinc phthalocyanine, and therapeutically effective analogs and derivatives of the same.

12. Topoisomerase Inhibitors

The anti-CDCP1 antibodies may be conjugated to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer. Inc.) and topotecan (Hycamtin, GlaxoSmithKline Pharmaceuticals). Representative examples of DNA topoisomerase 11 inhibitors include, but are not limited to, amsacrine, daunorubicin, doxotrubicin, epipodophyllotoxins, ellipticines, epirubicin, etoposide, razoxane, and teniposide.

13. Tyrosine Kinase Inhibitors

The anti-CDCP1 antibodies may be conjugated to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

14. Additional Agents

Many other types of agents are well known to one of ordinary skill in the art, and the anti-CDCP1 antibodies may be conjugated to any agent available to one of ordinary skill in the art. Agents include, but are not limited to, cytotoxic agents, cytostatic agents, anti-angiogenic agents, debulking agents, chemotherapeutic agents, radiotherapy and radiotherapeutic agents, targeted anti-cancer agents, biological response modifiers, therapeutic antibodies, cancer vaccines, cytokines, hormone therapies, radiation therapy and anti-metastatic agents, and immunotherapeutic agents.

In some implementations, the therapeutic agent is an anti-cancer agent. Examples of anti-cancer agents include, but are not limited to, cytochalasin B, gramicidin D, ethidium bromide, emetine, mitomycin, etoposide, tenoposide, vincristine, vinblastine, colchicin, doxorubicin, daunorubicin, dihydroxy anthracin, dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof.

In other implementations, the therapeutic agent is a may tansinoid cell-killing agent, e.g., $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl) maytansine (DM4). DM1 is a sulfhydryl-containing derivative of maytansine that can be linked to the peptide, e g., via a disulfide linker that releases DM1 when inside target cells. DM1 attached to an antibody with a thioether linker is called "emtansine" in its INN name (e.g., ado-trastuzumab emtansine). DM1 attached to an antibody with the N-succinimidyl 4-(2-pyridyldithio)pentanoate (SPP) linker is called "mertansine." DM4 attached with the N-succinimidyl 3-(2-pyridyldithio)butyrate (SPDB) linker is called "ravtansine." e.g., indatuximab ravtansine (BT062) targeting multiple myeloma, anetumab ravtansine (BAY94-9343) targeting mesothelin (to treat mesothelioma), and coltuximab ravtansine (SAR3419) targeting CD19 to treat acute lymphoblastic leukemia (ALL). DM4 attached with the sSPDB linker is called "soravtansine" (e.g., mirvetuximab soravtansine) Compared to DM1, the DM4 metabolites can also cross the cellular membrane and, upon diffusion, induce the extermination of surrounding cells, a phenomenon known as a bystander effect. These cytotoxic agents (e.g., DM1 and DM4) are described, e.g., in U.S. Pat. No. 8,557,956, and Bouchard. Hervé, Christian Viskov, and Carlos Garcia-Echeverria. "Antibody—drug conjugates—a new wave of cancer drugs." Bioorganic & medicinal chemistry letters 24.23. 5357-5363 (2014), each of which is incorporated by reference in its entirety.

The disulfide linkers can display greater stability in storage and in serum than other linkers. Maytansinoids, and in particular DM1 and DM4, are cytotoxic agents that effects cell killing by preventing the formation of microtubules and depolymerization of extant microtubules. They are 100- to 1000-fold more cytotoxic than anticancer agents such as doxorubicin, methotrexate, and vinca alkyloid, which are currently in clinical use. Alternatively, the antigen binding agents can be coupled to a taxane, a calicheamicin, a proteosome inhibitor, or a topoisomerase inhibitor. [(1R)-3-methyl-1-[[(2S)-1-oxo-3-phenyl-2-[(3-mercaptoacetyl) amino]propyl]amino]butyl]boronic acid is a suitable proteosome inhibitor. N,N'-bis[2-(9-methylphenazine-1-carboxamido)ethyl]-1,2-ethanediamine is a suitable topoisomerase inhibitor.

In some implementations, the therapeutic agents are cytotoxins, for example, dolastatins and auristatins, amanitins such as alpha-amanitin, beta-ananitin, gamma-amanitin or epsilon-amanitin. DNA minor groove binding agents such as duocarmycin derivatives and modified pyrrolobenzodiazepine dimers, splicing inhibitors such as meayamycin analogs or derivatives (e.g., FR901464 as set forth in U.S. Pat. No. 7,825,267), tubular binding agents such as epothilone analogs and paclitaxel and DNA damaging agents such as calicheamicins and esperamicins.

Auristatins include auristatin E, auristatin EB (AEB), auristatin EFP (AEFP), monomethyl auristatin E (MMAE). MMAE is a potent antimitotic agent that inhibits cell division by blocking the polymerization of tubulin. MMAE is 100-100n times more potent than doxorubicin (Adriamycin/Rubex) and it is usually linked to a monoclonal antibody that recognizes a specific marker expression in cancer cells and directs MMAE to a specific, targeted cancer cell. Auristatins, including MMAE, are described in U.S. Patent Publication No. 20060074008. U.S. Patent Publication No 2006022925; U.S. Pat. Nos. 7,691,962; 5,635,483; Int J. Oncol. 15:367-72 (199)); Molecular Cancer Therapeutics, vol. 3. No. 8, pp. 921-932 (2004); Doronina, et al. "Development of potent monoclonal antibody auristatin conjugates for cancer therapy," Nature biotechnology 21.7 (2003): 778-784; and Francisco, et al. "cAC10-vcMMAE, an anti-CD30-monomethyl auristatin E conjugate with potent and selective antitumor activity." Blood 102 4 (2003): 1458-1465, each of which is incorporated by reference in its entirety.

In some embodiments, the therapeutic agent is a DNA allkylator, e.g., indolinobenzodiazepine pseudodimers (also known as IGN). The IGN family of DNA-acting payload agents, including DGN462, are designed to effectively alkylate DNA, while avoiding the delayed toxicity that can develop with agents that cross-link DNA in addition to alkylating it. A description of IGN can be found in, e.g., Miller et al. "A New Class of Antibody-Drug Conjugates with Potent DNA Alkylating Activity," Molecular cancer therapeutics, molcanther-0184 (2016); U.S. Patent Publication No. 20160095938; and in U.S. Pat. No. 8,765,740; each of which is incorporated by reference in its entirety.

In some embodiments, the therapeutic agents include, but are not limited to, antimetabolites (e.g., methotrexate, 6-mercaptopurine, 6-thioguanine, cytarabine, and 5-fluorouracil decarbazine), alkylating agents (e, g., mechlorethamine, thioepa, chlorambucil, melphalan, carmustine (BCNU) and lomustine (CCNU), busulfan, dibromomannitol, streptozotocin, and cisdichlorodiamine platinum (11) (DDP) cisplatin), anthracyclines (e.g., daunorubicm (formerly daunomycin) and doxorubicin), antibiotics (e.g., dactinomycin (formerly actinomycin t bleomycin, and anthramycin (AMC)), and anti-mitotic agents (e.g., vincristine and vinblastine).

Examples for cytotoxic drugs are, without limitation, maytansinoids (e.g., emtansine, mertansine), calicheamicins (e.g., ozogamicin), auristatins (e.g., monomethyl auristatin E), pyrrolobenzodiazepines, ansamitocins, doxorubicins, daunorubicins, taxanes, bromodeoxyuridine (BUdR), 5-iododeoxyuridine (IUdR), bromodeoxycytidine, fluorodeoxyuridine (FudR), hydroxyurea, and cisplatin. In one embodiment, the agent is pyrrolobenzodiazepine (PBD).

In some implementations, the therapeutic agents are enzymatically active toxins. Enzymatically active toxins and fragments thereof include, but are not limited to, diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP S), *Momordica charantia* inhibitor, curcin, crotin, *Saponaria officinalis* inhibitor, gelonin, mitogillin, restrictocin, phenomycin, and enomycin. In some embodiments, the antigen binding agent is conjugated to CC-1065 (see U.S. Pat. Nos. 5,475,092, 5,585,499, and 5,846,545). Procedures for preparing enzymatically active polypeptides of the immunotoxins are described, e.g., in WO 1984/03508 and WO 1985/03508, which are hereby incorporated herein by reference in their entireties. Examples of cytotoxic moieties that can be conjugated to the antibodies include adriamycin, chlorambucil, daunomycin, methotrexate, neocarzinostatin, and platinum.

A therapeutic agent attached to an antibody as described herein can also include agents that are derived from, or that beneficially modulate, host biological processes, such as interferons, tumor growth factors, tumor necrosis factors, growth factors such as granulocyte macrophage colony-stimulating factor (GM-CSF), granulocyte-colony stimulating factor (G-CSF), and interleukins, for example, interleukin-2, interleukin-6, interleukin-7 and interleukin-12, and the like. A therapeutic agent attached to an antigen binding agent as described herein may also comprise an agent that damages DNA and/or prevents cells from multiplying, such as genotoxins. Genotoxins include, but are not limited to, alkylating agents, antimetabolites, DNA cutters, DNA binders, topoisomerase poisons, and spindle poisons. Examples of alkylating agents include lomustine, carmustine, streptozocin, mechlorethamine, melphalan, uracil nitrogen mustard, chlorambucil, cyclosphamide, iphosphamide, cisplatin, carboplatin, mitomycin, thiotepa, dacarbazin, procarbazine, hexamethyl melamine, triethylene melamine, busulfan, pipobroman, mitotane, and other platine derivatives.

Additional examples of cytotoxic peptides or proteins include Idarubicin; CRM9 (e.g., FN18-CRM9, Knechtle et al., Transplantation, 1997; 63:1-6); or pokeweed antiviral protein. In some embodiments, the cytotoxic protein is a bacterial toxin, e.g., diphtheria toxin (DT) or portions or variants thereof, e.g., Met1-Thr387, e.g., as described in Aullo et al., EMBO J., 11(2):575-83 (1992); Abi-Habib et al., Blood, 104(7):2143-2148 (2004); Perentesis et al., Proc. Natl. Acad. Sci. USA 85:8386-8390 (1988); Zettlemeissl et al., Gene. 41(1):103-111 (1986); US 2009/0010966; US2009/0041797; U.S. Pat. Nos. 5,843,711; 7,585,942; 7,696,338; or US2008/0166375; monomethyl auristatin E; or *Pseudomonas* exotoxin (PE), or portions or variants thereof, e.g., as described in U.S. Pat. Nos. 4,545,985; 4,892,827; 5,458,878; 7,314,632; Song et al., Protein Expression and Purification, 44(1):52-57 (2005); Theuer et al., J. Biol. Chem., 267(24):16872-16877 (1992); Heimbrook et al., Proc Natl Acad Sci USA, 87(12):4697-4701 (1990); Debinski et al., Mol Cell Biol., 11(3):1751-1753 (1991); and Chaudhary et al., Proc. Nadl. Acad. Sci. USA. 87:308-312 (1990).

In some implementations, the cytotoxic protein is a plant toxin, e.g., a plant holotoxin (e.g., class II ribosome-inactivating proteins such as ricin (e.g., deglycosylated ricin A chain (dgA)), abrin, mistletoe lectin, or modeccin) or hemitoxin (class I ribosome-inactivating proteins, e.g., PAP, saporin, bryodin 1, bouganin, or gelonin), or fragments or variants thereof that retain cytotoxic activity. See. e.g., Neville et al., J Contr Rel., 1993; 24:133-141; Vallera, Blood, 1994; 83:309-317; Vitetta et al., Immunology Today, 1993; 14:252-259; Kreitman et al., AAPS J., 2006; 8(3): E532-E551).

In some embodiments, the cytotoxic or cytostatic agent is maytansinoid. DGN462, benzodiazepine, taxoid. CC-1065, duocarmycin, calicheamicin, dolastatin, auristatin, tomaymycin, or leptomycin. In some embodiments, the cytotoxic or cytostatic agent is mertansine/emtansine (DM1), ravtansine/soravtansinc (DM4), indolino-benzodiazepine, or monomethyl auristatin E (MMAE), SN-38, monomethyl auristatin phenylalanine (MMAF), doxorubicin, tubulysin (AZ13599185), pyrrolobenzodiazepine (PBD). Amberstatin-269, or topoisomerase inhibitor (DXd). Some of these agents are described, e.g., in U.S. Pat. No. 8,557,966.

The antibody drug conjugates include an antibody or antigen-binding fragment thereof that binds to CDCP1. The antibody can be any of the antibodies described herein. In some embodiments, the therapeutic agent in the antibody drug conjugates can be a microtubule inhibitor, e.g., N-deacetyl-$N^{2'}$-(4-mercapto4-methyl-1-oxopentyl) maytansine (DM4), monomethyl auristatin E (MMAE), or a DNA alkylator, e.g., indolinobenzodiazepine pseudodimers (IGN) (Table 1). The linker that links the therapeutic agent and the antibody or antigen-binding fragment can be D-Ala-L-Ala dipeptide anilino (D-Ala-L-Ala dpa), N-succinimidyl 4-(2-pyridyldithio)-2-sulfobutanoate (sSPDB), or maleimido-caproyl-valine-citrulline (MC-VC). In some embodiments, the therapeutic agent is DM4, and the linker is selected from the group consisting of D-Ala-L-Ala dpa, sSPDB, and MC-VC. In some embodiments, the therapeutic agent is MMAE, and the linker is selected from the group consisting of D-Ala-L-Ala dpa, sSPDB, and MC-VC. In some embodiments, the therapeutic agent is IGN, and the linker is selected from the group consisting of D-Ala-L-Ala dpa, sSPDB, and MC-VC.

The antibody and the antibody drug conjugates described herein can be used to treat various cancers, including, but are not limited to, cancers of the stomach, colon, rectum, mouth/pharynx, larynx, liver, pancreas, lung, breast, cervix uteri, corpus uteri, ovary, prostate, testis, bladder, skin, bone, kidney, head, neck, and throat, Hodgkins disease, non-Hodgkins leukemia, sarcomas, choriocarcinoma, lymphoma, brain/central nervous system, and neuroblastoma (e.g., pediatric neuroblastoma), etc. In some embodiments, the antibody drug conjugates described in the present disclosure can be used to treat breast cancer (e.g., TNBC), colon cancer, and small cell lung cancer (Table 1). For example, a CDCP1 antibody that is linked to DM4 by a D-Ala-L-Ala dpa linker or sSPDB linker can be used to treat triple negative breast cancer or colon cancer. In some embodiments, the CDCP1 antibody disclosed in the present disclosure can also be linked to IGN by the linker D-Ala-L-Ala dpa. These ADCs can be used to treat colon cancer and small cell lung cancer. Furthermore, the CDCP1 antibody that is linked to MMAE by MC-VC can be used to treat TNBC and small cell lung cancer.

TABLE 1

| Indication | Payload Class | Payload | Linker |
|---|---|---|---|
| Triple negative breast cancer | Microtubule inhibitors | DM4 | Cleavable peptide (D-Ala-L-Ala dpa)<br>Charged hindered disulfide (sSPDB) |

TABLE 1-continued

| Indication | Payload Class | Payload | Linker |
|---|---|---|---|
| (TNBC) | | MMAE | maleimido-caproyl-valine-citrulline (MC-VC) |
| Colon Cancer | DNA alkylator | IGN | Cleavable peptide (D-Ala-L-Ala dpa) |
| | Microtubule inhibitors | DM4 | Cleavable peptide (D-Ala-L-Ala dpa) Charged hindered disulfide (sSPDB) |
| | | MMAE | maleimido-caproyl-valine-citrulline (MC-VC) |
| Small Cell Lung Cancer (SCLC) | DNA alkylator | IGN | Cleavable peptide (D-Ala-L-Ala dpa) |

The antibodies can also be coupled to high energy radiation emitters, for example, a radioisotope, such as $^{131}I$, a γ-emitter, which, when localized at the target site, e.g., tumor site, results in a killing of several cell diameters. See, e.g., Order, "Analysis, Results, and Future Prospective of the Therapeutic Use of Radiolabeled Antibody in Cancer Therapy," in *Monoclonal Antibodies for Cancer Detection and Therapy*, R. W. Baldwin et al. (eds.), pp 303-316 (Academic Press 1985). Other suitable radioisotopes include α-emitters, such as $^{212}Bi$, $^{213}Bi$, and $^{211}At$, and β-emitters, such as $^{186}Re$ and $^{90}Y$. $Lu^{117}$ may also be used as both an imaging and cytotoxic agent.

The antibodies can also be conjugated or fused to viral surface proteins present on viral particles. For example, an antigen binding agent could be fused (e.g., to form a fusion protein) to a viral surface protein. Alternatively, an antigen binding agent could be chemically conjugated (e.g., via a chemical linker) to a viral surface protein. Preferably, the virus is one that fuses with endocytic membranes, e.g., an influenza virus, such that the virus is internalized along with the antigen binding agents and thereby enters and kills the tumor cells. The virus can be genetically engineered as a cellular toxin. For example, the virus could express or induce the expression of genes that are toxic to cells, e.g., cell death promoting genes. Preferably, such viruses would be incapable of viral replication.

In some implementations, antibodies can be conjugated with a prodrug that is activated only when in close proximity with a prodrug activator. The prodrug activator is conjugated with a second antigen binding agent, preferably one that binds to a non-competing site on the same target receptor or target cell. Drug-prodrug pairs suitable for use are known in the art, see, e.g., in Blakely et al., Cancer Research, 56:32873292 (1996).

Additional information regarding cytotoxic agents, linkers, and production of antibody-drug conjugates may be found, e.g., in WO 2013/055990, WO 2013/055993, WO 2012/123423. WO 2012/041805, WO 2011/130613, WO 2011/130616, WO 2009/117531, WO 2007/103288. WO 2007/011968, WO 2007/008603, WO 2007/008848, WO 2006/132670, WO 2006/065533. WO 2005/084390, WO 2005/082023, WO 2005/081711, WO 2005/077090, WO 2005/070457, WO 2004/010957, WO 2003/026577, WO 2012/177837, WO 2012/1445112, WO 2012/138749, WO 2012/135517, WO 2012/135522, WO 2012/128868, WO 2012/112708, WO 2012/112687. WO 2012/078868, WO 2012/061590, WO 2010/141566, WO 2010/126551, WO 2010/126552, WO 2010/091150, WO 2009/134870, WO 2009/134977, WO 2009/134952, WO 2009/134976, WO 2009/080831, WO 2007/056550, WO 2007/024536, WO 2006/086733, WO 2006/078809. WO 2006/078368, WO 2005/037992, WO 2005/020883, WO 2004/110498, WO 2004/103272, WO 2004/016801, WO 2004/013093, WO 2002/098883, WO 2001/024763, U.S. Pat. Nos. 9,061,074, 9,345,785, 9,428,585, 7,553,816, 8,288,352, 9,504,756, 8,609,105, 7,745,394, 8,039,273, 8,992,932, 8,343,928, 8,987,209, 8,697,688, 8,841,425, 9,090,629, 9,434,748, 9,353,127, 9,289,512, 9,376,500, 9,125,896, 9,498,541, 9,469,655, 9,375,488, and 9,289,509, each of which are incorporated herein by reference in its entirety.

Other agents include, but are not limited to, abrin (e.g, abrin A chain), alpha toxin, *Aleurites fordii* proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *Momordica charantia* inhibitor, neomycin, onconase, phenomycin, *Phytolaca americana* proteins (PAPI, PAPII, and PAP-S), pokeweed antiviral protein, *Pseudomonas* endotoxin, *Pseudomonas* exotoxin (e.g. exotoxin A chain (from *Pseudomonas aeruginosa*)), restrictocin, ricin A chain, ribonuclease (Rnase), *Sapaonaria officinalis* inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]). HDAC inhibitors (vorinostat (Zolinza, Merck & Company. Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar. Lundbeck Inc.), hydroxyurea, levamisole, mitotane (Lysodren, Bristol-Myers Squibb), and tretinoin (Renova, Valeant Pharmaceuticals Inc.).

It should be noted that the aforementioned groups of drug moieties that may be used in the anti-CDCP1 ADCs are not exclusive, in that certain examples of drugs may be found in more than one category, e.g., ansamitocins are both mitotic inhibitors and antitumor antibiotics.

All stereoisomers of the above drug moieties are contemplated for use herein, i.e, any combination of R and S configurations at the chiral carbons of D.

The above agents (i.e., naked agents not conjugated to an antibody) may also be used in combination therapies with the anti-CDCP1 antibodies described herein. In one embodiment, anti-CDCP1 antibodies or ADCs are used with any of the foregoing agents in a combination therapy to treat cancer, where the agent is administered prior to, at the same time as, or following administration of the anti-CDCP1 antibody or ADC to the subject.

B. Anti-CDCP1 ADCs: Exemplary Linkers

An anti-CDCP1 ADC comprises an anti-CDCP1 antibody and at least one drug(s), whereby the antibody and the at least one drug are conjugated by a linker. The term "linker," as used herein, refers to a chemical moiety that may be bifunctional or multifunctional, and is used to attach an antibody to a drug moiety. A linker may include one conjugating component or may include multiple components.

For example, the linker may include a spacer, which is a moiety that extends the drug linkage to avoid, for example, shielding the active site of the antibody or improving the solubility of the ADC. Other examples of components of linkers include a stretcher unit and an amino acid unit.

Two methods are commonly used for conjugating drugs to antibodies: alkylation of reduced interchain cysteine disulfides through an enzymatically non-cleavable maleimido or simple and cleavable disulfide linker, and acylation of lysines by cleavable linear amino acids.

In one aspect, a linker covalently attaches an antibody to a drug moiety. An ADC is prepared using a linker having reactive functionality for binding to the antibody and the drug. For example, a cysteine thiol, or an amine, e.g., N-terminus or amino acid side chain such as lysine, of the antibody may form a bond with a functional group of the linker.

In one aspect, a linker has a functionality that is capable of reacting with a free cysteine present on an antibody to form a covalent bond. Nonlimiting exemplary such reactive functionalities include maleimide, haloacetamides, □-haloacetyl, activated esters such as succinimide esters, 4-nitrophenyl esters, pentafluorophenyl esters, tetrafluorophcnyl esters, anhydrides, acid chlorides, sulfonyl chlorides, isocyanates, and isothiocyanates. See, e.g., the conjugation method at page 766 of Klussman, et al (2004), Bioconjugate Chemistry 15(4):765-773.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

Suitable linkers include, for example, cleavable and non-cleavable linkers. A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020). A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a a valine-citrulline (Val-Cit) linker, an Ala-Val linker, or a Phe-Lys linker. These linkers are known in the art, and are described, e.g., in U.S. Pat. No. 6,214,345. One advantage of using intracellular proteolytic release of the therapeutic agent is that the agent is typically attenuated when conjugated and the serum stabilities of the conjugates are typically high.

Linkers are preferably stable extracellularly in a sufficient manner to be therapeutically effective. Before transport or delivery into a cell, the ADC is preferably stable and remains intact, i.e. the antibody remains conjugated to the drug moiety. Linkers that are stable outside the target cell may be cleaved at some efficacious rate once inside the cell. Thus, an effective linker will: (i) maintain the specific binding properties of the antibody; (ii) allow delivery, e.g., intracellular delivery, of the drug moiety; and (iii) maintain the therapeutic effect, e.g., cytotoxic effect, of a drug moiety.

In one embodiment, the linker is cleavable under intracellular conditions, such that cleavage of the linker sufficiently releases the drug from the antibody in the intracellular environment to be therapeutically effective. In some embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999*, Pharm. Therapeutics* 83:67-123; Neville et al., 1989*, Biol. Chem.* 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999. Pharm. Therapeutics 83:67-123). Most typical are peptidyl linkers that are cleavable by enzymes that are present in CDCP1-cxpressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the linker is a malonate linker (Johnson et al., 1995, Anticancer Res. 15:1387-93), a maleim idobenzoyl linker (Lau et al., 1995. *Bioorg-Med-Chem.* 3(10):1299-1304), or a 3'-N-amide analog (Lau et al., 1995. *Bioorg-Med-Chem.* 3(10): 1305-12).

In some implementations, the antigen binding agents can be directly conjugated to radioisotopes or may comprise macrocyclic chelators useful for conjugating radio-metal ions. In some embodiments, the macrocyclic chelator is 1,4,7,10-tetraazacyclododecane-N,N',N",N"-tetraacetic acid (DOTA), which can be attached to the antibody via a linker molecule. These linkers are known in the art and are described, e.g., in Denardo et al., 1998. Clin Cancer Res., 4:2483; Peterson et al., 1999. Bioconjug. Chem., 10:553; and Zimmerman et al., 1999, Nucl. Med. Biol., 26:943, each of which is incorporated by reference in its entirety.

In yet other embodiments, the linker unit is not cleavable and the drug is released, for example, by antibody degradation. See U.S. Publication No. 20050238649 incorporated by reference herein in its entirety. An ADC comprising a non-cleavable linker may be designed such that the ADC remains substantially outside the cell and interacts with certain receptors on a target cell surface such that the binding of the ADC initiates (or prevents) a particular cellular signaling pathway.

In some embodiments, the linker is N-succinimidyl 4-(2-pyridyldithio)pentanoate (SPP), N-succinimidyl 4-(2-pyridyldithio)-2-sulfopentanoate (sulfo-SPP), N-succinimidyl 4-(maleimidomethyl) cyclohexanecarboxylate (SMCC), N-sulfosuccinimidyl 4-(maleimidomethyl)cyclohexanecarboxylate (sulfoSMCC), N-succinimidyl-4-(iodoacetyl)-aminobenzoate (SIAB), or N-succinimidyl-[(N-maleimidopropionamido)-tetraethyleneglycol]ester (NHS-PEG4-maleimide). Some of these linkers are described, e.g., in U.S. Pat. No. 8,557,966.

In some embodiments, the linker is substantially hydrophilic linker (e.g., PEG4Mal and sulfo-SPDB). A hydrophilic linker may be used to reduce the extent to which the drug may be pumped out of resistant cancer cells through MDR (multiple drug resistance) or functionally similar transporters.

In other embodiments, upon cleavage, the linker functions to directly or indirectly inhibit cell growth and/or cell proliferation. For example, in some embodiments, the linker, upon cleavage, can function as an intercalating agent, thereby inhibiting macromolecular biosynthesis (e.g. DNA replication. RNA transcription, and/or protein synthesis).

In other embodiments, the linker is designed to facilitate bystander killing (the killing of neighboring cells) through diffusion of the linker-drug and/or the drug alone to neighboring cells. In other, embodiments, the linker promotes cellular internalization.

The presence of a sterically hindered disulfide can increase the stability of a particular disulfide bond, enhancing the potency of the ADC. Thus, in one embodiment, the linker includes a sterically hindered disulfide linkage. A sterically hindered disulfide refers to a disulfide bond present within a particular molecular environment, wherein the environment is characterized by a particular spatial arrangement or orientation of atoms, typically within the same molecule or compound, which prevents or at least partially inhibits the reduction of the disulfide bond. Thus, the presence of bulky (or sterically hindering) chemical moieties and/or bulky amino acid side chains proximal to the disulfide bond prevents or at least partially inhibits the disulfide bond from potential interactions that would result in the reduction of the disulfide bond.

Notably, the aforementioned linker types are not mutually exclusive. For example, in one embodiment, the linker used in the anti-CDCP1 ADCs described herein is a non-cleavable linker that promotes cellular internalization.

In some embodiments, the ADC has the following formula (formula I):

$$Ab\text{-}(L\text{-}D)_n \qquad (1)$$

or a pharmaceutically acceptable salt or solvate thereof; wherein Ab is the antibody, e.g., anti-CDCP1 antibody, and (L-D) is a Linker-Drug moiety. The Linker-Drug moiety is made of L—which is a Linker, and -D, which is a drug moiety having, for example, cytostatic, cytotoxic, or otherwise therapeutic activity against a target cell, e.g., a cell expressing CDCP1; and n is an integer from 1 to 20.

In some embodiments, n ranges from 1 to 8, 1 to 7, 1 to 6, 1 to 5, 1 to 4, 1 to 3, 1 to 2, or is 1.

In some embodiments, the –D moieties are the same. In yet another embodiment, the –D moieties are different.

In some embodiments, a linker component comprises an "amino acid unit." In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B. C and D, or a plasmin protease.

In one embodiment, the amino acid unit is valine-citrulline (vc or val-cit). In another aspect, the amino acid unit is phenylalanine-lysine (i.e., fk). In yet another aspect of the amino acid unit, the amino acid unit is N-methylvaline-citrulline. In yet another aspect, the amino acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

Another approach for the generation of ADCs involves the use of heterobifunctional cross-linkers which link the anti-CDCP1 antibody to the drug moiety. Examples of cross-linkers that may be used include N-succinimidyl 4-(5-nitro-2-pyridyldithio)-pentanoate or the highly water-soluble analog N-sulfosuccinimidyl 4-(5-nitro-2-pyridyldithio)-pentanoate, N-succinimidyl-4-(2-pyridyldithio) butyrate (SPDB). N-succinimidyl-4-(5-nitro-2-pyridyldithio) butyrate (SNPB), and N-sulfosuccinimidyl-4-(5-nitro-2-pyridyldithio) butyrate (SSNPB), N-succinimidyl-4-methyl-4-(5-nitro-2-pyridyldithio)pentanoate (SMNP). N-succinimidyl-4-(5-N,N-dimethylcarboxamido-2-pyridyldithio) butyrate (SCPB) or N-sulfosuccinimidyl 4-(5-N,N-dimethylcarboxamido-2-pyridyldithio) butyrate (SSCPB)). The antibodies may be modified with the cross-linkers N-succinimidyl 4-(5-nitro-2-pyridyldithio)-pentanoate, N-sulfosuccinimidyl 4-(5-nitro-2-pyridyldithio)-pentanoate, SPDB, SNPB, SSNPB, SMNP, SCPB, or SSCPB can then react with a small excess of a particular drug that contains a thiol moiety to give excellent yields of an ADC (see also U.S. Pat. No. 6,913,748, incorporated by reference herein).

In one embodiment, charged linkers (also referred to as pro-charged linkers) are used to conjugate anti-CDCP1 antibodies to drugs to form ADCs. Charged linkers include linkers that become charged after cell processing. The presence of a charged group(s) in the linker of a particular ADC or on the drug after cellular processing provides several advantages, such as (i) greater water solubility of the ADC, (ii) ability to operate at a higher concentration in aqueous solutions, (iii) ability to link a greater number of drug molecules per antibody, potentially resulting in higher potency, (iv) potential for the charged conjugate species to be retained inside the target cell, resulting in higher potency, and (v) improved sensitivity of multidrug resistant cells, which would be unable to export the charged drug species from the cell. Examples of some suitable charged or pro-charged cross-linkers and their synthesis are shown in FIGS. 1 to 10 of U.S. Pat. No. 8,236,319, and are incorporated by reference herein. Preferably, the charged or pro-charged cross-linkers are those containing sulfonate, phosphate, carboxyl or quaternary amine substituents that significantly increase the solubility of the ADCs, especially for ADCs with 2 to 20 conjugated drugs. Conjugates prepared from linkers containing a pro-charged moiety would produce one or more charged moieties after the conjugate is metabolized in a cell.

Additional examples of linkers that can be used with the compositions and methods include valine-citrulline; maleimidocaproyl; amino benzoic acids; p-aminobenzylcarbamoyl (PAB); lysosomal enzyme-cleavable linkers; maleimidocaproyl-polyethylene glycol (MC(PEG)6-OH); N-methyl-valine citrulline; N-succinimidyl 4-(N-maleimidomethyl)cyclohexane-1-carboxylate (SMCC); N-Succinimidyl 4-(2-pyridyldithio)butanoate (SPDB); and N-Succinimidyl 4-(2-pyridylthio)pentanoate (SPP) (See also US 2011/0076232). Another linker for use includes an avidin-biotin linkage to provide an avidin-biotin-containing ADC (See also U.S. Pat. No. 4,676,980. PCT publication Nos. WO1992/022332A2, WO1994/016729A1, WO1995/015770A1, WO1997/031655A2, WO1998/035704A1, WO1999/019500A, WO2001/09785A2, WO2001/090198A1, WO2003/093793A2, WO2004/050016A2, WO2005/081898A2, WO2006/083562A2, WO2006/089668A1, WO2007/150020A1, WO2008/135237A1, WO2010/111198A1, WO2011/057216A1, WO2011/058321A1, WO20121027494A1, and EP77671B1), wherein some such linkers are resistant to biotinidase cleavage. Additional linkers that may be used include a cohesin/dockerin pair to provide a cohesion-dockerin-containing ADC (See PCT publication Nos. WO2008/097866A2, WO2008/097870A2, WO2008/103947A2, and WO2008/103953A2).

Additional linkers may contain non-peptide polymers (examples include, but are not limited to, polyethylene glycol, polypropylene glycol, polyoxyethylated polyols, polyvinyl alcohol, polysaccharides, dextran, polyvinyl ethyl ether, PLA (poly(lactic acid)), PLGA (poly(lactic acid-glycolic acid)), and combinations thereof, wherein a preferred polymer is polyethylene glycol) (See also PCT publication No. WO2011/000370). Additional linkers are also described in WO 2004-010957, U.S. Publication No. 20060074008. U.S. Publication No. 20050238649, and U.S. Publication No. 20060024317, each of which is incorporated by reference herein in its entirety).

For an ADC comprising a maytansinoid, many positions on maytansinoids can serve as the position to chemically link the linking moiety. In one embodiment, maytansinoids comprise a linking moiety that contains a reactive chemical group are C-3 esters of maytansinol and its analogs where the linking moiety contains a disulfide bond and the chemical reactive group comprises a N-succinimidyl or N-sulfosuccinimidyl ester. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol.

The conjugation of the drug to the antibody via a linker can be accomplished by any technique known in the art. A number of different reactions are available for covalent attachment of drugs and linkers to antibodies. This may be accomplished by reaction of the amino acid residues of the antibody, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody. Also available for attachment of drugs to antibodies is the Schiff base reaction. This method involves the periodate oxidation of a drug that contains glycol or hydroxy groups, thus forming an aldehyde which is then reacted with the binding agent. Attachment occurs via formation of a Schiff base with amino groups of the antibody. Isothiocyanates can also be used as coupling agents for covalently attaching drugs to antibodies. Other techniques are known to the skilled artisan and within the scope of the disclosure.

In certain embodiments, an intermediate, which is the precursor of the linker, is reacted with the drug under appropriate conditions. In certain embodiments, reactive groups are used on the drug or the intermediate. The product of the reaction between the drug and the intermediate, or the derivatized drug, is subsequently reacted with the anti-CDCP1 antibody under appropriate conditions. The synthesis and structure of exemplary linkers, strelcher units, amino acid units, self-immolative spacer units are described in U.S. Patent Application Publication Nos. 20030083263, 20050238649 and 20050009751, each if which is incorporated herein by reference.

Stability of the ADC may be measured by standard analytical techniques such as mass spectroscopy, HPLC, and the separation/analysis technique LC/MS.

Additional information regarding cytotoxic agents, linkers, and production of antibody-drug conjugates may be found, e.g., in WO 2013/055990, WO 2013/055993, WO 2012/123423, WO 2012/041805, WO 2011/130613, WO 2011/130616, WO 2009/117531, WO 2007/103288, WO 2007/011968, WO 2007/008603, WO 2007/008848, WO 2006/132670, WO 2006/065533. WO 2005/084390, WO 2005/082023, WO 2005/081711, WO 2005/077090, WO 2005/070457. WO 2004/010957, WO 2003/026577, WO 2012/177837, WO 2012/1445112, WO 2012/138749, WO 2012/135517, WO 2012/135522, WO 2012/128868, WO 2012/112708, WO 2012/112687, WO 2012/078868, WO 2012/061590, WO 2010/141566, WO 2010/126551, WO 2010/126552, WO 2010/091150, WO 2009/134870, WO 2009/134977, WO 2009/134952, WO 2009/134976. WO 2009/080831, WO 2007/056550, WO 2007/024536, WO 2006/086733, WO 2006/078809. WO 2006/078368, WO 2005/037992, WO 2005/020883, WO 2004/110498, WO 2004/103272, WO 2004/016801, WO 2004/013093, WO 2002/098883, WO 2001/024763, U.S. Pat. Nos. 9,061,074, 9,345,785, 9,428,585, 7,553,816, 8,288,352, 9,504,756, 8,609,105, 7,745,394, 8,039,273, 8,992,932, 8,343,928, 8,987,209, 8,697,688, 8,841,425, 9,090,629, 9,434,748, 9,353,127, 9,289,512, 9,376,500, 9,125,896, 9,498,541, 9,469,655, 9,375,488, and 9,289,509, the entire contents of each of which are incorporated herein by reference.

IV. Uses of Anti-CDCP1 Antibodies and Anti-CDCP1 ADCs

The antibodies and antibody portions (and ADCs) preferably are capable of neutralizing human CDCP1 activity both in vivo and in vitro. Accordingly, such antibodies and antibody portions can be used to inhibit hCDCP1 activity, e.g., in a cell culture containing hCDCP1, in human subjects or in other mammalian subjects having CDCP1 with which an antibody disclosed herein cross-reacts. In one embodiment, the disclosure provides a method for inhibiting hCDCP1 activity comprising contacting hCDCP1 with an antibody or antibody portion such that hCDCP1 activity is inhibited. For example, in a cell culture containing, or suspected of containing hCDCP1, an antibody or antibody portion can be added to the culture medium to inhibit hCDCP1 activity in the culture.

In another embodiment, disclosed herein is a method for reducing hCDCP1 activity in a subject, advantageously from a subject suffering from a CDCP1 associated disorder, e.g., cancer such as breast cancer, lung cancer, small cell lung cancer, liver cancer, pancreatic cancer, ovarian cancer, kidney cancer, and colon cancer, or a disorder in which CDCP1 activity is detrimental. The disclosure provides methods for reducing CDCP1 activity in a subject suffering from such a disease or disorder, which method comprises administering to the subject an antibody or antibody portion of the disclosure such that CDCP1 activity in the subject is reduced. Preferably, the CDCP1 is human CDCP1, and the subject is a human subject. Alternatively, the subject can be a mammal expressing a CDCP1 to which antibodies of the disclosure are capable of binding. Still further the subject can be a mammal into which CDCP1 has been introduced (e.g., by administration of CDCP1 or by expression of a CDCP1 transgene). Antibodies of the disclosure can be administered to a human subject for therapeutic purposes. Moreover, antibodies of the disclosure can be administered to a non-human mammal expressing a CDCP1 with which the antibody is capable of binding for veterinary purposes or as an animal model of human disease. Regarding the latter, such animal models may be useful for evaluating the therapeutic efficacy of antibodies of the disclosure (e.g., testing of dosages and time courses of administration).

As used herein, the term "a disorder in which CDCP1 activity is detrimental" is intended to include diseases and other disorders in which the presence of CDCP1 in a subject suffering from the disorder has been shown to be or is suspected of being either responsible for the pathophysiology of the disorder or a factor that contributes to a worsening of the disorder. Accordingly, a disorder in which CDCP1 activity is detrimental is a disorder in which reduction of CDCP1 activity is expected to alleviate the symptoms and/or progression of the disorder. Such disorders may be evidenced, for example, by an increase in the concentration of CDCP1 in a biological cell, fluid or tissue of a subject suffering from the disorder (e.g., an increase in the concentration of CDCP1 in a tumor, serum, plasma, synovial fluid, etc. of the subject), which can be detected, for example, using an anti-CDCP1 antibody as described above.

Non-limiting examples of disorders that can be treated with the antibodies, or antigen binding fragments thereof, include those disorders discussed below. For example, suitable disorders include, but are not limited to, a variety of cancers including, but not limited to, breast cancer, lung cancer, small cell lung cancer, liver cancer, pancreatic cancer, ovarian cancer, kidney cancer, and colon cancer.

In one aspect, the disclosure features methods that include administering an antibody or composition (e.g., a cell composition, antibody-drug conjugate, or antibody-radioisotope conjugate) disclosed herein to a subject in need thereof (e.g., a subject having, or identified or diagnosed as having, a cancer characterized by expression or (overexpression) of CDCP1, or a cancer characterized by the presence of CDCP1 on the surface of the cancer cells (e.g., a subject identified using any of the methods described herein), e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some implementations, the subject is identified as being a subject that expresses CDCP1 (e.g., using any of the methods described herein) or has an elevated level of a CDCP1 protein (e.g., as compared to reference level, e.g., a level of a CDCP1 protein produced by a healthy subject, a level of a CDCP1 protein produced by a non-cancerous, e.g., primary, cell, or a threshold level of a CDCP1 protein, in which a determined level of a CDCP1 protein that is above this value indicates that the subject should be administered an antibody described herein, an antibody-drug conjugate described herein, and/or other therapy). In some embodiments, the compositions and methods disclosed herein can be used for treatment of patients at risk for a cancer.

In some implementations, the subject has a cancer characterized by the presence of CDCP1 on the cancer cell surface. In some cases. CDCP1 proteins are translocated from the cytoplasm to the cell surface, or to cell surface CDCP1 rafts. Thus, the quantity of CDCP1 in a cancer cell may be similar to the quantity of CDCP1 in a normal cell. In some cases, the tumor cells expressing CDCP1 proliferate, therefore the quantity of CDCP1 in tumor tissue is higher relative to the quantity of CDCP1 in normal tissue.

In yet another aspect, the disclosure features methods of inhibiting or decreasing proliferation of a cell (e.g., a cell that expresses (e.g., overexpresses) CDCP1, or a cell characterized by the presence of CDCP1 on the cell surface) that include contacting the cell with an antibody, antibody-drug conjugate, nucleic acid, composition, or cell disclosed herein. In another aspect, the disclosure features methods of inhibiting or decreasing proliferation of a cancer cell (e.g., a cancer cell that overexpresses CDCP1, or a cancer cell characterized by having CDCP1 on the cell surface) that include contacting the cancer cell with an antibody, antibody-drug conjugate, nucleic acid, composition, or cell disclosed herein. A cell can be identified as overexpressing CDCP1 protein using any of the methods described herein. In some embodiments, a cell can also be identified as having CDCP1 on the cell surface using any of the methods described herein. In some implementations, the cell death induced by the antibody is complement-dependent cytotoxicity and/or cell-dependent cell cytotoxicity. In some implementations, the antibody is conjugated to a therapeutic agent (e.g., a cytotoxic agent) and the cell death is induced by the endocytosis of the antibody into the cancer cells, which in turn triggers the death of the cancer cells. In some implementations, the methods include the step of administering to a subject (e.g., a subject in need thereof) an effective amount of an antibody, nucleic acid, composition, or cell disclosed herein, thereby selectively inducing cell death.

Other examples of cancers that may be treated using the compositions and methods disclosed herein include, but are not limited to carcinoma, lymphoma, blastoma, sarcoma, and leukemia or lymphoid malignancies. More particular examples of such cancers include but are not limited to breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, lung cancer, small cell lung cancer, non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma. Kaposi's sarcoma, epidermoid cancer, environmentally induced cancers including those induced by asbestos, hematologic malignancies including, for example, multiple myeloma. B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma. T-cell lymphoma, and precursor T-lymphoblastic lymphoma, and any combinations of said cancers. PVNS, acute myeloid leukemia, adrenocortico carcinoma, ladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma. The present invention is also applicable to treatment of metastatic cancers.

In one embodiment, the antibodies and ADCs disclosed herein are used to treat a solid tumor. e.g., inhibit growth of or decrease size of a solid tumor, overexpressing CDCP1 or which is CDCP1 positive. In another embodiment, the antibodies and ADCs disclosed herein are used to treat breast cancer, lung cancer, small cell lung cancer, liver cancer, pancreatic cancer, ovarian cancer, kidney cancer, and colon cancer. Diseases and disorders described herein may be treated by anti-CDCP1 antibodies or ADCs, as well as pharmaceutical compositions comprising such anti-CDCP1 antibodies or ADCs.

In certain embodiments, the antibodies and ADCs disclosed herein are administered to a subject in need thereof in order to treat advanced cancers likely to exhibit elevated levels of CDCP1.

In certain embodiments, the disclosure includes a method for inhibiting or decreasing solid tumor growth in a subject having a solid tumor, said method comprising administering an anti-CDCP1 antibody or ADC described herein, to the subject having the solid tumor, such that the solid tumor growth is inhibited or decreased. In further embodiments, the solid tumor is an CDCP1 expressing solid tumor. In certain embodiments the anti-CDCP1 antibodies or ADCs described herein are administered to a subject having cancer, alone or in combination with an additional agent, e.g., radiation and/or chemotherapy, an immune checkpoint inhibitor, or a PARP inhibitor.

In certain embodiments, the disclosure includes a method for inhibiting or decreasing solid tumor growth in a subject having a solid tumor which was identified as a CDCP1 expressing or CDCP1 expressing tumor, said method comprising administering an anti-CDCP1 antibody or ADC described herein, to the subject having the solid tumor, such that the solid tumor growth is inhibited or decreased. Methods for identifying CDCP1 expressing tumors are known in the art, and include FDA-approved tests and validation assays. For example, these assays may use primers that are specific for the CDCP1 gene and/or cDNA and result in the amplification of the CDCP1 gene/cDNA, or a portion thereof. The amplified PCR products may be subsequently analyzed, for example, by gel electrophoresis using standard methods known in the art to determine the size of the PCR products. Such tests may be used to identify tumors that may be treated with the methods and compositions described herein.

In another aspect, this application features a method of treating (e.g., curing, suppressing, ameliorating, delaying or preventing the onset of, or preventing recurrence or relapse of) or preventing a CDCP1-associated disorder, in a subject. The method includes: administering to the subject a CDCP1 binding agent (particularly an antagonist), e.g., an anti-CDCP1 antibody or fragment thereof as described herein, in an amount sufficient to treat or prevent the CDCP1-associated disorder. The CDCP1 antagonist, e.g., the anti-CDCP1 antibody or fragment thereof, can be administered to the subject, alone or in combination with other therapeutic modalities as described herein.

Antibodies or ADCs, or antigen binding portions thereof, can be used alone or in combination to treat such diseases. It should be understood that the antibodies or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody. The additional agent also can be an agent that imparts a beneficial attribute to the therapeutic composition, e.g., an agent which affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the antibodies of the disclosure and at least one additional agent selected from the lists below. The combination can also include more than one additional agent, e.g., two or three additional agents if the combination is such that the formed composition can perform its intended function.

The combination therapy can include one or more CDCP1 antagonists, e.g., anti-CDCP1 antibodies or fragments thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, or radiosensitizers, as described in more herein.

In a particular embodiment, the anti-CDCP1 antibodies disclosed herein are used in combination with an anti-cancer agent or an antineoplastic agent. The terms "anti-cancer agent" and "antineoplastic agent" refer to drugs used to treat malignancies, such as cancerous growths. In one embodiment, the anti-CDCP1 antibodies or ADCs of the invention are administered in combination with one or more immune checkpoint inhibitors (e.g., antibody or small molecule immune checkpoint inhibitors) for the treatment of a cancer. In some embodiments, the immune checkpoint inhibitor is an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, IDO1, lDO2, ICOS (inducible T cell costimulator), KIR, LAIR1, LIGHT, MARCO (macrophage receptor with collageneous structure), PS (phosphatidylserine), OX-40, SLAM, TIGHT, VISTA, or any combinations thereof. In some embodiments, the immune checkpoint inhibitor is an anti-CTLA-4, PD-L1, or PD-1 antibody therapy such as, but not limited to Yervoy@ (ipilimumab: Bristol-Myers Squibb), Opdivo@ (nivolumab; Bristol-Myers Squibb), Keytrudat (pembrolizumab: Merck), and Tecentriq®, (atezolizumab; Roche).

In some embodiments, the anti-CDCP1 antibodies disclosed herein are used in combination with an inhibitor of the PI3K-AKT mTOR pathway, e.g., rapamycin, temsirolimus, everolimus, ridaforolimus, Torin1, Torin2, PP242, KU63794. WYE354, NVP-BEZ235. XL765, GDC-0491, GDC-0980. GSK2126458, AZD8055, OSI-027, CH5132799, PF-05212384, or ZSTK474. See also WO 2012/054748; U.S. Pat. No. 8,394,818; McCubrey et al., 2012, Oncotarget, 3:1068-1111.

In one embodiment, the anti-CDCP1 antibodies, bispecific antibodies, or ADCs disclosed herein are administered in combination with a PARP (poly ADP ribose polymerase) inhibitor. PARP inhibitors are well known to those of ordinary skill in the art and include, but are not limited to, Niraparib. Olaparib, Rucaparib, Iniparib. Talazoparib, Veliparib, CEP 9722. E7016, BGB-290, and 3-aminobenazamine.

Drug therapy may be used alone, or in combination with other treatments such as surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone.

In particular embodiments, the anti-CDCP1 antibodies or ADCs can be administered alone or with another anti-cancer agent which acts in conjunction with or synergistically with the antibody to treat the disease associated with CDCP1 activity. Such anti-cancer agents include, for example, agents well known in the art (e.g., cytotoxins, chemotherapeutic agents, small molecules and radiation). Examples of anti-cancer agents include, but are not limited to, Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Other anti-cancer agents include, but are not limited to, those disclosed in U.S. Pat. No. 7,598,028 and International Publication No. WO2008/100624, the contents of which are hereby incorporated by reference. One or more anti-cancer agents may be administered either simultaneously or before or after administration of an antibody or antigen binding portion thereof.

In particular embodiments of the invention, the anti-CDCP1 antibodies or ADCs described herein can be used in a combination therapy with an inhibitor of NAMPT (see examples of inhibitors in US 2013/0303509; AbbVie. Inc., incorporated by reference herein) to treat a subject in need thereof. NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD. In one embodiment, anti-CDCP1 antibodies and ADCs described herein are administered in combination with a NAMPT inhibitor for the treatment of cancer in a subject.

In particular embodiments, the anti-CDCP1 antibodies or ADCs described herein can be used in a combination therapy with SN-38, which is the active metabolite of the topoisomerase inhibitor irinotecan.

The pharmaceutical compositions may include a "therapeutically effective amount" or a "prophylactically effective amount" of an antibody or antibody portion. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated, each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an ADC, an antibody or antibody portion is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another aspect, this application provides a method for detecting the presence of CDCP1 in a sample in vitro (e.g., a biological sample, such as serum, plasma, tissue, biopsy). The subject method can be used to diagnose a disorder, e.g., a cancer. The method includes: (i) contacting the sample or a control sample with the anti-CDCP1 antibody or fragment thereof as described herein; and (ii) detecting formation of a complex between the anti-CDCP1 antibody or fragment thereof, and the sample or the control sample, wherein a statistically significant change in the formation of the complex in the sample relative to the control sample is indicative of the presence of CDCP1 in the sample.

Given their ability to bind to human CDCP1, the anti-human CDCP1 antibodies, or portions thereof, (as well as ADCs thereof) can be used to detect human CDCP1 (e.g., in a biological sample, such as serum or plasma), using a conventional immunoassay, such as an enzyme linked immunosorbent assays (ELISA), an radioimmunoassay (RIA) or tissue immunohistochemistry. In one aspect, the disclosure provides a method for detecting human CDCP1 in a biological sample comprising contacting a biological sample with an antibody, or antibody portion, and detecting either the antibody (or antibody portion) bound to human CDCP1 or unbound antibody (or antibody portion), to thereby detect human CDCP1 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

Alternative to labeling the antibody, human CDCP1 can be assayed in biological fluids by a competition immunoassay utilizing rhCDCP1 standards labeled with a detectable substance and an unlabeled anti-human CDCP1 antibody. In this assay, the biological sample, the labeled rhCDCP1 standards and the anti-human CDCP1 antibody are combined and the amount of labeled rhCDCP1 standard bound to the unlabeled antibody is determined. The amount of human CDCP1 in the biological sample is inversely proportional to the amount of labeled rhCDCP1 standard bound to the anti-CDCP1 antibody. Similarly, human CDCP1 can also be assayed in biological fluids by a competition immunoassay utilizing rhCDCP1 standards labeled with a detectable substance and an unlabeled anti-human CDCP1 antibody.

In yet another aspect, this application provides a method for detecting the presence of CDCP1 in vivo (e.g., in vivo imaging in a subject). The subject method can be used to diagnose a disorder, e.g., a CDCP1-associated disorder. The method includes: (i) administering the anti-CDCP1 antibody or fragment thereof as described herein to a subject or a control subject under conditions that allow binding of the antibody or fragment to CDCP1; and (ii) detecting formation of a complex between the antibody or fragment and CDCP1, wherein a statistically significant change in the formation of the complex in the subject relative to the control subject is indicative of the presence of CDCP1.

Diagnostics and Imaging

The antibodies of the present disclosure can also be used in various diagnostic, and imaging methods. For example, the antibodies of the disclosure can be used in any known assay method, such competitive binding assays, direct and indirect sandwich assays, and immunoprecipitation assays (see. e.g., Zola, Monoclonal Antibodies: A Manual of Techniques, pp. 147-158 (CRC Press. Inc., 1987). For use in such methods, e.g., for use in in vitro assays, the antibodies can be detectably labeled, e.g., with a fluorophore such as Fluorescein isothiocyanate (FITC) or phycoerythrin or with an enzyme substrate, such as a substrate for horse radish peroxidase, for easy detection.

As discussed herein, the antibodies of the disclosure also can be used for in vivo diagnostic assays and in vivo imaging. In some implementations, the antibody is labeled with a radionucleotide (such as $^{3}H$, $^{111}In$, $^{14}C$, $^{32}P$, or $^{123}I$) so that the cells or tissue of interest can be localized and/or imaged using immunoscintigraphy. Methods of conjugating labels to an antibody are known in the art. In other implementations of the disclosure, antibodies disclosed herein need not be labeled, and the presence thereof can be detected using a labeled antibody, which binds to the antibody.

For example, the disclosure provides methods of detecting a CDCP1 protein in a sample (e.g., a sample containing mammalian cells, e.g., a biopsy sample) that include contacting a sample with an antibody disclosed herein and detecting binding of the antibody to any CDCP1 protein in the sample. Some implementations further include recording the detection or non-detection of CDCP1 protein (e.g., the presence, the detection, the non-detection, and/or level of a CDCP1 protein) in the clinical records of a subject from whom the sample was obtained.

In some implementations, the clinical record is stored on a computer-readable medium, e.g., a disc, tape, or computer memory. Some implementations further include administering any one of the antibodies described herein to a subject identified as having detectable CDCP1 protein or an elevated level of a CDCP1 protein (e.g., as compared to a reference level, e.g., a level of a CDCP1 protein produced by a non-cancerous cell) in his or her sample. Some implementations further include performing further testing for the presence of cancer (e.g., any of the methods for further testing for the presence of cancer described herein) on a subject identified as having detectable CDCP1 protein or an elevated level of a CDCP1 protein. Additional examples of reference values are described herein.

Also provided are methods of imaging one or more cancer cells (e.g., a cancer cell that overexpresses CDCP1 or a cancer cell characterized by having CDCP1 on the cell surface, e.g., breast cancer (e.g., triple-negative breast cancer), carcinoid cancer, cervical cancer, endometrial cancer, glioma, head and neck cancer, liver cancer, lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy cell) in a subject (e.g., a subject in need thereof, e.g., a subject identified as being at risk for developing a cancer, a subject suspected of having a cancer, or a subject already diagnosed or identified as having a cancer), that include administering to a subject an antibody that is conjugated to a detectable label (e.g., any of the examples of detectable labels described herein) and imaging the presence of the cancer cell by detecting the detectable label in the subject. In some implementations, the detectable label is a fluorophore, a metalloporphyrin, a paramagnetic metal, a superparamagnetic metal, a magnetic particle (e.g., 10-20 nm in diameter), a nitroxide stable free radical, or ferrioxamine methane sulfonate, or a metal, e.g., gold.

The methods of detection and diagnosis can be performed on any biological sample (e.g., a sample containing mammalian cells), e.g., a sample from an individual having a cancer or suspected of having a cancer. The biological sample can be, e.g., a biopsy (e.g., needle biopsy), tissue section, or a bodily fluid (e.g., lung gavage, urine, saliva, blood, tears, semen, or breast milk).

The antibody can also be used as staining reagent in pathology, following techniques that are well known in the art.

Such detection of specific binding by the antibody to the sample (e.g., detection of an antibody: sample complex) can be made by any known method including, without limitation, western blotting analysis, immunohistochemistry (IHC) analysis, immunofluorescence (IF) analysis, flow cytometry analysis, FACS analysis, ELISA, and immunoprecipitation. See, generally. Immunological Methods, Vols. I and II (Lefkovits and Pernis, eds., Academic Press, N Y, 1979 and 1981, herein incorporated by reference.

Cellular extracts of the foregoing biological samples may be prepared, either crude or partially (or entirely) purified, in accordance with standard techniques, and used in the methods of the disclosure. Alternatively, biological samples comprising whole cells, e.g, circulating tumor cells (CTCs), can be utilized in assay formats such as immunohistochemistry (IHC), flow cytometry (FC), and immunofluorescence (IF).

V. Pharmaceutical Compositions

The disclosure also provides pharmaceutical compositions comprising an antibody, or antigen binding portion thereof, or ADC and a pharmaceutically acceptable carrier. The pharmaceutical compositions comprising antibodies or ADCs are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies. In another embodiment, the pharmaceutical composition comprises one or more antibodies or ADCs and one or more prophylactic or therapeutic agents other than antibodies or ADCs for treating a disorder in which CDCP1 activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions or ADCs can be incorporated into pharmaceutical compositions suitable for administration to a subject. Typically, the pharmaceutical composition comprises an antibody or antibody portion and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion or ADC.

Various delivery systems are known and can be used to administer one or more antibodies or ADCs or the combination of one or more antibodies and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos, WO 92/19244, WO 97/32572, WO 97/44013, WO 98/31346, and WO 99/66903, each of which is incorporated herein by reference their entireties. In one embodiment, an antibody, combination therapy, or a composition is administered using Alkermes AIR® pulmonary drug delivery technology (Alkermes, Inc., Cambridge. Mass.). In a specific embodiment, prophylactic or therapeutic agents are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies antagonists is administered locally to the affected area to a subject to prevent, treat, manage, and/or ameliorate a disorder or a symptom thereof. In another embodiment, an effective amount of one or more antibodies is administered locally to the affected area in combination with an effective amount of one or more therapies (e.g., one or more prophylactic or therapeutic agents) other than an antibody of a subject to prevent, treat, manage, and/or ameliorate a disorder or one or more symptoms thereof.

A pharmaceutical composition is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the method of the disclosure comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the prophylactic or therapeutic agents, or pharmaceutical compositions is packaged in a hermetically sealed container such as an ampoule or sachette indicating the quantity of the agent. In one embodiment, one or more of the prophylactic or therapeutic agents, or pharmaceutical compositions is supplied as a dry sterilized lyophilized powder or water free concentrate in a hermetically sealed container and can be reconstituted (e.g., with water or saline) to the appropriate concentration for administration to a subject. The antibodies and antibody-portions or ADCs can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

EXAMPLES

The following examples are provided to illustrate, but not to limit, the invention.

Example 1. Preparation of Monoclonal Antibodies

Monoclonal antibodies were obtained by immunization of rabbits with rabbit splenocytes expressing full-length CDCP1 or immunization of mice engineered with the capacity to produce fully human immunoglobulins with recombinant extracellular domain of CDCP1. Additionally, antibody 41A10 was partially humanized to produce antibody ATF3. Sequences of the 41A10 antibodies are disclosed in Table 2.

TABLE 2

| Ab | Isotype | VH DNA | VH | VL DNA | VL |
|---|---|---|---|---|---|
| 41A10 | Rabbit IgG | CAGGAGCAGCTGGAGGAGTCCGGGGGAGACCTGGTCAAGCCTGGGGCATCCCTGACACTCACCTGCAAGTCCTCTGGAATCGACTTCAGCAGTGCCTATTACATGTGCTGGGTCCGCCAGGCTCCCGGGAAGGGGCTGGAGTGGATCGCATGCATTTATACTGGTAGCACTTACTACGCGAACTGGGCGAAAGGCCGATTCACCATCTCCAAAACCTCGTCGACCACGGTGACTCTGCAAATGACCAGTCTGACAGCCGCGGACACGGCCACTTATTTTTGTGCCAGAGATCCTATTGGTTATATGTTTGACTTGTGGGGCCCAGGCACCCTACTCACCGTCTCCTCA (SEQ ID NO: 402) | QEQLEESGGDLVKPGASLTLTCKSSGIDFSSAYYMCWVRQAPGKGLEWIACIYTGSTYYANWAKGRFTISKTSSTTVTLQMTSLTAADTATYFCARDPIGYMFDLWGPGTLLTVSS (SEQ ID NO: 403) | GCATTCGAGTTGACCCAGACTCCAGCCTCCGTGGAGGCAGATGTGGGAGGCACAGTCACCATCAAGTGCCAGGCCAGTCAGAACATTTACAGCAATTTAGCCTGGTATCAACAGAAACCAGGGCAGCCTCCCAAGCTCCTGATCTATGGTGCATCCACTCTGGCATCTGGGGTCTCATCGCGGTTCAGAGGCAGTGGATCTGGGACAGAGTTCACTCTCACCATCAGCGACCTGGAGTGTGCCGATGCTGCCACTTACTACTGTCAGGGCGGTGATGATGATAGTTATGCTTTCGGCGGAGGGACCGAGGTGGTGGTCAAAG (SEQ ID NO: 404) | AFELTQTPASVEADVGGTVTIKCQASQNIYSNLAWYQQKPGQPPKLLIYGASTLASGVSSRFRGSGSGTEFTLTISDLECADAATYYCQGGDDDSYAFGGGTEVVVK (SEQ ID NO: 405) |

Example 2. Generation of Antibodies Against the CDCP1 Extracellular Domain

Experiments were performed to generate fully human antibodies against CDCP1 extracellular domain. The following methods were used in the examples.

Recombinant CDCP1 Cloning

Human CDCP1 cDNA was purchased from Origene (RC220633. Rockville. MD) and named BBP374. The encoded protein was aligned with GenBank CDCP1_HUMAN sequence and found to differ at two positions: Q525R and D709G.

Ectodomains of human, cynomolgus monkey, rat, and mouse were cloned by either PCR (human) or synthetic genes (monkey, rat, mouse). The synthetic genes were based on GenBank sequences (Table 3). All DNA sequences were cloned into appropriate CMV-based expression vectors with non-native signal peptides and C-terminal histidine tags for purification.

TABLE 3

Source of CDCP1 protein sequences

| Species | GenBank Protein Reference |
|---|---|
| Human | CDCP1_HUMAN |
| Cynomolgus monkey | XP_005546930 |
| Rat | NP_001100339 |
| Mouse | CDCP1_MOUSE |

The Origene® BBP374 construct was used to express full-length human CDCP1 protein (M1-E836) on the surface of HEK-293 cells. In addition, a series of human CDCP1 constructs were generated to screen antibody binding properties and epitopes (see Table 4).

TABLE 4

CDCP1 cell-surface expression vectors

| Plasmid name | Sequence feature | Comment |
|---|---|---|
| BBP374 | M1-E836 Q525R D709G (plus Myc-DDK) | Native CDCP1 |
| pMSCV/FLCDCP1 | M1-E836 Q525R D709G (plus Myc-DDK | Native CDCP1 |
| pMSCV/ClvCDCP1 (N342) | K343-E836 Q525R D709G (plusMyc-DDK) | |

A series of CDCP1 constructs were generated to secrete portions of the ectodomain from CHO cells. These plasmids were cloned (see Table 5) to assist with biophysical evaluations.

TABLE 5

CDCP1 ectodomain expression vectors

| Plasmid name | Species | Sequence feature (plus 8xHis (SEQ ID NO: 406)) | Comment |
|---|---|---|---|
| BBP476 | Human | F30-T667 | Full ectodomain |
| BBP463 | Human | F30-T667 Q525R | Full ectodomain with Q525R SNP |
| BBP477 | Human | F30-T667 R368GS K369GS Q525R | Impaired R368-K369 cleavage |
| BBP464 | Human | F30-R368 | Distal domain |
| BBP465 | Human | K343-T667 Q525R | Proximal domain |
| BBP467 | Human | C221-E544 Q525R | CUB1/CUB2 domain |
| BBP468 | Cynomolgus | F30-T667 | Full monkey ectodomain |
| BBP469 | Rat | S30-T667 | Full rat ectodomain |
| BBP470 | Mouse | S30-T663 | Full mouse ectodomain |

Cloning VH and VL Sequences from Hybridomas

For determination of CDR sequences, total RNA was isolated from hybridoma cells using an RNeasy® kit (Qiagen. Hilden, Germany). First and second-strand cDNA synthesis was performed using a OneTaq®) One-Step RT-PCR kit (New England BioLabs, Ipswich, MA). PCR products were separated by agarose electrophoresis and fragments were excised and purified by a QIAquick® gel extraction kit (Qiagen. Hilden, Germany). Fragments were cloned directly into expression vectors with BspQI (New England BioLabs, Ipswich, MA) by Golden Gate cloning techniques. Four colonies from each reaction were scaled up for miniprep-scale plasmid purification by SequeMid® DNA Purification Kit (Aline Biosciences. Woburn, MA).

Identification of Functional, Recombinant VH and VL Sequences

For each hybridoma, four plasmids encoding the recombinant heavy chain were paired with four plasmids encoding the recombinant light chain. These plasmid pairs were transfected into HEK-293 cells in 96-well plates. Five days later conditioned medium from each pairing was screened by ELISA for binding to the target.

From each hybridoma there were 16 wells of transfected cells. Based on ELISA data, one pairing (of the 16) was chosen from each hybridoma. The colonies containing plasmids that were used for the chosen pairing were cultured and plasmid DNA was purified at the maxiprep-scale (Qiagen). These plasmids were subjected to DNA sequence determination and analysis.

Transient Expression System

The CDCP1 recombinant proteins and anti-CDCP1 antibodies were expressed in Chinese hamster ovary (CHO) cells using recommended transfection and media components of the ExpiCHO system (Invitrogen, Carlsbad, CA). Cell culture supernatants were harvested 14 days post-transfection, centrifuged, and filtered (0.22 um) prior to purification.

Purification of Recombinant His-Tagged Proteins

Conditioned medium from CHO cell cultures was clarified, filtered, and loaded onto an ÄKTAprime plus system with a 5 mL HisTrap™ FF column (GE Healthcare). Fractions were collected, analyzed by SDS-PAGE, pooled, and dialyzed against PBS.

Antibody Purification

Conditioned medium from CHO cell cultures was clarified, filtered, and purified by loading onto an ÄKTA pure system with a 5 mL MabSelect SuRe® column (GE Healthcare). Antibodies were eluted with 100 mM glycine, pH 3.5 and neutralized with 1M Tris-Cl, pH 8.5.

Recombinant Antibody Analyses

Concentration: Concentration of recombinant antibodies was determined on a Fortebio Octet using Protein A tips and a human IgG1 antibody for the standard curve.

Purity testing by SDS-PAGE: Purity testing was performed by sodium dodecyl sulfate polyacrylamide gel electrophoresis (SDS-PAGE) of reduced and non-reduced samples. Samples (10 ug) were mixed with loading buffer (+/−β-mercaptoethanol), heated, and electrophoresed on a 4-20% gel (Invitrogen). Bands were visualized by Coomassie InstantBlue® (Expedeon) staining.

Purity testing by Endotoxin: Endotoxin concentrations were measured by the Limulus amoebocyte lysate (LAL) kinetic turbidometric method using the Endosafe-PTSr system (Charles River Laboratories).

Purity testing by HPLC-SEC: Samples were screened for aggregation or other forms of antibody on a 1260 Infinity System (Agilent) with a TSKgel UltraSW® Aggregate Guard column and HPLC column (Tosoh Bioscience). Samples and standards were detected by absorbance at 280 nm. Comparison against the standard curve provided the molar mass of sample components.

Affinity: The affinity of antibodies to various recombinant CDCP1 molecules was determined on an Octet Red (Pall, ForteBio) instrument. After loading reagents into a 96-well plate, the Octet Red with Protein A-conjugated biosensors was programmed as follows: 30 seconds for baseline #1; 120 seconds to immobilize the antibody; 30 seconds for baseline #2; 300 seconds for association of antibody to recombinant CDCP1; and 300-600 seconds for dissociation of recombinant CDCP1 from the antibody.

Epitope binning: Binding competition among different antibodies was determined using a real-time, interferometry assay on an Octet Red (Pall, ForteBio) instrument with Protein A-conjugated biosensors. To assess whether two antibodies competed for binding to a recombinant CDCP1 protein, the assay was performed as follows. Protein A biosensors were first submerged into wells containing 20 ug/mL of individual monoclonal antibodies for 10 minutes. Following the capture step, the biosensors were dipped briefly (30 sec) into buffer and then any unoccupied sites on the biosensor were saturated by submerging them for 5 minutes into wells containing 200 ug/mL of an irrelevant monoclonal antibody. The Octet biosensors were then dipped briefly (30 sec) in buffer before immersion for 5 minutes into wells containing recombinant CDCP1. The biosensors were dipped briefly (30 sec) in buffer before immersion for 5 minutes into wells containing a second recombinant antibody.

For the control case where the second antibody was the same as the rust, there was no increase in signal, because there was no additional binding to the recombinant target. For the control case where buffer was used instead of the first antibody, no recombinant target bound the non-quenching antibody on the biosensor and no second antibody bound the biosensor. For cases where a boost in signal was seen with the second antibody, the two antibodies were determined not to compete. For cases where no boost in signal was seen with the second antibody, the two antibodies were determined to compete for binding.

Immunofluorescence (IF) Based High Content Screening (HCS)

High content immunofluorescence was used to identify wells that contain immunoglobulin that preferentially bound CDCP1. Briefly, HCT116 cells (CDCP1+) and MCF7 cells (CDCP1-) seeded 24 hours before the assay were incubated for 45 minutes at 37° C. with hybridoma supernatant diluted 2-fold in DMEM+10% fetal bovine serum (FBS). After incubation, cells were fixed in 4% formaldehyde, washed with PBS, permeabilized with 0.3% Triton®-X-100, and labeled with anti human Alexa® 488 secondary antibodies for 1 hour at room temperature. Unbound secondary antibody was removed with PBS washes, and cells were stained with DNA dye (propidium iodide and Hoechst 33342).

Potential hits were initially identified via low-resolution, high throughput screening using a TTP Labtech Acumen eX3® (TIT Labtech. Cambridge, MA), quantifying the fluorescence differential for each sample on both positive and negative cell lines. Those hits were subsequently verified and the subcellular localization of each sample was characterized using a Thermo ArrayScan VTi® (Thermo Fisher Scientific, Waltham. MA) to obtain high-resolution images of both cell lines.

Wells containing immunoglobulin that preferentially bound the CDCP1 were analyzed again on 2931 cells or 293T cells over-expressing full length (FL) CDCP1 and cleaved-CDCP1 to confirm CDCP1 specificity and to determine epitope localization.

Determination of Epitope Localization of CDCP1 Antibodies

Two proteolytic cleavage sites (R368 and N342) in the CDCP1 ECD were identified using mass spectrometry technology. 293T cells stably transfected with DNA constructs expressing full length (FL) CDCP1 and cleaved (Clv) CDCP1 (AA343-836) expresses these proteins on the cell surface. As shown in FIG. 1B, Abl binds to FL-CDCP1 only, therefore its epitope is likely to be in the distal region (AA30-342). Ab2 binds to both 293T/FL-CDCP1 and 2931/Clv-CDCP1, therefore its epitope is likely to be in the proximal region (AA343-667). Antibodies that can bind both 2931/FL-CDCP1 and 2931/Clv-CDCP1 (AA343-836) have epitopes localized in the proximal region of CDCP1 ECD (AA343-667). In contrast, antibodies that can only bind 293T/FL-CDCP1 have epitopes localized to the distal region of CDCP1 ECD (AA30-342) (FIGS. 1A-1C).

Results

Fully human antibodies against CDCP1 extracellular domain (ECD) were generated by standard hybridoma procedures. Briefly, mice were immunized with recombinant full length CDCP1 ECD or a cleaved form of ECD. Splenocytes were fused with the mouse myeloma cell line X63-Ag8.653. Clones producing antibodies against CDCP1 ECD were identified by immunofluorescence (IF) based high content screening (HCS) on HCT116 cells endogenously expressing CDCP1 and MCF7 cells not expressing CDCP1. CDCP1 specificity as well as ECD binding region was then determined by IF-HCS on 293T cells over-expressing full length (FL) CDCP1 and cleaved-CDCP1 (14342). The resulting CDCP1 specific clonal hybridomas were cryopreserved in freezing medium and stored in liquid nitrogen.

Forty hybridoma hits were selected and successfully converted to recombinant human IgG1 antibody against CDCP1 including 21 Abs binding to distal region (AA.30-342) and 17 Abs binding to proximal region (AA343-667). Biological characterization of these antibodies include target internalization/degradation capabilities and matripase-mediated R368 cleavage blockade. Biophysical characterization of these antibodies include: cross-reactivity against human and Cynomolgus CDCP1, epitope competition binning, aggregation, degradation, stickiness and sequence liability.

Eighteen recombinant monoclonal human antibodies were selected for epitope binning assay, kinetic analysis against human and Cynomolgus CDCP1 (FIG. 15). The properties of these antibodies are summarized in FIG. 16 and FIG. 17, and the sequences of these antibodies are shown in FIG. 18. FIG. 19, and FIG. 20.

FIG. 16 and FIG. 17, show the affinity of the antibodies to CDCP1. Affinity was measured by dissociation constant ($K_d$). $K_d$ is the ratio of the rate constant of the off rate ($k_{off}$) divided by the rate constant of the on rate ($k_{on}$). The lower the value of $K_d$, the higher affinity of the antibody for the target molecule. FIG. 16 shows $K_d$ for cynomolgus monkey CDCP1 and affinity to murine CDCP1. FIG. 17 shows $K_d$ for human CDCP1, $K_d$ for cynomolgus monkey CDCP1, and affinity to murine CDCP1. FIG. 18 shows the amino acid sequence of the heavy chain variable region (VH) and the light chain variable region (VL) of the 40 anti-CDCP1 antibodies. FIG. 19 shows the nucleotide sequence of the heavy chain variable region and the light chain variable region of these antibodies. FIG. 20 shows the amino acid sequence of the complementary determining regions in the heavy chain variable region and complementary determining regions in the light chain variable region of the 40 anti-CDCP1 antibodies.

Example 3. CDCP1 is Highly Expressed and Phosphorylated in Multiple Solid Tumors Experiments were performed to determine CDCP1 expression and phosphorylation in multiple solid tumors. The following methods were used in this example.

Phospho-Tyrosine Peptide Profiling by PhosphoScan™

Tissue specimens were taken infra-operatively and snap frozen in liquid nitrogen. An average of 15 milligrams of peptides were prepared from 0.2-0.5 grams of resected frozen ovarian tissues by homogenization, trypsin digestion and Sep-pak® C18 column purification. The methods are described, e.g., in, Rush, John, et al. "Immunoaffinity profiling of tyrosine phosphorylation in cancer cells." *Nature Biotechnology.* 23.1 (2005): 94-101; and Gu. Ting-Lei, et al. "Survey of tyrosine kinase signaling reveals ROS kinase fusions in human cholangiocarcinoma," PloS one 6.1 (2011): e15640.

Peptides containing phospho-tyrosine (pY) were isolated by immuno-precipitation with a monoclonal antibody against phospho-tyrosine (pY100), concentrated on reverse-phase micro tips, and analyzed by liquid chromatography tandem mass spectrometry (LC-MS/MS). Briefly, samples were collected with an LTQ-Orbitraprm mass spectrometer, using a top-ten method, a dynamic exclusion repeat count of 1, and a repeat duration of 30 seconds. MS and MS/MS spectra were collected in the Orbitrap and LTQ component of the mass spectrometer, respectively. SORCERER-SE-QUEST™ (v4.0.3 (c) 2008. Sage-N Research, Inc., Milpitas, CA) searches were done against the NCBI human RefPept database downloaded on Jan. 6, 2009 (containing 37,742 proteins) or Mar. 1, 2010 (containing 36.500 proteins), allowing for serine, threonine and tyrosine phosphorylation (STY+80) and methionine oxidation (M+16) as differential modifications.

Clustering and Ranking Analysis

To assess potentially aberrant tyrosine phosphorylation of proteins in tumor tissues, spectral counts per protein were summed and normalized to the amount of peptide subjected to pY immuno-precipitation (15 mg). Elevated spectral count in each tumor sample was calculated by subtracting an average spectral count in normal tissues. Elevated pY spectral count proteins, representing elevated tyrosine phosphorylation, observed in tumor samples were used as the basis for hierarchical clustering using the Pearson correlation distance metric and average linkage (MultiExperiment Viewer version 4.4). Proteins with elevated phosphorylation in tumors were ranked based on the average value of elevated spectral count in corresponding tumors. GenePattern 3.0 software package (Broad Institute of MIT and Harvard, Cambridge. MA) was used for Comparative Marker Selection analysis.

Results

Using an unbiased and global phospho-proteomic approach, the PhosphoScan® program. CDCP1 was found to be differentially expressed in breast, colon, lung, pancreatic, ovarian, and kidney cancer as compared to normal tissue. Additionally, differential CDCP1 tyrosine phosphorylation was detected in breast, colon, lung, and ovarian cancer. CDCP1 is among the most differentially phosphorylated proteins identified in breast cancer, non-small cell lung cancer, liver cancer and colon cancer. Particularly. CDCP1 is highly phosphorylated in malignant breast tumor tissue when compared with benign breast tumor. These results show that CDCP1 is highly expressed in multiple solid tumors and is a suitable target for cancer treatment using the ADCs described herein.

Example 4. CDCP1 is Overexpressed in Triple Negative Breast Cancer (TNBC) and Colorectal Cancer (CRC)

Experiments were performed to determine CDCP1 expression in TNBC and CRC. The following methods were used in this example.

4 μm FFPE tissue sections or tissue microarrays (TMA) slides were de-paraffinized and rehydrated through xylene and graded ethanol, respectively. Antigen retrieval was performed in a Decloaking Chamber (Biocare Medical. Concord, CA) using 1.0 mM EDTA, pH 8.0. Slides were then quenched in 3% $H_2O_2$ for 10 minutes, washed in deionized $H_2O$ and blocked with Tris buffered saline/0.5% Tween-20 (TBST)/5% goat serum in a humidified chamber for 60 minutes. Sections were then exposed to anti-CDCP1 antibody overnight at 4° C. Detection was performed with SignalStain® Boost IHC Detection Reagent (Cell Signaling Technology, Danvers. MA) for 30 minutes. All slides were exposed to NovaRed® (Vector Laboratories, Inc., Burlingame. CA) for 1 minute before they were rinsed, dehydrated, cleared and cover-slipped. An immunohistochemistry (IHC) score was given to each specimen using a qualitative scoring method. The scoring method categorizes different levels of IHC staining into different groups, including negative (−), weak (1+), moderate (2+), and strong (3+ or more). The method of determining the IHC scores is described in. e.g., Fedchenko. Nickolay, and Janin Reifenrath. "Different approaches for interpretation and reporting of immunohistochemistry analysis results in the bone tissue—a review." *Diagnos. Pathol.,* 9 (1): 221 (2014), which is incorporated herein by reference in its entirety.

Immunohistochemistry (IHC) analysis further revealed 86% of 26 primary TNBC tumor tissue over-express CDCP1 (IHC score of 2+ or more). In tumor, CDCP1 is localized predominantly on the cell surface. 7/7 metastatic lymph node specimens from TNBC patients overexpressed CDCP1 (IHC score of 2+ or more). In addition, 2 relapsed TNBC tumors overexpressed CDCP1.

In colon cancer, 12 primary tumor specimen and 4 metastatic specimen of colorectal cancer harvested from liver, lung or pancreas exhibited high level of membrane expression of CDCP1 (Table 6).

TABLE 6

Overexpression of CDCP1 in Primary, Metastatic and/or Relapsed Tumors of TNBC and CRC

| Indication | Tissue Type | Total No. | IHC 0 | IHC 1+ | IHC 2+ | IHC ≥3+ | # of tissue IHC ≥2+ |
|---|---|---|---|---|---|---|---|
| TNBC | Primary tumor | 26 | 0 | 4 | 12 | 12 | 24 (86%) |
| TNBC | Normal adjacent tissue | 5 | 5 | | | | 0 (0%) |
| TNBC | Lymph node metastatic tumor | 7 | | | 3 | 4 | 7 (100%) |
| TNBC | Relapsed tumor | 2 | | | 1 | 1 | 2 (100%) |
| CRC | Primary tumor | 12 | | | | 12 | 12 (100%) |
| CRC | Metastatic tumor (liver, lung, pancreas) | 4 | | | | 4 | 4 (100%) |

These results confirm that CDCP1 is overexpressed in primary, metastatic, and relapsed tumors, which are thus suitable targets for cancer therapy using the ADCs described herein.

Example 5. CDCP1 is Expressed in Other Subtypes of Breast Cancer

Immunohistochemistry (IHC) analysis revealed that CDCP1 is overexpressed in 5/5 ductal carcinoma in situ (DCIS), 5/5 luminal A breast cancer, 4/4 Her2+ breast cancer tumor specimens (Table 7). In addition, 2 tissue microarray containing 138 and 149 storable tumor tissue cores from invasive ductal carcinoma (IDC) patients with known Her2 expression status were examined for CDCP1 expression by immunohistochemistry analysis. High level of CDCP1 expression was detected in 46-57% of Her 2 over-expressing tumor specimen versus 18% or 54% of Her 2 low tumor specimens (Table 7).

TABLE 7

Overexpression of CDCP1 in several subtypes of breast cancer specimen

| Type of BrCa specimen | Total No. | IHC 0 | IHC 1+ | IHC 2+ | IHC ≥3+ | # of tissue IHC ≥2+ |
|---|---|---|---|---|---|---|
| DCIS | 5 | 0 | 0 | 3 | 2 | 5 (100%) |
| Luminal A | 5 | 0 | 0 | 2 | 3 | 5 (100%) |

TABLE 7-continued

Overexpression of CDCP1 in several subtypes of breast cancer specimen

| Type of BrCa specimen | Total No. | IHC 0 | IHC 1+ | IHC 2+ | IHC ≥3+ | # of tissue IHC ≥2+ |
|---|---|---|---|---|---|---|
| Her2+ breast cancer | 4 | 0 | 0 | 2 | 2 | 4 (100%) |
| IDC tissue microarrays (TMA-1) (Her2 expression IHC 0-1+) | 66 | 39 | 16 | 9 | 2 | 11 (18%) |
| IDC tissue microarrays (TMA-1) (Her2 expression IHC 2-3+) | 72 | 19 | 20 | 23 | 10 | 33 (46%) |
| IDC tissue microarrays (TMA-2) (Her2 expression IHC 0-1+) | 81 | 11 | 26 | 18 | 26 | 44 (54%) |
| IDC tissue microarrays (TMA-2) (Her2 expression IHC 2-3+) | 68 | 11 | 13 | 15 | 24 | 39 (57%) |

Example 6. CDCP1 is Expressed in Other Types of Solid Tumors

Immunohistochemistry (IHC) analysis revealed that CDCP1 is overexpressed in other types of solid tumors. In ovarian serous carcinoma, CDCP1 overexpression is detected in 95% of the 18 primary tumors and 72% of the 11 relapsed tumors. In ovarian clear cell carcinoma, CDCP1 is overexpressed in 5/5 samples. Among 36 Non-Small Cell Lung Cancer (NSCLC), 8 pancreatic cancer and 14 prostate cancer specimens, 86%, 100% and 79% of them overexpressed CDCP1, respectively. 20% of the 20 Small Cell Lung Cancer (SCLC) specimen overexpressed CDCP1 (Table 8).

TABLE 8

Overexpression of CDCP1 in other types of solid tumors

| Indication | Tissue Type | Total | 0 | 1+ | 2+ | ≥3+ | # of tissue IHC ≥2+ |
|---|---|---|---|---|---|---|---|
| Ovarian serous carcinoma | Primary tumor | 18 | 0 | 1 | 5 | 12 | 17 (95%) |
| Recurrent serous carcinoma | Relapsed tumor | 11 | 1 | 2 | 4 | 4 | 8 (72%) |
| Ovarian clear cell carcinoma | Primary tumor | 5 | 0 | 0 | 0 | 5 | 5 (100%) |
| NSCLC | Primary tumor | 36 | 3 | 2 | 10 | 21 | 31 (86%) |
| Pancreatic Cancer | Primary tumor | 8 | 0 | 0 | 3 | 5 | 8 (100%) |
| Prostate Cancer | Primary tumor | 14 | 0 | 3 | 3 | 8 | 11 (79%) |
| SCLC | Primary tumor | 20 | 8 | 8 | 2 | 2 | 4 (20%) |

Example 7. CDCP1 is Expressed in TNBC. Her2+ Breast Cancer and CRC Cell Lines A panel of TNBC, Her2+ breast cancer and CRC cell lines were examined for their surface CDCP1 expression using a mouse monoclonal anti-CDCP1 antibody directly conjugated to fluorochrome phycoerythrin (PE) (Biolegend, San Diego. CA, Cat. No. 324006). Antigen density was determined using BD Quantibrite™ Beads PE Fluorescence Quantitation Kit (BD Cat. No. 340495).

Flow cytometry analysis was performed for five TNBC cell lines MDA-231, BT549, DU4475. MDA-468 and HCC1187 using a mouse monoclonal anti-CDCP1 antibody directly conjugated to fluorochrome PE. A breast cell line MCF7 was used as a negative control. The estimated cell surface CDCP1 density was 89439 for MDA231, 202780 for BT549, 67543 for DU4475, 34340 for MDA468, 20255 for HCC1187, and 0 for MCF7 (negative control). Thus, cell surface CDCP1 density was estimated at 20255-202780 for tested TNBC cell lines.

Flow cytometry analysis was also performed for two Her2+ breast cancer cell lines BT474 and SKBR3 using a mouse monoclonal anti-CDCP1 antibody directly conjugated to fluorochrome PE. A breast cell line MCF7 was used as a negative control. The estimated cell surface CDCP1 density was 67543 for B1474, 1101 for SKBR3, and 0 for MCF7 (negative control). Thus, cell surface CDCP1 density was estimated at 1101-67543 for tested Her2+ breast cancer cell lines.

Furthermore, flow cytometry analysis was performed for three colorectal cancer cell lines SW48, HCT116 and HCT8, using a mouse monoclonal anti-CDCP1 antibody directly conjugated to fluorochrome PE. The estimated cell surface CDCP1 density was 69161 for SW48, 99921 for HCT116, and 25118 for HCT8. Thus, cell surface CDCP1 density was estimated at 25100-99900 for tested CRC cells.

These results show that CDCP1 is present on the cell surface of cells from various cancer cell lines, and suggest that the ADCs described herein that target CDCP1 can be used to treat different types of cancers.

Example 8. In Vitro Target Internal Nation/Degradation Assay

After confirming the target specificity of an antibody, the ability of an antibody to induce CDCP1 internalization and degradation is assessed by incubating test antibodies at ~10 ug/ml with live HCT116 cells plated in 384 well plates for 30 minutes, 2 hours, and overnight. Cells were then fixed with 4% formaldehyde in PBS at room temperature for 15 minutes, the plates were then washed three times with PBS, and blocked with 5% normal goat serum in PBS-T, mouse monoclonal antibody CUB1 was then added in Ab dilution buffer at 0.5 ug/ml to the wells. The plates were then incubated at 4° C. overnight. On the next day, plates were developed with anti-human IgG A488 and anti-mouse IgG A555 secondary antibodies and imaged using an array scanner.

The live cell immunofluorescence assay was performed with two human monoclonal antibodies, 27H10 and 38E11.

27H10 induces CDCP1 internalization and degradation, whereas 38E11 binds to the cell surface CDCP1 and does not induced target internalization and degradation. 19 out of 40 recombinant antibodies (FIG. 16) which likely bind to proximal region (AA343-667) bind to surface CDCP1 without internalizing the target, as indicated by membranous staining of both human antibody and CUB1 antibody; while 21 out of 40 recombinant antibodies (FIG. 16) which likely bind to distal region (AA30-342) can cause strong intracellular punctate staining as well as target degradation indicated by diminished antibody signal at 2 hours and overnight time points.

In summary, this example shows that certain CDCP1 antibodies can induce CDCP1 internalization and degradation.

Example 9. Identification of Specific Epitope Bins in Both Distal and Proximal Regions of CDCP1

Experiments were performed to identify specific epitope bins in both distal and proximal regions of CDCP1. The following methods were used in the examples.

R368 Cleavage Blocking Assay

CDCP1 can be proteolytically cleaved by matriptase at the C-terminal side of R368.

Antibodies that can block CDCP1 cleavage at R368 can inhibit cancer cell metastasis in mouse models. To determine if any of the human antibodies generated can block this cleavage, recombinant CDCP1 ECD (AA30-667) with a C-terminal His tag were first incubated with the antibodies described in the examples at a protein/antibody ratio of 1:3 on ice for 1 hour, matriptase was then added to each reaction at S:E ratio of 50:1 and incubated at 37° C. for 1.5 hour. The reaction was then boiled in SDS loading buffer and analyzed by Western Blot using anti-His tag antibody, which detects both FL and Clv ECD.

Figures 2A, 2B, 2C:
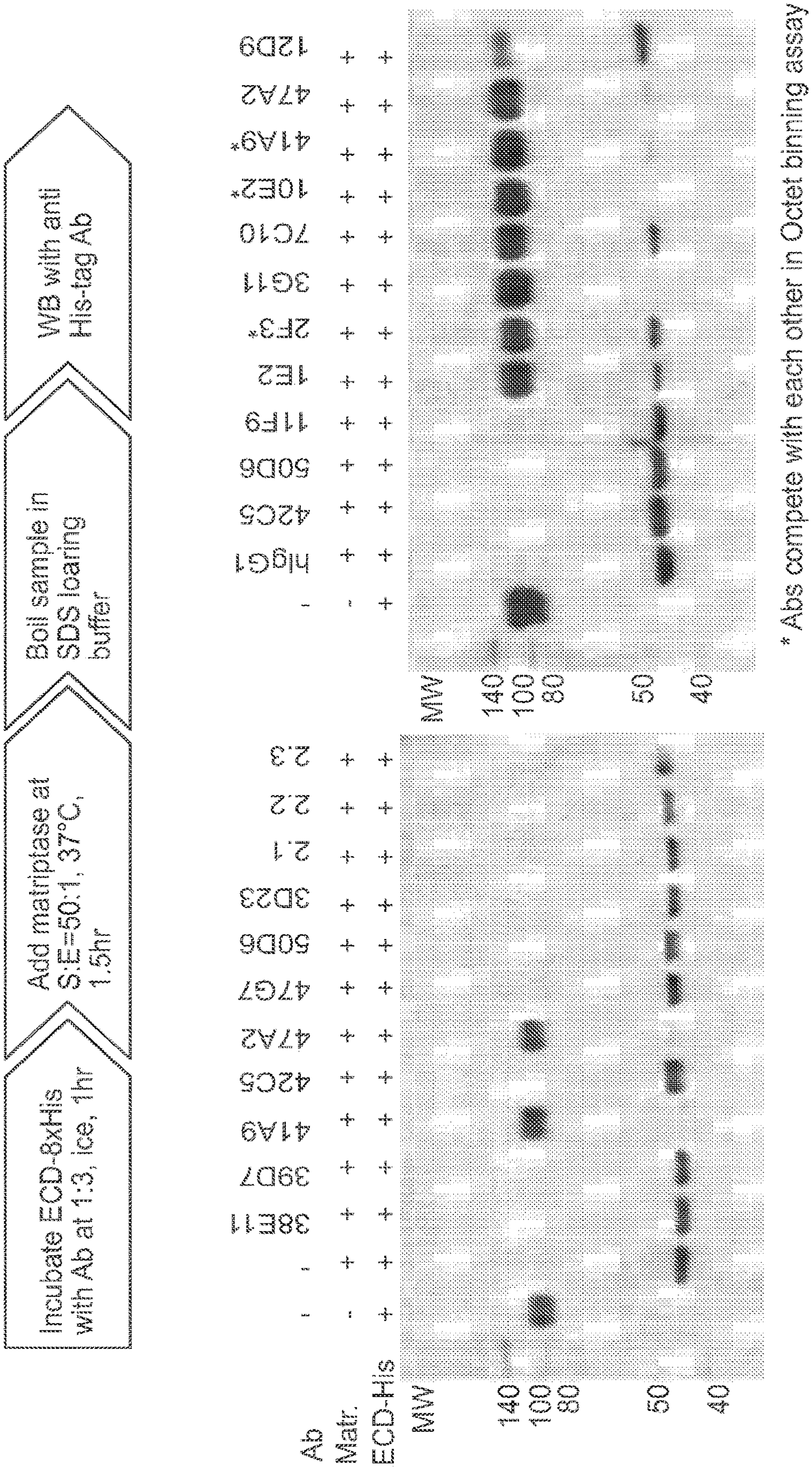
FIG. 2A is a schematic diagram showing a protocol for a R368 cleavage blocking assay. This Figure discloses "8×His" as SEQ ID NO: 406.
FIGS. 2B-2C are images of Western blots showing the results of a R368 cleavage blocking assay.

As shown in FIGS. 2A-2C, some human antibodies can block matriptase cleavage of CDCP1, indicating that these antibodies are binding epitopes near the R368 cleavage site and interfere with matriptase binding. 8 out of 20 recombinant human antibodies were found to be R368 cleavage blockers. Therefore, these antibodies are in a special epitope bin that most likely resides in the proximal region (AA343-667).

Identification of N342 Clv-CDCP1 Preferred Antibodies

Figure 3:
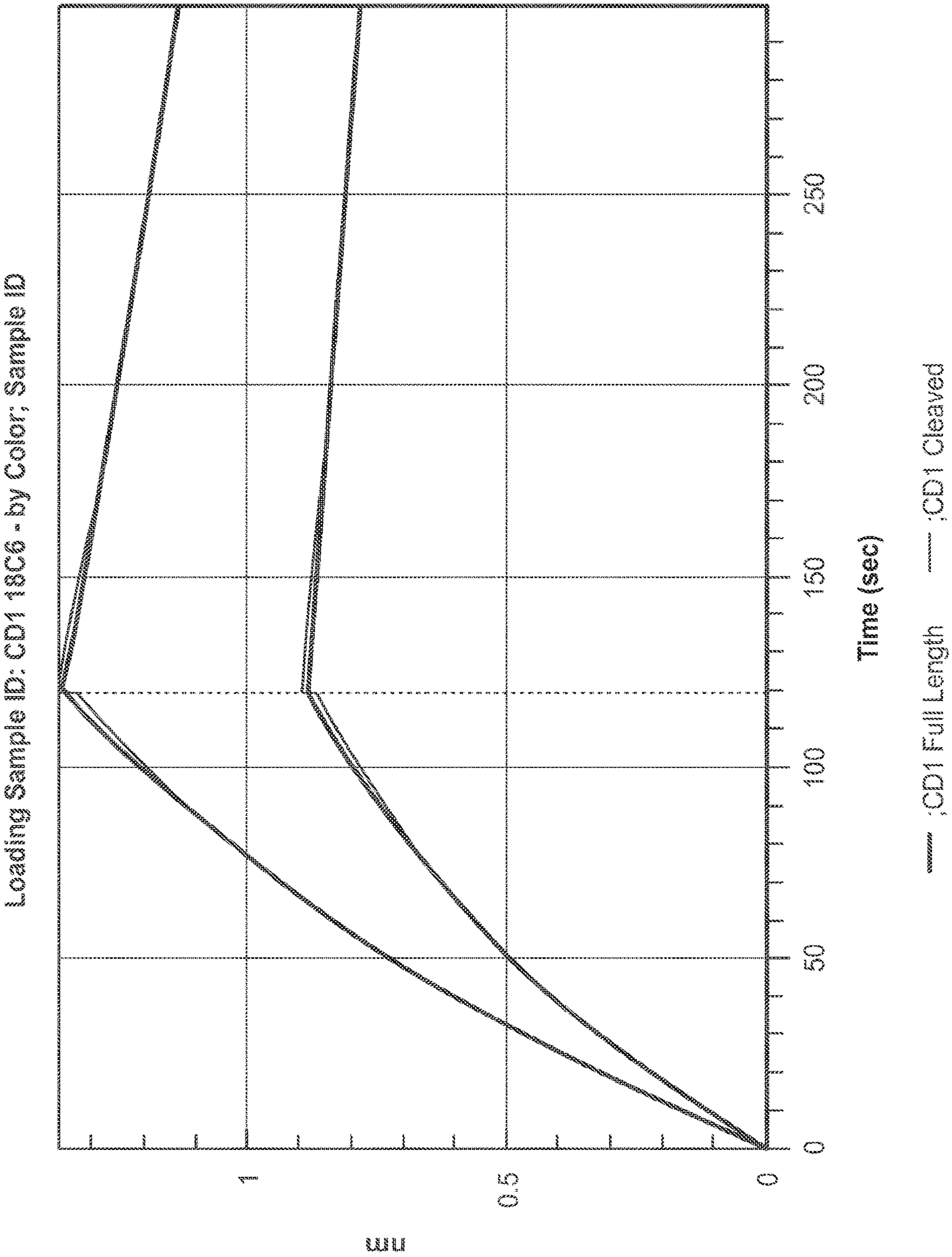
FIG. 3 is a graph showing that 18C6 antibody binds to cleaved CDCP (AA343-836) (Clv-CDCP1(N342)) at a higher affinity than to full length CDCP1.
Figure 4:
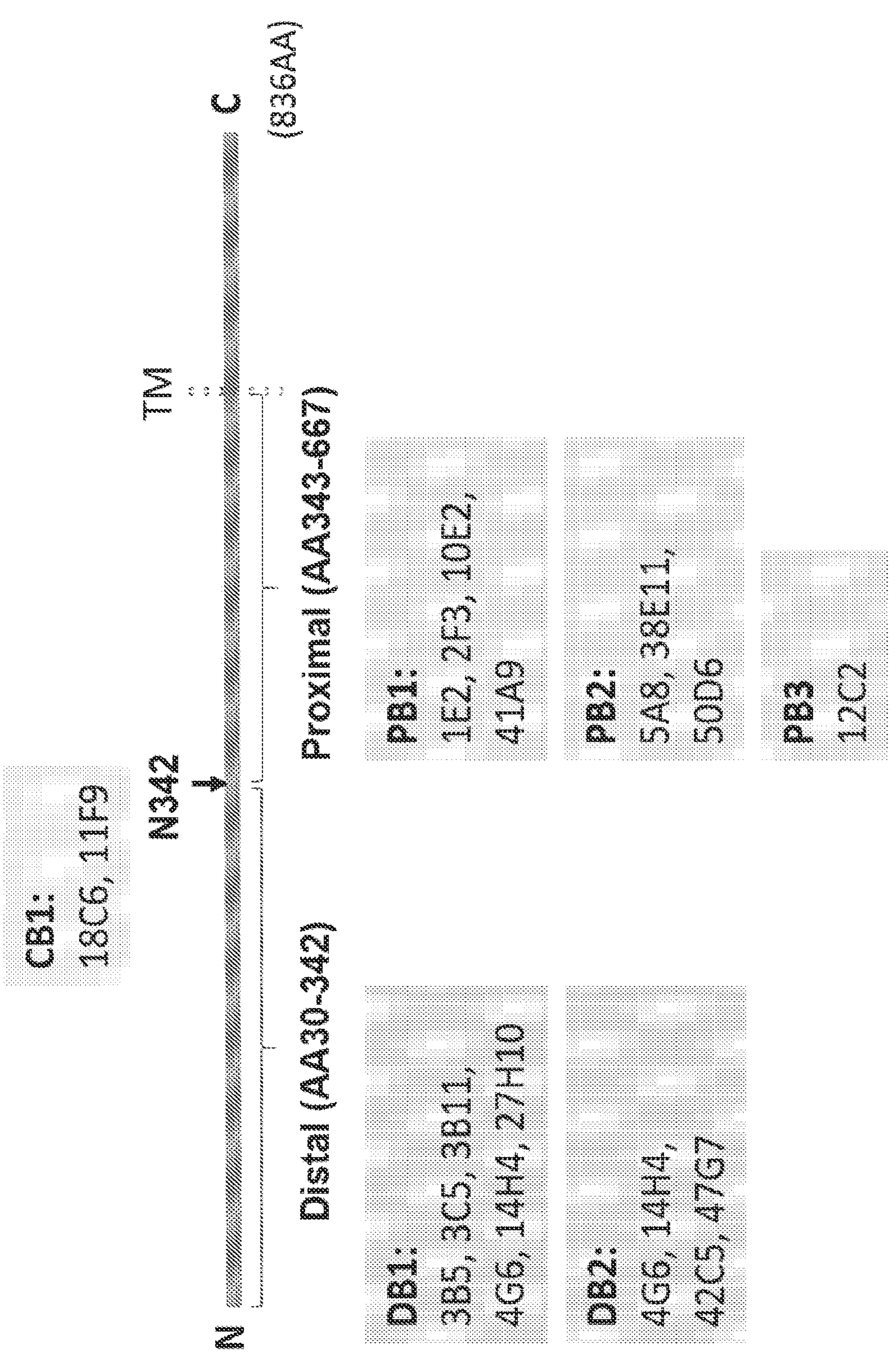
FIG. 4 is a schematic diagram showing distinct epitope bins for 18 selected recombinant human antibodies.
Figures 5A, 5B, 5C, 5D, 5E:
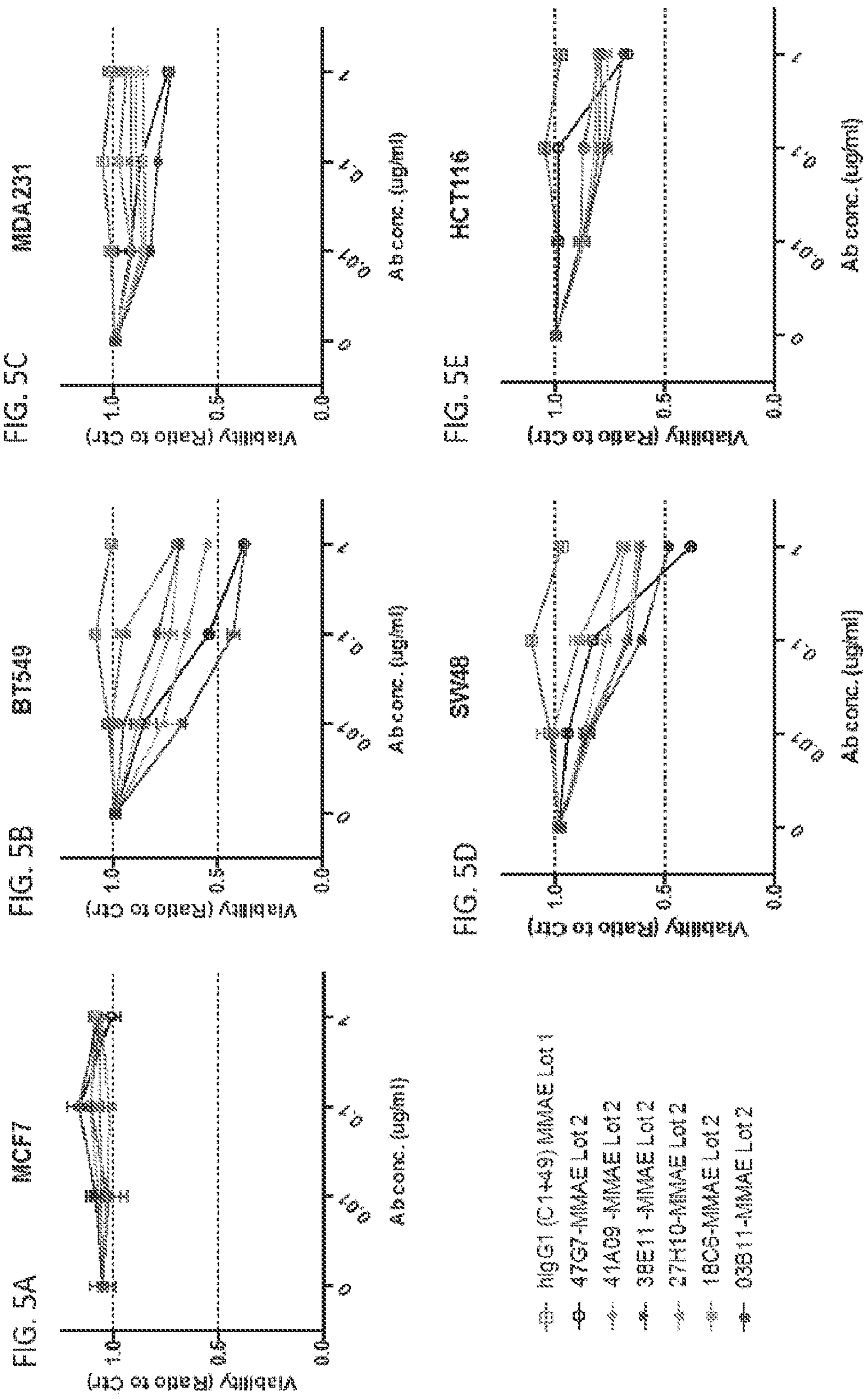
FIGS. 5A-5E are graphs showing the in vitro killing effect of antibody vcMMAE conjugates on cells from BrCa cell lines MCF7, BT549, MDA231, and cells from CRC cell lines SW48 and HCT116, wherein the antibodies in the antibody vcMMAE conjugates are hIgG1, 47G7, 41A09, 38E11, 27H10, 18C6, and 03B11.

Two of the antibodies bind better to Clv-CDCP1 (N342) than to FL-CDCP1, indicating that these antibodies might bind to special epitopes enriched or specific to Clv-CDCP1 (N342). Both an immunofluorescence assay using 293T cells overexpressing FL and Clv CDCP1 (N342) as well as an Octet kinetics assay using recombinant FL-ECD and Clv-ECD (N342) demonstrated Clv-CDCP1 preference of these two antibodies (FIG. 3). Sequence analysis of these two antibodies. 18C6 and 11F9, revealed that they belong to the same VDJ family, which indicates that they most likely bind to the same epitope.

Results

Combining epitope binning results from Octet and biological analysis of recombinant monoclonal human antibodies, six distinct epitope bins were identified (FIG. 4) including two in the distal region (AA30-342): DB1 and DB2; three in the proximal region (AA343-667): PB1, PB2 and PB3; and one N342 cleaved form preferred bin: CBI.

Example 10. In Vitro Target Modulation in Cultured Cancer Cell Lines

In addition to target internalization and degradation, other aspects of target modulation by the disclosed antibodies were assessed in several cell based assays. TNBC cell line B1549 and CRC cell line SW48 were seeded in 6 well plates at ~70% confluency and were incubated with 5 ug/ml recombinant human monoclonal antibodies against CDCP1 diluted in complete culture medium for 0, 0.5, 1, 4, 6 hours and overnight. Cells were then harvested in SDS-loading buffer and subjected to western blot analysis using the following antibodies: anti-CDCP1 (Cat. No. 4115, Cell Signaling Technology. Danvers, MA), anti-phosphoCDCP1 (pY734) (Cat. No. 9050, Cell Signaling Technology. Danvers, MA), anti-PKCδ (Cat. No. 9616. Cell Signaling Technology, Danvers, MA), anti-PKCδ (pY311) (Cat. No. 2055. Cell Signaling Technology, Danvers, MA), anti-Erk (Cat. No. 4695, Cell Signaling Technology, Danvers. MA) and anti-Erk (pT202/Y204) (Cat. No. 4370. Cell Signaling Technology, Danvers, MA).

Table 9 summarizes the results generated in BT549 and SW48 cells. As shown in Table 9, in both B1549 and SW48 cells, antibodies that can internalize CDCP1 in immunofluorescence assay can induce CDCP1 phosphorylation and PKCδ phosphorylation, indicating that these antibodies act as CDCP1 agonists. Consistent with results from the immunofluorescence analysis, these antibodies also caused subsequent CDCP1 degradation at later time points. In contrast, the three antibodies that do not induce CDCP1 internalization in the immunofluorescence assay did not increase CDCP1 phosphorylation or PKCδ phosphorylation.

TABLE 9

In vitro target modulation and signaling effects of human CDCP1 antibodies

| Ab | Epitope localization | In vitro internalization | p-CDCP1 (Y734) | CDCP1 degradation | p-PKCD (Y311) |
|---|---|---|---|---|---|
| 03B11 | Distal (AA30-342) | Yes | Yes | Yes | Yes |
| 27H10 | Distal (AA30-342) | Yes | Yes | Yes | Yes |
| 47G7 | Distal (AA30-342) | Yes | Yes | Yes | Yes |
| 41A9 | Proximal (AA343-667) | No | No | No | No |
| 38E11 | Proximal (AA343-667) | No | No | No | No |
| 18C06 | Proximal (AA343-667) | No | No | No | No |

Example 11. Conjugation of Human Antibodies to vcMMAE

Human monoclonal antibodies against CDCP1 were conjugated to vcMMAE. The methods were described, e.g., in Doronina. Svetlana O., et al. "Development of potent monoclonal antibody auristatin conjugates for cancer therapy." Nature biotechnology 21.7 (2003): 778-784; and Francisco, Joseph A., el al. "cAC10-vcMMAE, an anti-CD30-monomethyl auristatin E conjugate with potent and selective antitumor activity." Blood 102.4 (2003): 1458-1465.

Each antibody was mixed with dithiothreitol (DTI) at room temperature for 30 minutes, and the buffer was exchanged by Amicon spin columns (30 kDa) into PBS pH 7.0 with 2 mM EDTA. The antibody concentration was quantified by A280. They were then diluted to 1.5 mg/ml in PBS pH 7.0 and 2 mM EDTA. A 4-fold molar excess of maleimidocaproyl-Val-Cit-MMAE (vc-MMAE) was then added to the reduced antibody at room temperature for 1 hour. The reaction mixture was then dialyzed against IX PBS pH 8.0 and filter sterilized. The drug:mAb ratio (DAR) was then calculated based on spec readings at A280 and A248 on an absorption spectroscopy. The method of calculating DAR is described in detail, e.g., in Hamblett, Kevin J., et al. "Effects of drug loading on the antitumor activity of a monoclonal antibody drug conjugate," Clinical Cancer Research 10.20 (2004): 7063-7070.

Example 12. In Vitro Cancer Cell Killing Assay

Human antibodies conjugated to vc-MMAE were tested for their effect on growing TNBC and CRC cancer cells.

TNBC cell lines. BT549, MDA-MB-231, which express CDCP1, breast cancer cell line MCF7, which does not express CDCP1, and CRC cell lines, SW48 and HCT116, which express CDCP1, were seeded onto 96 well plate at 2000-4000 cells/well. 24 hours later, Ab-vcMMAE bearing a drug antibody ratio (DAR) of 3.7-4.3 was added to the wells in complete culture medium so that the final Ab-vcMMAE concentration in the well is 0.001, 0.01, 0.1 and 1.0 ug/ml. Each treatment was replicated in 2-3 wells. 72 hours later, cell viability was measured by CellTiter Glo® Luminescent Cell viability assay (Promega, Madison. WI) according to manufacturer's instructions. Cell viability was graphed by Prism® software using ratio of cell viability of test conditions to that of control wells that were incubated with growth medium.

As shown in FIGS. 5A-5E, while none of the human Ab-vcMMAE could kill MCF7, which does not express CDCP1, they showed varying degrees of killing effects on BT549. MDA231, SW48, and HCT116 cells. Noticeably, antibodies that can induce internalization in the immunofluorescence assay (3811-MMAE. 27H10-MMAE, and 47G7-MMAE) exhibited a better killing effect (50-60% in BT549, 35-60% in SW48) than the ones (41A9-MMAE, 38E11-MMAE, 18C6-MMAE) that do not (35% in BT549, 35-40% in SW48).

Example 13. In Vitro ADCC Assay

The capability of a few human antibodies of inducing antibody dependent cytotoxicity (ADCC) was tested using an ADCC Reporter Bioassay (Promega. Madison, WI). BT549 or SW48 cells were plated at $1\times10^4$ cells per well 24 hours in advance of treatment in sterile 96-well black cell culture microplate (GrenierBio. Kremsmunster, Austria). Culture medium was aspirated in advance of treatment and 25 ul of RPMI 1640 supplemented with 4% ultra-low IgG FBS was added to cells. Human monoclonal antibodies were diluted in assay medium and added to cells in 25 ul/well in duplicate to achieve final antibody concentrations of 0, 0.0001, 0.001, 0.01, 0.1, and 1.0 ug/ml. Engineered Jurkat effector cells were thawed at 37° C. for 2 minutes into assay medium and added to the cells at an effector/target ratio of 7.5:1. The mixed cell culture was incubated at 37° C., 5% $CO_2$ for 6 hours. Cell viability was analyzed using Bio-Glo luciferase assay reagent as directed in technical manual. Relative Light Units (RLU) readout was graphed using Prism® software.

Figures 6A, 6B, 6C:
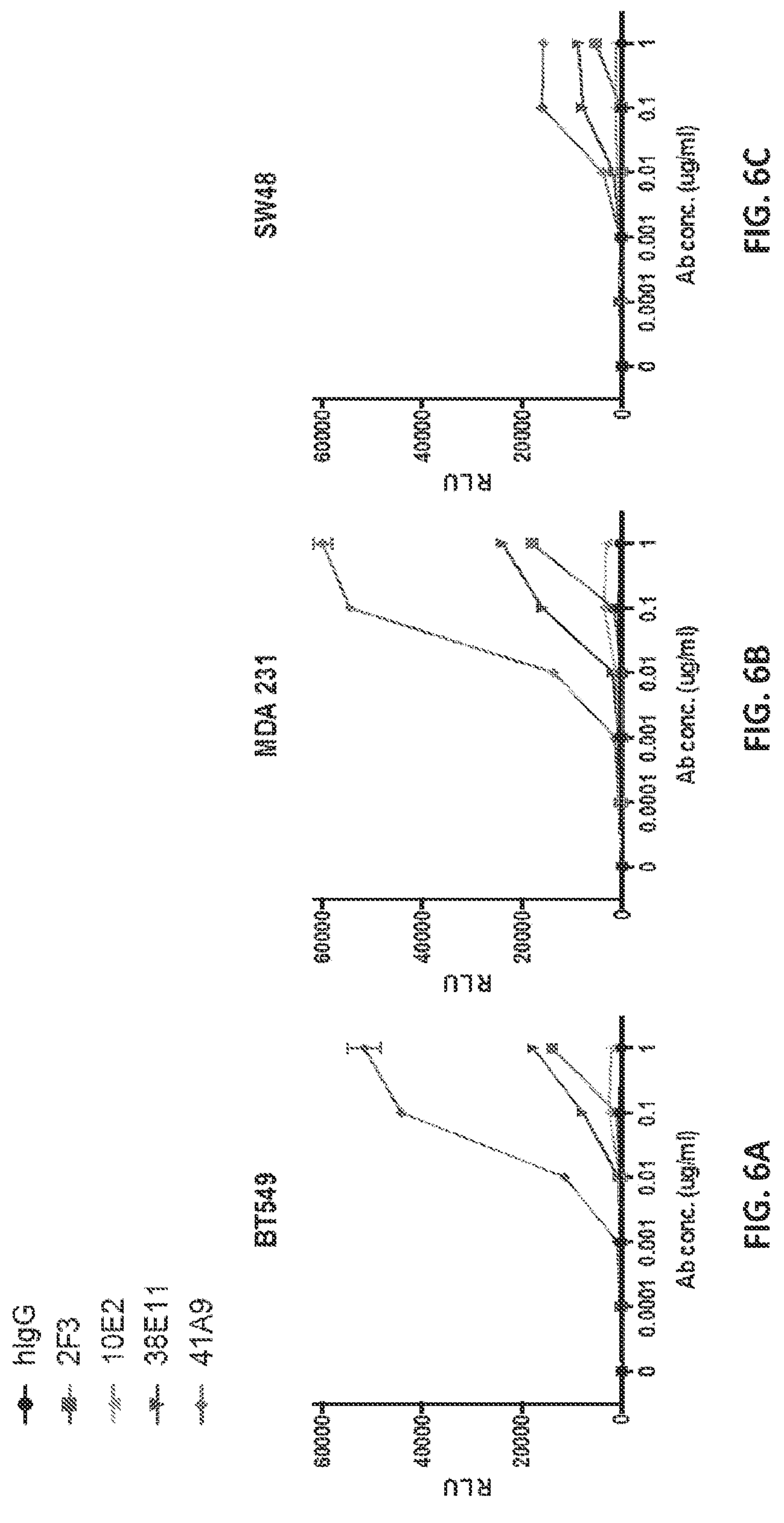
FIGS. 6A-6C are graphs showing antibody dependent cytotoxicity (ADCC) effects of hIgG (control) and human CDCP1 antibodies 2F3, 10E2, 38E11, and 41A9 on cells from TNBC cell lines BT549 and MDA231, and cells from CRC cell line SW48.
Figures 7A, 7B, 7C:
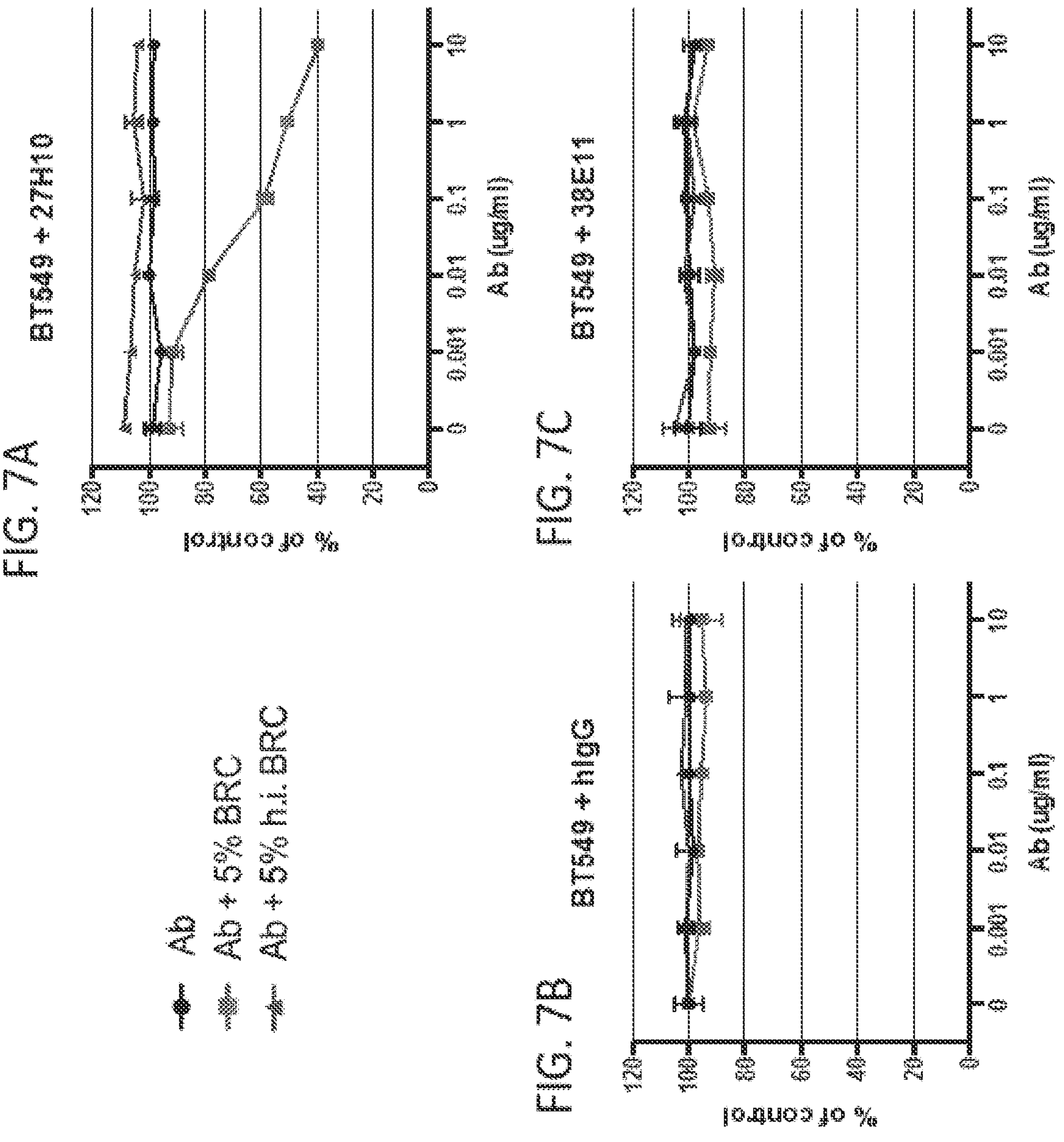
FIGS. 7A-7G are graphs showing complement-dependent cytotoxicity (CDC) effect of hIgG (control) and human CDCP1 antibodies 27H10, 38E11, 3B11, 47G7, 41A9 and 18C6 on BT549 cells.
Figure 7D:
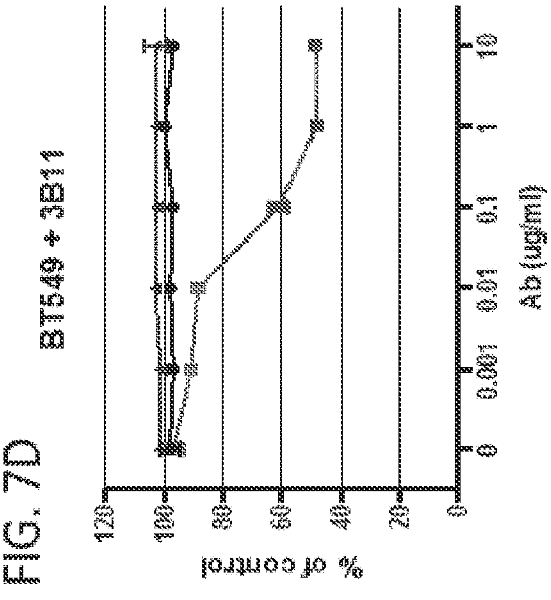
Figure 7E:
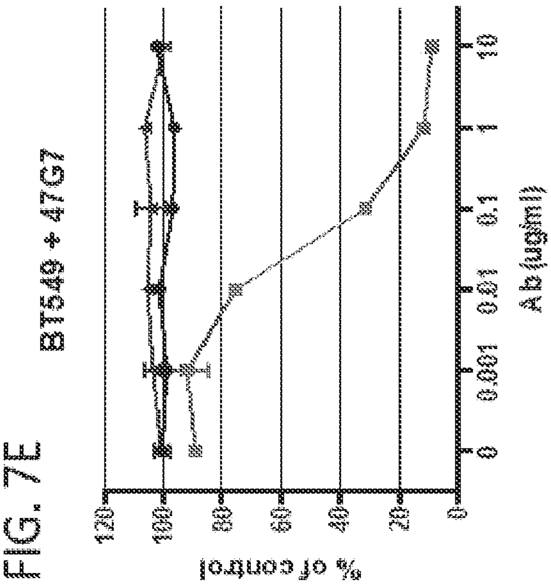
Figure 7F:
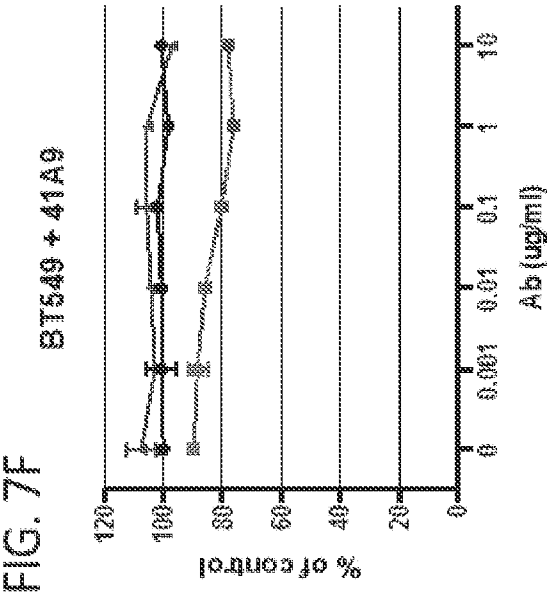
Figure 7G:
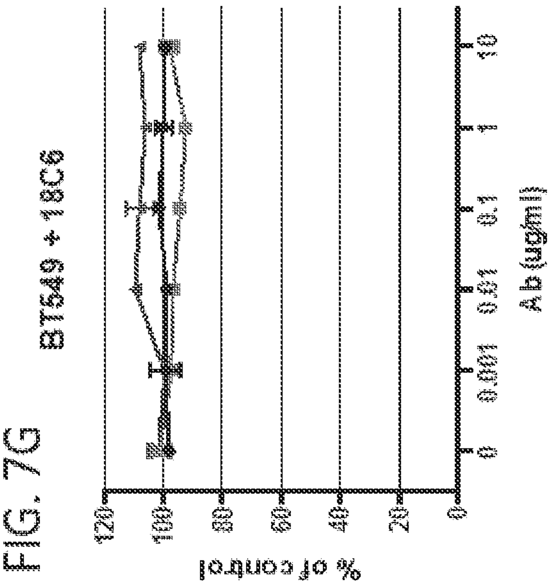

As shown in FIGS. 6A-6C, among tested antibodies, 41A9 was identified as the antibody with highest ADCC activity in both TNBC cell lines, BT549 and MDA231, as well as CRC cells SW48. 38E11 also exhibited ADCC activity in these cell lines.

Example 14. In Vitro CDC Assay

The capability of six human antibodies, which bind to different epitopes in distal and proximal regions, of complement dependent cytotoxicity (CDC) is tested. BT549 or SW48 cells were plated at $1\times10^4$ cells per well in sterile 96-well black cell culture microplate (GrenierBio, Kremsmünster. Austria) in 50 ul RPMI 1640 supplemented with 5% heat inactivated ultra low IgG FBS (Life Technologies, Carlsbad. CA) assay medium. Human monoclonal antibodies were diluted in assay medium and added to cells in 25 ul/well in duplicate and incubated at 37° C. 5% $CO_2$ for 15 minutes. Active and heat-inactivated baby rabbit complement was added to experimental wells at a final concentration of 5%. The final antibody concentrations of diluted antibodies are 0, 0.001, 0.01, 0.1, 1.0, and 10.0 ug/ml. All wells normalized with assay medium to a final volume of 100 ul and incubated at 37° C. 5% $CO_2$ for 6 hours. Cell viability was analyzed using Cell Titer Glo 2.0 (Promega, Madison, WI) assay reagent as directed in technical manual. Results were graphed as percent of control wells using Prism® software. Ultra low IgG FBS for assay medium and negative control baby rabbit complement were heat inactivated at 56° C. for 30 minutes.

As shown in FIGS. 7A-7G, antibodies that can induce CDCP1 internalization in cell culture, 3B11, 27H10, 47G7, induced a stronger CDC effect than those which do not. The dose-dependent CDC effect is complement dependent as indicated by inactivation of such activity when heat inactivated baby rabbit complement (BRC) was used in the assay.

Example 15. In Vivo Antibody Tumor Penetration and Target Degradation

Mice with HCT116 xenograft tumors of 400-500 $mm^3$ in size received 5 mg/kg control antibodies (rabbit isotype control IgG or an anti-DDR 1 rabbit monoclonal antibody) or 41A10, a rabbit monoclonal antibody against distal region of CDCP1, by tail intravenous injection. 4 and 24 hours after i.v. injection, tumors were harvested and processed into FFPE blocks. FFPE sections were then analyzed by an IHC antibody binding to C-terminus of CDCP1. While tumors treated with isotype control antibodies show strong and even CDCP1 staining, tumor treated with 41A10 exhibited massive CDCP1 clearance. The target clearance can be seen around blood vessel as early as 4 hours after i.v. injection, indicating efficient tumor penetration and target degradation by 41A10 in this CRC twnor model. Thus, 41A10 (Rb) induced CDCP1 degradation in HCT116 xenograft tumors.

Example 16. Conjugated CDCP1 Antibodies Cause Tumor Regression: Triule Negative Breast Cancer Since the rabbit antibody 41A10 exhibited efficient tumor penetration and target clearance in vivo, the ability of conjugated 41A10, 41A10-vcMMAE was tested in a MDA231 xenografts, a TNBC tumor model.

MDA231 xenograft tumors were generated by injecting 2.5x10e6 MDA231 cells in the presence of matrigel subcutaneously into 6-8 weeks old female Ncr-nude mice (Taconic, Hudson. NY). When most tumors reached 20) $mm^3$ in size (~3 weeks after cell inoculation), mice are randomized into 4 treatment groups of 8-10 mice using an R studio script designed to group the animals so that the average tumor size and standard deviation of the tumor size between groups are comparable.

Figure 8A:
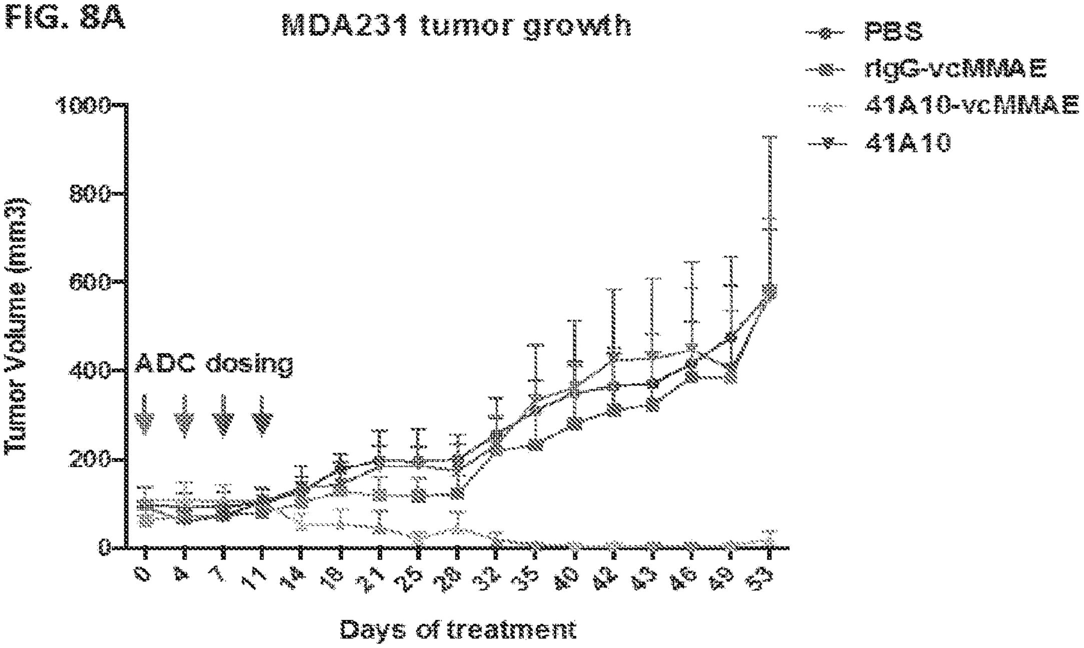
FIG. 8A is a graph showing the antibody vcMMAE conjugate (41A10-vcMMAE) inhibited tumor growth in mice xenografted with cells from TNBC cell line MDA231 in vivo.
Figure 8B:
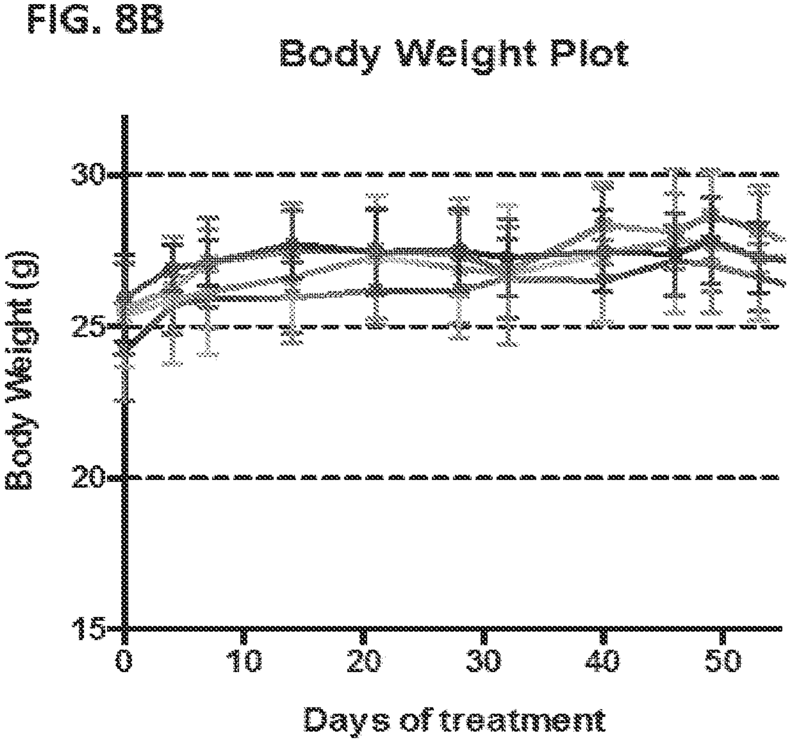
FIG. 8B is a graph showing body weight plot for mice with MDA231 tumor treated with the antibody vcMMAE conjugate (41A10-vcMMAE).

The animals were then injected intravenously with 41A10 antibody, the antibodies conjugated to MMAE, a rabbit IgG isotype control antibody (No. 3900, Cell Signaling Technology, Danvers. MA) conjugated to MMAE, and PBS vehicle. ADCs were administered at 5 mg/kg for 4 doses over a period of 10 days, naked antibodies were administered at 10 mg/kg 2 times a week until the end of the study (a total of 15 doses). Tumor volume was estimated by 0.52×Length×width×width. As shown in FIGS. 8A and 8B, while naked antibody 41A10 exhibited no effect on tumor growth in MDA-231 xenografts, 41A10-MMAE exhibited >150% tumor growth inhibition. Although 41A10 cross reacts with mouse CDCP1, 41A10-MMAE treated mice are healthy and active, as shown by the stable body weight and normal activities.

Example 17. Conjugated CDCP1 Antibodies Cause Tumor Regression: Colon Carcinoma The human CDCP1 antibodies conjugated MMAEs were tested to demonstrate their effect on tumor growth in vivo in a model of colon carcinoma. CRC tumor model SW48 xenografts were generated by injecting $2.5\times10^6$ SW48 cells in the presence of matrigel subcutaneously into 6-8 weeks old female Ncr-nude mice (Taconic). When most tumors reach 200 $mm^3$ in size (~3 weeks after cell inoculation), mice are randomized into 8 treatment groups of 8-10 mice using an R studio script designed to group the animals so that the average tumor size and standard deviation of the tumor size between groups are comparable. The animals were then injected intravenously with PBS, human IgG1 (isotype control)-MMAE and CDCP1 Ab-MMAEs that showed in vitro cell killing effect at 5 mg/kg. The i.v. treatment was repeated 3 more times over a period of 10 days. Following treatment, tumor volumes and mouse weights were monitored until tumors exceed 800 $mm^3$. Mice that showed a 15% or more weight loss or became lethargic are taken out of the study.

Figure 9:
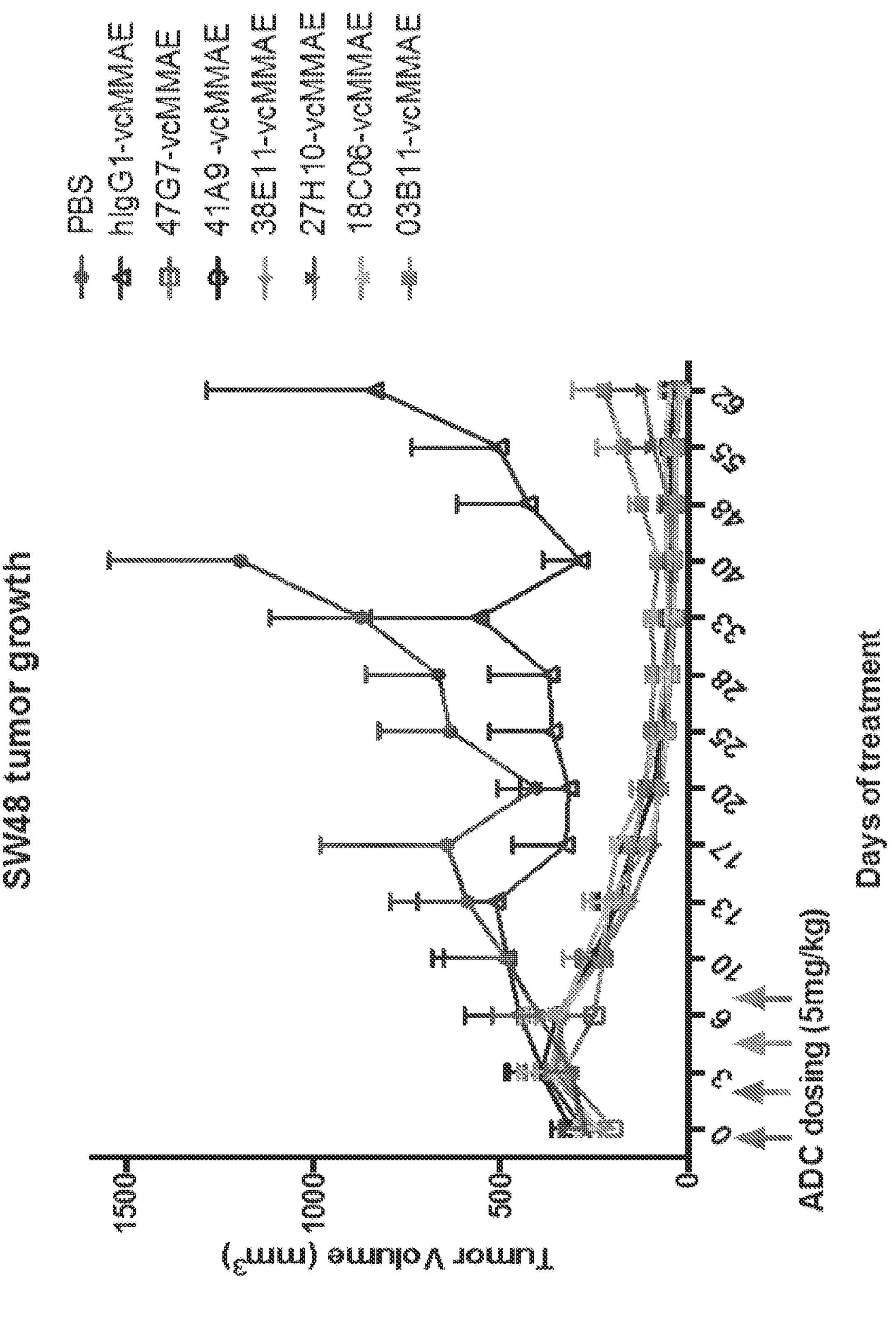
FIG. 9 is a graph showing human CDCP1 antibodies conjugated with vcMMAE inhibited SW48 tumor growth in mice in vivo, wherein the antibodies in the antibody vcMMAE conjugates are hIgG1 (control), 47G7, 41A09, 38E11, 27H10, 18C6, and 03B11.

As shown in FIG. 9, all six human antibody MMAE conjugates exhibited significant tumor growth inhibition (180-250%) in SW48 tumors.

Example 18. Antibody Drug Conjugates Cause Tumor Regression in TNBC Tumor Models The human CDCP1 antibodies 18C6, 27H10, 38E11 and 41A9 conjugated with vcMMAE were also tested to demonstrate their effect on tumor growth in TNBC tumor model. TNBC tumor model MDA231 xenografts were generated by injecting $2.5\times10^6$ corresponding cultured cells in the presence of matrigel subcutaneously into 6-8 weeks old female Ncr-nude mice (Taconic). When most tumors reach 250-300 $mm^3$ in size (~3 weeks after cell inoculation), mice are randomized into treatment groups of 8-10 mice using an R studio script designed to group the animals so that the average tumor size and standard deviation of the tumor size between groups are comparable.

The animals were then injected intravenously with vehicle, human IgG1 (isotype control)-MMAE and 4 human CDCP1 ADCs (18C6-MMAE, 27H10-MMAE, 38E11-MMAE and 41A9 MMAE) at 5 mg/kg. The i.v. treatment was repeated 3 times over a period of 10 days. Following treatment, tumor volumes and mouse weights were monitored until tumors exceed 1500 $mm^3$. Mice that showed a 15% or more weight loss or become lethargic were taken out of the study.

Figure 10:
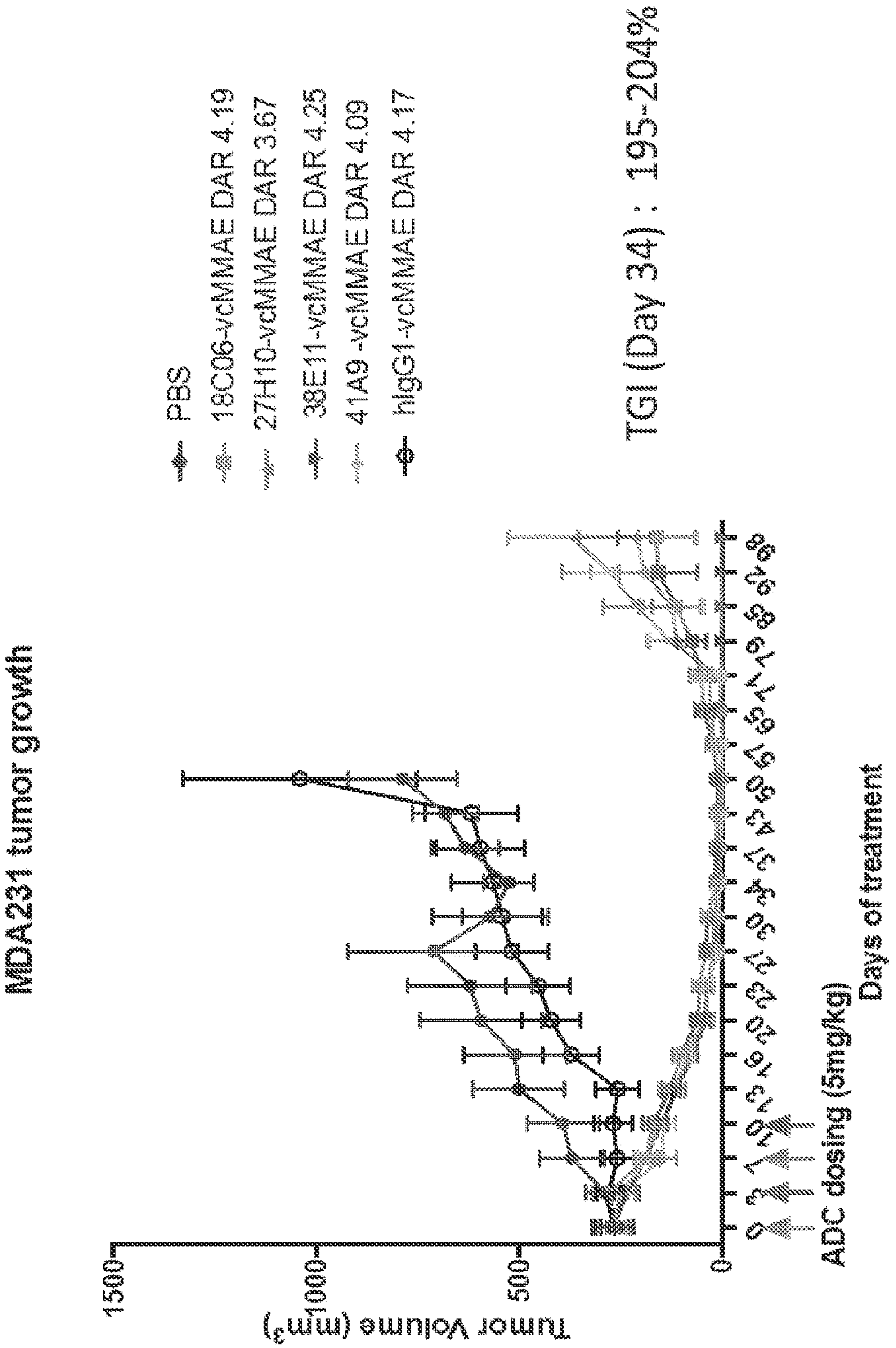
FIG. 10 is a graph showing that human CDCP1 antibodies conjugated with vcMMAE inhibited tumor growth in mice xenografted with cells from TNBC cell line MDA231 in vivo, wherein the antibodies in the conjugates are 18C6, 27H10, 38E11, 41A9, and hIgG1.

The four human antibody MMAE conjugates caused complete tumor regression in the TNBC model MDA231 xenografts at 5 mg/kg (FIG. 10).

Example 19. Antibody Drug Conjugates Cause Tumor Regression in CRC Tumor Models The human CDCP1 antibodies 18C6, 27H10, 38E11 and 41A9 conjugated with vcMMAE were also tested to demonstrate their effect on tumor growth in CRC tumor model. CRC tumor model SW48 xenografts were generated by injecting $2.5\times10^6$ corresponding cultured cells in the presence of matrigel subcutaneously into 6-8 weeks old female Ncr-nude mice (Taconic). When most tumors reach 250-300 $mm^3$ in size (~12 days after cell inoculation), mice are randomized into treatment groups of 8-10 mice using an R studio script designed to group the animals so that the average tumor size and standard deviation of the tumor size between groups are comparable.

The animals were then injected intravenously with vehicle, human IgG1 (isotype control)-MMAE and 4 human CDCP1 ADCs (18C6-MMAE, 27H10-MMAE, 38E11-MMAE and 41A9 MMAE) at 5 mg/kg. The i.v. treatment was repeated 3 times over a period of 10 days. Following treatment, tumor volumes and mouse weights were monitored until tumors exceed 1500 $mm^3$. Mice that showed a 15% or more weight loss or become lethargic are taken out of the study.

Figure 11:
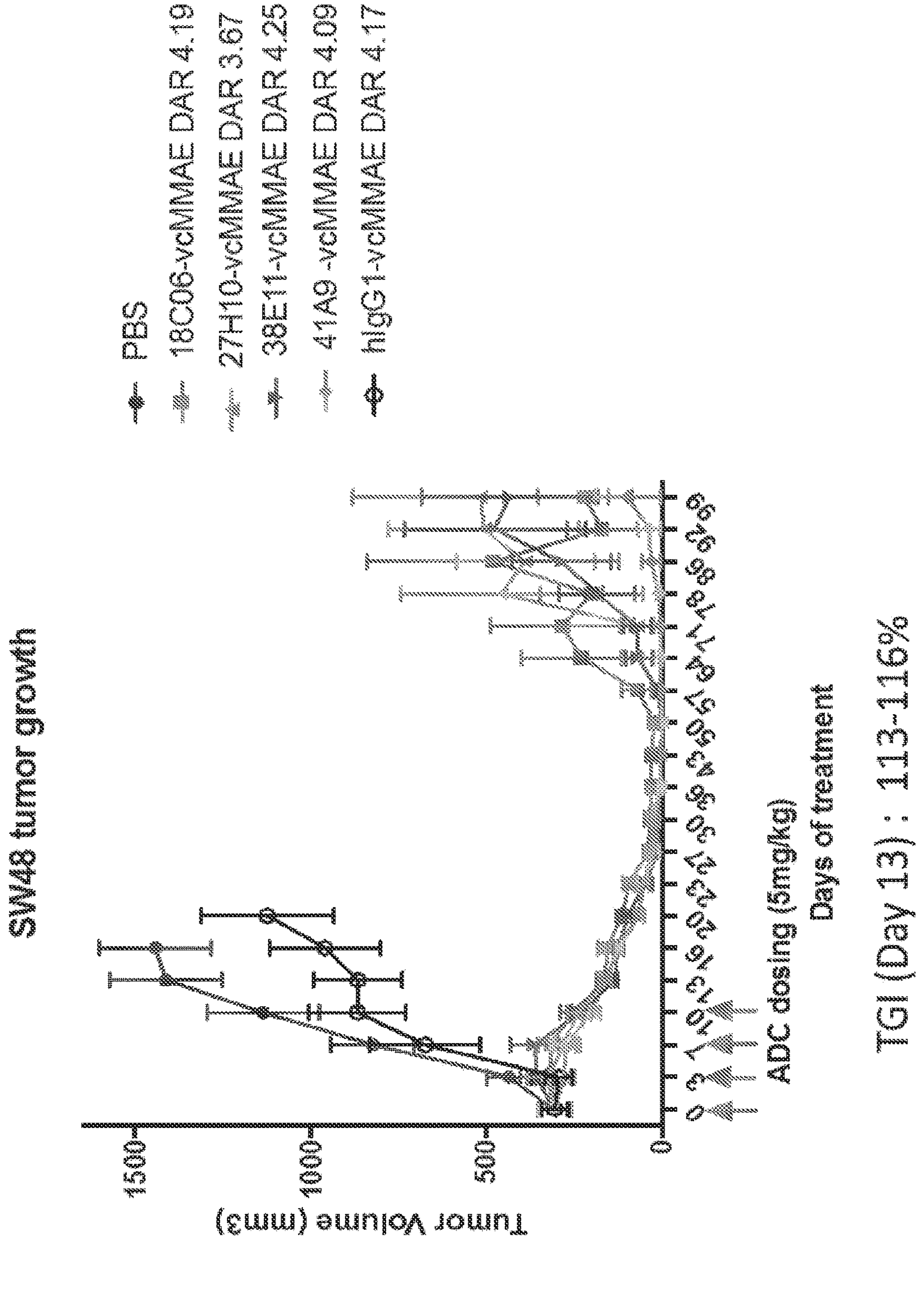
FIG. 11 is a graph showing that human CDCP1 antibodies conjugated with vcMMAE caused regression of established SW48 tumors in mice in vivo, wherein the antibodies in the conjugates are 18C6, 27H10, 38E11, 41A9, and hIgG1.
Figure 12:
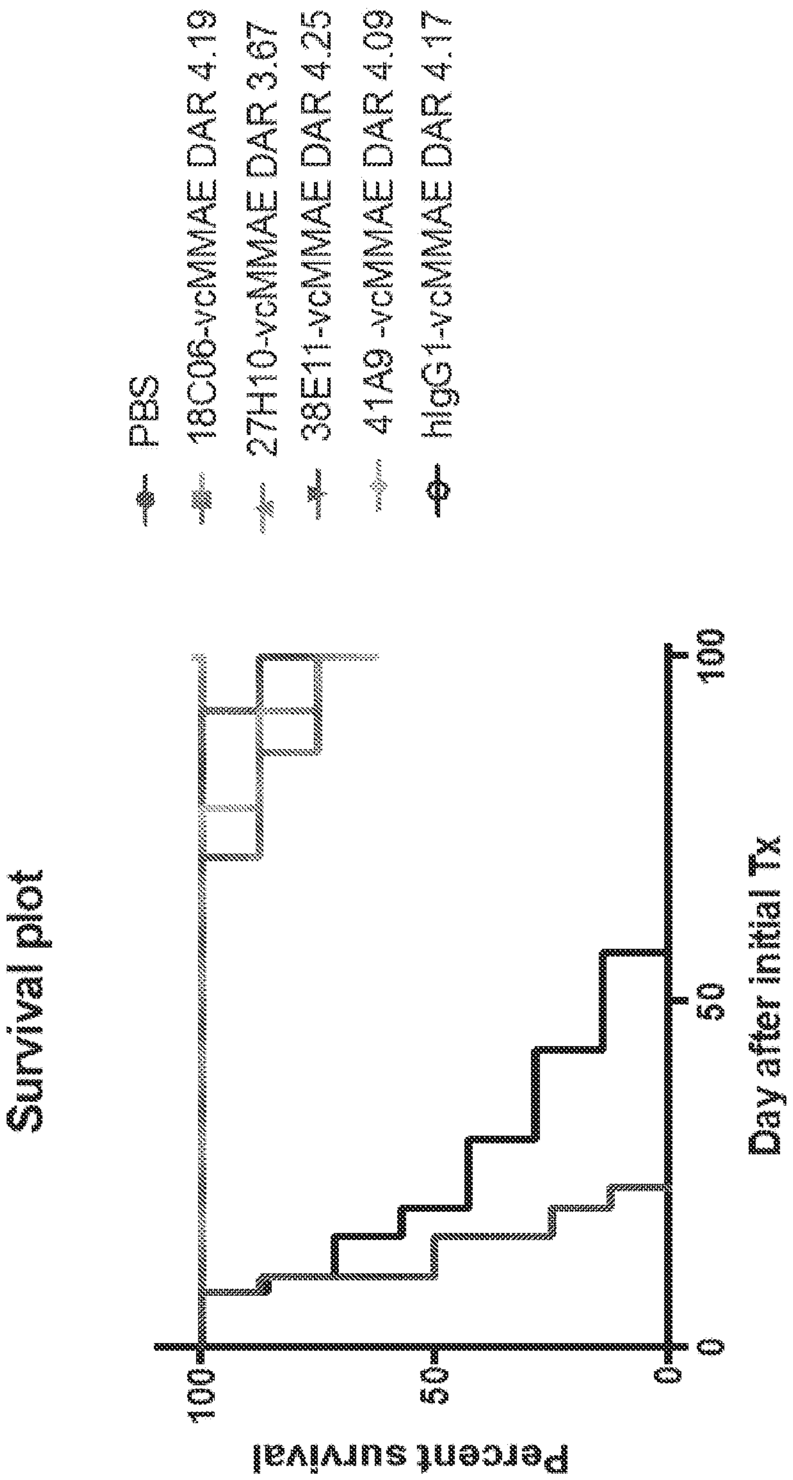
FIG. 12 is a graph showing the survival plot for mice with SW48 tumors treated with the antibody vcMMAE conjugates as shown in FIG. 11.
Figure 13A:
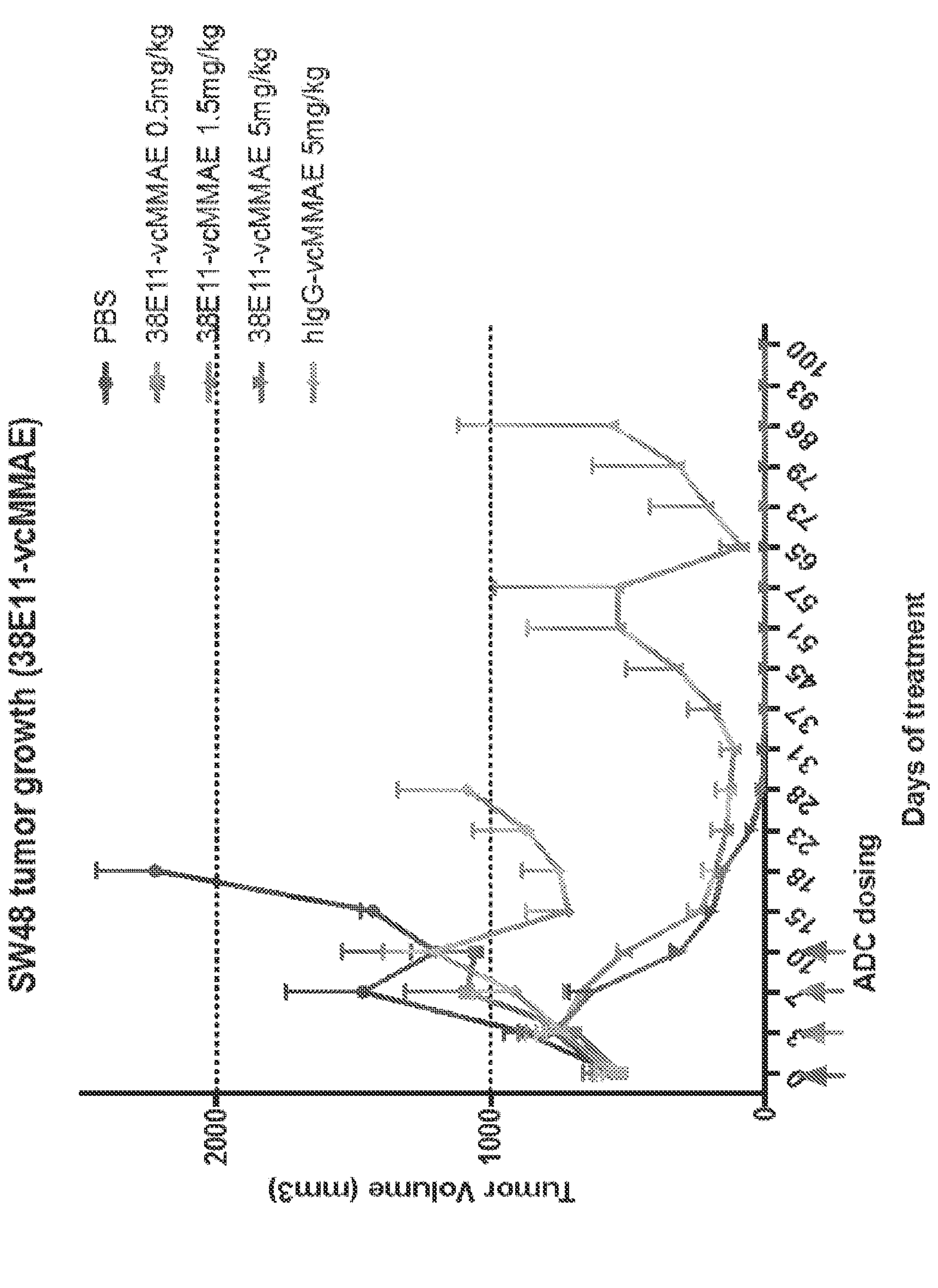
FIG. 13A is a graph showing dose-dependent tumor growth inhibitory effects of 38E11-MMAE on SW48 tumors in mice.
Figure 13B:
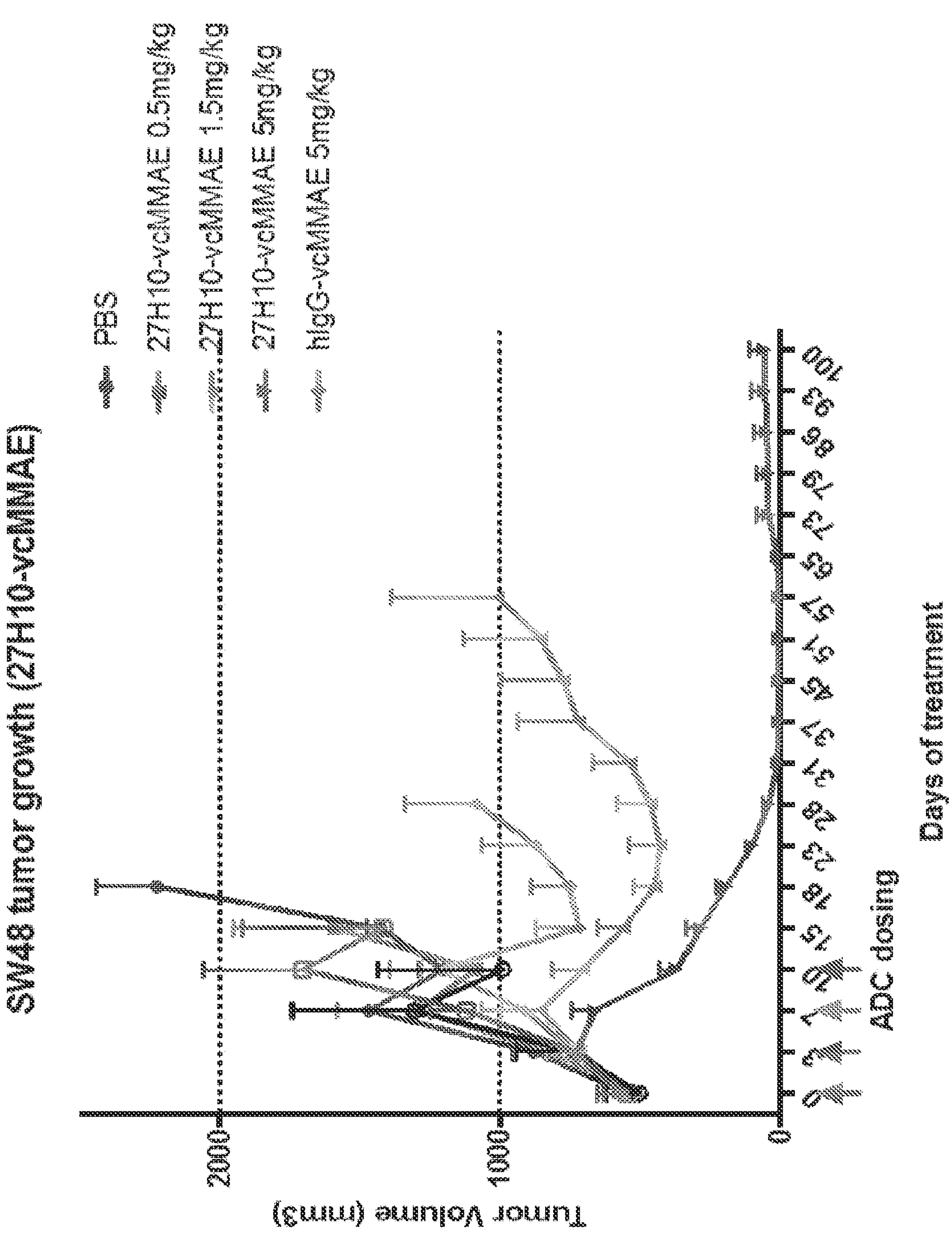
FIG. 13B is a graph showing dose-dependent tumor growth inhibitory effects of 27H10-MMAE on SW48 tumors in mice.
Figure 13C:
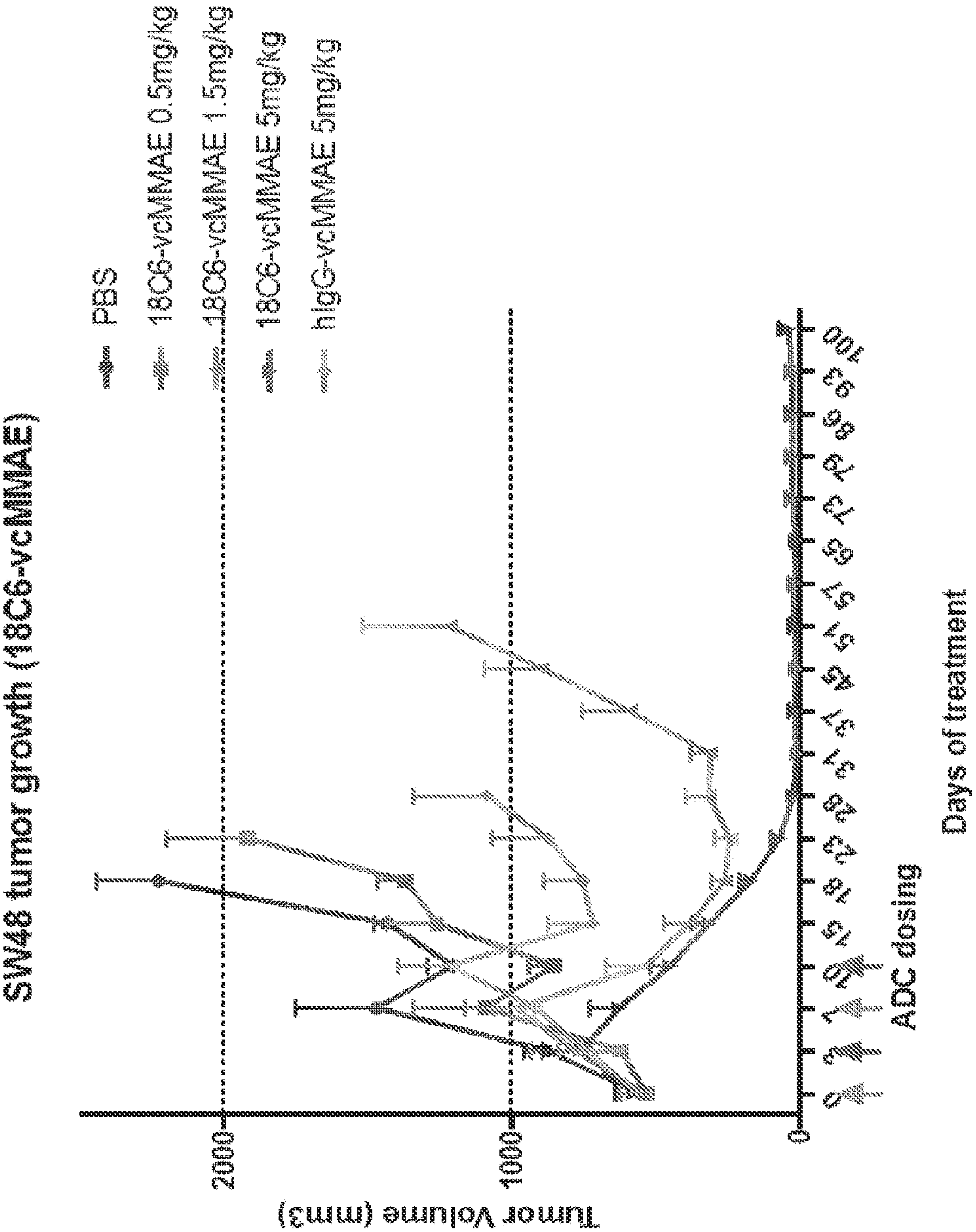
FIG. 13C is a graph showing dose-dependent tumor growth inhibitory effects of 18C6-MMAE on SW48 tumors in mice.
Figure 13D:
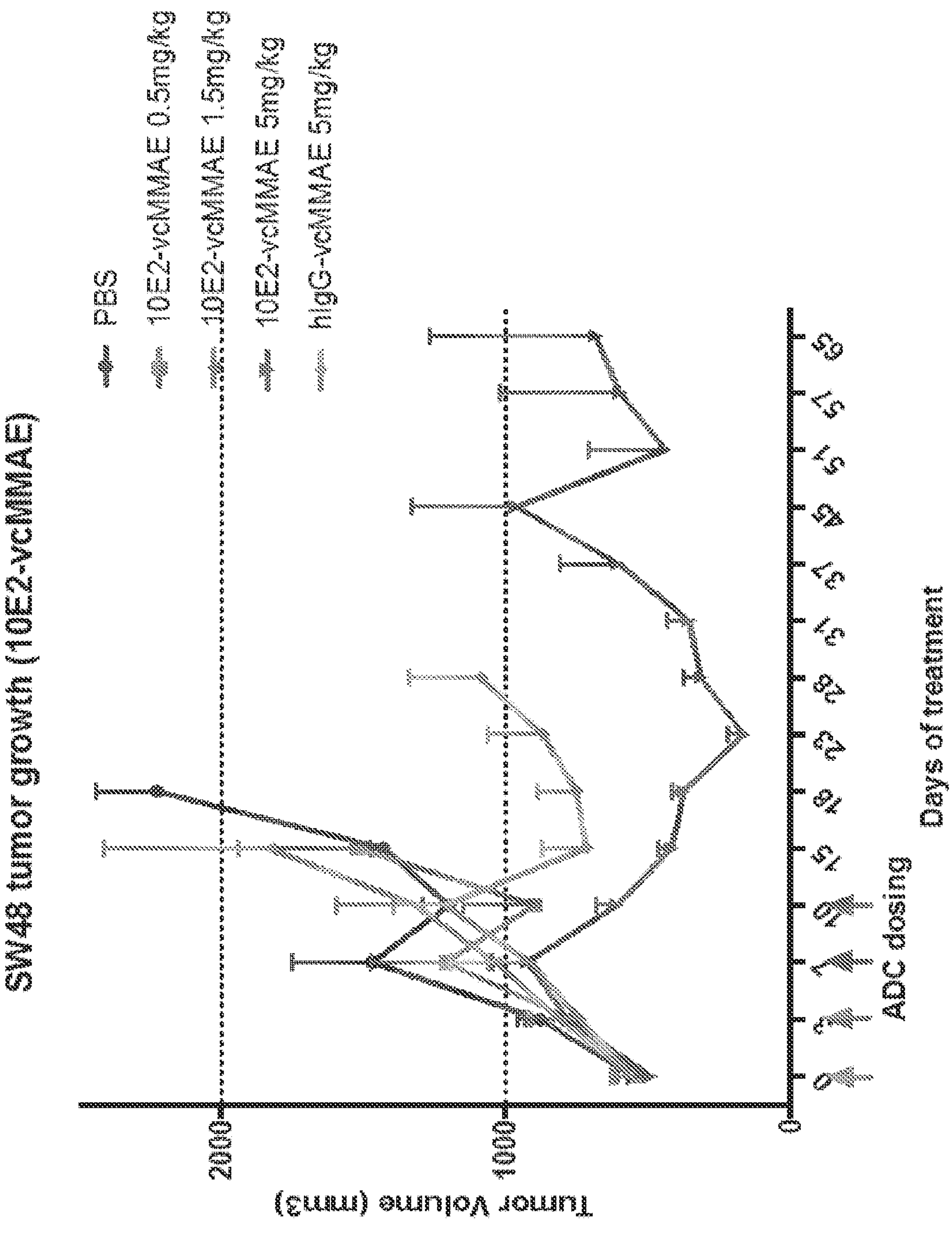
FIG. 13D is a graph showing dose-dependent tumor growth inhibitory effects of 10E2-MMAE on SW48 tumors in mice.
Figure 14A:
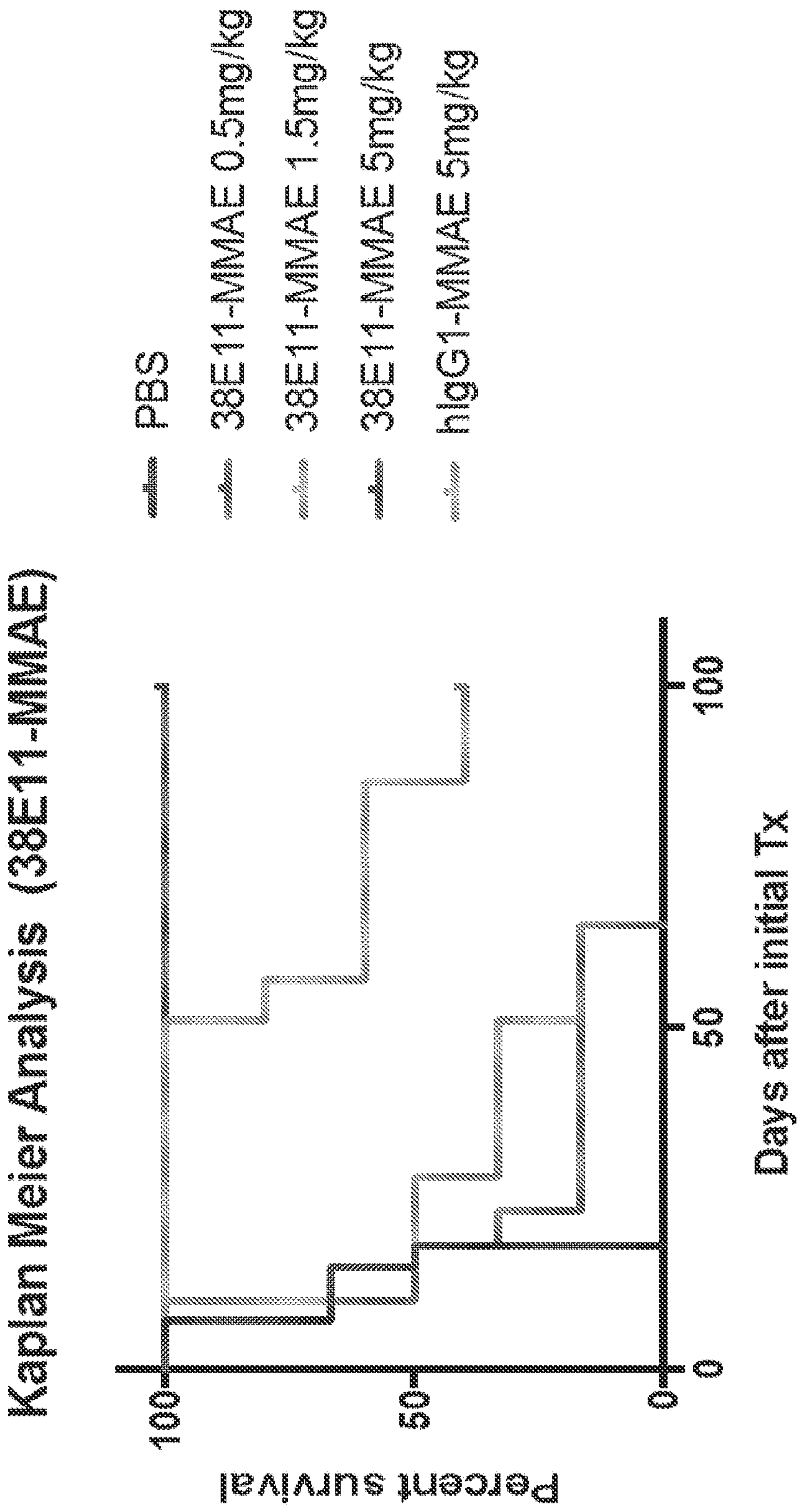
FIG. 14A is a graph showing Kaplan Meier analysis of SW48 tumor bearing mice treated with PBS, hlgG1-MMAE, or 38E11-MMAE at 0.5, 1.5, 5 mg/kg.
Figure 14B:
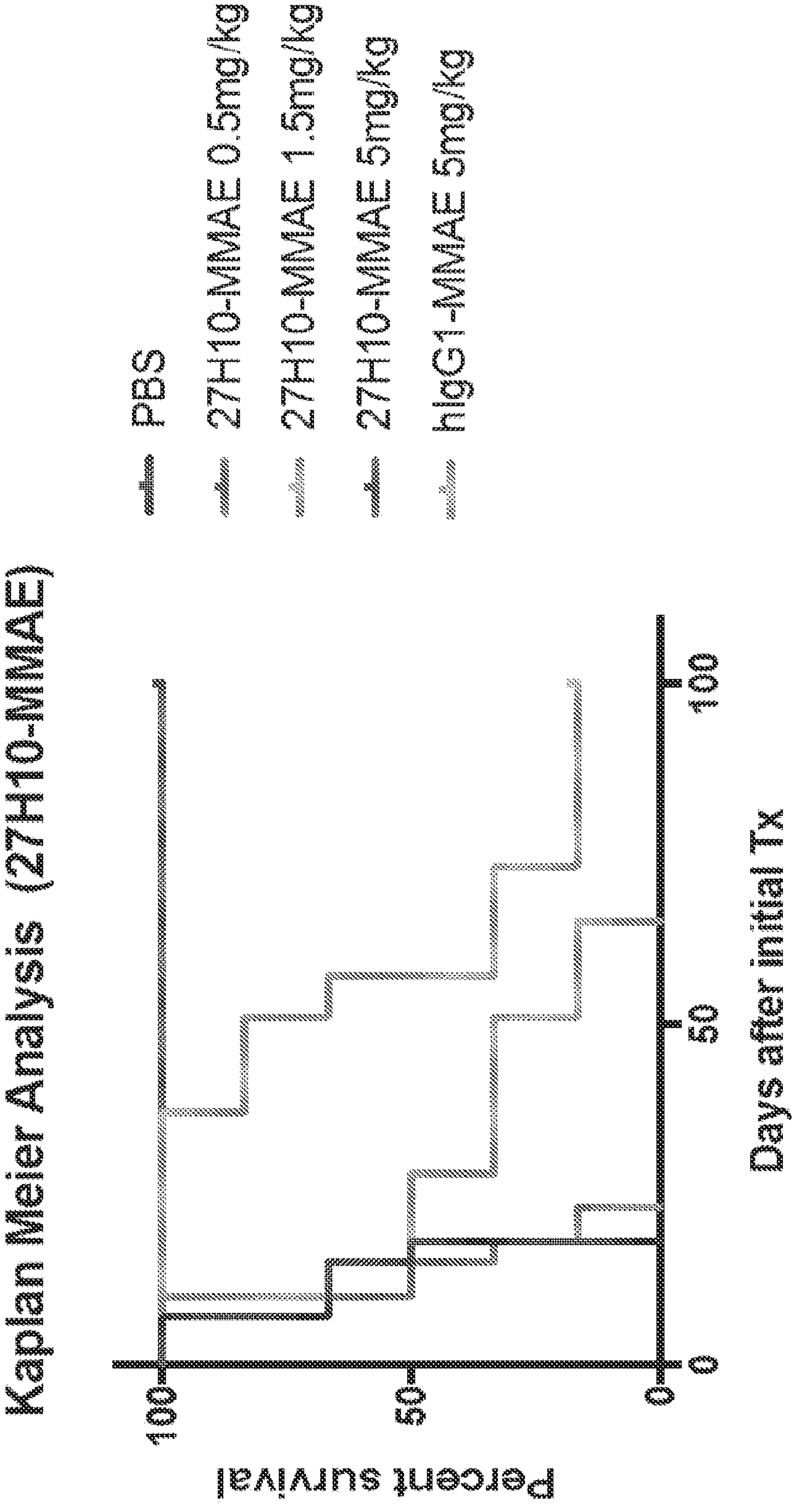
FIG. 14B is a graph showing Kaplan Meier analysis of SW48 tumor bearing mice treated with PBS, hlgG1-MMAE, or 27H10-MMAE at 0.5, 1.5.5 mg/kg.
Figure 14C:
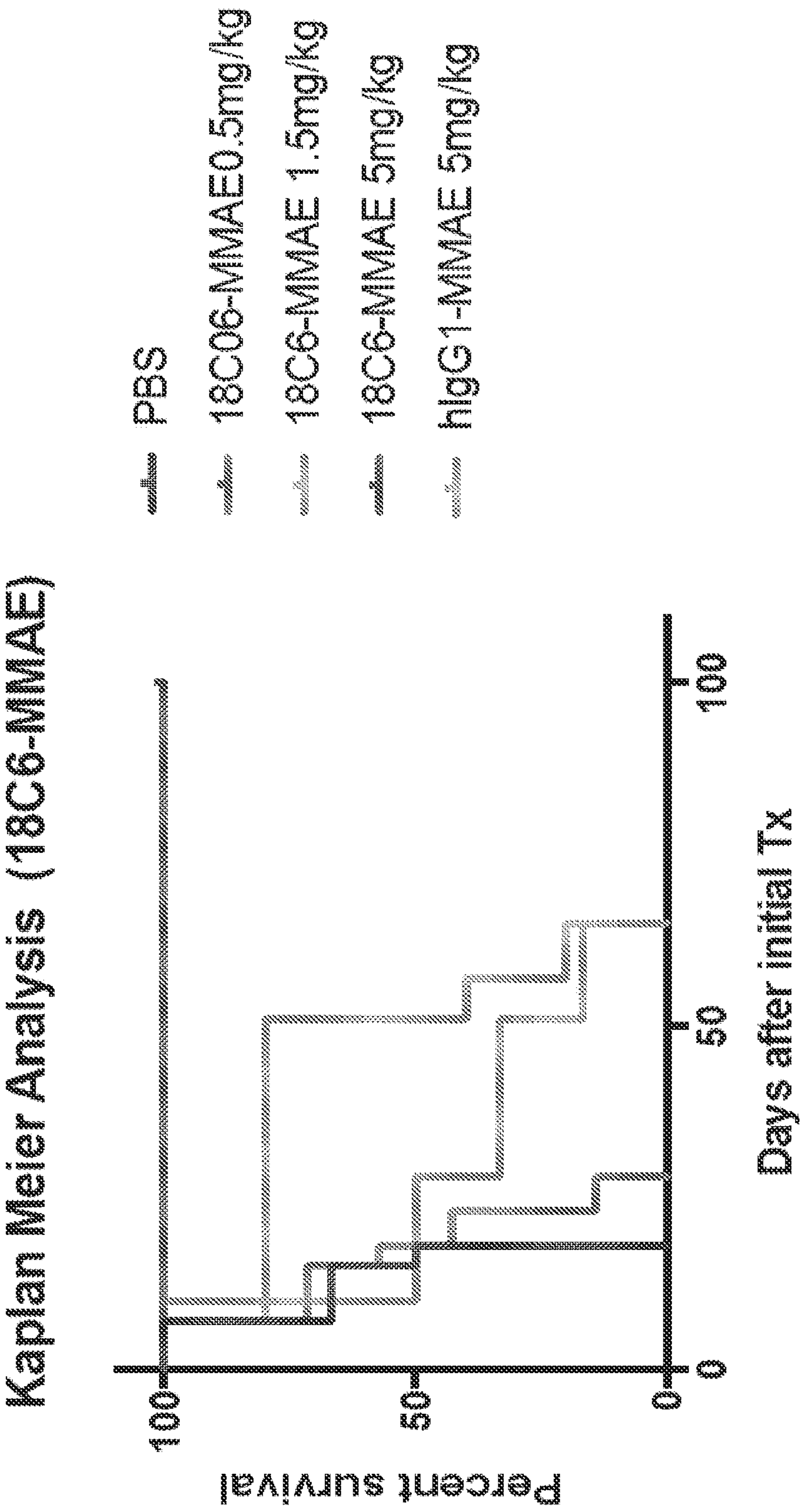
FIG. 14C is a graph showing Kaplan Meier analysis of SW48 tumor bearing mice treated with PBS, hlgG1-MMAE, or 18C6-MMAE at 0.5, 1.5, 5 mg/kg.
Figure 14D:
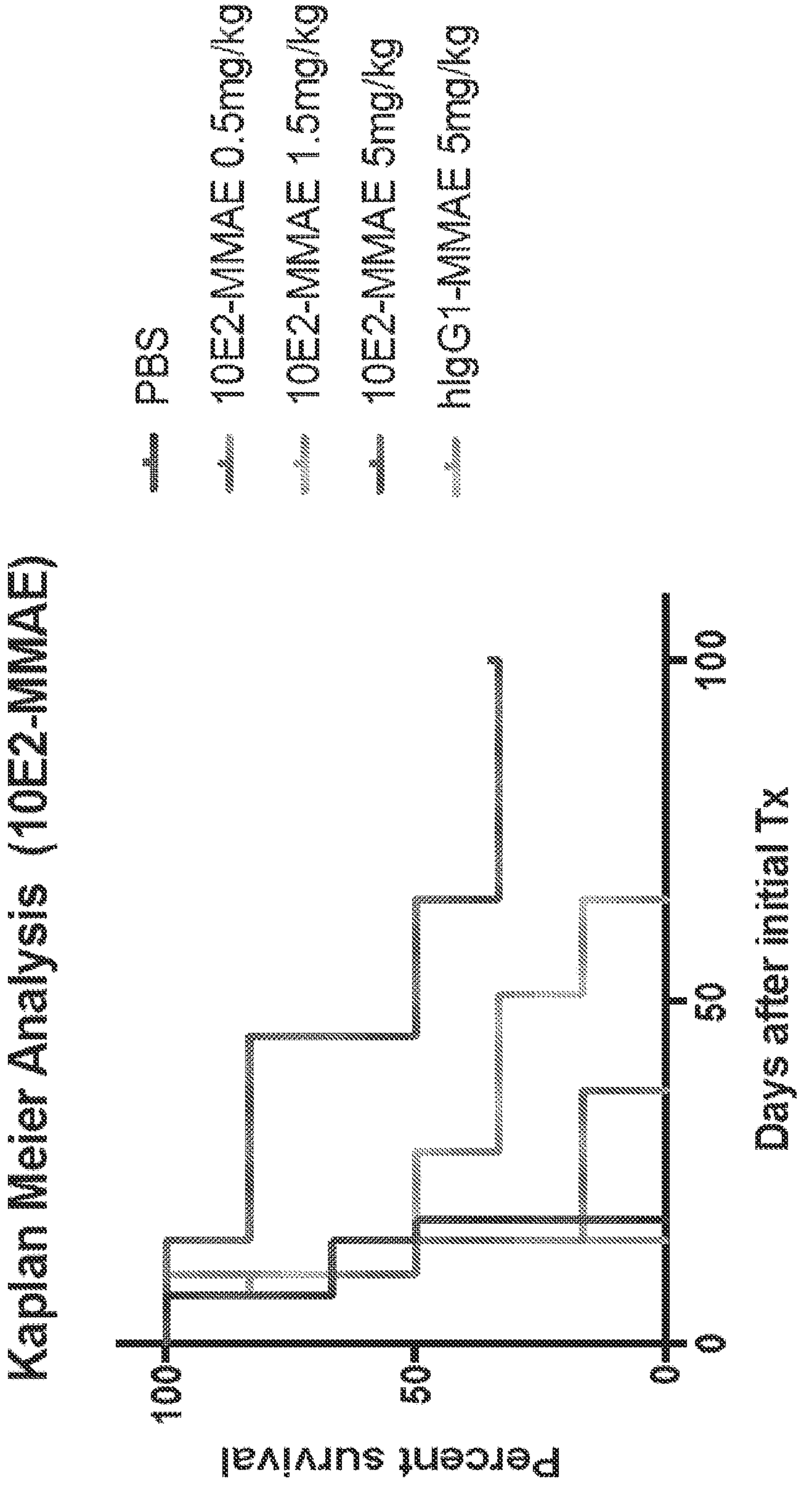
FIG. 14D is a graph showing Kaplan Meier analysis of SW48 tumor bearing mice treated with PBS, hlgG1-MMAE, or 10E2-MMAE at 0.5, 1.5, 5 mg/kg.

The 4 ADCs caused complete tumor regression and a significant prolonged survival in colon cancer model SW48 tumors (FIG. 11). Median of Time to Event (TTE) of CDCP1 ADC treated groups is 100 days versus 13 and 20 days in vehicle and isotype control treated groups, respectively (FIG. 12).

Example 20. Dose-Dependent Tumor Growth Inhibitory Effects of Anti-CDCP1 Antibodies Conjugated to MMAE on SW48 Xenograft Tumors in Mice Four human CDCP1 antibodies conjugated to MMAE were tested to demonstrate their dose dependent inhibitory effects on tumor growth in SW48 models. The CRC tumor model SW48 xenografts were generated by injecting $2.5\times10^6$ corresponding cultured cells in the presence of matrigel subcutaneously into 6-8 weeks old female Ncr-nude mice (Taconic. Hudson, NY). When most tumors reach 250-300 $mm^3$ in size, mice are randomized into treatment groups of 6-8 mice using an R studio script designed to group the animals so that the average tumor size and standard deviation of the tumor size between groups are comparable.

The animals were then injected intravenously with vehicle, human IgG1 (isotype control)-MMAE and 4 human CDCP1 ADCs (18C6-MMAE, 27H10-MMAE, 38E11-MMAE and 41A9-MMAE) at 0.5, 1.5 and 5 mg/kg. The intravenous administration was repeated 3 times over a period of 10 days. Following the treatment, tumor volumes and mouse weights were monitored until tumors exceeded 1500 $mm^3$. Mice that showed a 15% or more weight loss or become lethargic were taken out of the study. Tumor growth inhibition (TGI) was assessed when the number of animals in the vehicle group (control group) was reduced to <75% and was calculated by the following:

$$TGI=[1-(TV_{tx}^{Day\ x}-TV_{tx}^{Initial})/(TV_{veh}^{Day\ x}-TV_{veh}^{Initial})]\times100\%$$

wherein, $TV_{tx}^{Initial}$ is the initial tumor volume in the treatment group, $TV_{tx}^{Day\ x}$ is the tumor volume in the treatment group at Day X, $TV_{veh}^{Initial}$ is the initial tumor volume in the vehicle group and $TV_{veh}^{Day\ x}$ is the tumor volume in the vehicle group at Day X.

Three out of four human antibody MMAE conjugates, 38E11-MMAE, 27H10-MMAE and 18C6-MMAE, exhibited dose dependent inhibitory effects on SW48 tumor growth: at 5 mg/kg, they caused complete tumor regression without tumor regrowth 100 days after initial dosing (FIGS.

13A-13D); at 1.5 mg/kg these ADCs caused significant tumor growth inhibition: 121%, 106% and 117%, respectively, as well as significant prolonged survival, reflected by the median time to the end point (TTE) as 86.57 and 51 days, respectively; at 0.5 mg/kg, no obvious tumor growth inhibitory effect was observed for any of the ADCs. Among the 4 ADCs, 10E2-MMAE was the least efficacious one with a TGI of 86% and median TTE of 55 days at 5 mg/kg (Table 10, FIGS. 13A-13D and 14A-14D).

TABLE 10

Dose dependent tumor growth inhibitory effects of 4 ADCs on established SW48 tumors

| Treatment | DAR (drug:mAb ratio) | TGI on Day 18 | Median TTE (time to the end point ) |
|---|---|---|---|
| PBS | NA | NA | 16.5 |
| hIgG1-MMAE 5 mg/kg | 4.16 | Unmeasurable | 19 |
| 38E11-MMAE 0.5 mg/kg | 4.25 | Unmeasurable | 14 |
| 38E11-MMAE 1.5 mg/kg | 4.25 | 121% | 86 |
| 38E11-MMAE 5 mg/kg | 4.25 | 125% | 100 |
| 27H10-MMAE 0.5 mg/kg | 3.67 | Unmeasurable | 12.5 |
| 27H10-MMAE 1.5 mg/kg | 3.67 | 106% | 57 |
| 27H10-MMAE 5 mg/kg | 3.67 | 123% | 100 |
| 18C06-MMAE0.5 mg/kg | 4.19 | 50% | 18 |
| 18C6-MMAE 1.5 mg/kg | 4.19 | 117% | 51 |
| 18C6-MMAE 5 mg/kg | 4.19 | 124% | 100 |
| 10E2-MMAE 0.5 mg/kg | 4.16 | Unmeasurable | 12.5 |
| 10E2-MMAE 1.5 mg/kg | 4.16 | Unmeasurable | 12.5 |
| 10E2-MMAE 5 mg/kg | 4.16 | 86.80% | 55 |

Example 21. Conjugation of Human Antibodies to Pyrrolobenzodiazepine (PBD)

Human monoclonal antibodies against CDCP1 were conjugated to Pyrrolobenzodiazepine (PBD) as previously described (Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press. Totowa, NJ) Briefly, each antibody was partially reduced with an appropriate molar amount of TCEP for 2 hrs at 37° C. After incubation, the antibodies were cooled to room temperature and a 6-fold molar excess of PBD was added to the partially reduced antibody for 1 hour. After this incubation, the entire mixture was run over a gel filtration column to remove free drug. A fraction of the eluate was then used for concentration and DAR determination using A280 and HIC respectively.

Example 22. In Vitro Killing Activity of 38E11 Conjugated to MMAE or PBD on Prostate and Lung Cancer Cells Human antibodies conjugated to MMAE or PBD as described above are tested for their effect on growing prostate and non-small cell lung cancer cells. Prostate cell lines, DU 145, LNCAP, and PC3, and NSCLC cells, which express CDCP1, breast cancer cell line MCF7, which does not express CDCP1, were seeded onto 96 well plate at 1000-2000 cells/well. 24 hrs later, 38E11-vcMMAE and isotype control hIgG-vcMMAE bearing a drug antibody ratio (DAR) of 3.9 and 4.2, respectively, or 38E11-PBD and isotype control hIgG-PBD bearing a drug antibody ratio (DAR) of 2.3 and 2.9, respectively, were added to the wells in complete culture medium so that the final Ab-PBD concentration in the well is 0.001, 0.01, 0.1 and 1 ug/ml. Each treatment was replicated in 2 wells. 96 hrs later, cell viability was measured by CellTiter Glo Luminescent Cell viability assay (Promega) according to manufacturer's instructions. Cell viability was graphed by Prism using ratio of cell viability of test conditions to that of control wells that are treated with growth medium only.

Figure 21A:
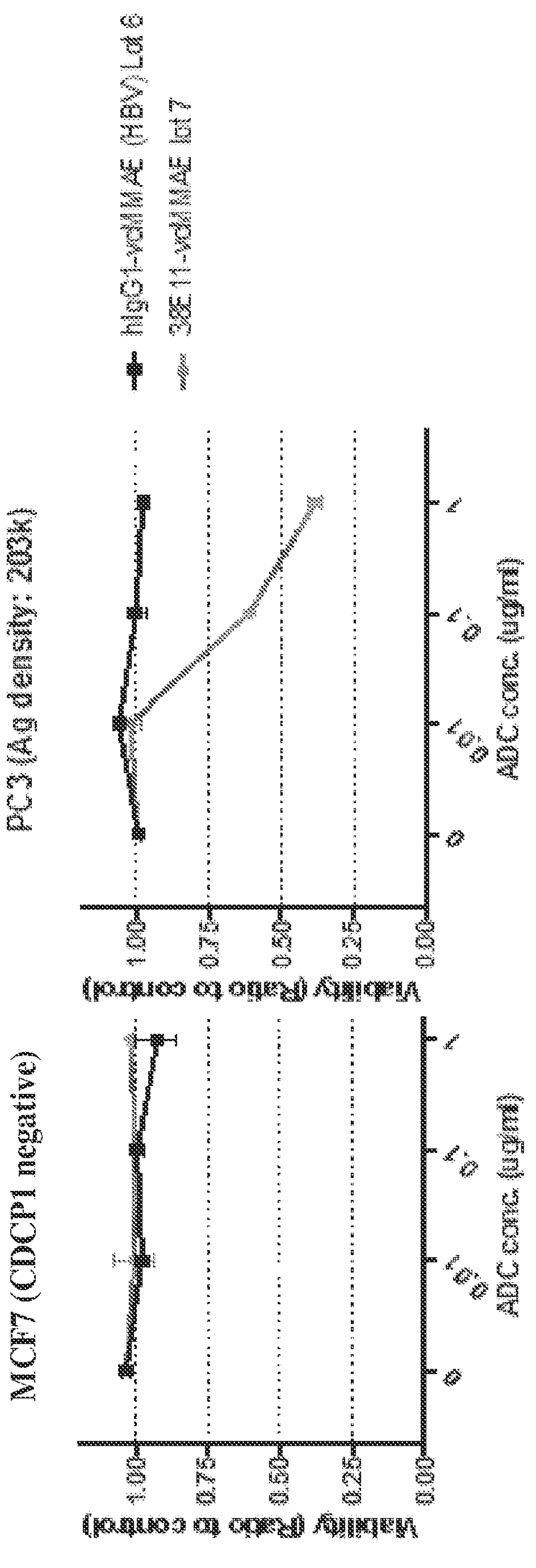
FIGS. 21A and 21B are graphs showing the in vitro killing effect of hIgG1-vcMMAE and 38E11-vcMMAE on prostate cancer cells.
Figure 21B:
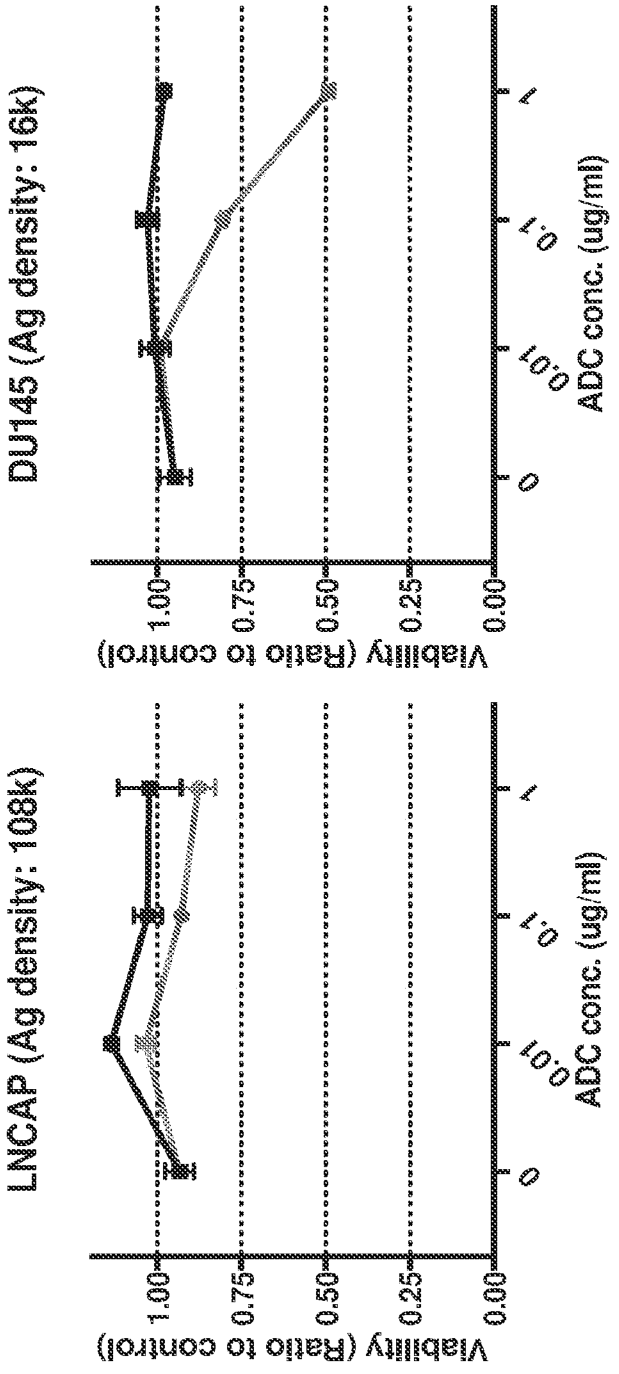

As shown in FIGS. 21A-21B, while 38E11-vcMMAE exhibited no effect on MCF7 cells, which does not express CDCP1, it exhibited killing effects on prostate cancer cell lines, PC3 and DU145, with EC50 of 0.1 μg/ml and 1 μg/ml, respectively. LNCAP shows no sensitivity to 38E11-vcMMAE.

Figure 22A:
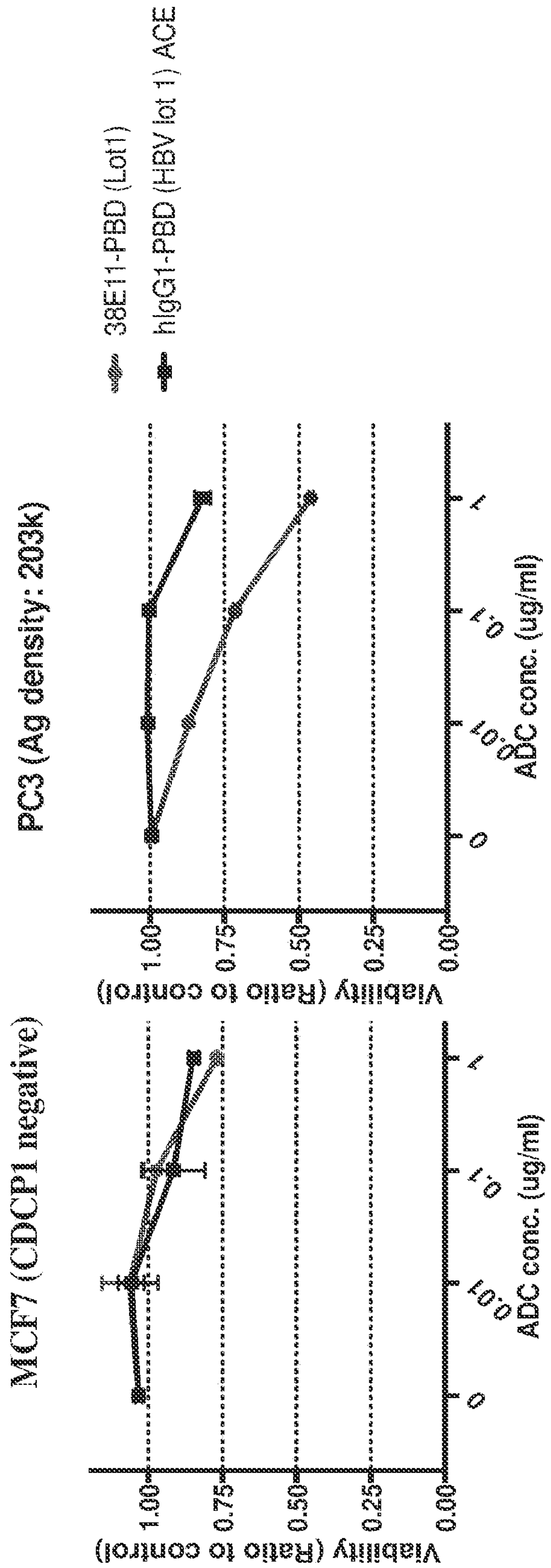
FIGS. 22A and 22B are graphs showing the in vitro killing effect of hIgG1-PBD and 38E11-PBD on prostate cancer cells.
Figure 22B:
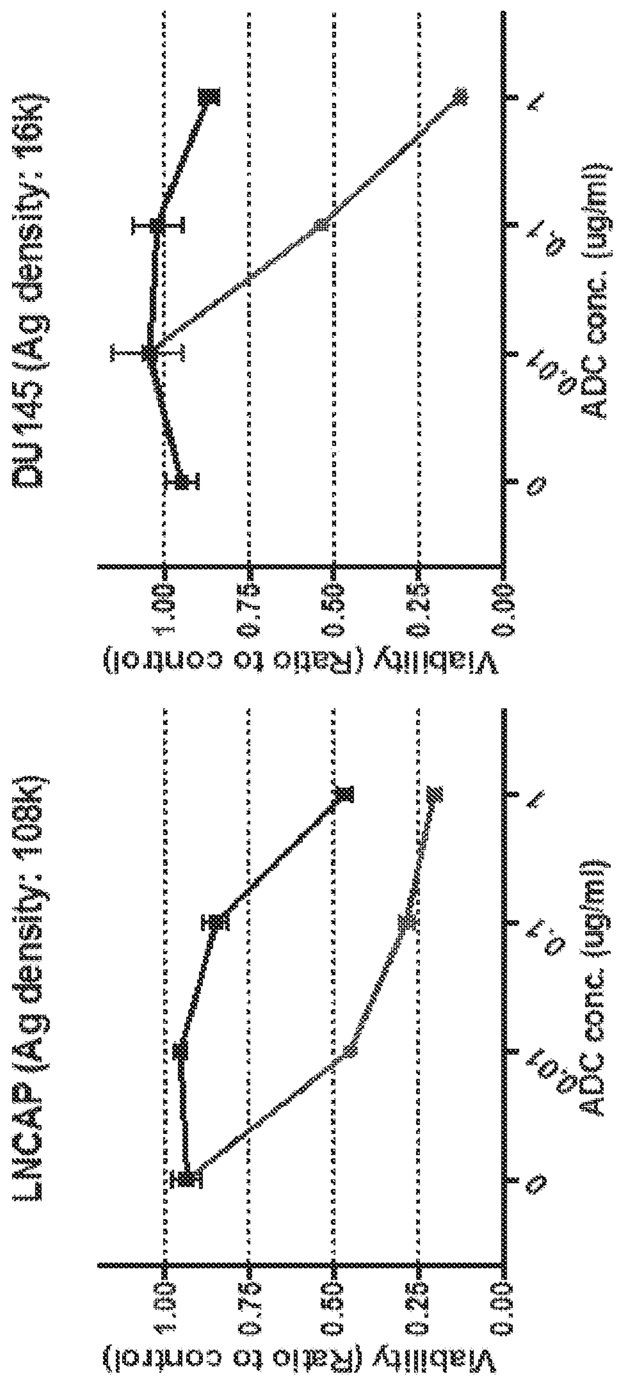

As shown in FIGS. 22A-22B, while 38E11-PBD exhibited no effect on MCF7 cells, which does not express CDCP1, it exhibited varying degree of killing effects on prostate cancer cell lines, PC3, DU145 and LNCAP, with EC50 of 1 μg/ml, 0.1 μg/ml and 0.01 μg/ml, respectively.

Figure 23A:
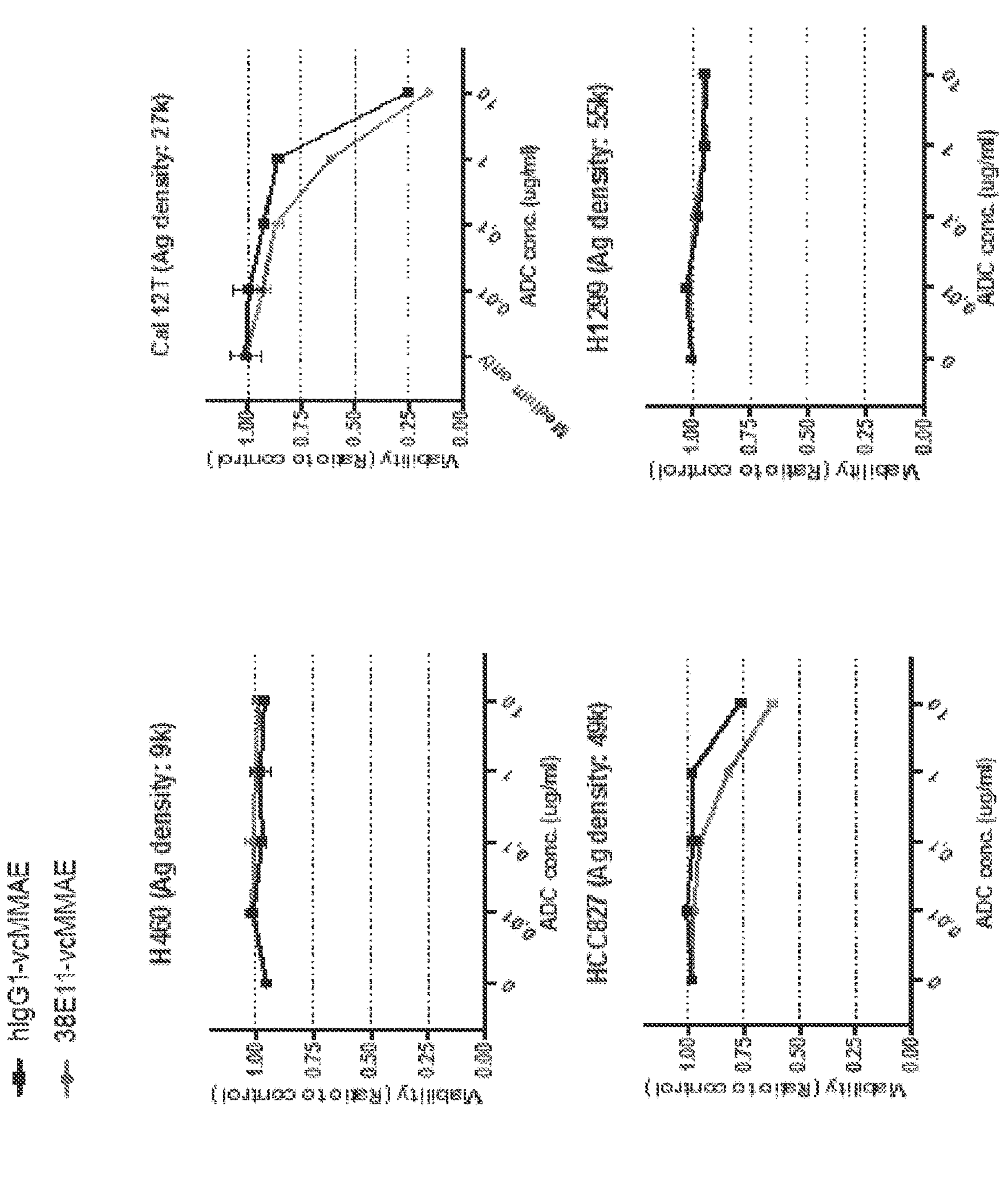
FIGS. 23A and 23B are graphs showing the in vitro killing effect of hIgG1-vcMMAE and 38E11-vcMMAE on NSLC cells.
Figure 23B:
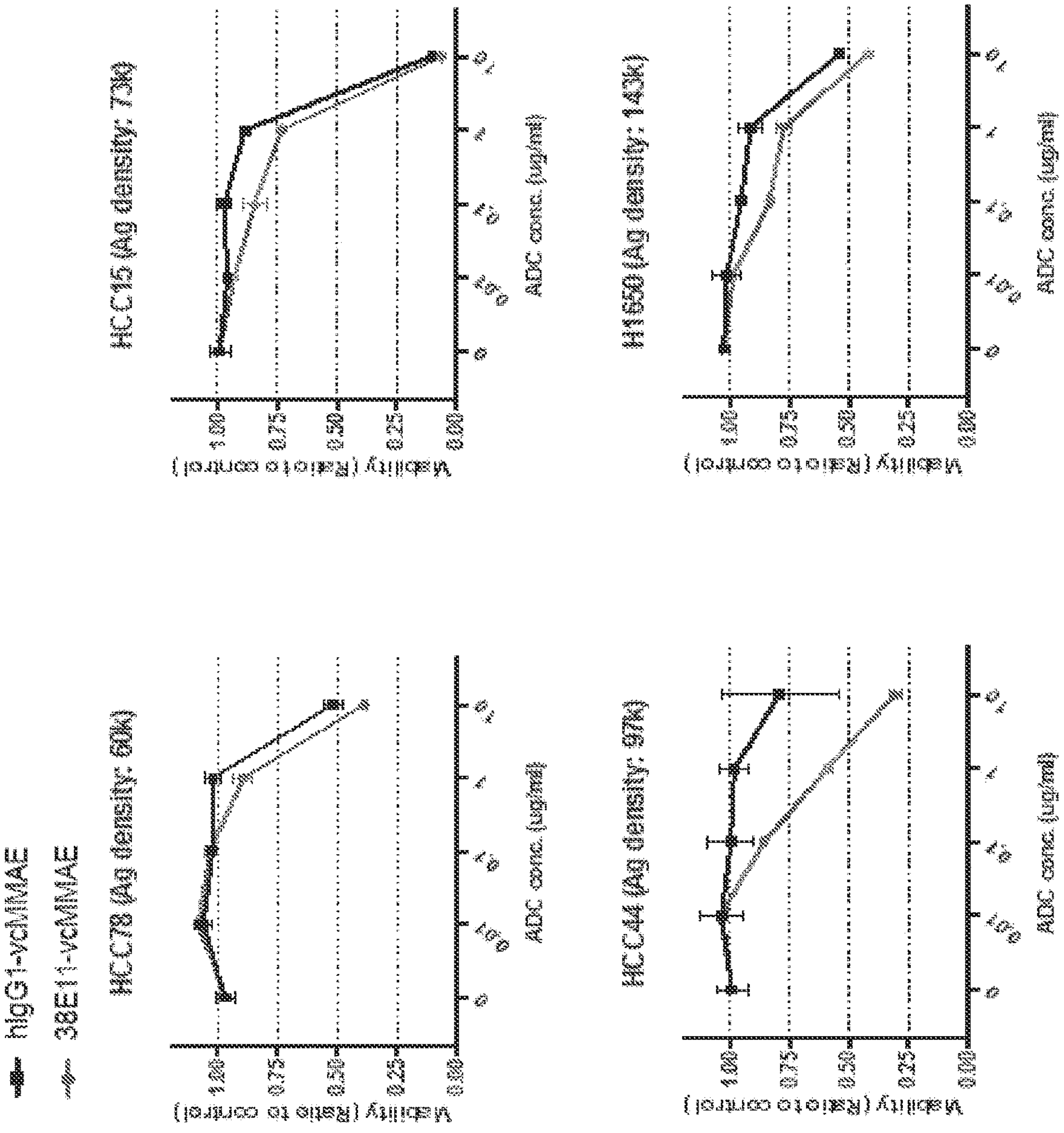

As shown in FIGS. 23A-23B, while 38E11-vcMMAE exhibited varying killing effects on NSCLC cell lines, Cal-12T, HCC78, HCC827, HCC44, HCC15 and H1650 cells, with EC50 more than 1 μg/ml. In contrast, NSCLC cell lines H460 and H1299 showed no sensitivity to 38E11 vcMMAE.

Figure 24A:
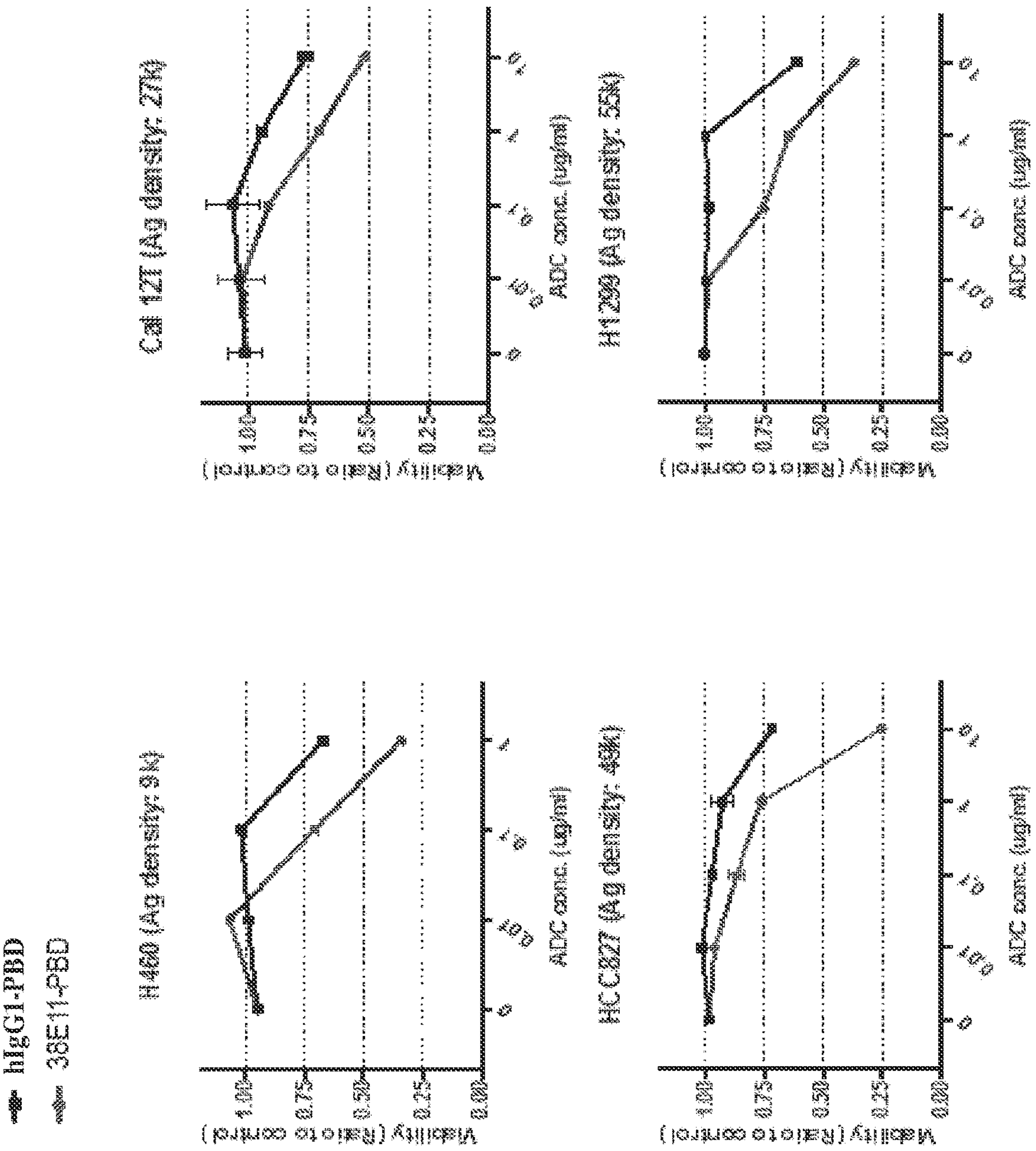
FIGS. 24A and 24B are graphs showing the in vitro killing effect of hlgG1-PBD and 38E11-PBD on NSLC cells.
Figure 24B:
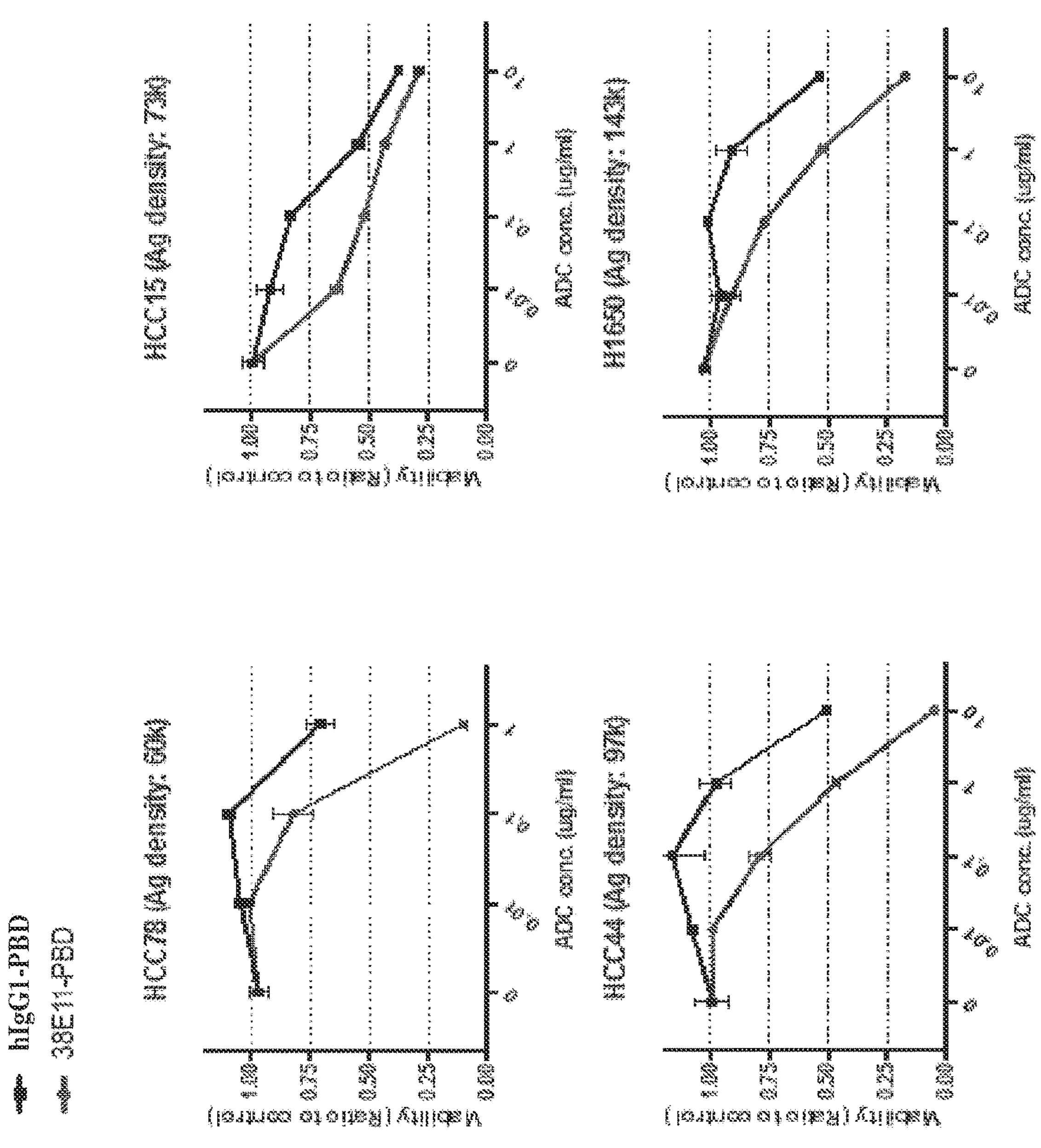

As shown in FIGS. 24A-24B, while 38E11-PBD exhibited varying killing effects on NSCLC cell lines, with EC50 of ~0.1 μg/ml in H460 and HCC15 cells, and EC50 of ~1 μg/ml in HCC15, HCC44 and H1650 cells, and EC50 of more than 1 μg/ml inCal-12T, HCC827, H1299.

Example 23. Conjugation of Human Antibodies to Pyrrolobenzodiazepine and Auristatin-E Payloads Human monoclonal antibodies against CDCP1 were conjugated to the valine-alanine-pyrrolobenzodiazepine. MA-PEG8-VA-PAB-SG3199 (PBD) or maleimidocaproyl-valine-citrulline-p-aminobenzoyloxycarbonyl-monomethyl auristatin E (MMAE) as previously described (Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press. Totowa. NJ) Briefly, each antibody was partially reduced with an appropriate molar amount of TCEP for 2 hrs at 37° C. After incubation, the antibodies were cooled to room temperature and a 6-fold molar excess of PBD or MMAE was added to the partially reduced antibody for 1 hour. After this incubation, the entire mixture was run over a gel filtration column to remove free drug. A fraction of the eluate was then used for concentration and DAR determination using A280 and HIC respectively.

Example 24. Dose-Dependent Tumor Growth Inhibitory Effects of 38E11 and hIgG1 Conjugated to MMAE on TNBC PDX Tumors in Mice Eight monoclonal CDCP1 antibodies conjugated to MMAE and human IgG1 were tested to demonstrate their dose dependent inhibitory effects on tumor growth in TNBC PDX models. Xenograft tumors for each PDX model were initiated from Cryo-preserved PDX tumor tissue using trocar needle method into 3-5 stock mice. Tumor volume was monitored and calculated using the formula:

$$\text{Tumor Volume (mm}^3\text{)}=0.52\times L\times W^2$$

where L=length and W=width in mm of a tumor. Tumor length and width represent the two longest perpendicular axes in the x/y plane of each tumor measured by an electronic caliper to the nearest 0.1 mm.

When tumor volume of stock mice reach 800-1000 mm3, tumors were harvested for re-implantation into 12-15 pre-study mice. Pre-study mice are implanted unilaterally on the left flank with tumor fragments harvested from stock mice. Pre-study tumor volumes are recorded for each experiment beginning seven to ten days after implantation. When tumors reach an average tumor volume of approximately 150-300 $mm^3$ animals are matched by tumor volume into treatment or control groups to be used for dosing.

Human monoclonal antibodies against CDCP1, 38E11, and a human IgG1 isotype control antibody (against Hepatitis B virus. HBV) were conjugated to the anti-mitotic payload, valine-citrulline-monomethylauristatin E (vcMMAE) as previously described in Stefano. J. E., et al. (2013) *Micro- and Mid-Scale Maleimide-Based Conjugation of Cytotoxic Drugs to Antibody Hinge Region Thiols for Tumor Targeting*; and Ducry L. (eds) *Antibody-Drug Conjugates. Methods in Molecular Biology* (*Methods and Protocols*), vol. 1045. Humana Press, Totowa, NJ. Briefly, each antibody was partially reduced with an appropriate molar amount of TCEP for 2 hrs at 37° C. After incubation, the antibodies were cooled to room temperature and a 6-fold molar excess of vcMMAE or PBD was added to the partially reduced antibody for 1 hour. After this incubation, the entire mixture was run over a gel filtration column to remove free drug. A fraction of the eluate was then used for concentration and DAR determination using A280 and HIC respectively. Conjugated antibodies are stored in PBS at 4° C. Dilutions of 1 mg/ml ADCs were made in PBS and stored at 4° C. before and during mouse treatment under sterile conditions.

The treatment plan is summarized in the Table 11. For each group, treatments were administered intravenously (i.v.) 2 times per week for 2 weeks (2×/wk for 2 wks). Specifically, doses were administered on Day 0, 3, 7 and 10. Group I received vehicle (PBS), Groups 2 and 3 received 1.5 mg/kg or 5 mg/kg of 38E11-vcMMAE, respectively. Group 4 received 5 mg/kg isotype control hIgG1-vcMMAE. Each dose of drug was given in a volume of 0.15 ml so that each mouse received indicated doses, assuming a body weight of 30 grams for each mouse.

TABLE 11

Treatment Design for TNBC PDX Efficacy Study

| Group | -n- | Agent | Dose (mg/kg/dose) | Dose Volume (mL/kg) | ROA | Schedule | Total Number of Doses |
|---|---|---|---|---|---|---|---|
| 1 | 2 | PBS | — | 5 | IV | BIW × 2 | 4 |
| 2 | 1 | 38E11-vcMMAE | 1.5 | 5 | IV | BIW × 2 | 4 |
| 3 | 1 | 38E11-vcMMAE | 5 | 5 | IV | BIW × 2 | 4 |
| 4 | 1 | hIgG-vcMMAE | 5 | 5 | IV | BIW × 2 | 4 |

Figure 25A:
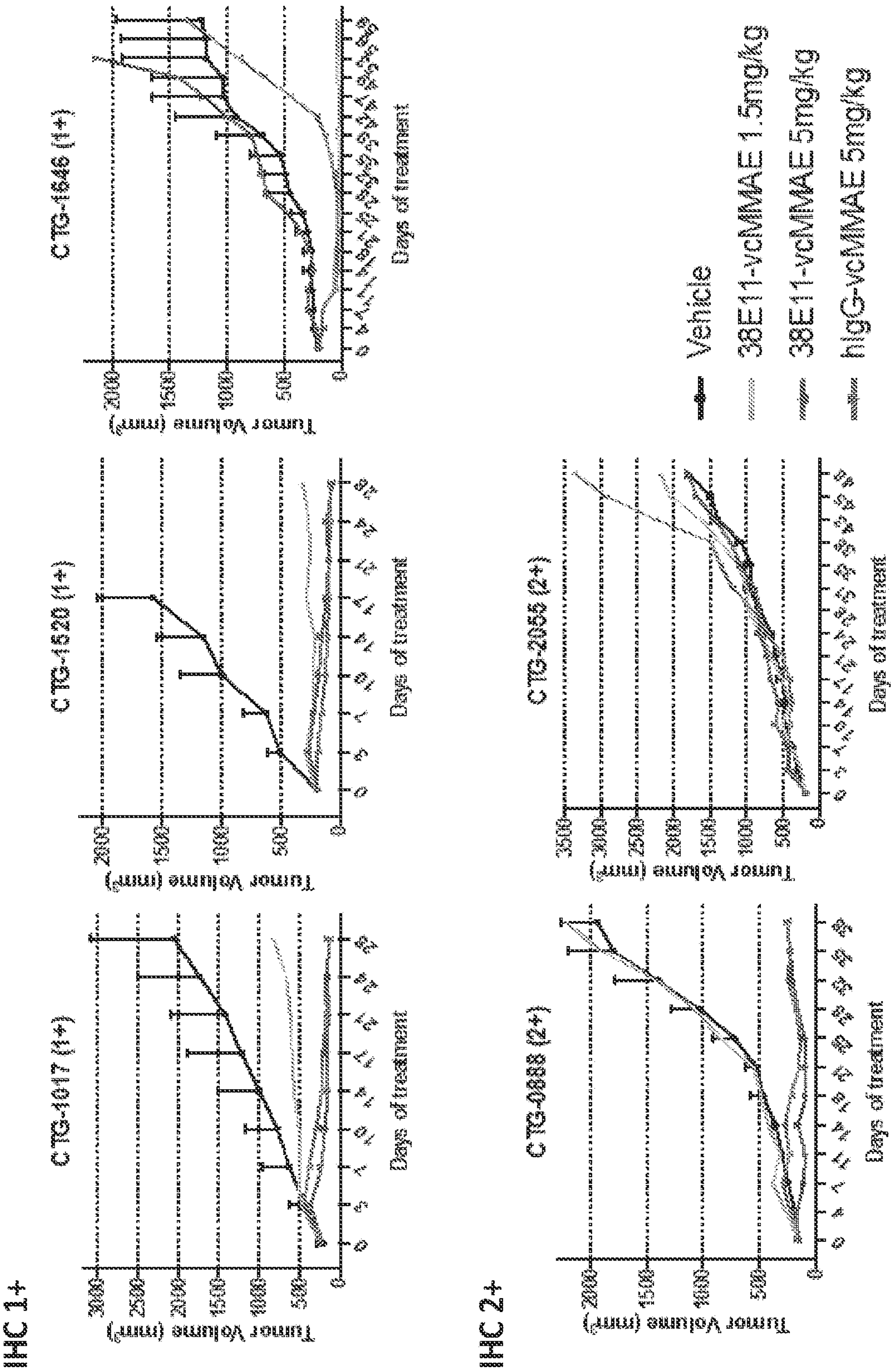
FIGS. 25A and 25B are graphs showing the tumor growth of eight TNBC PDX models in response to 38E11-vcMMAE and hIgG-vcMMAE.
Figure 25B:
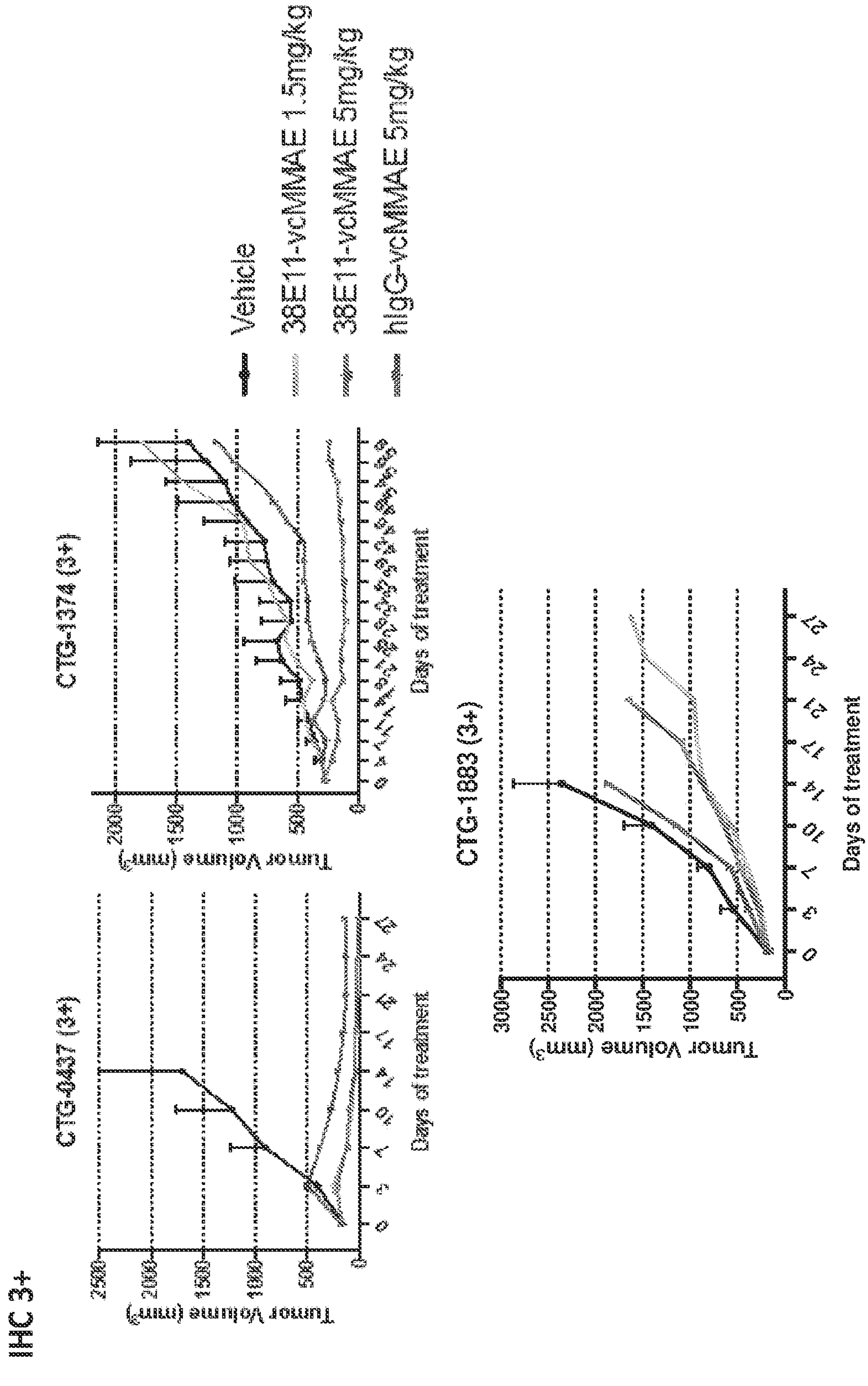
Figure 26A:
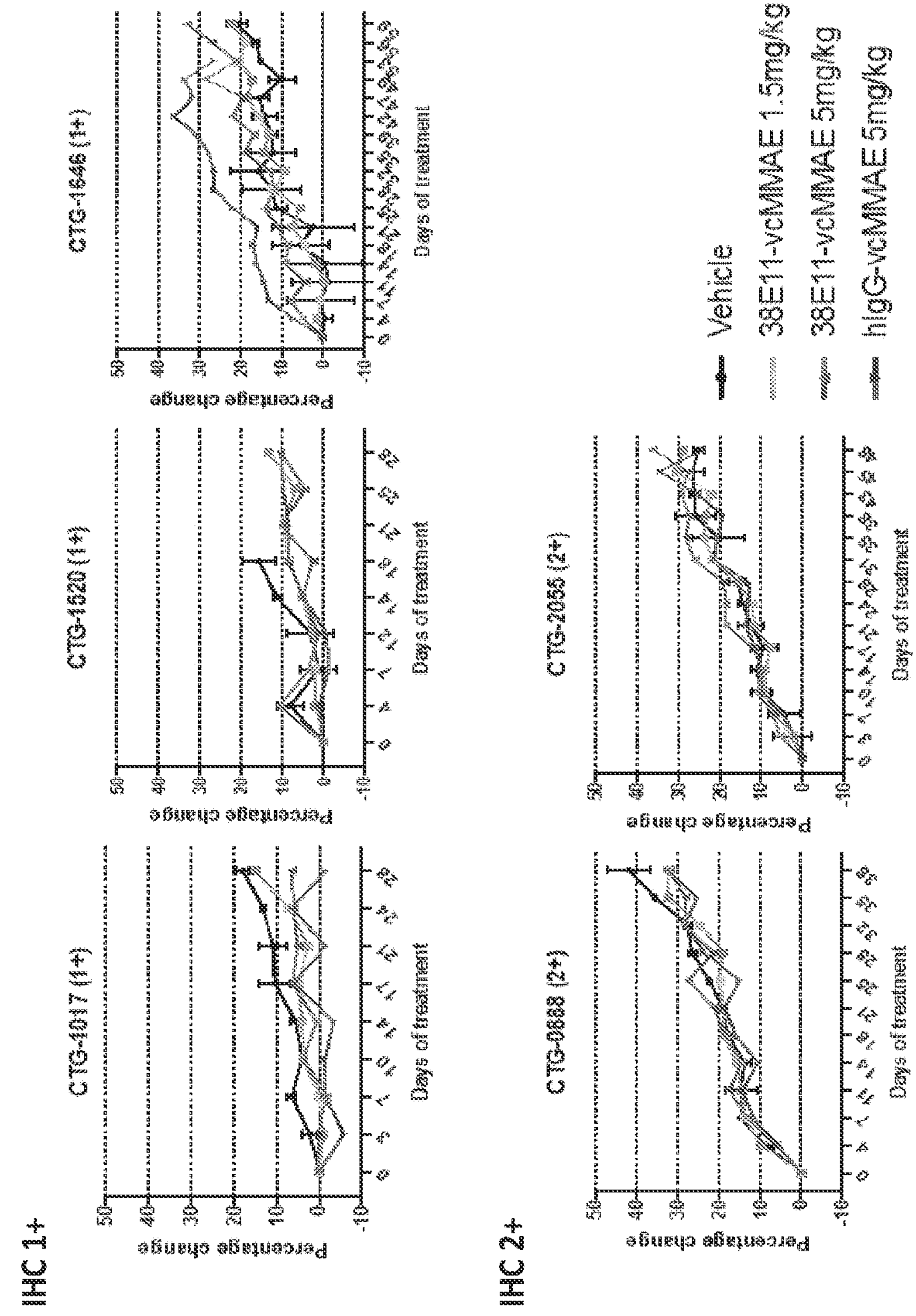
FIGS. 26A and 26B are graphs showing the body weight plots of eight TNBC PDX models in response to 38E11-vcMMAE and hIgG-vcMMAE.
Figure 26B:
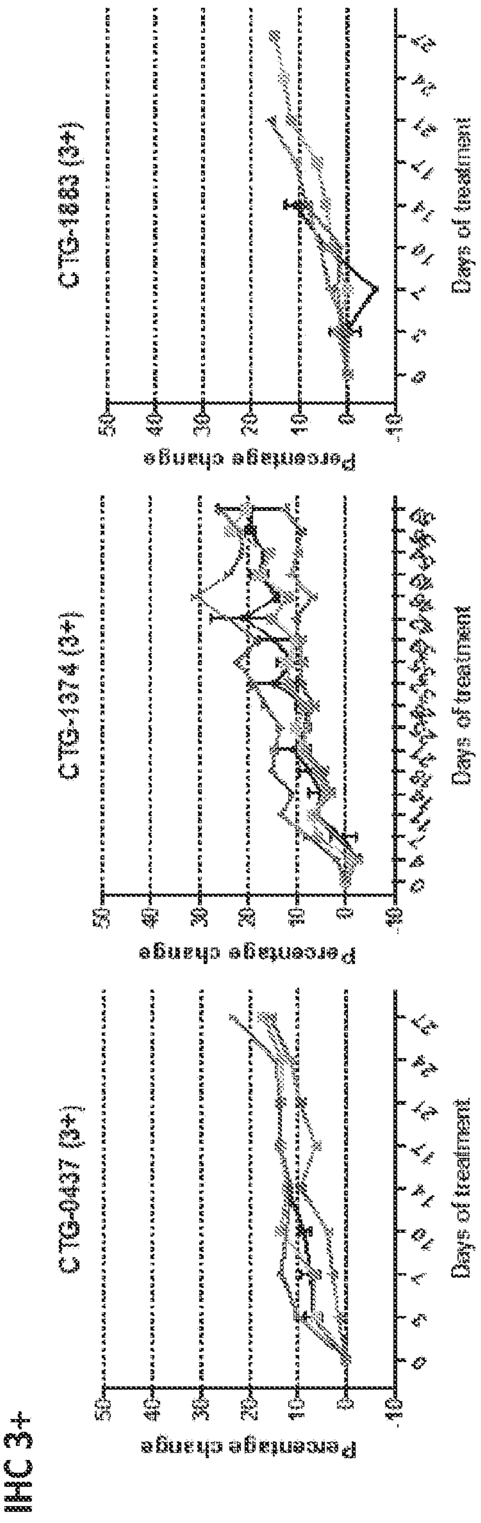

Eight TNBC PDX models (CTG-1017, CTG-1520, CTG-1646, CTG-0888, CTG-0437, CTG-1374 and CTG-1883) were dosed and analyzed. The response of each of the eight models to different treatment are summarized in Table 12. FIGS. 25A-25B shows the tumor growth curves of these 8 models. FIGS. 26A-26B shows the body weight change of mice from these eight models throughout the study.

TABLE 12

Response Summary of MDA-MB-231 Xenograft Efficacy Study

| | | | % tumor size vs vehicle (positive no.) or % regression (negative no.) | | |
|---|---|---|---|---|---|
| Model ID | Tumor Status | Target expression | 38E11-vcMMAE 1.5 mg/kg | 38E11-vcMMAE 5 mg/kg | hIgG-vcMMAE 5 mg/kg |
| CTG-1017 | Primary | 1+ | 31% | −29% | −35% |
| CTG1520 | Relapsed | 1+ | 0% | −52% | −38% |
| CTG-1646 | Primary | 1+ | −86% | −83% | 59% |
| CTG-0888 | Relapsed | 2+ | 102% | −10% | −46% |
| CTG-2055 | Relapsed | 2+ | 51% | 70% | 92% |
| CTG-0437 | Mets | 3+ | −87% | −87% | −24% |
| CTG-1374 | Primary | 3+ | 45% | −60% | −7% |
| CTG-1883 | Primary | 3+ | 17% | 29% | 54% |

Response of INK PDX models to 38E11-vcMMAE and hIgG-vcMMAE

Seven out of eight TNBC PDX models (CTG-1017, CTG-1520, CTG-1646, CTG-0888, CTG-(1437. CTG-1374 and CTG-1883) responded to 38E11-vcMMAE at 5 mg/kg. These models showed response of ΔT/ΔC<20% or regression or disease control as shown in Table 12 and FIGS. 25A-25B. Four out of eight models (CTG-1520, CTG-1646, CTG-0437, and CTG-1883) responded to 38E11-vcMMAE at 1.5 mg/kg. These models showed response of ΔT/ΔC<20% or regression or disease control as shown in Table 12 and FIGS. 25A-25B. Seven out of eight TNBC PDX models (CTG-1017. CTG-1520. CTG-0888, CTG-0437, and CTG-1374) responded to hIgG-vcMMAE at 5 mg/kg. These models showed response of ΔT/ΔC<20% or regression or disease control as shown in Table 12 and FIGS. 25A-25B.

INCORPORATION BY REFERENCE

The contents of all references, patents, pending patent applications and published patents, and Accession Numbers, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
Sequence total quantity: 406
SEQ ID NO: 1           moltype = AA  length = 115
FEATURE                Location/Qualifiers
REGION                 1..115
                       note = Description of Artificial Sequence: Synthetic
                        polypeptide
source                 1..115
                       mol_type = protein
                       organism = synthetic construct
SEQUENCE: 1
EVQLLESGGD LVQPGGSLRL SCAASGFTFN SYAMSWVRQA PGKGLEWVSV LSGSGGDIHY  60
ADSVKGRFTV SRDNSKNMLY LQMNSLRAED TAVYFCAQQW PQGYWGQGTL VTVSS       115

SEQ ID NO: 2           moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 2
DIQMTQSPSS LSASVGDRVT ITCRASQGIS IYLAWFQQKP GKVPKLLIYA ASTLQSGVPS  60
RFSGSGSGTD FTLTISSLQP EDVATYYCQK YNSAPFTFGP GTKVEIK                107

SEQ ID NO: 3           moltype = DNA  length = 431
FEATURE                Location/Qualifiers
misc_feature           1..431
                       note = Description of Artificial Sequence: Synthetic
                        polynucleotide
source                 1..431
                       mol_type = other DNA
                       organism = synthetic construct
SEQUENCE: 3
atggaattgg ggctgagctg tctttttctt gtggctattt taaaaggtgt ccagtgtgag  60
gtgcagctgt tggagtctgg gggagacttg gtacagcctg gggggtccct gagactctcc  120
tgtgcagcct ctggattcac ctttaacagc tatgccatga gctgggtccg ccaggctcca  180
gggaaggggc tggagtgggt ctcagttctc agtggtagtg gtggtgacat acactacgca  240
gactccgtga agggccggtt caccgtctcc agagacaatt ccaagaatat gctgtatctg  300
caaatgaaca gcctgagagc cgaagacacg gccgtttatt tctgtgcgca acagtggcca  360
cagggctact ggggccaggg aaccctggtc accgtctcct cagcctccac caagggccca  420
tcggtcttcc c                                                       431

SEQ ID NO: 4           moltype = DNA  length = 390
FEATURE                Location/Qualifiers
misc_feature           1..390
                       note = Description of Artificial Sequence: Synthetic
                        polynucleotide
source                 1..390
                       mol_type = other DNA
                       organism = synthetic construct
SEQUENCE: 4
atgaggctcc ttgctcagct cctgggactc ctgctgccct ggctcccaga taccagatgt  60
gacatccaga tgacccagtc tccatcctcc ctgtctgcat ctgtaggaga cagagtcacc  120
atcacttgcc gggcgagtca gggcattagc atttatttag cctggtttca gcagaaacca  180
gggaaagttc ctaagctcct gatctatgct gcatccactt tgcaatcagg ggtcccatct  240
cggttcagtg gcagtggatc tgggacagat ttcactctca ccatcagcag cctgcagcct  300
gaagatgttg caacttatta ctgtcaaaag tataacagtg ccccattcac tttcggccct  360
gggaccaagg tggagatcaa acgaactgtg                                   390

SEQ ID NO: 5           moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 5
GFTFNSYAMS                                                         10

SEQ ID NO: 6           moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 6
```

-continued

```
VLSGSGGDIH YADSV                                            15

SEQ ID NO: 7            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 7
AQQWPQGY                                                    8

SEQ ID NO: 8            moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 8
RASQGISIYL A                                                11

SEQ ID NO: 9            moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 9
AASTLQS                                                     7

SEQ ID NO: 10           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 10
QKYNSAPFT                                                   9

SEQ ID NO: 11           moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 11
QVQLVESGGG VVQPGRSLRL SCAASGFTFS SYGMHWVRQA PGKGLEWVAI IWYDGSNKYY  60
ADSVKGRFTI SRDNSKNTLY LQMNSLRAED TAVYYCAKDP SYSSGYYLFD FWGQGTLVTV  120
SS                                                          122

SEQ ID NO: 12           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 12
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPLTFGG GTKVEIK             107

SEQ ID NO: 13           moltype = DNA  length = 452
FEATURE                 Location/Qualifiers
misc_feature            1..452
                        note = Description of Artificial Sequence: Synthetic
                         polynucleotide
source                  1..452
                        mol_type = other DNA
                        organism = synthetic construct
SEQUENCE: 13
atggagttgg gactgagctg ggttttcctc gttgctcttt taagaggtgt ccagtgtcag  60
gtgcagctgg tggagtctgg gggaggcgtg gtccagcctg ggaggtccct gagactctcc  120
tgtgcagcgt ctggattcac cttcagtagc tatggcatgc actgggtccg ccaggctcca  180
```

-continued

```
ggcaaggggc tggagtgggt ggcaattata tggtatgatg gaagtaataa atactatgca  240
gactccgtga agggccgatt caccatctcc agagacaatt ccaagaacac gttgtatctg  300
caaatgaaca gcctgagagc cgaggacacg gccgtttatt actgtgcgaa agatccctcg  360
tacagcagtg gctactacct ctttgacttc tggggtcagg gaaccctggt caccgtctcc  420
tcagcccaaa caacagcccc atctgtctat cc                                452

SEQ ID NO: 14           moltype = DNA  length = 336
FEATURE                 Location/Qualifiers
misc_feature            1..336
                        note = Description of Artificial Sequence: Synthetic
                         polynucleotide
source                  1..336
                        mol_type = other DNA
                        organism = synthetic construct
SEQUENCE: 14
gaaatagtga tgacgcagtc tccagccacc ctgtctgtgt ctccagggga aagagccacc  60
ctctcctgca gggccagtca gagtgttagc agcaacttag cctggtacca gcagaaacct  120
ggccaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ctgtcagcag tataataact ggccgctcac tttcggcgga  300
gggaccaagg tggagatcaa acgggctgat gctgca                            336

SEQ ID NO: 15           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 15
GFTFSSYGMH                                                         10

SEQ ID NO: 16           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 16
IIWYDGSN                                                           8

SEQ ID NO: 17           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 17
AKDPSYSSGY YLFDF                                                   15

SEQ ID NO: 18           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 18
RASQSVSSNL A                                                       11

SEQ ID NO: 19           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 19
GASTRAT                                                            7

SEQ ID NO: 20           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
```

```
SEQUENCE: 20
QQYNNWPLT                                                         9

SEQ ID NO: 21           moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 21
EVQVLESGGG LVQPGGSLRL SCAASGFTFS SYVMSWVRQA PGKGLEWVSG ISGSGGSTHY  60
ADSVKGRFTI SRDNSKNTLY LQMNSLRAED TALYYCAQQW PQGYWGQGTL VTVSS       115

SEQ ID NO: 22           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 22
DIQMTQSPSS LSASVGDRVT ITCRASQDIS IYLAWFQQKP GKVPKVLIYA ASTLQSGVPS  60
RFSGSGTGTD FTLTISSLQP EDVATYFCQK YNSAPFTFGP GTKLEIK                107

SEQ ID NO: 23           moltype = DNA  length = 431
FEATURE                 Location/Qualifiers
misc_feature            1..431
                        note = Description of Artificial Sequence: Synthetic
                         polynucleotide
source                  1..431
                        mol_type = other DNA
                        organism = synthetic construct
SEQUENCE: 23
atggagtttg ggcttagctg gcttttttctt gtggctattt taaaaggtgt ccagtgtgag  60
gtgcaggtgt tggagtctgg gggaggcttg gtacagcctg gggggtccct gagactctcc  120
tgtgcagcct ctggattcac ctttagcagc tatgtcatga gctgggtccg ccaggctcca  180
gggaaggggc tggagtgggt ctcaggtatc agtggtagtg gtggtagcac acactacgca  240
gactccgtga agggccggtt caccatctcc agagacaatt ccaagaacac gctgtatctg  300
caaatgaaca gcctgagagc cgaggacacg gccctttatt actgtgcgca gcagtggcca  360
cagggctact ggggccaggg aaccctggtc accgtctcct cagcctccac caagggccca  420
tcggtcttcc c                                                       431

SEQ ID NO: 24           moltype = DNA  length = 396
FEATURE                 Location/Qualifiers
misc_feature            1..396
                        note = Description of Artificial Sequence: Synthetic
                         polynucleotide
source                  1..396
                        mol_type = other DNA
                        organism = synthetic construct
SEQUENCE: 24
atggacatga gggtcctcgc tcagctcctg ggactcctgc tgctctggct cccagatacc  60
agatgtgaca tccagatgac ccagtctcca tcctccctgt ctgcatctgt aggagacaga  120
gtcaccatca cttgccgggc gagtcaggac attagcattt atttagcctg gtttcagcag  180
aaaccaggga aagttcctaa ggtcctgatc tatgctgcat ccactttgca atcaggggtc  240
ccatctcggt tcagtggcag tggaactggg acagatttca ctctcaccat cagcagcctg  300
cagcctgaag atgttgcgac ttatttctgt caaaagtata acagtgcccc attcactttc  360
ggccctggga ccaagctgga gatcaaacga actgtg                            396

SEQ ID NO: 25           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 25
GFTFSSYVMS                                                        10

SEQ ID NO: 26           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
```

-continued

```
SEQUENCE: 26
GISGSGGSTH YADSV                                                  15

SEQ ID NO: 27           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 27
AQQWPQGY                                                          8

SEQ ID NO: 28           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 28
RASQDISIYL A                                                      11

SEQ ID NO: 29           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 29
AASTLQS                                                           7

SEQ ID NO: 30           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 30
QKYNSAPFT                                                         9

SEQ ID NO: 31           moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 31
QVQLVQSGAE VKKPGSSVKV SCKASGGTFS SYAMSWVRQA PGQGLEWMGG IIPILGTTNY  60
AQKFQGRVTI TADKSTSTAY MELSSLRSED TAVYYCAREG LYAFDIWGQG TMVTVSS     117

SEQ ID NO: 32           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 32
DIQMTQSPSS LSASVGDRVT ITCRASQSIS SYLNWYQQKP GKAPKFLIYV ASSLQSGVPS  60
RFSGRGSGTD FTLTISSLQP EDFATYYCQQ SYSTPWTFGQ GTKVEIK               107

SEQ ID NO: 33           moltype = DNA  length = 408
FEATURE                 Location/Qualifiers
misc_feature            1..408
                        note = Description of Artificial Sequence: Synthetic
                         polynucleotide
source                  1..408
                        mol_type = other DNA
                        organism = synthetic construct
SEQUENCE: 33
atggactgga tttggaggat cctctttgtg gtggcagcag ctacaggtgt ccagtcccag  60
gtgcagctgg tgcagtctgg ggctgaggtg aagaagcctg ggtcctcggt gaaggtctcc  120
tgcaaggctt ctggaggcac cttcagcagt tatgctatga gctgggtgcg acaggcccct  180
```

-continued

```
ggacaagggc ttgagtggat gggagggatc atccctatcc ttggtacaac aaactacgca  240
cagaagttcc agggcagagt cacgattacc gcggacaaat ccacgagcac agcctacatg  300
gagctgagca gcctgagatc tgaggacacg gccgtgtatt actgtgcgag agaggggctc  360
tatgcttttg atatctgggg ccaagggaca atggtcaccg tctcctca              408

SEQ ID NO: 34          moltype = DNA  length = 387
FEATURE                Location/Qualifiers
misc_feature           1..387
                       note = Description of Artificial Sequence: Synthetic
                        polynucleotide
source                 1..387
                       mol_type = other DNA
                       organism = synthetic construct
SEQUENCE: 34
atggacatga gggtgcctgc tcagctcctg gggctcctgc tactctggct ccgaggtgcc  60
agatgtgaca tccagatgac ccagtctcca tcctccctgt ctgcatctgt aggagacaga  120
gtcaccatca cttgccgggc aagtcagagc attagcagct atttaaattg gtatcagcag  180
aaaccaggga aagcccctaa gttcctgatc tatgttgcat ccagtttgca aagtggggtc  240
ccatcaaggt tcagtggcag gggatctggg acagatttca ctctcaccat cagcagtctg  300
caacctgaag attttgcaac ttactactgt caacagagtt acagtacccc gtggacgttc  360
ggccaaggga ccaaggtgga gatcaaa                                     387

SEQ ID NO: 35          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 35
GGTFSSYAMS                                                        10

SEQ ID NO: 36          moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 36
GIIPILGTTN YAQ                                                    13

SEQ ID NO: 37          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 37
AREGLYAFDI                                                        10

SEQ ID NO: 38          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 38
RASQSISSYL N                                                      11

SEQ ID NO: 39          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 39
VASSLQS                                                           7

SEQ ID NO: 40          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
```

-continued

```
SEQUENCE: 40
QQSYSTPWT                                                  9

SEQ ID NO: 41           moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 41
QVQLQQWDAG LLKPSETLSL TCAVYGGSFS SYYWSWIRQP PGKGLEWIGE INHSGSTSYN  60
PSLKSRVTIS IDTSKNQFSL KLNSMTAADT AVYFCAASPY FDYWGQGTLV TVSS        114

SEQ ID NO: 42           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 42
DIQLTQSPSF LSASVGDRVT ITCRASQGIS SYLAWYQQKP GKAPKLLIYA ASTLQSGVPS  60
RFSGSGSGTE FTLTISSLQP EDFATYYCQQ LNSYPRTFGQ GTKVEIK                107

SEQ ID NO: 43           moltype = DNA  length = 399
FEATURE                 Location/Qualifiers
misc_feature            1..399
                        note = Description of Artificial Sequence: Synthetic
                         polynucleotide
source                  1..399
                        mol_type = other DNA
                        organism = synthetic construct
SEQUENCE: 43
atgaagcacc tgtggttctt cctcctcctg gtggcagctc ccagatgggt cctgtcccag  60
gtgcagctac agcagtggga cgcaggactg ttgaagcctt cggagaccct gtccctcacc  120
tgcgctgtct atggtgggtc cttcagtagt tactactgga gctggatccg ccagcccccc  180
gggaaggggc tggagtggat tggggaaatc aatcatagtg gaagcaccag ctacaacccg  240
tccctcaaga gtcgagtcac catatcaata gacacgtcca agaaccagtt ctccctgaag  300
ctgaactcta tgaccgccgc ggacacggct gtgtatttct gtgcggcttc cccatacttt  360
gactactggg gccagggaac cctggtcacc gtctcctca                        399

SEQ ID NO: 44           moltype = DNA  length = 387
FEATURE                 Location/Qualifiers
misc_feature            1..387
                        note = Description of Artificial Sequence: Synthetic
                         polynucleotide
source                  1..387
                        mol_type = other DNA
                        organism = synthetic construct
SEQUENCE: 44
atggacatga gggtgcccgc tcagctcctg gggctcctgc tgctctggct cccaggtgcc  60
agatgtgaca tccagttgac ccagtctcca tccttcctgt ctgcatctgt aggagacaga  120
gtcaccatca cttgccgggc cagtcagggc attagcagtt atttagcctg gtatcagcaa  180
aaaccaggga aagcccctaa gctcctgatc tatgctgcat ccactttgca aagtggggtc  240
ccatcaaggt tcagcggcag tggatctggg acagaattca ctctcacaat cagcagcctg  300
cagcctgaag attttgcaac ttattactgt caacagctta atagttaccc tcggacgttc  360
ggccaaggga ccaaggtgga gatcaaa                                      387

SEQ ID NO: 45           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 45
GGSFSSYYWS                                                 10

SEQ ID NO: 46           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 46
```

```
EINHSGSTSY NPSL                                                 14

SEQ ID NO: 47           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 47
AASPYFDY                                                        8

SEQ ID NO: 48           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 48
RASQGISSYL A                                                    11

SEQ ID NO: 49           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 49
AASTLQS                                                         7

SEQ ID NO: 50           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 50
QQLNSYPRT                                                       9

SEQ ID NO: 51           moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 51
QVQLVESGGG VVQPGRSLRL SCVVSGFTLS SYGMHWVRQA PGKGLEWVAV IWYDGSDKYY  60
ADSVKGRFTI SRDNSKNTLY LQMNSLRAED TAVYYCARDD WGFDYWGQGT LVTVSS      116

SEQ ID NO: 52           moltype = AA  length = 104
FEATURE                 Location/Qualifiers
REGION                  1..104
                        note = Description of Artificial Sequence: Synthetic
                         polypeptide
source                  1..104
                        mol_type = protein
                        organism = synthetic construct
SEQUENCE: 52
DIQLTQSPSF LSASVGDRVT ITCRASQDIS NYLAWYQQKP GKAPKLLISA STLQSGVPSR  60
FSGSGSGTEF ILTISSLQPE DFATYYCQHL NSYPFGQGTK VEIK                  104

SEQ ID NO: 53           moltype = DNA  length = 434
FEATURE                 Location/Qualifiers
misc_feature            1..434
                        note = Description of Artificial Sequence: Synthetic
                         polynucleotide
source                  1..434
                        mol_type = other DNA
                        organism = synthetic construct
SEQUENCE: 53
atggagtttg ggctgagctg ggttttcctc gttgctcttt taagaggtgt ccagtgtcag  60
gtgcagttgg tggagtctgg gggaggcgtg gtccagcctg ggaggtccct gagactctcc  120
tgtgtagtgt ctggattcac cctcagtagc tatggcatgc actgggtccg ccaggctcca  180
ggcaaggggc tggagtgggt ggcagttatt tggtatgatg gaagtgataa atattatgca  240
```

-continued

```
gactccgtga agggccgatt caccatctcc agagacaatt ccaagaacac actatatctg  300
caaatgaaca gcctgagagc cgaggacacg gctgtgtatt actgtgcgag agatgactgg  360
ggctttgact actggggcca gggaaccctg gtcaccgtct cctcagcctc caccaagggc  420
ccatcggtct tccc                                                    434

SEQ ID NO: 54          moltype = DNA  length = 381
FEATURE                Location/Qualifiers
misc_feature           1..381
                       note = Description of Artificial Sequence: Synthetic
                        polynucleotide
source                 1..381
                       mol_type = other DNA
                       organism = synthetic construct
SEQUENCE: 54
atgagggtcc tcgctcagct cctggggctc ctgctgctct ggctcccagg tgctagatgt  60
gacatccagt tgacccagtc tccatccttc ctgtctgcat ctgtaggaga cagagtcacc  120
atcacttgcc gggccagtca ggacattagc aattatttag cctggtatca gcaaaaacca  180
gggaaagccc ctaagctcct gatctctgca tccactttgc aaagtggggt cccctcaagg  240
ttcagcggca gtggatctgg gacagaattc attctcacaa tcagcagcct gcagcctgaa  300
gattttgcaa cttattactg tcaacacctt aatagttatc cttttggcca ggggaccaag  360
gtggagatca aacgaactgt g                                            381

SEQ ID NO: 55          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 55
GFTLSSYGMH                                                         10

SEQ ID NO: 56          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 56
VIWYDGSD                                                           8

SEQ ID NO: 57          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 57
ARDDWGFDY                                                          9

SEQ ID NO: 58          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 58
RASQDISNYL A                                                       11

SEQ ID NO: 59          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 59
SASTLQS                                                            7

SEQ ID NO: 60          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
```

```
SEQUENCE: 60
QHLNSYP                                                     7

SEQ ID NO: 61          moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 61
EVQLVESGGG LVQPGGSLRL SCAASGFTFS RYWMNWVRQA PGKGLEWVAN IKQDGSEKDY  60
VDSVKGRFTI SRDNAKNSLF LQMSSLRAED TAVYYCARVM YSSGWSFDYW GQGTLVTVSS  120

SEQ ID NO: 62          moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 62
DIVMTQSPLS LPVTPGEPAS ISCRSSRSLL HSSGYNFLDW FLQKPGQSPQ LLIFLGSDRA  60
SGVPDRFSGS GSGTDFTLKI SRVETEDVGV YYCMQALQTP ITFGQGTRLE IK          112

SEQ ID NO: 63          moltype = DNA  length = 489
FEATURE                Location/Qualifiers
misc_feature           1..489
                       note = Description of Artificial Sequence: Synthetic
                        polynucleotide
source                 1..489
                       mol_type = other DNA
                       organism = synthetic construct
SEQUENCE: 63
atggagttgg ggctgagctg ggttttcctt gttgctattt tagaaggtgt ccagtgtgag  60
gtgcagctgg tggagtctgg gggaggcttg gtccagcctg gggggtccct gagactctcc  120
tgtgcagcct ctggattcac ctttagtagg tattggatga actgggtccg ccaggctcca  180
gggaaggggc tggagtgggt ggccaacata aagcaagatg gaagtgagaa agactatgtg  240
gactctgtga agggccgatt caccatctcc agagacaacg ccaagaactc actgtttctg  300
caaatgagca gcctgagagc cgaggacacg gctgtgtatt actgtgcgag agtaatgtat  360
agcagtggct ggtcctttga ctactggggc cagggaaccc tggtcaccgt ctcctcagcc  420
tccaccaagg gcccatcggt cttccctctg gcaccctcct ccaagagcac ctctgggggc  480
acagcggcc                                                   489

SEQ ID NO: 64          moltype = DNA  length = 508
FEATURE                Location/Qualifiers
misc_feature           1..508
                       note = Description of Artificial Sequence: Synthetic
                        polynucleotide
source                 1..508
                       mol_type = other DNA
                       organism = synthetic construct
SEQUENCE: 64
atggagactg ggctgcgctg gcttctcctg gtcgctgtgc tcaaaggtgt ccaggggacc  60
atgaggctcc ttgctcagct cctggggctg ctaatgctct gggtctctgg atccagtggg  120
gatattgtga tgactcagtc tccactctcc ctgcccgtca cccctggaga gccggcctcc  180
atctcctgca ggtctagtcg gagcctccta catagtagtg gatacaactt tttggattgg  240
ttcctgcaga agccagggca gtctccacag ctcctgatct tttgggttc  tgatcgggcc  300
tccggggtcc ctgacaggtt cagtggcagt ggatcaggca cagattttac actgaaaatc  360
agcagagtgg agactgagga tgttggagtt tattactgca tgcaagctct acaaactcct  420
atcaccttcg gccaagggac acgactggag attaaacgaa ctgtggctgc accatctgtc  480
ttcatcttcc ctccatctga tgagcagt                              508

SEQ ID NO: 65          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 65
GFTFSRYWMN                                                  10

SEQ ID NO: 66          moltype = AA  length = 8
FEATURE                Location/Qualifiers
REGION                 1..8
                       note = Description of Artificial Sequence: Synthetic peptide
```

```
source                  1..8
                        mol_type = protein
                        organism = synthetic construct
SEQUENCE: 66
NIKQDGSE                                                  8

SEQ ID NO: 67           moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 67
ARVMYSSGWS FDY                                            13

SEQ ID NO: 68           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 68
RSSRSLLHSS GYNFLD                                         16

SEQ ID NO: 69           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 69
LGSDRAS                                                   7

SEQ ID NO: 70           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 70
MQALQTPIT                                                 9

SEQ ID NO: 71           moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 71
EVQLVESGGG LVQPGGSLRL SCAASGFTFS SYWMSWVRQA PGKGLEWVAN IKQDGSEKDY  60
VDSVKGRFTI SRDNAKNSLY LQMNSLRVED TAVYYCAREG GSSGWTFDYW GQGTLVTVSS  120

SEQ ID NO: 72           moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 72
DIVMTQSPLS LPVTPGEPAS ISCRSSQSLL HSSGHNFLDW YLQKPGQSPQ LLIYLGSNRA  60
SGVPDRFSGS GSGTDFTLKI SRVEAEDVGV YYCMQALQTP PTFGQGTKLE IK          112

SEQ ID NO: 73           moltype = DNA  length = 446
FEATURE                 Location/Qualifiers
misc_feature            1..446
                        note = Description of Artificial Sequence: Synthetic
                         polynucleotide
source                  1..446
                        mol_type = other DNA
                        organism = synthetic construct
SEQUENCE: 73
```

```
atggaattgg ggctgtgctg ggttttcctt gttgctattt tagaaggtgt ccagtgtgag  60
gtgcagctgg tggagtctgg gggaggcttg gtccagcctg gggggtccct gagactctcc  120
tgtgcagcct ctggattcac ctttagtagc tattggatga gctgggtccg ccaggctcca  180
gggaaggggc tggagtgggt ggccaacata aagcaagatg gaagtgagaa agactatgtg  240
gactctgtga agggccgatt caccatctcc agagacaacg ccaagaactc actgtatctg  300
caaatgaaca gcctgagagt cgaggacacg gctgtgtatt actgtgcgag agagggggt  360
agcagtggct ggacttttga ctactggggc cagggaaccc tggtcaccgt ctcctcagcc  420
tccaccaagg gcccatcggt cttccc                                      446

SEQ ID NO: 74          moltype = DNA  length = 405
FEATURE                Location/Qualifiers
misc_feature           1..405
                       note = Description of Artificial Sequence: Synthetic
                        polynucleotide
source                 1..405
                       mol_type = other DNA
                       organism = synthetic construct
SEQUENCE: 74
atgaggctcc ctgctcagct cctggggctg ctaatgctct gggtctctgg atccagtggg  60
gatattgtga tgactcagtc tccactctcc ctgcccgtca cccctggaga gccggcctcc  120
atctcctgca ggtctagtca gagcctcctg catagtagtg gacacaactt tttggattgg  180
tacctgcaga agccagggca gtctccacag ctcctgatct atttgggttc taatcgggcc  240
tccggggtcc ctgacaggtt cagtggcagt ggatcaggca cagattttac actgaaaatc  300
agcagagtgg aggctgagga tgttggggtt tattactgca tgcaagctct acaaactcct  360
ccgacgttcg gccaagggac caagctggag atcaaacgaa ctgtg                 405

SEQ ID NO: 75          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 75
GFTFSSYWMS                                                        10

SEQ ID NO: 76          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 76
NIKQDGSE                                                          8

SEQ ID NO: 77          moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 77
AREGGSSGWT FDY                                                    13

SEQ ID NO: 78          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 78
RSSQSLLHSS GHNFLD                                                 16

SEQ ID NO: 79          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 79
LGSNRAS                                                           7

SEQ ID NO: 80          moltype = AA  length = 9
FEATURE                Location/Qualifiers
REGION                 1..9
```

```
                          note = Description of Artificial Sequence: Synthetic peptide
source                    1..9
                          mol_type = protein
                          organism = synthetic construct
SEQUENCE: 80
MQALQTPPT                                                          9

SEQ ID NO: 81             moltype = AA  length = 118
FEATURE                   Location/Qualifiers
REGION                    1..118
                          note = Description of Artificial Sequence: Synthetic
                           polypeptide
source                    1..118
                          mol_type = protein
                          organism = synthetic construct
SEQUENCE: 81
QVQLQESGPG QVKPSETLSL TCTVSGGSIS SSFWSWIRQP PGKGLEWIGY IYYSESTNYN  60
PSLKRRVTLS VDTSKNQFSL KLTSVTTADT AVYYCARNIG VAGLFDYWGQ GTLVTVSS    118

SEQ ID NO: 82             moltype = AA  length = 107
FEATURE                   Location/Qualifiers
REGION                    1..107
                          note = Description of Artificial Sequence: Synthetic
                           polypeptide
source                    1..107
                          mol_type = protein
                          organism = synthetic construct
SEQUENCE: 82
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPLTFGG GTKVEIK                107

SEQ ID NO: 83             moltype = DNA  length = 440
FEATURE                   Location/Qualifiers
misc_feature              1..440
                          note = Description of Artificial Sequence: Synthetic
                           polynucleotide
source                    1..440
                          mol_type = other DNA
                          organism = synthetic construct
SEQUENCE: 83
atgaaacatc tgtggttctt ccttctcctg gtggcagctc ccagatgggt cctgtcccag  60
gtgcagctgc aggagtcggg cccaggacag gtgaagcctt cggagaccct gtccctcacc  120
tgcactgtct ctggtggctc catcagtagt tccttctgga gctggatccg gcagccccca  180
gggaagggac tggagtggat tgggtatatc tattacagtg agagcaccaa ctacaacccc  240
tccctcaaga gacgagtcac cttatcagtg gacacgtcca agaaccagtt ctccctgaag  300
ctgacctctg tgaccactgc ggacacggcc gtgtattact gtgcgagaaa tataggagtg  360
gctggtctct ttgactactg gggccaggga accctggtca ccgtctcctc agcctccacc  420
aagggcccat cggtcttccc                                              440

SEQ ID NO: 84             moltype = DNA  length = 390
FEATURE                   Location/Qualifiers
misc_feature              1..390
                          note = Description of Artificial Sequence: Synthetic
                           polynucleotide
source                    1..390
                          mol_type = other DNA
                          organism = synthetic construct
SEQUENCE: 84
atggaagccc cagctcagct tctcttcctc ctgctactct ggctcccaga taccactgga  60
gaaatagtga tgacgcagtc tccagccacc ctgtctgtgt ctccagggga aagagccacc  120
ctctcctgca gggccagtca gagtgttagc agcaacttag cctggtacca gcagaaacct  180
ggccaggctc ccaggctcct catctatggt gcatccacca gggccactgg tatcccagcc  240
aggttcagtg gcagtgggtc tgggacagag ttcactctca ccatcagcag cctgcagtct  300
gaagattttg cagtttatta ctgtcagcag tataataact ggccgctcac tttcggcgga  360
gggaccaagg tggagatcaa acgaactgtg                                   390

SEQ ID NO: 85             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 85
GGSISSSFWS                                                         10

SEQ ID NO: 86             moltype = AA  length = 14
FEATURE                   Location/Qualifiers
REGION                    1..14
```

-continued

```
                        note = Description of Artificial Sequence: Synthetic peptide
source                  1..14
                        mol_type = protein
                        organism = synthetic construct
SEQUENCE: 86
YIYYSESTNY NPSL                                                     14

SEQ ID NO: 87           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 87
ARNIGVAGLF DY                                                       12

SEQ ID NO: 88           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 88
RASQSVSSNL A                                                        11

SEQ ID NO: 89           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 89
GASTRAT                                                             7

SEQ ID NO: 90           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 90
QQYNNWPLT                                                           9

SEQ ID NO: 91           moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 91
QVQLQESGPG LVKPSETLSL TCTVSGGSIS SYYWSWIRQP PGKGLEWIGY IYYSGSTNYN  60
PSLKSRVTIS VDTSKNQFSL KLSSVTAADT AVYYCARNIG VAGLFDYWGQ GTLVTVSS    118

SEQ ID NO: 92           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 92
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPLTFGG GTKLEIK                107

SEQ ID NO: 93           moltype = DNA  length = 468
FEATURE                 Location/Qualifiers
misc_feature            1..468
                        note = Description of Artificial Sequence: Synthetic
                         polynucleotide
source                  1..468
                        mol_type = other DNA
                        organism = synthetic construct
```

```
SEQUENCE: 93
atgaaacacc tgtggttctt ccttctcctg gtggcagctc ccagatgggt cctgtcccag  60
gtgcagctgc aggagtcggg cccaggactg gtgaagcctt cggagaccct gtccctcacc  120
tgcactgtct ctggtggctc catcagtagt tactactgga gctggatccg gcagccccca  180
gggaagggac tggagtggat tgggtatatc tattacagtg ggagcaccaa ctacaacccc  240
tccctcaaga gtcgagtcac catatcagta gacacgtcca agaaccagtt ctccctgaag  300
ctgagctctg tgaccgctgc ggacacggcc gtgtattact gtgcgagaaa tataggagtg  360
gctggtctct ttgactactg gggccaggga accctggtca ccgtctcctc agcctccacc  420
aagggcccat cggtcttccc tctggcaccc tcctccaaga gcacctct              468

SEQ ID NO: 94          moltype = DNA  length = 416
FEATURE                Location/Qualifiers
misc_feature           1..416
                       note = Description of Artificial Sequence: Synthetic
                        polynucleotide
source                 1..416
                       mol_type = other DNA
                       organism = synthetic construct
SEQUENCE: 94
atggaaaccc cagcgcagct tctcttcctc ctgctactct ggctcccaga taccactgga  60
gaaatagtga tgacgcagtc tccagccacc ctgtctgtgt ctccagggga aagagccacc  120
ctctcctgca gggccagtca gagtgttagc agcaacttag cctggtacca gcagaaacct  180
ggccaggctc ccaggctcct catctatggt gcatccacca gggccactgg tatcccagcc  240
aggttcagtg gcagtgggtc tgggacagag ttcactctca ccatcagcag cctgcagtct  300
gaagattttg cagtttatta ctgtcagcag tataataact ggccgctcac tttcggcgga  360
gggaccaagc tggagatcaa acgaactgtg gctgcaccat ctgtcttcat cttccc      416

SEQ ID NO: 95          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 95
GGSISSYYWS                                                         10

SEQ ID NO: 96          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 96
YIYYSGSTNY NPSL                                                    14

SEQ ID NO: 97          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 97
ARNIGVAGLF DY                                                      12

SEQ ID NO: 98          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 98
RASQSVSSNL A                                                       11

SEQ ID NO: 99          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 99
GASTRAT                                                            7

SEQ ID NO: 100         moltype = AA  length = 9
FEATURE                Location/Qualifiers
```

```
REGION                1..9
                      note = Description of Artificial Sequence: Synthetic peptide
source                1..9
                      mol_type = protein
                      organism = synthetic construct
SEQUENCE: 100
QQYNNWPLT                                                              9

SEQ ID NO: 101        moltype = AA  length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 101
QVQLVESGGG VVQPGRSLRL SCAASGFTFS SYGMHWVRQA PGKGLEWVAV VWYDGTIKYY  60
ADSVKGRFTI SRDNPKNTLY LQMNSLRAED TAVYYCASQY SSGWHTDFFD VWGQGTMVTV  120
SS                                                                 122

SEQ ID NO: 102        moltype = AA  length = 107
FEATURE               Location/Qualifiers
REGION                1..107
                      note = Description of Artificial Sequence: Synthetic
                       polypeptide
source                1..107
                      mol_type = protein
                      organism = synthetic construct
SEQUENCE: 102
DIQMTQSPST LSASVGDRVT ITCRASQSIS TWLAWYQQKP GKAPKFLIYK ASSLESGVPS  60
RFSGSGSGTE FTLTISSLQP DDFATYYCQQ YSGYSLTFGG GTKVEIK                107

SEQ ID NO: 103        moltype = DNA  length = 452
FEATURE               Location/Qualifiers
misc_feature          1..452
                      note = Description of Artificial Sequence: Synthetic
                       polynucleotide
source                1..452
                      mol_type = other DNA
                      organism = synthetic construct
SEQUENCE: 103
atggagtttg ggctgagctg ggttttcctc gttgctcttt taagaggtgt ccagtgtcag  60
gtgcagttgg tggagtctgg gggaggcgtg gtccagcctg ggaggtccct gagactctcc  120
tgtgcagcgt ctggattcac cttcagtagc tatggcatgc actgggtccg tcaggctcca  180
ggcaaggggc tggagtgggt ggcagttgta tggtatgacg gaactataaa atactatgca  240
gactccgtga agggccgatt caccatctcc agagacaatc ccaaaaacac actgtatctc  300
caaatgaata gcctgagagc cgaggacacg gctgtgtatt actgtgcgag ccagtatagc  360
agtggctggc acaccgattt ttttgacgtc tggggccaag ggacaatggt caccgtctcc  420
tcagcctcca ccaagggccc atcggtcttc cc                                452

SEQ ID NO: 104        moltype = DNA  length = 399
FEATURE               Location/Qualifiers
misc_feature          1..399
                      note = Description of Artificial Sequence: Synthetic
                       polynucleotide
source                1..399
                      mol_type = other DNA
                      organism = synthetic construct
SEQUENCE: 104
atggacatga gggtcctcgc tcagctcctg gggctcctgc tgctctggct cccaggtgcc  60
aaatgtgaca tccagatgac ccagtctcct tccaccctgt ctgcatctgt aggagacaga  120
gtcaccatca cttgccgggc cagtcagagt attagtacct ggttggcctg gtatcagcag  180
aaaccaggga aagcccctaa gttcctgatc tataaggcgt ctagtttaga aagtggggtc  240
ccatcaaggt tcagcggcag tggatctggg acagaattca ctctcaccat cagcagcctg  300
cagcctgatg attttgcaac ttattactgc caacagtata gtggttattc gctcactttc  360
ggcggaggga ccaaggtgga gatcaaacga actgtggct                         399

SEQ ID NO: 105        moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 105
GFTFSSYGMH                                                         10

SEQ ID NO: 106        moltype = AA  length = 8
```

-continued

```
FEATURE                Location/Qualifiers
REGION                 1..8
                       note = Description of Artificial Sequence: Synthetic peptide
source                 1..8
                       mol_type = protein
                       organism = synthetic construct
SEQUENCE: 106
VVWYDGTI                                                             8

SEQ ID NO: 107         moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 107
ASQYSSGWHT DFFDV                                                     15

SEQ ID NO: 108         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 108
RASQSISTWL A                                                         11

SEQ ID NO: 109         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 109
KASSLES                                                              7

SEQ ID NO: 110         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 110
QQYSGYSLT                                                            9

SEQ ID NO: 111         moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 111
QVQLVESGGG VVQPGRSLRL SCAASGFTFS SYGMHWVRQA PGKGLEWVAV IWYAGSNKYY  60
ADSVKGRFTI SRDNSKNTLY LQMNSLRAED TAVYYCAGWD FDYWGQGTLV TVSS        114

SEQ ID NO: 112         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 112
EIVLTQSPAT LSLSPGERAT LSCRASQTVP NYLAWYQQKP GQAPRLLIYD ASNRATDIPA  60
RFSGSGSGTD FTLTISSLEP EDFAVYYCQQ RANWPPITFG QGTRLEIK                108

SEQ ID NO: 113         moltype = DNA  length = 471
FEATURE                Location/Qualifiers
misc_feature           1..471
                       note = Description of Artificial Sequence: Synthetic
                        polynucleotide
source                 1..471
```

-continued

```
                        mol_type = other DNA
                        organism = synthetic construct
SEQUENCE: 113
atggagttgg ggctgagctg ggttttcctc gttgctcttt taagaggtgt ccagtgtcag  60
gtgcagctgg tggagtctgg gggaggcgtg gtccagcctg ggaggtccct gagactctcc  120
tgtgcagcgt ctggattcac cttcagtagc tatggcatgc actgggtccg ccaggctcca  180
ggcaaggggc tggagtgggt ggcagttata tggtatgctg gaagtaataa atactatgca  240
gactccgtga agggccgatt caccatctcc agagacaatt ccaagaacac gctgtatctg  300
caaatgaaca gcctgagagc cgaggacacg gctgtgtatt actgtgcggg ttgggacttt  360
gactactggg gccagggaac cctggtcacc gtctcctcag cctccaccaa gggcccatcg  420
gtcttccctc tggcaccctc ctccaagagc acctctgggg gcacagcggc c           471

SEQ ID NO: 114          moltype = DNA  length = 496
FEATURE                 Location/Qualifiers
misc_feature            1..496
                        note = Description of Artificial Sequence: Synthetic
                         polynucleotide
source                  1..496
                        mol_type = other DNA
                        organism = synthetic construct
SEQUENCE: 114
atggagactg ggctgcgctg gcttctcctg gtcgctgtgc tcaaaggtgt ccaggggacc  60
atggaagccc cagctcagct tctcttcctc ctgctactct ggctcccaga taccaccgga  120
gaaattgtgt tgacacagtc tccagccacc ctgtctttgt ctccagggga aagagccacc  180
ctctcctgca gggccagtca gactgttccc aattacttag cctggtacca acagaaacct  240
ggccaggctc ccaggctcct catctatgat gcatcgaata gggccactga catcccagcc  300
agattcagtg gcagtgggtc tgggacagac ttcactctca ccatcagcag cctagagcct  360
gaagattttg cagtttatta ctgtcagcag cgtgccaact ggcctccgat caccttcggc  420
caagggacac gactggagat taaacgaact gtggctgcac catctgtctt catcttccct  480
ccatctgatg agcagt                                                  496

SEQ ID NO: 115          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 115
GFTFSSYGMH                                                         10

SEQ ID NO: 116          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 116
VIWYAGSN                                                           8

SEQ ID NO: 117          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 117
AGWDFDY                                                            7

SEQ ID NO: 118          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 118
RASQTVPNYL A                                                       11

SEQ ID NO: 119          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 119
```

```
DASNRAT                                                          7

SEQ ID NO: 120          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 120
QQRANWPPIT                                                       10

SEQ ID NO: 121          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 121
QVQLQQWGAG LLKPSETLSL TCAVYGGSFS DYYWSWIRQP PGKGLEWIGE INHSGSTNYN  60
PSLKSRVTIS VDTSKNQFSL KLSSVTAADT AVYYCARDYD VLTGHFYYYY GMDVWGQGTT  120
VTVSS                                                            125

SEQ ID NO: 122          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 122
EIVLTQSPAT LSLSPGERAT LSCRASQSVR RYLAWYQQKP GQAPRLLIYD ASNRATGIPA  60
RFSGSGSGTD FTLTISSLEP EDFAVYYCQQ RNNWPLTFGG GTKLEIK                107

SEQ ID NO: 123          moltype = DNA  length = 504
FEATURE                 Location/Qualifiers
misc_feature            1..504
                        note = Description of Artificial Sequence: Synthetic
                         polynucleotide
source                  1..504
                        mol_type = other DNA
                        organism = synthetic construct
SEQUENCE: 123
atgaagcacc tgtggttctt cctcctcctg gtggcagctc ccagatgggt cctgtcccag  60
gtgcagctac agcagtgggg cgcaggactg ttgaagcctt cggagaccct gtccctcacc  120
tgcgctgtct atggtgggtc cttcagtgat tactactgga gctggatccg ccagccccca  180
gggaaggggc tggagtggat tggggaaatc aatcatagtg gaagcaccaa ttacaacccg  240
tccctcaaga gtcgagtcac catatcagta gacacgtcca agaaccagtt ctccctgaag  300
ctgagctctg tgaccgccgc ggacacggct gtgtattact gtgcgaggga ttacgatgtt  360
ttgactggtc atttctacta ctactacggt atggacgtct ggggccaagg gaccacggtc  420
accgtctcct cagcctccac caagggccca tcggtcttcc ctctggcacc ctcctccaag  480
agcacctctg ggggcacagc ggcc                                       504

SEQ ID NO: 124          moltype = DNA  length = 433
FEATURE                 Location/Qualifiers
misc_feature            1..433
                        note = Description of Artificial Sequence: Synthetic
                         polynucleotide
source                  1..433
                        mol_type = other DNA
                        organism = synthetic construct
SEQUENCE: 124
atggaaaccc cagcgcagct tctcttcctc ctgctactct ggctcccaga taccaccgga  60
gaaattgtgt tgacacagtc tccagccacc ctgtctttgt ctccagggga aagagccacc  120
ctctcctgca gggccagtca gagtgttaga agatacttag cctggtacca acagaaacct  180
ggccaggctc ccaggctcct catctatgat gcatccaaca gggccactgg catcccagcc  240
aggttcagtg gcagtgggtc tgggacagac ttcactctca ccatcagcag cctagagcct  300
gaagattttg cagtttatta ctgtcagcag cgtaacaact ggccgctcac tttcggcgga  360
gggaccaagc tggagatcaa acgaactgtg gctgcaccat ctgtcttcat cttccctcca  420
tctgatgagc agt                                                   433

SEQ ID NO: 125          moltype = AA  length = 10
FEATURE                 Location/Qualifiers
REGION                  1..10
                        note = Description of Artificial Sequence: Synthetic peptide
source                  1..10
```

```
                        mol_type = protein
                        organism = synthetic construct
SEQUENCE: 125
GGSFSDYYWS                                                 10

SEQ ID NO: 126          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 126
EINHSGSTNY NPSL                                            14

SEQ ID NO: 127          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 127
ARDYDVLTGH FYYYYGMDV                                       19

SEQ ID NO: 128          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 128
RASQSVRRYL A                                               11

SEQ ID NO: 129          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 129
DASNRAT                                                    7

SEQ ID NO: 130          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 130
QQRNNWPLT                                                  9

SEQ ID NO: 131          moltype = AA  length = 128
FEATURE                 Location/Qualifiers
REGION                  1..128
                        note = Description of Artificial Sequence: Synthetic
                         polypeptide
source                  1..128
                        mol_type = protein
                        organism = synthetic construct
SEQUENCE: 131
QVQLVESGGG VVQPGRSLRL SCAASGFSFS DYGIHWVRQA PGKGLEWVAV IWYDGSNKYY  60
ADSVKGRFTI SRDNSKNTLY LQVNSLIAED TAVYYCARDR GYSSGWYVDY YYYGMDVWGQ  120
GTTVTVSS                                                   128

SEQ ID NO: 132          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 132
DIVMTQSPLS LPVTPGEPAS ISCRSSQSLL HSNGYNYLDW YLQKPGQSPQ ILIYLGSNRA  60
SGVPDRFSGS GSGTDFTLKI SRVEAEDVGV YYCMQALQTP WTFGQGTKLE IK          112
```

```
SEQ ID NO: 133          moltype = DNA  length = 480
FEATURE                 Location/Qualifiers
misc_feature            1..480
                        note = Description of Artificial Sequence: Synthetic
                         polynucleotide
source                  1..480
                        mol_type = other DNA
                        organism = synthetic construct
SEQUENCE: 133
atggaactgg ggctccgctg ggttttcctc gttgctcttt taagaggtgt ccagtgtcag  60
gtgcagttgg tggagtctgg gggaggcgtg gtccagcctg ggaggtccct gagactctcc  120
tgtgcagcgt ctggattctc cttcagtgac tatggcatac actgggtccg ccaggctcca  180
ggcaaggggc tggagtgggt ggcagttata tggtatgatg gaagtaataa atactatgca  240
gactccgtga agggccgatt caccatctcc agagacaatt ccaagaacac gctgtatctg  300
caagtgaaca gcctgatagc cgaggacacg gctgtgtatt actgtgcgag agatcggggg  360
tatagcagtg gctggtacgt agactactac tactacggta tggacgtctg gggccaaggg  420
accacggtca ccgtctcctc agcctccacc aagggcccat cggtcttccc tctggcaccc  480

SEQ ID NO: 134          moltype = DNA  length = 454
FEATURE                 Location/Qualifiers
misc_feature            1..454
                        note = Description of Artificial Sequence: Synthetic
                         polynucleotide
source                  1..454
                        mol_type = other DNA
                        organism = synthetic construct
SEQUENCE: 134
atggacatga gggtgcccgt tcagctcctg gggctgctaa tgctctgggt ctctggatcc  60
agtggggata ttgtgatgac tcagtctcca ctctccctgc ccgtcacccc tggagagccg  120
gcctccatct cctgcaggtc tagtcagagc ctcctgcata gtaatggata caactatttg  180
gattggtacc tgcagaagcc agggcagtct ccacaaatcc tgatctattt gggctctaat  240
cgggcctccg gggtccctga caggttcagt ggcagtggat caggcacaga ttttacactg  300
aaaatcagca gagtggaggc tgaggatgtt ggggtttatt actgcatgca agctctacaa  360
actccgtgga cgttcggcca agggaccaag ctggagatca aacgaactgt ggctgcacca  420
tctgtcttca tcttccctcc atctgatgag cagt                             454

SEQ ID NO: 135          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 135
GFSFSDYGIH                                                        10

SEQ ID NO: 136          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 136
VIWYDGSN                                                          8

SEQ ID NO: 137          moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 137
ARDRGYSSGW YVDYYYYGMD V                                           21

SEQ ID NO: 138          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 138
RSSQSLLHSN GYNYLD                                                 16

SEQ ID NO: 139          moltype = AA  length = 7
FEATURE                 Location/Qualifiers
```

```
REGION                1..7
                      note = Description of Artificial Sequence: Synthetic peptide
source                1..7
                      mol_type = protein
                      organism = synthetic construct
SEQUENCE: 139
LGSNRAS                                                           7

SEQ ID NO: 140        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 140
MQALQTPWT                                                         9

SEQ ID NO: 141        moltype = AA  length = 126
FEATURE               Location/Qualifiers
REGION                1..126
                      note = Description of Artificial Sequence: Synthetic
                       polypeptide
source                1..126
                      mol_type = protein
                      organism = synthetic construct
SEQUENCE: 141
EVQVLESGGG LVQPGGSLRL SCAASGFTFS NYAMNWVRQA PGKGLEWVSA ISGGGGSTYY  60
ADSVKGRATI SRDNSENTLY LQMNSLRAED TAVYYCAKTS SGWYDSYYDY YGLDVWGQGT  120
TVTVSS                                                            126

SEQ ID NO: 142        moltype = AA  length = 107
FEATURE               Location/Qualifiers
REGION                1..107
                      note = Description of Artificial Sequence: Synthetic
                       polypeptide
source                1..107
                      mol_type = protein
                      organism = synthetic construct
SEQUENCE: 142
DIQLTQSPSF LSASVGDRVT ITCRASQGIS NYLAWYQQKP GKVPKLLIYA VSTLQSGVPS  60
RFSGSGSGTE FTLTISSLQP EDFATYYCQQ LNSYPFTFGG GTKLEIK               107

SEQ ID NO: 143        moltype = DNA  length = 492
FEATURE               Location/Qualifiers
misc_feature          1..492
                      note = Description of Artificial Sequence: Synthetic
                       polynucleotide
source                1..492
                      mol_type = other DNA
                      organism = synthetic construct
SEQUENCE: 143
atggagttgg ggctgagctg gctgtttctt gtggctattt taaaaggtgt ccactgtgag  60
gtgcaggtat tggagtctgg gggaggcttg gtacaacctg gggggtccct gagactctcc  120
tgtgcagcct ctggattcac ctttagcaac tatgccatga actgggtccg ccaggctcca  180
gggaaggggc tggaatgggt ctcagctatt agtggtggtg gtggtagcac atattacgca  240
gactccgtga agggccgagc caccatctcc agagacaatt ccgagaacac gctgtatctg  300
caaatgaaca gcctgagagc cgaggacacg gccgtatatt actgtgcgaa aaccagcagt  360
ggctggtacg actcttacta cgactactac ggtttggacg tctggggcca agggaccacg  420
gtcaccgtct cctcagcctc caccaagggc ccatcggtct tccctctggc accctcctcc  480
aagagcacct ct                                                     492

SEQ ID NO: 144        moltype = DNA  length = 422
FEATURE               Location/Qualifiers
misc_feature          1..422
                      note = Description of Artificial Sequence: Synthetic
                       polynucleotide
source                1..422
                      mol_type = other DNA
                      organism = synthetic construct
SEQUENCE: 144
atggacatga gagtcctcgc tcagctcctg gggctcctgc tgctctggct cccaggtgcc  60
agatgtgaca tccagttgac ccagtctcca tccttcctgt ctgcatctgt aggagacaga  120
gtcaccatca cttgccgggc cagtcagggc attagcaatt atttagcctg gtatcagcaa  180
aaaccaggga aagtccctaa gctcctgatc tatgctgtat ccactttgca aagtggggtc  240
ccatcaaggt tcagcggcag tggatctggg acagaattca ctctcacaat cagcagcctg  300
cagcctgaag attttgcaac ttattactgt caacagctta atagttaccc gttcactttc  360
ggcggaggga ccaagctgga gatcaaacga actgtggctg caccatctgt cttcatcttc  420
cc                                                                422
```

```
SEQ ID NO: 145          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 145
GFTFSNYAMN                                                        10

SEQ ID NO: 146          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 146
AISGGGGSTY YADSV                                                  15

SEQ ID NO: 147          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 147
AKTSSGWYDS YYDYYGLDV                                              19

SEQ ID NO: 148          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 148
RASQGISNYL A                                                      11

SEQ ID NO: 149          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 149
AVSTLQS                                                           7

SEQ ID NO: 150          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 150
QQLNSYPFT                                                         9

SEQ ID NO: 151          moltype = AA  length = 126
FEATURE                 Location/Qualifiers
REGION                  1..126
                        note = Description of Artificial Sequence: Synthetic
                         polypeptide
source                  1..126
                        mol_type = protein
                        organism = synthetic construct
SEQUENCE: 151
EVQLLESGGG LVQPGGSLRL SCAASGFTFS NYAMNWVRQA PGKGLEWVSA ISGGGGSTYY  60
ADSVKGRFTI SRDNSKNTLY LQMNSLRAED TAVYYCAKES ITMVRGVMDY YGMDVWGQGT  120
TVTVSS                                                            126

SEQ ID NO: 152          moltype = AA  length = 107
FEATURE                 Location/Qualifiers
REGION                  1..107
                        note = Description of Artificial Sequence: Synthetic
                         polypeptide
```

```
source                  1..107
                        mol_type = protein
                        organism = synthetic construct
SEQUENCE: 152
DIQLTQSPSF LSASVGDRVT ITCRASQGIS SYLAWYQQKP GKAPKLLIYA ASTLQGGVPS  60
RFSGSGSGTE FTLTISSLQP EDFATYYCQH LNRFPRTFGQ GTKVEIK               107

SEQ ID NO: 153          moltype = DNA  length = 492
FEATURE                 Location/Qualifiers
misc_feature            1..492
                        note = Description of Artificial Sequence: Synthetic
                         polynucleotide
source                  1..492
                        mol_type = other DNA
                        organism = synthetic construct
SEQUENCE: 153
atggagtttg gactgagctg gctttttctt gtggctattt taaaaggtgt ccagtgtgag  60
gtgcagctgt tggaatctgg gggaggcttg gtacagcctg gggggtccct gagactctcc  120
tgtgcagcct ctggattcac ctttagcaac tatgccatga actgggtccg ccaggctcca  180
gggaaggggc tggagtgggt ctcagctatt agtggtggtg gtggtagcac atactacgca  240
gactccgtga agggccggtt caccatctcc agagacaatt ccaagaacac actgtatctg  300
cagatgaaca gcctgagagc cgaggacacg gccgtatatt actgtgcgaa agaaagtatt  360
actatggttc ggggagttat ggactactac ggtatggacg tctggggcca agggaccacg  420
gtcaccgtct cctcagcctc caccaagggc ccatcggtct tccctctggc accctcctcc  480
aagagcacct ct                                                      492

SEQ ID NO: 154          moltype = DNA  length = 422
FEATURE                 Location/Qualifiers
misc_feature            1..422
                        note = Description of Artificial Sequence: Synthetic
                         polynucleotide
source                  1..422
                        mol_type = other DNA
                        organism = synthetic construct
SEQUENCE: 154
atggacatga gagtcctcgc tcagctcctg gggctcctgc tgctctggct cccaggtgcc  60
agatgtgaca tccagttgac ccagtctcca tccttcctgt ctgcatctgt aggagacaga  120
gtcaccatca cttgccgggc cagtcagggc attagcagtt atttagcctg gtatcagcaa  180
aaaccaggga aagcccctaa gctcctgatc tatgctgcat ccactttgca aggtggggtc  240
ccatcgaggt tcagcggcag tggatctggg acagaattca ctctcacaat cagcagcctg  300
cagcctgaag attttgcaac ttattactgt caacacctta atcgtttccc tcggacgttc  360
ggccaaggga ccaaggtgga gatcaaacga actgtggctg caccatctgt cttcatcttc  420
cc                                                                 422

SEQ ID NO: 155          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 155
GFTFSNYAMN                                                         10

SEQ ID NO: 156          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 156
AISGGGGSTY YADSV                                                   15

SEQ ID NO: 157          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 157
AKESITMVRG VMDYYGMDV                                               19

SEQ ID NO: 158          moltype = AA  length = 11
FEATURE                 Location/Qualifiers
REGION                  1..11
                        note = Description of Artificial Sequence: Synthetic peptide
source                  1..11
```

```
                        mol_type = protein
                        organism = synthetic construct
SEQUENCE: 158
RASQGISSYL A                                                 11

SEQ ID NO: 159          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 159
AASTLQG                                                      7

SEQ ID NO: 160          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 160
QHLNRFPRT                                                    9

SEQ ID NO: 161          moltype = AA  length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 161
EVQLLESGGG LVQPGGSLRL SCAASGFTFS NYAMSWVRQA PGKGLEWVSA ISGRGGSTYY  60
ADSVKGRFTI SRDNSKNTLY LQMNSLRAED TAVYYCAKDI VVVPAAKGYV MDAWGQGASV  120
TVSS                                                         124

SEQ ID NO: 162          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 162
EIVMTQSPAT LSVSPGERAT LSCRASQSVS SNLAWYQQKP GQAPRLLIYG ASTRATGIPA  60
RFSGSGSGTE FTLTFSSLQS EDFVVYYCQQ YNNWPLTFGQ GTRLEIK              107

SEQ ID NO: 163          moltype = DNA  length = 429
FEATURE                 Location/Qualifiers
misc_feature            1..429
                        note = Description of Artificial Sequence: Synthetic
                         polynucleotide
source                  1..429
                        mol_type = other DNA
                        organism = synthetic construct
SEQUENCE: 163
atggagttgg ggctgagctg gcttttttctt gtggctattt taaaaggtgt ccagtgtgag  60
gtgcaactgt tggagtctgg gggaggcttg gtacagcctg gggggtccct gagactctcc  120
tgtgcagcct ctggattcac ctttagcaac tatgccatga gctgggtccg ccaggctcca  180
gggaaggggc tggagtgggt ctctgctatt agtggtcgtg gtggtagcac atactacgca  240
gactccgtga agggccggtt caccatctcc agagacaatt ccaagaacac gctgtatctg  300
caaatgaaca gcctgagagc cgaggacacg gccgtatatt actgtgcgaa agatattgta  360
gtagtaccag ctgctaaggg ctatgttatg gatgcctggg gtcaaggagc ttcggtcacc  420
gtctcctca                                                    429

SEQ ID NO: 164          moltype = DNA  length = 381
FEATURE                 Location/Qualifiers
misc_feature            1..381
                        note = Description of Artificial Sequence: Synthetic
                         polynucleotide
source                  1..381
                        mol_type = other DNA
                        organism = synthetic construct
SEQUENCE: 164
atggaaaccc cagcgcagct tctcttcctc ctgctactct ggctcccaga taccactgga  60
gaaatagtga tgacgcagtc tccagccacc ctgtctgtgt ctccagggga aagagccacc  120
```

```
ctctcctgca gggccagtca gagtgttagc agcaacttag cctggtacca gcagaaacct  180
ggccaggctc ccaggctcct catctatggt gcttccacca gggccactgg tatcccagcc  240
aggttcagtg gcagtgggtc tgggacagag ttcactctca ccttcagcag cctgcagtct  300
gaagattttg tagtttatta ctgtcagcag tataataact ggcctctcac cttcggccaa  360
gggacacgac tggagattaa a                                            381

SEQ ID NO: 165         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 165
GFTFSNYAMS                                                         10

SEQ ID NO: 166         moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 166
AISGRGGSTY YADSV                                                   15

SEQ ID NO: 167         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 167
AKDIVVVPAA KGYVMDA                                                 17

SEQ ID NO: 168         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 168
RASQSVSSNL A                                                       11

SEQ ID NO: 169         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 169
GASTRAT                                                            7

SEQ ID NO: 170         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 170
QQYNNWPLT                                                          9

SEQ ID NO: 171         moltype = AA  length = 126
FEATURE                Location/Qualifiers
REGION                 1..126
                       note = Description of Artificial Sequence: Synthetic
                        polypeptide
source                 1..126
                       mol_type = protein
                       organism = synthetic construct
SEQUENCE: 171
QEQLVESGGG VVQPGRSLRL SCVTSGFTFS SYGMHWVRQA PGKGLEWVAV IWYDGTNKYY  60
ADTVKGRFTI SRDNSKNTLY LQMNSLRAED TGVYYCAREG CDTISCPYYY YGMDVWGQGT  120
TITVSS                                                             126
```

```
SEQ ID NO: 172         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 172
DILMTQSPSS LSASVGDRVT ITCRASQGIN YYLAWYQQKP GKVPKLLIYT ASTLQSGVPS  60
RFSGSGSGTD FTLTISSLQP EDVATYFCQK YNSAPFTFGP GTKLEIK                107

SEQ ID NO: 173         moltype = DNA  length = 464
FEATURE                Location/Qualifiers
misc_feature           1..464
                       note = Description of Artificial Sequence: Synthetic
                        polynucleotide
source                 1..464
                       mol_type = other DNA
                       organism = synthetic construct
SEQUENCE: 173
atggagttgg ggctgagctg ggttttcctc gttgctcttt taagaggtgt ccagtgtcag  60
gagcagctgg tggagtctgg gggaggcgtg gtccagcctg ggaggtccct gagactctcc  120
tgtgtaacgt ctggattcac cttcagtagc tatggcatgc actgggtccg ccaggctcca  180
ggcaaggggc tggagtgggt ggcagttata tggtatgatg ggactaataa atactatgca  240
gacaccgtga agggccgatt caccatctcc agagacaatt ccaagaacac gctgtatctg  300
caaatgaaca gcctgagagc cgaggacacg ggtgtgtatt attgtgcgag agaggggtgt  360
gatactatca gctgcccta ctattactac ggtatggacg tctggggcca agggaccacg  420
atcaccgtct cctcagcctc caccaagggc ccatcggtct tccc                   464

SEQ ID NO: 174         moltype = DNA  length = 390
FEATURE                Location/Qualifiers
misc_feature           1..390
                       note = Description of Artificial Sequence: Synthetic
                        polynucleotide
source                 1..390
                       mol_type = other DNA
                       organism = synthetic construct
SEQUENCE: 174
atgagggtcc tcgctcagct cctgggactc ctgctgctct ggctcccaga taccagatgt  60
gacatcctga tgacccagtc tccatcctcc ctgtctgcat ctgtaggaga cagagtcacc  120
atcacttgcc gggcgagtca gggcattaac tattatttag cctggtatca gcagaaacca  180
gggaaagttc ctaagctcct gatttatact gcatccactt tgcaatcagg ggtcccatct  240
cgcttcagtg gcagtggatc tgggacagat ttcactctca ccatcagcag cctgcagcct  300
gaagatgttg caacttattt ctgtcaaaag tataacagtg ccccattcac tttcggccct  360
gggaccaagc tggagatcaa acgaactgtg                                   390

SEQ ID NO: 175         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 175
GFTFSSYGMH                                                         10

SEQ ID NO: 176         moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 176
VIWYDGTNKY YADTV                                                   15

SEQ ID NO: 177         moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 177
AREGCDTISC PYYYYGMDV                                               19

SEQ ID NO: 178         moltype = AA  length = 11
FEATURE                Location/Qualifiers
```

-continued

```
REGION                1..11
                      note = Description of Artificial Sequence: Synthetic peptide
source                1..11
                      mol_type = protein
                      organism = synthetic construct
SEQUENCE: 178
RASQGINYYL A                                                    11

SEQ ID NO: 179        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 179
TASTLQS                                                         7

SEQ ID NO: 180        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 180
QKYNSAPFT                                                       9

SEQ ID NO: 181        moltype = AA  length = 121
FEATURE               Location/Qualifiers
REGION                1..121
                      note = Description of Artificial Sequence: Synthetic
                       polypeptide
source                1..121
                      mol_type = protein
                      organism = synthetic construct
SEQUENCE: 181
EVQLLESGGG LVQPGGSLRL SCAASGFTFS SYAMSWVRQA PGKGLEWVSA ISGSGNSAYY  60
ADSVKGRFTI SRDNSKNTLF LQMNSLRADD TAVYYCASSS GWYLVYYFDL WGRGTLVTVS  120
S                                                               121

SEQ ID NO: 182        moltype = AA  length = 107
FEATURE               Location/Qualifiers
REGION                1..107
                      note = Description of Artificial Sequence: Synthetic
                       polypeptide
source                1..107
                      mol_type = protein
                      organism = synthetic construct
SEQUENCE: 182
EIVMTQSPAT LSVSPGERGT LSCRASQSVS SNLAWYQQKP GQAPRLLIYG ASIRATGIPA  60
RFSGSGSGTE FILTINSLQS EDFAVYYCQQ YNNWPLTVGG GTKVEIK             107

SEQ ID NO: 183        moltype = DNA  length = 449
FEATURE               Location/Qualifiers
misc_feature          1..449
                      note = Description of Artificial Sequence: Synthetic
                       polynucleotide
source                1..449
                      mol_type = other DNA
                      organism = synthetic construct
SEQUENCE: 183
atggagttgg ggctgagctg gctttttctt gtggctattt taaaaggtgt ccagtgtgag  60
gtgcagctgt tggagtctgg gggaggcttg gtacagcctg gggggtccct gagactctcc  120
tgtgcagcct ctggattcac ctttagcagc tatgccatga gctgggtccg ccaggctcca  180
gggaaggggc tggagtgggt ctcagctatt agtggtagtg gtaatagcgc atactacgca  240
gactccgtga agggccggtt caccatctcc agagacaatt ccaagaatac gctgtttctc  300
caaatgaaca gcctgagagc cgacgacacg gccgtatatt attgtgcgtc tagcagtggc  360
tggtacctag tctactactt cgatctctgg ggccgtggca ccctggtcac cgtctcctca  420
gcctccacca agggcccatc ggtcttccc                                 449

SEQ ID NO: 184        moltype = DNA  length = 502
FEATURE               Location/Qualifiers
misc_feature          1..502
                      note = Description of Artificial Sequence: Synthetic
                       polynucleotide
source                1..502
                      mol_type = other DNA
                      organism = synthetic construct
```

```
SEQUENCE: 184
atggaagccc cagcacagct tctcttcctc ctgctactct ggctcccaga taccactgga  60
gaaatagtga tgacgcagtc tccagccacc ctgtctgtgt ctccagggga aagaggcacc  120
ctctcctgca gggccagtca gagtgttagt agcaacttag cctggtacca gcagaaacct  180
ggccaggctc ccaggctcct catctatggt gcatccatcc gggccactgg tatcccagcc  240
aggttcagtg gcagtgggtc tgggacagag ttcattctca ccatcaacag cctgcagtct  300
gaagattttg cagtttatta ctgtcaacag tataataact ggccgctcac tgtcggcgga  360
gggaccaagg tggagatcaa acgaactgtg gctgcaccat ctgtcttcat cttccctcca  420
tctgatgagc agttgaaatc tggaactgcc tctgttgtgt gcctgctgaa taacttctat  480
cccagagagg ccaaagtaca gt                                          502

SEQ ID NO: 185         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 185
GFTFSSYAMS                                                        10

SEQ ID NO: 186         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 186
AISGSGNSAY YADSVKG                                                17

SEQ ID NO: 187         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 187
SSGWYLVYYF DL                                                     12

SEQ ID NO: 188         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 188
RASQSVSSNL A                                                      11

SEQ ID NO: 189         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 189
GASIRAT                                                           7

SEQ ID NO: 190         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 190
QQYNNWPLT                                                         9

SEQ ID NO: 191         moltype = AA  length = 115
FEATURE                Location/Qualifiers
REGION                 1..115
                       note = Description of Artificial Sequence: Synthetic
                        polypeptide
source                 1..115
                       mol_type = protein
                       organism = synthetic construct
```

```
SEQUENCE: 191
EVQLLESGGG LVQPGGSLRL SCAASGFTFS SYAMSWVRQA PGKGLEWVSG ISGSGGNTHY  60
ADSVKGRFTI SRDNSKNTLY LQMNSLRAED TALYYCAQQW PQGYWGQGTL VTVSS       115

SEQ ID NO: 192         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 192
DIQMTQSPSS LSASVGDRVT ITCRASQGIS IYLAWFQQKP GKVPKLLIYA ASTLQSGVPS  60
RFSGSGSGTD FTLTISSLQP EDFATYYCQK YNSAPFTFGP GTKLEIK               107

SEQ ID NO: 193         moltype = DNA  length = 431
FEATURE                Location/Qualifiers
misc_feature           1..431
                       note = Description of Artificial Sequence: Synthetic
                        polynucleotide
source                 1..431
                       mol_type = other DNA
                       organism = synthetic construct
SEQUENCE: 193
atggagttgg ggctgagctg gcttttttctt gtggctattt taaaaggtgt ccagtgtgag  60
gtgcagctgt tggagtctgg gggaggcttg gtacagcctg gggggtccct gagactctcc  120
tgtgcagcct ctggattcac ctttagcagc tatgccatga gctgggtccg ccaggctcca  180
gggaaggggc tggagtgggt ctcaggtatc agtggtagtg gtggtaacac acactacgca  240
gactccgtga agggccggtt caccatctcc agagacaatt ccaagaacac gctgtatctg  300
caaatgaaca gcctgagagc cgaggacacg gccctatatt actgtgcgca gcagtggcca  360
cagggctact ggggccaggg aaccctggtc accgtctcct cagcctccac caagggccca  420
tcggtcttcc c                                                       431

SEQ ID NO: 194         moltype = DNA  length = 396
FEATURE                Location/Qualifiers
misc_feature           1..396
                       note = Description of Artificial Sequence: Synthetic
                        polynucleotide
source                 1..396
                       mol_type = other DNA
                       organism = synthetic construct
SEQUENCE: 194
atggacatga gggtcctcgc tcagctcctg ggactcctgc tgctctggct cccagaaacc  60
agatgtgaca tccagatgac ccagtctcca tcctccctgt ctgcatctgt aggagacaga  120
gtcaccatca cttgccgggc gagtcagggc attagcattt atttagcctg gtttcagcag  180
aaaccaggga aagttcctaa gctcctgatc tatgctgcat ccactttgca atcaggggtc  240
ccatctcggt tcagtggcag tggatctggg acagatttca ctctcaccat cagcagcctg  300
cagcctgaag attttgcaac ttattactgt caaaagtata acagtgcccc attcactttc  360
ggccctggga ccaagctgga gatcaaacga actgtg                            396

SEQ ID NO: 195         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 195
GFTFSSYAMS                                                         10

SEQ ID NO: 196         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 196
GISGSGGNTH YADSVKG                                                 17

SEQ ID NO: 197         moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 197
```

```
QWPQGY                                                                    6

SEQ ID NO: 198          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 198
RASQGISIYL A                                                              11

SEQ ID NO: 199          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 199
AASTLQS                                                                   7

SEQ ID NO: 200          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 200
QKYNSAPFT                                                                 9

SEQ ID NO: 201          moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 201
EVQLLESGGG LVQPGGSLGL SCAASGFTFS NYIMSWVRQA PGKGLEWVSG ISGSGGSTHY  60
AGSVKGRFTI SRDNSKNTLN LQMNSLRVED TAVYHCVQQW PQGYWGQGTL VTVSS       115

SEQ ID NO: 202          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 202
DIQMTQSPSS LSASVGDRVT ITCRASQGIT IYLAWFQQKP GKVPKLLIYA ASTLQSGVPS  60
RFSGSGSGTD FTLTISSLQP EDVATYYCQK YNSAPFTFGP GTKLEIK                107

SEQ ID NO: 203          moltype = DNA  length = 431
FEATURE                 Location/Qualifiers
misc_feature            1..431
                        note = Description of Artificial Sequence: Synthetic
                         polynucleotide
source                  1..431
                        mol_type = other DNA
                        organism = synthetic construct
SEQUENCE: 203
atggaactgg ggctccgctg gctttttctt gtggctattt taaaaggtgt ccagtgtgag  60
gtgcagttgt tggagtctgg gggaggcttg gtacagcctg gggggtccct gggactctcc  120
tgtgcagcct ctggattcac cttcagcaac tatatcatga gctgggtccg ccaggctcca  180
gggaaggggc tggagtgggt ctcaggtatc agtggtagtg gtggtagcac acactacgca  240
ggctccgtga agggccggtt caccatctcc agagacaatt ccaagaacac gctgaatctg  300
caaatgaaca gcctgagagt cgaggacacg gccgtctatc actgtgtgca gcagtggcca  360
cagggctact ggggccaggg aaccctggtc accgtctcct cagcctccac caagggccca  420
tcggtcttcc c                                                       431

SEQ ID NO: 204          moltype = DNA  length = 396
FEATURE                 Location/Qualifiers
misc_feature            1..396
                        note = Description of Artificial Sequence: Synthetic
                         polynucleotide
```

```
source                  1..396
                        mol_type = other DNA
                        organism = synthetic construct
SEQUENCE: 204
atggacatga gggtccccgc tcagctcctg ggactcctgc tgctctggct cccagatacc  60
agatgtgaca tccagatgac ccagtctcca tcctccctgt ctgcatctgt aggagacaga  120
gtcaccatca cttgccgggc gagtcagggc attaccattt atttagcctg gtttcagcag  180
aaaccaggga aagttcctaa gctcctgatc tatgctgcat ccactttgca atcaggggtc  240
ccatctcggt tcagtggcag tggatctggg acagatttca ctctcaccat cagcagcctg  300
cagcctgagg atgttgcaac ttattactgt caaaagtata acagtgcccc attcactttc  360
ggccctggga ccaagctgga gatcaaacga actgtg                            396

SEQ ID NO: 205          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 205
GFTFSNYIMS                                                         10

SEQ ID NO: 206          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 206
GISGSGGSTH YAGSVKG                                                 17

SEQ ID NO: 207          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 207
QWPQGY                                                             6

SEQ ID NO: 208          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 208
RASQGITIYL A                                                       11

SEQ ID NO: 209          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 209
AASTLQS                                                            7

SEQ ID NO: 210          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 210
QKYNSAPFT                                                          9

SEQ ID NO: 211          moltype = AA  length = 115
FEATURE                 Location/Qualifiers
REGION                  1..115
                        note = Description of Artificial Sequence: Synthetic
                         polypeptide
source                  1..115
                        mol_type = protein
```

-continued

```
                         organism = synthetic construct
SEQUENCE: 211
EVQLLESGGG LVQPGGSLRL SCAASGFTFS SYAMSWVRLA PGKGLEWVSG LSGSGGDTHY  60
AGSVKGRFTI SRDNSKNTLY LQMNSLRAED TALYYCAQQW PQGYWGQGTL VTVSS       115

SEQ ID NO: 212          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 212
DIQMTQSPSS LSASVGDRVT ITCRASQGIS IYLAWFQQKP GKVPKLLIYA ASTLQSGVPS  60
RFSGSGSGTD FTLTISSLQP EDVATYYCQK YNSAPFTFGP GTKLEIK                107

SEQ ID NO: 213          moltype = DNA  length = 431
FEATURE                 Location/Qualifiers
misc_feature            1..431
                        note = Description of Artificial Sequence: Synthetic
                         polynucleotide
source                  1..431
                        mol_type = other DNA
                        organism = synthetic construct
SEQUENCE: 213
atggagtttg ggctgagctg gctttttctt gtggctattt taaaaggtgt ccaatgtgag  60
gtacaactgt tggagtctgg gggaggcttg gtacagcctg gggggtccct gagactctcc  120
tgtgcagcct ctggattcac ctttagcagc tatgccatga gctgggtccg cctggctcca  180
gggaagggac tggagtgggt ctcaggtctc agtggtagtg gtggtgacac acactacgca  240
ggctccgtga agggccggtt caccatctcc agagacaatt ccaagaacac gctgtatctg  300
caaatgaaca gcctgagagc cgaagacacg gccttatatt actgtgcgca gcagtggcca  360
cagggctact ggggccaggg aaccctggtc accgtctcct cagcctccac caagggccca  420
tcggtcttcc c                                                       431

SEQ ID NO: 214          moltype = DNA  length = 396
FEATURE                 Location/Qualifiers
misc_feature            1..396
                        note = Description of Artificial Sequence: Synthetic
                         polynucleotide
source                  1..396
                        mol_type = other DNA
                        organism = synthetic construct
SEQUENCE: 214
atggacatga gggtcctcgc tcagctcctg ggactcctgc tgctctggct cccagatacc  60
agatgtgaca tccagatgac ccagtctcca tcctccctgt ctgcatctgt aggagacaga  120
gtcaccatca cttgccgggc gagtcagggc attagcattt atttagcctg gtttcagcag  180
aaaccaggga aagttcctaa gctcctgatc tatgctgcat ccactttgca atcaggggtc  240
ccatctcggt tcagtggcag tggatctggg acagatttca ctctcaccat cagcagcctg  300
cagcctgaag atgttgcaac ttattactgt caaaagtata acagtgcccc attcactttc  360
ggccctggga ccaagctgga gatcaaacga actgtg                            396

SEQ ID NO: 215          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 215
GFTFSSYAMS                                                         10

SEQ ID NO: 216          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 216
GLSGSGGDTH YAGSVKG                                                 17

SEQ ID NO: 217          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
```

```
SEQUENCE: 217
QWPQGY                                                      6

SEQ ID NO: 218         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 218
RASQGISIYL A                                                11

SEQ ID NO: 219         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 219
AASTLQS                                                     7

SEQ ID NO: 220         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 220
QKYNSAPFT                                                   9

SEQ ID NO: 221         moltype = AA  length = 115
FEATURE                Location/Qualifiers
REGION                 1..115
                       note = Description of Artificial Sequence: Synthetic
                        polypeptide
source                 1..115
                       mol_type = protein
                       organism = synthetic construct
SEQUENCE: 221
EVQLLESGGG LVQPGESLRL SCAASGFTFS SYAMSWVRQA PGKGLEWVSG ISGSGGSTHY  60
ADSVKGRFTI SRDNSKNTLY LQMNSLRAED TAAYYCAQQW PQGHWGQGIL VTVSS       115

SEQ ID NO: 222         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 222
DIQMTQSPSS LSASVGDRVT ITCRASQDIS IYLAWFQQRP GKVPKLLIYA ASTLQSGVPS  60
RFSGSGSGTD FTLTISSLQP EDVATYYCQK YNSDPFTFGP GTKVEIK              107

SEQ ID NO: 223         moltype = DNA  length = 431
FEATURE                Location/Qualifiers
misc_feature           1..431
                       note = Description of Artificial Sequence: Synthetic
                        polynucleotide
source                 1..431
                       mol_type = other DNA
                       organism = synthetic construct
SEQUENCE: 223
atggagtttg ggctgagctg gctttttctt gtggctattt taaaaggtgt ccagtgtgag  60
gtgcagctgt tggagtctgg gggaggcttg gtacagcctg gggaatccct gagactctcc  120
tgtgcagcct ctggattcac ctttagcagc tatgccatga gctgggtccg ccaggctcca  180
gggaaggggc tggagtgggt ctcaggtatc agtggtagtg gtggtagcac acactacgca  240
gactccgtga agggccggtt caccatctcc agagacaatt ccaagaacac gctgtatctg  300
caaatgaaca gcctgagagc cgaggacacg gccgcatatt actgtgcgca gcagtggcca  360
cagggccact ggggccaggg aatcctggtc accgtctcct cagcctccac caagggccca  420
tcggtcttcc c                                                431

SEQ ID NO: 224         moltype = DNA  length = 399
FEATURE                Location/Qualifiers
misc_feature           1..399
                       note = Description of Artificial Sequence: Synthetic
```

```
                         polynucleotide
source                  1..399
                        mol_type = other DNA
                        organism = synthetic construct
SEQUENCE: 224
atggacatga gggtcctcgc tcagctcctg ggactcctgc tgctctggct cccagatacc  60
agatgtgaca tccagatgac ccagtctcca tcctccctgt ctgcatctgt aggagacaga  120
gtcaccatca cttgccgggc gagtcaggac attagcattt atttagcctg gtttcagcag  180
agaccaggga aagttcctaa gctcctgatc tatgctgcat ccactttgca atcaggggtc  240
ccatctcggt tcagtggcag tggatctggg acagatttca ctctcaccat cagcagcctg  300
cagcctgaag atgttgcaac ttattactgt caaaagtata acagtgaccc attcactttc  360
ggccctggga ccaaggtgga gatcaaacga actgtggct                         399

SEQ ID NO: 225          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 225
GFTFSSYAMS                                                         10

SEQ ID NO: 226          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 226
GISGSGGSTH YADSVKG                                                 17

SEQ ID NO: 227          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 227
QWPQGH                                                             6

SEQ ID NO: 228          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 228
RASQDISIYL A                                                       11

SEQ ID NO: 229          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 229
AASTLQS                                                            7

SEQ ID NO: 230          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 230
QKYNSDPFT                                                          9

SEQ ID NO: 231          moltype = AA  length = 115
FEATURE                 Location/Qualifiers
REGION                  1..115
                        note = Description of Artificial Sequence: Synthetic
                         polypeptide
source                  1..115
```

```
                        mol_type = protein
                        organism = synthetic construct
SEQUENCE: 231
EVQLLESGGG LVQPGGSLRL SCAASGFTFS SYAMSWVRQA PGKGLEWVSV LSGSGDDTHY  60
ADSVKGRFTI SRDNSKNTLY LQMNSLRAED TAVYYCAHQW PQGYWGQGTL VTVSS       115

SEQ ID NO: 232          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 232
DIQMTQSPSS LSASVGDRVT ITCRASQDIS IYLAWFHQKP GKVPKLLIYA ASTLQSGVPS  60
RFSGSGSGTD FTLTISSLQP EDVAAYYCQK YNSAPFTFGP GTKLEIK                107

SEQ ID NO: 233          moltype = DNA  length = 431
FEATURE                 Location/Qualifiers
misc_feature            1..431
                        note = Description of Artificial Sequence: Synthetic
                         polynucleotide
source                  1..431
                        mol_type = other DNA
                        organism = synthetic construct
SEQUENCE: 233
atggaactgg ggctccgctg gctttttctt gtggctattt taaaaggtgt ccagtgtgag  60
gtgcagctgt tggagtctgg gggaggctta gtacagcctg gggggtccct gagactctcc  120
tgtgcagcct ctggattcac ctttagcagc tatgccatga gctgggtccg ccaggctcca  180
gggaaggggc tggagtgggt ctcagttctc agtggtagtg gtgatgacac acactacgca  240
gactccgtga agggccggtt caccatctcc agagacaatt ccaagaacac gctgtatctg  300
caaatgaaca gcctgagagc cgaggacacg gccgtatatt actgtgcgca ccagtggcca  360
cagggctact ggggccaggg aaccctggtc accgtctcct cagcctccac caagggccca  420
tcggtcttcc c                                                       431

SEQ ID NO: 234          moltype = DNA  length = 399
FEATURE                 Location/Qualifiers
misc_feature            1..399
                        note = Description of Artificial Sequence: Synthetic
                         polynucleotide
source                  1..399
                        mol_type = other DNA
                        organism = synthetic construct
SEQUENCE: 234
atggacatga gggtccccgc tcagctcctg ggactcctgc tgctctggct cccagatacc  60
agatgtgaca tccagatgac ccagtctcca tcctccctgt ctgcatctgt aggagacaga  120
gtcaccatca cttgccgggc gagtcaggac attagcattt atttagcctg gtttcaccag  180
aaaccaggga aagttcctaa gctcctgatc tatgctgcat ccactttgca atcaggggtc  240
ccatctcggt tcagtggcag tggatctggg acagatttca ctctcaccat cagcagcctg  300
cagcctgaag atgttgcagc ttattactgt caaaagtata acagtgcccc attcactttc  360
ggccctggga ccaagctgga gatcaaacga actgtggct                         399

SEQ ID NO: 235          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 235
GFTFSSYAMS                                                         10

SEQ ID NO: 236          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 236
VLSGSGDDTH YADSVKG                                                 17

SEQ ID NO: 237          moltype = AA  length = 6
FEATURE                 Location/Qualifiers
REGION                  1..6
                        note = Description of Artificial Sequence: Synthetic peptide
source                  1..6
                        mol_type = protein
```

```
                        organism = synthetic construct
SEQUENCE: 237
QWPQGY                                                                6

SEQ ID NO: 238          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 238
RASQDISIYL A                                                          11

SEQ ID NO: 239          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 239
AASTLQS                                                               7

SEQ ID NO: 240          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 240
QKYNSAPFT                                                             9

SEQ ID NO: 241          moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 241
EVQLLESGGG LVQPGGSLRL SCAASGFTFS SYVMSWVRQT PGKGLEWVSG ISGSGGSTHY  60
TDSVQGRFTI SRDNSKNTLY LQMNSLRAED TAVYYCVQQW PQGYWGQGTL VTVSS       115

SEQ ID NO: 242          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 242
DIQMTQSPSS LSATVGDRVT ITCRASQGIS IYLAWFQQKP GKVPKNLIYA ASTLQSGVPS  60
RFSGSGSGTD FTLTISSLQP EDFATYYCQK YNSAPFTFGP GTKLEIK               107

SEQ ID NO: 243          moltype = DNA  length = 431
FEATURE                 Location/Qualifiers
misc_feature            1..431
                        note = Description of Artificial Sequence: Synthetic
                         polynucleotide
source                  1..431
                        mol_type = other DNA
                        organism = synthetic construct
SEQUENCE: 243
atggagtttg ggctgagctg gctttttctt gtggctattt taaaaggtgt ccagtgtgag  60
gtgcagctgt tggagtctgg gggaggcttg gtacagcctg gggggtccct gagactctcc  120
tgtgcagcct ctggattcac ctttagcagc tatgtcatga gctgggtccg ccagactcca  180
gggaaggggc tggagtgggt ctcaggtatc agtggtagtg gtggtagcac acactacaca  240
gactccgtgc agggccggtt caccatctcc agagacaatt ccaagaacac gctgtatctg  300
caaatgaaca gcctgagagc cgaggacacg gccgtgtatt actgtgtgca gcagtggcca  360
cagggctact ggggccaggg aaccctggtc accgtctcct cagcctccac caagggccca  420
tcggtcttcc c                                                          431

SEQ ID NO: 244          moltype = DNA  length = 399
FEATURE                 Location/Qualifiers
misc_feature            1..399
```

```
                        note = Description of Artificial Sequence: Synthetic
                         polynucleotide
source                  1..399
                        mol_type = other DNA
                        organism = synthetic construct
SEQUENCE: 244
atggacatga gggtcctcgc tcagctcctg ggactcctgc tgctctggct cccagatacc  60
agatgtgaca tccagatgac ccagtctcca tcctccctgt ctgcaactgt aggagacaga  120
gtcaccatca cttgccgggc gagtcagggc attagcattt atttagcctg gtttcagcag  180
aaaccaggga aagttcctaa gaacctgatc tatgctgcat ccactttgca atcaggggtc  240
ccatctcggt tcagtggcag tggatctggg acagatttca ctctcaccat cagcagcctg  300
cagcctgaag attttgcaac ttattactgt caaaagtata acagtgcccc attcactttc  360
ggccctggga ccaagctgga gatcaaacga actgtggct                         399

SEQ ID NO: 245          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 245
GFTFSSYVMS                                                         10

SEQ ID NO: 246          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 246
GISGSGGSTH YTDSVQG                                                 17

SEQ ID NO: 247          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 247
QWPQGY                                                             6

SEQ ID NO: 248          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 248
RASQGISIYL A                                                       11

SEQ ID NO: 249          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 249
AASTLQS                                                            7

SEQ ID NO: 250          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 250
QKYNSAPFT                                                          9

SEQ ID NO: 251          moltype = AA  length = 119
FEATURE                 Location/Qualifiers
REGION                  1..119
                        note = Description of Artificial Sequence: Synthetic
                         polypeptide
```

-continued

```
source                  1..119
                        mol_type = protein
                        organism = synthetic construct
SEQUENCE: 251
EVQVLESGGG LVQPGESLRL SCAASGFTFN TYAMSWVRQA PGKGLEWVSA ISDNGGGTYN  60
ADSVKGRFTI SRDNSKNTLY LQMNSLRAED TAVYYCAKGE QWGAPFDYWG QGTLVTVSS   119

SEQ ID NO: 252          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 252
DIQMTQSPSS LSASVGDRVT ITCRASQGIS IYLAWYHQKP GKVPKLLIYA ASTLQSGVPS  60
RFSGSGSGTD FTLTISSLQP EDVATYYCQK YNSAPWTFGQ GTKLEIK                107

SEQ ID NO: 253          moltype = DNA  length = 414
FEATURE                 Location/Qualifiers
misc_feature            1..414
                        note = Description of Artificial Sequence: Synthetic
                         polynucleotide
source                  1..414
                        mol_type = other DNA
                        organism = synthetic construct
SEQUENCE: 253
atggagtttg ggctgagctg gctttttctt gtggctattt taaaaggtgt ccagtgtgag  60
gtgcaggtgt tggagtctgg gggaggcttg gtacagcctg gggagtccct gagactctcc  120
tgtgcagcct ctggattcac ctttaacacc tatgccatga gctgggtccg ccaggctcca  180
gggaaggggc tggagtgggt ctcagctatt agtgataatg gtggtggcac atacaacgca  240
gactccgtga agggccggtt caccatctcc agagacaatt ccaagaacac gctgtatctc  300
caaatgaaca gcctgagagc cgaggacacg gccgtatatt actgtgcgaa gggggagcag  360
tggggggccc cctttgacta ctggggccag ggaaccctgg tcaccgtctc ctca        414

SEQ ID NO: 254          moltype = DNA  length = 387
FEATURE                 Location/Qualifiers
misc_feature            1..387
                        note = Description of Artificial Sequence: Synthetic
                         polynucleotide
source                  1..387
                        mol_type = other DNA
                        organism = synthetic construct
SEQUENCE: 254
atggacatga gggtgcccgc tcagctcctg ggactcctgc tgctctggct cccagatacc  60
agatgtgaca tccagatgac ccagtctcca tcctccctgt ctgcatctgt aggagacaga  120
gtcaccatca cttgccgggc gagtcagggc attagcattt atttagcctg gtatcaccag  180
aaaccaggga aagttcctaa gctcctgatc tatgctgcat ccactttgca atcaggggtc  240
ccatctcggt tcagtggcag tggatctggg acagatttca ctctcaccat cagcagcctg  300
cagcctgaag atgttgcaac ttattactgt caaaagtata acagtgcccc gtggacgttc  360
ggccaaggga ccaagctgga gatcaaa                                      387

SEQ ID NO: 255          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 255
GFTFNTYAMS                                                         10

SEQ ID NO: 256          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 256
AISDNGGGTY NADSVKG                                                 17

SEQ ID NO: 257          moltype = AA  length = 10
FEATURE                 Location/Qualifiers
REGION                  1..10
                        note = Description of Artificial Sequence: Synthetic peptide
source                  1..10
                        mol_type = protein
```

```
                        organism = synthetic construct
SEQUENCE: 257
GEQWGAPFDY                                                10

SEQ ID NO: 258          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 258
RASQGISIYL A                                              11

SEQ ID NO: 259          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 259
AASTLQS                                                   7

SEQ ID NO: 260          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 260
QKYNSAPWT                                                 9

SEQ ID NO: 261          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 261
EVQLLESGGG LVQPGGSLRL SCAASGFTFS SYAMSWVRQA PGKGLEWVST ISGSGGSTYY  60
ADSVKGRFTI SRDNSKNTLY LQMNSLRAED TAVYYCATLD TAMAADAFAI WGQGTMVTVS  120
S                                                         121

SEQ ID NO: 262          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 262
DIVMTQSPLS LPVTPGEPAS ISCRSSQSLL HSNGYNYLDW YLQKSGQSPQ LLIYLGSNRA  60
SGVPDRFSGS GSGTDFTLKI SRVEAEDVGV YYCMQALLIP LYTFGQGTKL EIK         113

SEQ ID NO: 263          moltype = DNA  length = 420
FEATURE                 Location/Qualifiers
misc_feature            1..420
                        note = Description of Artificial Sequence: Synthetic
                         polynucleotide
source                  1..420
                        mol_type = other DNA
                        organism = synthetic construct
SEQUENCE: 263
atggaactgg ggctccgctg gcttttcttt gtggctattt taaaaggtgt ccagtgtgag  60
gtgcagttgt tggagtctgg gggaggcttg gtacagcctg gggggtccct gagactctcc  120
tgtgcagcct ctggattcac ctttagcagc tatgccatga gctgggtccg ccaggctcca  180
gggaaggggc tggagtgggt ctcaactatt agtggtagtg gtggtagcac atactacgca  240
gactccgtga agggccggtt caccatctcc agagacaatt ccaagaacac gctgtatctg  300
caaatgaaca gcctgagagc cgaggacacg gccgtatatt actgtgcgac cttggataca  360
gctatggccg ctgatgcttt tgctatctgg ggccaaggga caatggtcac cgtctcctca  420

SEQ ID NO: 264          moltype = DNA  length = 405
FEATURE                 Location/Qualifiers
misc_feature            1..405
```

```
                         note = Description of Artificial Sequence: Synthetic
                          polynucleotide
source                   1..405
                         mol_type = other DNA
                         organism = synthetic construct
SEQUENCE: 264
atggacatga gggtccctgc tcagctcctg gggctgctaa tgctctgggt ctctggatcc  60
agtggggata ttgtgatgac tcagtctcca ctctccctgc ccgtcacccc tggagagccg  120
gcctccatct cctgcaggtc tagtcagagc ctcctgcata gtaatggata caactatttg  180
gattggtacc tgcagaagtc agggcagtct ccacagctcc tgatctattt gggttctaat  240
cgggcctccg gggtccctga caggttcagt ggcagtggat caggcacaga ttttacactg  300
aaaatcagca gagtggaggc tgaggatgtt ggggtttatt actgcatgca agctctacta  360
attccgctgt acacttttgg ccaggggacc aagctggaga tcaaa                   405

SEQ ID NO: 265           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 265
GFTFSSYAMS                                                          10

SEQ ID NO: 266           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 266
TISGSGGSTY YADSVKG                                                  17

SEQ ID NO: 267           moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 267
LDTAMAADAF AI                                                       12

SEQ ID NO: 268           moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 268
RSSQSLLHSN GYNYLD                                                   16

SEQ ID NO: 269           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 269
LGSNRAS                                                             7

SEQ ID NO: 270           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 270
MQALLIPLY                                                           9

SEQ ID NO: 271           moltype = AA  length = 120
FEATURE                  Location/Qualifiers
REGION                   1..120
                         note = Description of Artificial Sequence: Synthetic
                          polypeptide
```

-continued

```
source                  1..120
                        mol_type = protein
                        organism = synthetic construct
SEQUENCE: 271
EVQLVESGGG LVQPGGSLRL SCAASGFTFS SYWMSWVRQV PGKGLEWVAN IKQDGSEKYY  60
VDSVKGRFTI SRDNAKNSLY LQMNSLRAED TAVYYCARDW RSSGWTLDYW GQGTLVTVSS  120

SEQ ID NO: 272          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 272
DIVMTQSPLS LPVTPGEPAS ISCRSSQSLL HSSGHNFLDW YLKKPGQSPQ LLIYLGSNRG  60
SGVPDRFSGS GSGTDFTLKI SRVEAEDVGV YYCMQALQTP RTFGQGTKLE IK          112

SEQ ID NO: 273          moltype = DNA  length = 489
FEATURE                 Location/Qualifiers
misc_feature            1..489
                        note = Description of Artificial Sequence: Synthetic
                         polynucleotide
source                  1..489
                        mol_type = other DNA
                        organism = synthetic construct
SEQUENCE: 273
atggagttgg ggctgtgctg ggttttcctt gttgctattt tagaaggtgt ccagtgtgag  60
gtgcagctgg tggagtctgg gggaggcttg gtccagcctg gggggtccct gagactctcc  120
tgtgcagcct ctggattcac ctttagtagc tattggatga gctgggtccg ccaggttcca  180
gggaaggggc tggagtgggt ggccaacata aagcaagatg gaagtgagaa atactatgtg  240
gactctgtga agggccgatt caccatctcc agagacaacg ccaagaactc actgtatctg  300
caaatgaaca gcctgagagc cgaggacacg gctgtttatt actgtgcgag agattggagg  360
agcagtggct ggaccttga ctactggggc cagggaaccc tggtcaccgt ctcctcagcc  420
tccaccaagg gcccatcggt cttccctctg gcaccctcct ccaagagcac ctctgggggc  480
acagcggcc                                                         489

SEQ ID NO: 274          moltype = DNA  length = 448
FEATURE                 Location/Qualifiers
misc_feature            1..448
                        note = Description of Artificial Sequence: Synthetic
                         polynucleotide
source                  1..448
                        mol_type = other DNA
                        organism = synthetic construct
SEQUENCE: 274
atgaggctcc ctgctcagct cctggggctg ctaatgctct gggtctctgg atccagtggg  60
gatattgtga tgactcagtc tccactctcc ctgcccgtca cccctggaga gccggcctcc  120
atctcctgca ggtctagtca gagcctcctg catagtagtg gacacaactt tttggattgg  180
tacctgaaaa agccagggca gtctccacaa ctcctgatct atttgggttc taatcggggc  240
tccggggtcc ctgacaggtt cagtggcagt ggttcaggca cagattttac actgaaaatc  300
agtagagtgg aggctgagga tgttggggtt tattactgca tgcaagctct acaaactcct  360
cggacgttcg gccaagggac caagctggag atcaaacgaa ctgtggctgc accatctgtc  420
ttcatcttcc ctccatctga tgagcagt                                    448

SEQ ID NO: 275          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 275
GFTFSSYWMS                                                        10

SEQ ID NO: 276          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 276
NIKQDGSEKY YVDSVKG                                                17

SEQ ID NO: 277          moltype = AA  length = 11
FEATURE                 Location/Qualifiers
REGION                  1..11
```

```
                         note = Description of Artificial Sequence: Synthetic peptide
source                   1..11
                         mol_type = protein
                         organism = synthetic construct
SEQUENCE: 277
DWRSSGWTLD Y                                                       11

SEQ ID NO: 278           moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 278
RSSQSLLHSS GHNFLD                                                  16

SEQ ID NO: 279           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 279
LGSNRGS                                                            7

SEQ ID NO: 280           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 280
MQALQTPRT                                                          9

SEQ ID NO: 281           moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 281
EVQLVESGGG LVQPGGSLRL SCAASGFTFS SYWMSWVRQA PGKGLEWVAN VKQDGSEKDY  60
VDSVKGRFTI SRDNAKNSLY LQMNSLRAED TAVYYCAREW NSSGWTFDYW GQGTLVTVSS  120

SEQ ID NO: 282           moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 282
DIVMTQSPLS LPVTPGEPAS ISCRSSQSLL HSTGYNFLDW YLQKPGQSPQ LLIFLGSNRA  60
SGVPDRFSGS GSGTDFTLKI SRVEAEDVGI YYCMQALQTP LTFGGGTKVE IK          112

SEQ ID NO: 283           moltype = DNA  length = 474
FEATURE                  Location/Qualifiers
misc_feature             1..474
                         note = Description of Artificial Sequence: Synthetic
                          polynucleotide
source                   1..474
                         mol_type = other DNA
                         organism = synthetic construct
SEQUENCE: 283
atggagtttt ggctgagctg ggttttcctt gttgctattt tagaaggtgt ccagtgtgag  60
gtgcagctgg tggagtctgg gggaggcttg gtccagcctg gggggtccct gagactctcc  120
tgtgcagcct ctggattcac ctttagtagc tattggatga gctgggtccg ccaggctcca  180
gggaaggggc tggagtgggt ggccaatgta aagcaagatg gaagtgagaa agactatgtg  240
gactctgtga agggccgatt caccatctcc agagacaacg ccaagaactc actgtatctg  300
caaatgaaca gcctgagagc cgaggacacg gctgtgtatt actgtgcgag agagtggaat  360
agcagtggct ggacgtttga ctactggggc cagggaaccc tggtcaccgt ctcctcagcc  420
tccaccaagg gcccatcggt cttccctctg gcaccctcct ccaagagcac ctct        474
```

-continued

```
SEQ ID NO: 284         moltype = DNA  length = 437
FEATURE                Location/Qualifiers
misc_feature           1..437
                       note = Description of Artificial Sequence: Synthetic
                        polynucleotide
source                 1..437
                       mol_type = other DNA
                       organism = synthetic construct
SEQUENCE: 284
atggacatga gggtgcccgc tcagctcctg gggctgctaa tgctctgggt ctctggatcc  60
agtggggata ttgtgatgac tcagtctcca ctctccctgc ccgtcacccc tggagagccg  120
gcctccatct cctgcaggtc tagtcagagc ctcctgcata gtactggata caactttttg  180
gattggtacc tgcagaagcc agggcagtct ccacagctcc tgatctttt gggttctaat   240
cgggcctccg gggtccctga caggttcagt ggcagtggat caggcacaga ttttacactg  300
aaaatcagca gagtggaggc tgaggatgtt gggatttatt actgcatgca agctctacaa  360
actccgctca ctttcggcgg agggaccaag gtggagatca aacgaactgt ggctgcacca  420
tctgtcttca tcttccc                                                 437

SEQ ID NO: 285         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 285
GFTFSSYWMS                                                        10

SEQ ID NO: 286         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 286
NVKQDGSEKD YVDSVKG                                                17

SEQ ID NO: 287         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 287
EWNSSGWTFD Y                                                      11

SEQ ID NO: 288         moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 288
RSSQSLLHST GYNFLD                                                 16

SEQ ID NO: 289         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 289
LGSNRAS                                                           7

SEQ ID NO: 290         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 290
MQALQTPLT                                                         9

SEQ ID NO: 291         moltype = AA  length = 128
```

-continued

```
FEATURE                Location/Qualifiers
REGION                 1..128
                       note = Description of Artificial Sequence: Synthetic
                        polypeptide
source                 1..128
                       mol_type = protein
                       organism = synthetic construct
SEQUENCE: 291
QVQLVESGGG VVQPGRSLRL SCAASGFTFS SYGMHWVRQA PGKGLEWVAV IWYDGSNKYY  60
ADSVKGRFTI SRDNSKNTLY LQMNSLRAED TAVYHCARDR VYYDGSGSYY NVGVMDVWGQ  120
GASVTVSS                                                          128

SEQ ID NO: 292         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 292
EIVMTQSPAT LSVSPGERAT LSCRASQSVS NNLAWYQQKP GQAPRLLIYG VSTRATGIPA  60
RFSGSGSGTE FTLIISSLQS EDFAGYYCQQ YNDWPLTFGG GTKLEIK               107

SEQ ID NO: 293         moltype = DNA  length = 470
FEATURE                Location/Qualifiers
misc_feature           1..470
                       note = Description of Artificial Sequence: Synthetic
                        polynucleotide
source                 1..470
                       mol_type = other DNA
                       organism = synthetic construct
SEQUENCE: 293
atggaactgg ggctccgctg ggttttcctc gttgctcttt taagaggtgt ccagtgtcag  60
gtgcagctgg tggagtctgg gggaggcgtg gtccagcctg ggaggtccct gagactctcc  120
tgtgcagcgt ctggattcac cttcagtagc tatggcatgc actgggtccg ccaggctcca  180
ggcaaggggc tggagtgggt ggcagttata tggtatgatg gaagtaataa atattatgca  240
gactccgtga agggccgatt caccatctcc agagacaatt ccaagaacac gctgtatctg  300
caaatgaaca gcctgagagc cgaggacacg gctgtgtatc actgtgcgag agatcgggtg  360
tattacgatg gttcggggag ttattataac gtgggtgtta tggatgtttg gggtcaagga  420
gcttcggtca ccgtctcctc agcctccacc aagggcccat cggtcttccc            470

SEQ ID NO: 294         moltype = DNA  length = 455
FEATURE                Location/Qualifiers
misc_feature           1..455
                       note = Description of Artificial Sequence: Synthetic
                        polynucleotide
source                 1..455
                       mol_type = other DNA
                       organism = synthetic construct
SEQUENCE: 294
atggacatga gggtccctgc tcagctcctc ttcctcctgc tactctggct cccagatacc  60
actggagaaa tagtgatgac gcagtctcca gccaccctgt ctgtgtctcc aggggaaaga  120
gccaccctct cctgcagggc cagtcagagt gttagcaaca acttagcctg gtaccagcag  180
aaacctggcc aggctcccag actcctcatt tatggtgtat ccactagggc cactggtatt  240
ccagccaggt tcagtggcag tgggtctggg acagagttca ctctcatcat cagcagcctg  300
cagtctgaag attttgcagg ttattactgt cagcagtata atgactggcc gctcactttc  360
ggcggaggga ccaagctgga gatcaaacga actgtggctg caccatctgt cttcatcttc  420
cctccatctg atgagcagtt gaaatctgga actgc                            455

SEQ ID NO: 295         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 295
GFTFSSYGMH                                                        10

SEQ ID NO: 296         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 296
VIWYDGSNKY YADSVKG                                                17
```

```
SEQ ID NO: 297          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 297
DRVYYDGSGS YYNVGVMDV                                         19

SEQ ID NO: 298          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 298
RASQSVSNNL A                                                 11

SEQ ID NO: 299          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 299
GVSTRAT                                                      7

SEQ ID NO: 300          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 300
QQYNDWPLT                                                    9

SEQ ID NO: 301          moltype = AA  length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 301
QVQLVESGGG VVQPGGSPRL SCAASGFTFS SYAMHWVRQA PGTGLEWVAL IYYDGSHEYY  60
SDSVKGRFTI SRDNSKNTLY LQMSSLRAED TAVYYCARDG GSGSHYPFDA FDIWGQGTMV  120
TVSS                                                         124

SEQ ID NO: 302          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 302
DIQMTQSPST LSASVGDRVT ITCRASQSIS SWLAWYQQKP GKAPNLLIYK ASSLESGVPS  60
RFSGSGSGTE FTLTISSLQP DDFATYYCQQ YNTYYTFGQG TKVEIK           106

SEQ ID NO: 303          moltype = DNA  length = 458
FEATURE                 Location/Qualifiers
misc_feature            1..458
                        note = Description of Artificial Sequence: Synthetic
                         polynucleotide
source                  1..458
                        mol_type = other DNA
                        organism = synthetic construct
SEQUENCE: 303
atggagttgg ggctgtgctg ggttttcctc gttgctcttt taagaggtgt ccagtgtcag  60
gtgcagttgg tggagtctgg gggaggcgtg gtccagcctg gggggtcccc gagactctcc  120
tgtgcagcgt ctggattcac cttcagtagt tatgccatgc actgggtccg ccaggctcca  180
ggcacggggc tggagtgggt ggcacttatt tactatgatg gaagtcatga atactattca  240
```

-continued

```
gactccgtga agggccgatt caccatctcc agagacaatt ccaagaacac gctgtatctg  300
caaatgagca gcctgagagc cgaggacacg gctgtgtatt actgtgcgag agacggcggt  360
tcggggagtc attacccctt tgatgctttt gatatctggg gccaagggac aatggtcacc  420
gtctcctcag cctccaccaa gggcccatcg gtcttccc                          458

SEQ ID NO: 304         moltype = DNA  length = 396
FEATURE                Location/Qualifiers
misc_feature           1..396
                       note = Description of Artificial Sequence: Synthetic
                        polynucleotide
source                 1..396
                       mol_type = other DNA
                       organism = synthetic construct
SEQUENCE: 304
atggacatga gggtcctcgc tcagctcctg gggctcctgc tgctctggct cccaggtgcc  60
aaatgtgaca tccagatgac ccagtctcct tccaccctgt ctgcatctgt aggagacaga  120
gtcaccatca cttgccgggc cagtcagagt attagtagct ggttggcctg gtatcagcag  180
aaaccaggga aagcccctaa cctcctgatc tataaggcgt ctagtttaga aagtggggtc  240
ccatcaaggt tcagcggcag tggatctggg acagaattca ctctcaccat cagcagcctg  300
cagcctgatg attttgcaac ttattactgc caacaatata atacttatta cacttttggc  360
caggggacca aggtggagat caaacgaact gtggct                            396

SEQ ID NO: 305         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 305
GFTFSSYAMH                                                         10

SEQ ID NO: 306         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 306
LIYYDGSHEY YSDSVKG                                                 17

SEQ ID NO: 307         moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 307
DGGSGSHYPF DAFDI                                                   15

SEQ ID NO: 308         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 308
RASQSISSWL A                                                       11

SEQ ID NO: 309         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 309
KASSLES                                                            7

SEQ ID NO: 310         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
```

```
SEQUENCE: 310
QQYNTYYT                                                            8

SEQ ID NO: 311         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 311
QVQLQESGPG LVKPSETLSL TCTVSGGSIS SYYWSWIRQF SGKGLEWIGY IYYTGRNNYN  60
PSLKSRVTIS VDTSKNQFSL KLSSVTAADS AVYYCAREGG WGPHFDYWGQ GTLVTVSS    118

SEQ ID NO: 312         moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 312
DIVMTQSPLS LPVTPGEPAS ISCRSSQSLL HSSGYNYLDW YLQKPGQSPQ LLIYLGSDRA  60
SGVPDRFRGS GSGTDFTLKI SRVEAEDVGI YYCMQALQIP YTFGQGTKLE IK          112

SEQ ID NO: 313         moltype = DNA  length = 483
FEATURE                Location/Qualifiers
misc_feature           1..483
                       note = Description of Artificial Sequence: Synthetic
                        polynucleotide
source                 1..483
                       mol_type = other DNA
                       organism = synthetic construct
SEQUENCE: 313
atgaaacatc tgtggttctt ccttctcctg gtggcagctc ccagatgggt cctgtcccag  60
gtgcagctgc aggagtcggg cccaggccta gtgaagcctt cggagaccct gtccctcacc  120
tgcactgtct caggtggctc catcagtagt tactactgga gctggatccg gcagttctca  180
gggaagggac tggagtggat tggctatatc tactacactg ggaggaacaa ctacaacccc  240
tccctcaaga gtcgagtcac catatcagta gacacgtcca agaaccagtt ctccctgaag  300
ctgagctctg tgaccgctgc ggactcggcc gtgtattact gtgcgagaga gggagggtgg  360
ggaccccact ttgactactg gggccaggga accctggtca ccgtctcctc agcctccacc  420
aagggcccat cggtcttccc tctggcaccc tcctccaaga gcacctctgg gggcacagcg  480
gcc                                                                 483

SEQ ID NO: 314         moltype = DNA  length = 448
FEATURE                Location/Qualifiers
misc_feature           1..448
                       note = Description of Artificial Sequence: Synthetic
                        polynucleotide
source                 1..448
                       mol_type = other DNA
                       organism = synthetic construct
SEQUENCE: 314
atgaggctcc ttgctcagct cctgaggctg ctaatgctct gggtctctgg atccagtggg  60
gatattgtga tgactcagtc tccactctcc ctgcccgtca cccctggaga gccggcctcc  120
atctcctgta ggtctagtca gagcctcctg catagtagtg gatacaacta tttggattgg  180
tacctgcaga agccagggca gtctccacag cttctgatct atttgggttc tgatcgggcc  240
tccggggtcc ctgacaggtt caggggcagt ggatcaggca cagattttac actgaaaatc  300
agcagagtgg aggctgagga tgttgggatt tattactgca tgcaagctct acaaattccg  360
tacacttttg gccaggggac caagctggag atcaaacgaa ctgtggctgc accatctgtc  420
ttcatcttcc ctccatctga tgagcagt                                      448

SEQ ID NO: 315         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 315
GGSISSYYWS                                                          10

SEQ ID NO: 316         moltype = AA  length = 16
FEATURE                Location/Qualifiers
REGION                 1..16
                       note = Description of Artificial Sequence: Synthetic peptide
source                 1..16
```

```
                        mol_type = protein
                        organism = synthetic construct
SEQUENCE: 316
YIYYTGRNNY NPSLKS                                                    16

SEQ ID NO: 317          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 317
EGGWGPHFDY                                                           10

SEQ ID NO: 318          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 318
RSSQSLLHSS GYNYLD                                                    16

SEQ ID NO: 319          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 319
LGSDRAS                                                              7

SEQ ID NO: 320          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 320
MQALQIPYT                                                            9

SEQ ID NO: 321          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 321
QVQLQQWGAG LLKPSETLSL TCAVYGGSFS DYYWSWIRQP PGKGLEWIGE INHSGSTNYN  60
PSLKSRVTIS VDTSKNQFSL KLSSVTAADT AVYYCARDYD VLTGHFYYYY GMDVWGQGTT  120
VTVSS                                                                125

SEQ ID NO: 322          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 322
DIQMTQSPSS LSASVGDRVT ITCRASQSIS SYLNWFQQKP GKAPKLLIYA ASSLQSGVPS  60
RFSGSGSGTD FTLTISSLQP EDFATYYCQQ SYTMPYTFGQ GTKLEIK                  107

SEQ ID NO: 323          moltype = DNA  length = 489
FEATURE                 Location/Qualifiers
misc_feature            1..489
                        note = Description of Artificial Sequence: Synthetic
                         polynucleotide
source                  1..489
                        mol_type = other DNA
                        organism = synthetic construct
SEQUENCE: 323
```

-continued

```
atgaagcacc tgtggttctt cctcctcctg gtggcagctc ccagatgggt cctgtcccag  60
gtgcagctac agcagtgggg cgcaggactg ttgaagcctt cggagaccct gtccctcacc  120
tgcgctgtct atggtgggtc cttcagtgat tactactgga gctggatccg ccagccccca  180
gggaaggggc tggagtggat tggggaaatc aatcatagtg gaagcaccaa ttacaacccg  240
tccctcaaga gtcgagtcac catatcagta gacacgtcca agaaccagtt ctccctgaag  300
ctgagctctg tgaccgccgc ggacacggct gtgtattact gtgcgaggga ttacgatgtt  360
ttgactggtc atttctacta ctactacggt atggacgtct ggggccaagg gaccacggtc  420
accgtctcct cagcctccac caagggccca tcggtcttcc ctctggcacc ctcctccaag  480
agcacctct                                                         489

SEQ ID NO: 324         moltype = DNA  length = 416
FEATURE                Location/Qualifiers
misc_feature           1..416
                       note = Description of Artificial Sequence: Synthetic
                        polynucleotide
source                 1..416
                       mol_type = other DNA
                       organism = synthetic construct
SEQUENCE: 324
atgaggctcc ctgctcagct cctggggctc ctgctactct ggctccgagg tgccagatgt  60
gacatccaga tgacccagtc tccatcctcc ctgtctgcat ctgtaggaga cagagtcacc  120
atcacttgcc gggcaagtca gagcattagc agctatttaa attggtttca gcagaaacca  180
gggaaagccc ctaagctcct gatctatgct gcatccagtt tgcaaagtgg ggtcccatca  240
aggttcagtg gcagtggatc tgggacagat ttcactctca ccatcagcag tctgcaacct  300
gaagattttg caacttacta ctgtcaacag agttacacta tgccgtacac ttttggccaa  360
gggaccaagc tggagatcaa acgaactgtg gctgcaccat ctgtcttcat cttccc      416

SEQ ID NO: 325         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 325
GGSFSDYYWS                                                        10

SEQ ID NO: 326         moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 326
EINHSGSTNY NPSLKS                                                 16

SEQ ID NO: 327         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 327
DYDVLTGHFY YYYGMDV                                                17

SEQ ID NO: 328         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 328
RASQSISSYL N                                                      11

SEQ ID NO: 329         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 329
AASSLQS                                                           7

SEQ ID NO: 330         moltype = AA  length = 9
FEATURE                Location/Qualifiers
```

-continued

```
REGION                  1..9
                        note = Description of Artificial Sequence: Synthetic peptide
source                  1..9
                        mol_type = protein
                        organism = synthetic construct
SEQUENCE: 330
QQSYTMPYT                                                         9

SEQ ID NO: 331          moltype = AA  length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 331
QVQLVESGGG VVQPGRSLRL SCAASGFTFS SYGMHWVRQA PGKGLEWVAL IWYDGSNKYY  60
ADSVQGRFTI SRDNSKNTLY LQMNSLRAED TAVYYCAVDY DILTGHVLYV MDAWGQGVSV  120
TVSS                                                              124

SEQ ID NO: 332          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 332
EIVLTQSPAT LSLSPGERAT LSCRASQSVT NYLAWFQQKP GQAPRLLIYD AFNRATGIPA  60
RFSGSGSGTD FTLTISSLEP EDFAIYYCQQ RSYWPLTFGG GTKLEIK                107

SEQ ID NO: 333          moltype = DNA  length = 429
FEATURE                 Location/Qualifiers
misc_feature            1..429
                        note = Description of Artificial Sequence: Synthetic
                         polynucleotide
source                  1..429
                        mol_type = other DNA
                        organism = synthetic construct
SEQUENCE: 333
atggaattgg ggctccgctg ggttttcctc gttgctcttt taagaggtgt ccagtgtcag  60
gtgcagctgg tggagtctgg gggaggcgtg gtccagcctg ggaggtccct gagactctcc  120
tgtgcagcgt ctggattcac cttcagtagc tatggcatgc actgggtccg ccaggctcca  180
ggcaaggggc tggagtgggt ggcacttata tggtatgatg gaagtaataa atactatgca  240
gactccgtgc agggccgatt caccatctcc agagacaatt ccaagaacac gctgtatctg  300
caaatgaaca gcctgagagc cgaggacacg gctgtgtatt actgtgcggt tgattacgat  360
attttgactg gtcatgtcct atatgttatg gatgcctggg gtcaaggagt ttcggtcacc  420
gtctcctca                                                         429

SEQ ID NO: 334          moltype = DNA  length = 381
FEATURE                 Location/Qualifiers
misc_feature            1..381
                        note = Description of Artificial Sequence: Synthetic
                         polynucleotide
source                  1..381
                        mol_type = other DNA
                        organism = synthetic construct
SEQUENCE: 334
atggaaaccc cagcgcagct tctcttcctc ctgctactct ggctcccaga taccaccgga  60
gaaattgtgt tgacacagtc tccagccacc ctgtctttgt ctccagggga aagagccacc  120
ctctcctgca gggccagtca gagtgttacc aactacttgg cctggttcca acagaaacct  180
ggccaggctc ccaggctcct catctatgat gcattcaaca gggccactgg catcccagcc  240
aggttcagtg gcagtgggtc tgggacagac ttcactctca ccatcagcag cctagagcct  300
gaagattttg caatttatta ctgtcagcag cgtagctact ggccgctcac tttcggcgga  360
gggaccaagc tggagatcaa a                                           381

SEQ ID NO: 335          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 335
GFTFSSYGMH                                                        10

SEQ ID NO: 336          moltype = AA  length = 17
```

```
FEATURE                Location/Qualifiers
REGION                 1..17
                       note = Description of Artificial Sequence: Synthetic peptide
source                 1..17
                       mol_type = protein
                       organism = synthetic construct
SEQUENCE: 336
LIWYDGSNKY YADSVQG                                                   17

SEQ ID NO: 337         moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 337
DYDILTGHVL YVMDA                                                     15

SEQ ID NO: 338         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 338
RASQSVTNYL A                                                         11

SEQ ID NO: 339         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 339
DAFNRAT                                                              7

SEQ ID NO: 340         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 340
QQRSYWPLT                                                            9

SEQ ID NO: 341         moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 341
QVQLVESGGG VVQPGRSLRL SCAASGFTFS NYGMNWVRQA PGKGLEWVAV IWYDGTIKYY  60
ADSVKGRFTI SRDNSKNTLY LQMISLRAED TAVYYCASEY SSGWYRGAFD IWGQGTMVTV  120
SS                                                                   122

SEQ ID NO: 342         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 342
DIQLTQSPSF LSASVGDRVT ITCRASQGIS SYLAWYQQKP GKAPKLLIYA ASTLQSGVPS  60
RFSGSGSGTE FTLTISSLQP EDFATYYCQQ LNSYPYTFGQ GTKVEIK                  107

SEQ ID NO: 343         moltype = DNA  length = 480
FEATURE                Location/Qualifiers
misc_feature           1..480
                       note = Description of Artificial Sequence: Synthetic
                        polynucleotide
```

```
source                  1..480
                        mol_type = other DNA
                        organism = synthetic construct
SEQUENCE: 343
atggagtttg ggctgagctg ggttttcctc gttgctcttt taagaggtgt ccagtgtcag  60
gtgcagctgg tggagtcggg gggaggcgtg gtccagcctg ggaggtccct gagactctcc  120
tgtgcagcgt ctggattcac cttcagtaac tatggcatga attgggtccg ccaggctcca  180
ggcaaggggc tggagtgggt ggcagttata tggtatgatg gaactattaa atactatgca  240
gactccgtga agggccgatt caccatctcc agagacaatt ccaagaacac gctgtatctg  300
caaatgatca gcctgagagc cgaggacacg gctgtgtatt actgtgcgag cgagtatagc  360
agtggctggt acaggggtgc ttttgatata tggggccaag ggacaatggt caccgtctcc  420
tcagcctcca ccaagggccc atcggtcttc cctctggcac cctcctccaa gagcacctct  480

SEQ ID NO: 344          moltype = DNA  length = 422
FEATURE                 Location/Qualifiers
misc_feature            1..422
                        note = Description of Artificial Sequence: Synthetic
                         polynucleotide
source                  1..422
                        mol_type = other DNA
                        organism = synthetic construct
SEQUENCE: 344
atggacatga gagtcctcgc tcagctcctg gggctcctgc tgctctggct cccaggtgcc  60
agatgtgaca tccagttgac ccagtctcca tccttcctgt ctgcatctgt aggagacaga  120
gtcaccatca cttgccgggc cagtcagggc attagcagtt atttagcctg gtatcagcaa  180
aaaccaggga aagcccctaa gctcctgatc tatgctgcat ccactttgca aagtggggtc  240
ccatcaaggt tcagcggcag tggatctggg acagaattca ctctcacaat cagcagcctg  300
cagcctgaag attttgcaac ttattactgt caacagctta atagttaccc gtacactttt  360
ggccagggga ccaaggtgga gatcaaacga actgtggctg caccatctgt cttcatcttc  420
cc                                                                 422

SEQ ID NO: 345          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 345
GFTFSNYGMN                                                         10

SEQ ID NO: 346          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 346
VIWYDGTIKY YADSVKG                                                 17

SEQ ID NO: 347          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 347
EYSSGWYRGA FDI                                                     13

SEQ ID NO: 348          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 348
RASQGISSYL A                                                       11

SEQ ID NO: 349          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 349
```

```
AASTLQS                                                      7

SEQ ID NO: 350         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 350
QQLNSYPYT                                                    9

SEQ ID NO: 351         moltype = AA  length = 125
FEATURE                Location/Qualifiers
REGION                 1..125
                       note = Description of Artificial Sequence: Synthetic
                        polypeptide
source                 1..125
                       mol_type = protein
                       organism = synthetic construct
SEQUENCE: 351
QVQLVESGGG VVQPGRSLRL SCAASGFTFS SYGMFWVRQT PGKGLEWVAN IWYDGSNKYY  60
TDSVKGRFTI SRDNSKNTLY LQMNSLRAGD TAVYYCARET YYYGSGSYGG GLDVWGQGTT  120
VTVSS                                                        125

SEQ ID NO: 352         moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 352
DIQMTQSPST LSASVGDRVT ITCRASQSIS SWLAWYQQKP GKAPKLLIYK ASSLESGVPS  60
RFSGSGSGTE FTLTISSLQP DDFATYYCQQ YYSYITFGQG TRLEIK           106

SEQ ID NO: 353         moltype = DNA  length = 504
FEATURE                Location/Qualifiers
misc_feature           1..504
                       note = Description of Artificial Sequence: Synthetic
                        polynucleotide
source                 1..504
                       mol_type = other DNA
                       organism = synthetic construct
SEQUENCE: 353
atggaattgg ggctgtgctg ggttttcctc gttgctcttt taagaggtgt ccagtgtcag  60
gtgcagctgg tggagtctgg gggaggcgtg gtccagcctg ggaggtccct gagactctcc  120
tgtgcagcgt ctggattcac cttcagtagt tatggcatgt tctgggtccg ccagactcca  180
ggcaaggggc tggagtgggt ggcaaatata tggtatgatg gaagcaataa atattataca  240
gactccgtga agggccgatt caccatctcc agagacaatt ccaagaacac gctgtatctg  300
caaatgaaca gcctgagagc cggggacacg gctgtatatt actgtgcgag agagacatat  360
tactatggtt cggggagtta tggggggggt ttggacgtct ggggccaagg gaccacggtc  420
accgtctcct cagcctccac caagggccca tcggtcttcc ctctggcacc ctcctccaag  480
agcacctctg ggggcacagc ggcc                                   504

SEQ ID NO: 354         moltype = DNA  length = 436
FEATURE                Location/Qualifiers
misc_feature           1..436
                       note = Description of Artificial Sequence: Synthetic
                        polynucleotide
source                 1..436
                       mol_type = other DNA
                       organism = synthetic construct
SEQUENCE: 354
atggacatga gggtcctcgc tcagctcctg gggctcctgc tgctctggct cccaggtgcc  60
aaatgtgaca tccagatgac ccagtctcct tccaccctgt ctgcttctgt aggagacaga  120
gtcaccatca cttgccgggc cagtcagagt attagtagct ggttggcctg gtatcagcag  180
aaaccaggga aagcccctaa gctcctgatc tataaggcgt ctagtttaga aagtggggtc  240
ccatcaaggt tcagcggcag tggatctggg acagaattca ctctcaccat cagcagcctg  300
cagcctgatg attttgcaac ttattactgc caacagtatt atagttatat caccttcggc  360
caagggacac gactggagat taaacgaact gtggctgcac catctgtctt catcttccct  420
ccatctgatg agcagt                                            436

SEQ ID NO: 355         moltype = AA  length = 10
FEATURE                Location/Qualifiers
REGION                 1..10
                       note = Description of Artificial Sequence: Synthetic peptide
source                 1..10
```

```
                        mol_type = protein
                        organism = synthetic construct
SEQUENCE: 355
GFTFSSYGMF                                                   10

SEQ ID NO: 356          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 356
NIWYDGSNKY YTDSVKG                                           17

SEQ ID NO: 357          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 357
ETYYYGSGSY GGGLDV                                            16

SEQ ID NO: 358          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 358
RASQSISSWL A                                                 11

SEQ ID NO: 359          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 359
KASSLES                                                      7

SEQ ID NO: 360          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 360
QQYYSYIT                                                     8

SEQ ID NO: 361          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 361
QVQLQESGPG LVKPSETLSL TCAVSGYSIS SGYYWGWIRQ PPGKGLEWIG SIYHSGSTYY  60
NPSLKSRVTI SVDTSKNQFS LKLSSVTAAD TAVYYCARDK ITVAAFDIWG QGTMVTVSS   119

SEQ ID NO: 362          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 362
DIQLTQSPSF LSASVGDRVT ITCRASQGIS SYLAWYQQKP GKAPKLLIYA ASTLQSGVPS  60
RFSGSGSGTE FTLTISSLQP EDFATYYCQQ LNSYPYTFGQ GTKLEIK             107
```

-continued

```
SEQ ID NO: 363         moltype = DNA  length = 443
FEATURE                Location/Qualifiers
misc_feature           1..443
                       note = Description of Artificial Sequence: Synthetic
                        polynucleotide
source                 1..443
                       mol_type = other DNA
                       organism = synthetic construct
SEQUENCE: 363
atgaagcatc tgtggttctt cctcctgctg gtggcagctc ccagatgggt cctgccccag  60
gtgcagctgc aggagtcggg cccaggactg gtgaagcctt cggagaccct gtccctcacc  120
tgcgctgtct ctggttactc catcagcagt ggttactact ggggctggat ccggcagccc  180
ccagggaagg ggctggagtg gattgggagt atctatcata gtgggagcac ctactacaac  240
ccgtccctca agagtcgagt caccatatca gtagacacgt ccaagaacca gttctccctg  300
aagctgagct ctgtgaccgc cgcagacacg gccgtgtatt actgtgcgag agataagata  360
acagtggctg cttttgatat ctggggccaa gggacaatgg tcaccgtctc ctcagcctcc  420
accaagggcc catcggtctt ccc                                         443

SEQ ID NO: 364         moltype = DNA  length = 399
FEATURE                Location/Qualifiers
misc_feature           1..399
                       note = Description of Artificial Sequence: Synthetic
                        polynucleotide
source                 1..399
                       mol_type = other DNA
                       organism = synthetic construct
SEQUENCE: 364
atggacatga gggtccccgc tcagctcctg gggctcctgc tgctctggct cccaggtgcc  60
agatgtgaca tccagttgac ccagtctcca tccttcctgt ctgcatctgt aggagacaga  120
gtcaccatca cttgccgggc cagtcagggc attagcagtt atttagcctg gtatcagcaa  180
aaaccaggga aagcccctaa gctcctgatc tatgctgcat ccactttgca aagtggggtc  240
ccatcaaggt tcagcggcag tggatctggg acagaattca ctctcacaat cagcagcctg  300
cagcctgaag attttgcaac ttattactgt caacagctta atagttaccc gtacactttt  360
ggccagggga ccaagctgga gatcaaacga actgtggct                        399

SEQ ID NO: 365         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 365
GYSISSGYYW G                                                      11

SEQ ID NO: 366         moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 366
SIYHSGSTYY NPSLKS                                                 16

SEQ ID NO: 367         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 367
DKITVAAFDI                                                        10

SEQ ID NO: 368         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 368
RASQGISSYL A                                                      11

SEQ ID NO: 369         moltype = AA  length = 7
FEATURE                Location/Qualifiers
REGION                 1..7
                       note = Description of Artificial Sequence: Synthetic peptide
```

-continued

```
source                  1..7
                        mol_type = protein
                        organism = synthetic construct
SEQUENCE: 369
AASTLQS                                                            7

SEQ ID NO: 370          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 370
QQLNSYPYT                                                          9

SEQ ID NO: 371          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 371
QVQLQESGPG LVKPSETLSL TCAVSGYSIS SDYYWGWIRQ PPGKGLEWIG SIYHSGSTYY  60
NTSLKSRVTI SLDTSKNQFS LKLTSVTAAD TAVYYCVREG TVGGHYYYYY GMDVWGQGTT  120
VTVSS                                                              125

SEQ ID NO: 372          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 372
EIVLTQSPAT LSLSPGERAT LSCRASQSVR SYLAWYQQKP GQAPRLLIYD ASKRATGIPA  60
RFSGSGSGTD FTLTISSLEP EDFAVYYCQQ RNSWPTFGGG TKVEIK                 106

SEQ ID NO: 373          moltype = DNA  length = 489
FEATURE                 Location/Qualifiers
misc_feature            1..489
                        note = Description of Artificial Sequence: Synthetic
                         polynucleotide
source                  1..489
                        mol_type = other DNA
                        organism = synthetic construct
SEQUENCE: 373
atgaagcatc tgtggttctt cctcctgctg gtggcagctc ccagatgggt cctgccccag  60
gtgcagctgc aggagtcggg cccaggactg gtgaagcctt cggagaccct gtccctcacc  120
tgcgctgtct ctggttactc catcagcagt gattactact ggggctggat ccggcagccc  180
ccagggaagg ggctggagtg gattgggagt atctatcata gtgggagcac ctactacaat  240
acgtccctca agagtcgagt caccatatca ctggacacgt ccaagaacca gttctccctg  300
aaactgacct ctgtgaccgc cgcagacacg gccgtgtatt attgtgtgag agagggaaca  360
gtgggtggcc attactacta ctactacggt atggacgtct ggggccaagg gaccacggtc  420
accgtctcct cagcctccac caagggccca tcggtcttcc ccctggcacc ctcctccaag  480
agcacctct                                                          489

SEQ ID NO: 374          moltype = DNA  length = 413
FEATURE                 Location/Qualifiers
misc_feature            1..413
                        note = Description of Artificial Sequence: Synthetic
                         polynucleotide
source                  1..413
                        mol_type = other DNA
                        organism = synthetic construct
SEQUENCE: 374
atggaaaccc cagcgcagct tctcttcctc ctgctactct ggctcccaga taccaccgga  60
gaaattgtgt tgacacagtc tccagccacc ctgtctttgt ctccagggga aagagccacc  120
ctctcctgca gggccagtca gagtgttaga agctacttag cctggtacca acagaaacct  180
ggccaggctc ccaggctcct catctatgat gcatccaaga gggccactgg catcccagcc  240
aggttcagtg gcagtgggtc tgggacagac ttcactctca ccatcagcag cctagagcct  300
gaagattttg cagtttatta ctgtcagcaa cgtaacagct ggcccacttt cggcggaggg  360
accaaggtgg agatcaaacg aactgtggct gcaccatctg tcttcatctt ccc         413

SEQ ID NO: 375          moltype = AA  length = 11
FEATURE                 Location/Qualifiers
```

```
REGION                  1..11
                        note = Description of Artificial Sequence: Synthetic peptide
source                  1..11
                        mol_type = protein
                        organism = synthetic construct
SEQUENCE: 375
GYSISSDYYW G                                                  11

SEQ ID NO: 376          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 376
SIYHSGSTYY NTSLKS                                             16

SEQ ID NO: 377          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 377
EGTVGGHYYY YYGMDV                                             16

SEQ ID NO: 378          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 378
RASQSVRSYL A                                                  11

SEQ ID NO: 379          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 379
DASKRAT                                                       7

SEQ ID NO: 380          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 380
QQRNSWPT                                                      8

SEQ ID NO: 381          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 381
EVHLLESGGG LVQPGGSLRL SCAASGFTFS SYAMSWVRQA PGKGLEWVSG IDSGGDTYYA  60
DSVKGRFTIS RDNSKNTLYL QMTSLRAEDT AVYYCAKDLY SSGWLAFDIW GQGTMVTVSS  120

SEQ ID NO: 382          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 382
```

```
DIQLTQSPSF LSASVGDRVT ITCRASQGIS SYLAWYQQKP GKAPKLLIYA ASTLQSGVPS  60
RFSGSGSGTE FTLTISSLQP EDFAIYYCQQ LNSYPLYTFG QGTKLEIK               108

SEQ ID NO: 383          moltype = DNA  length = 446
FEATURE                 Location/Qualifiers
misc_feature            1..446
                        note = Description of Artificial Sequence: Synthetic
                         polynucleotide
source                  1..446
                        mol_type = other DNA
                        organism = synthetic construct
SEQUENCE: 383
atggagtttg ggctgagctg gcttttttctt gtggctattt taaaaggtgt ccagtgtgag  60
gtgcacctgt tggagtctgg gggaggcttg gtacagcctg gggggtccct gagactctcc  120
tgtgcagcct ctggattcac ctttagcagc tatgccatga gttgggtccg ccaggctcca  180
gggaaggggc tggagtgggt ctcaggtatt gatagtggtg gtgacacata ctacgcagac  240
tccgtgaagg gccggttcac catctccaga gacaattcca agaacactct gtatctgcaa  300
atgaccagcc tgagagccga ggacacggcc gtatattact gtgcgaaaga tctatatagc  360
agtggctggt tggcttttga tatctggggc caagggacaa tggtcaccgt ctcctcagcc  420
tccaccaagg gcccatcggt cttccc                                       446

SEQ ID NO: 384          moltype = DNA  length = 399
FEATURE                 Location/Qualifiers
misc_feature            1..399
                        note = Description of Artificial Sequence: Synthetic
                         polynucleotide
source                  1..399
                        mol_type = other DNA
                        organism = synthetic construct
SEQUENCE: 384
atggacatga gggtcctcgc tcagctcctg gggctcctgc tgctctggct cccaggtgcc  60
agatgtgaca tccagttgac ccagtctcca tccttcctgt ctgcatctgt aggagacaga  120
gtcaccatca cttgccgggc cagtcagggc attagcagtt atttagcctg gtatcagcaa  180
aaaccaggga aagcccctaa gctcctgatc tatgctgcat ccactttgca aagtggggtc  240
ccatcaaggt tcagcggcag tggatctggg acagaattca ctctcacaat cagcagcctg  300
cagcctgaag attttgcaat ttattactgt caacagctta atagttatcc gctgtacact  360
tttggccagg ggaccaagct ggagatcaaa cgaactgtg                         399

SEQ ID NO: 385          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 385
GFTFSSYAMS                                                         10

SEQ ID NO: 386          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 386
GIDSGGDTYY ADSVKG                                                  16

SEQ ID NO: 387          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 387
DLYSSGWLAF DI                                                      12

SEQ ID NO: 388          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 388
RASQGISSYL A                                                       11

SEQ ID NO: 389          moltype = AA  length = 7
```

```
FEATURE               Location/Qualifiers
REGION                1..7
                      note = Description of Artificial Sequence: Synthetic peptide
source                1..7
                      mol_type = protein
                      organism = synthetic construct
SEQUENCE: 389
AASTLQS                                                               7

SEQ ID NO: 390        moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 390
QQLNSYPLYT                                                            10

SEQ ID NO: 391        moltype = AA  length = 120
FEATURE               Location/Qualifiers
REGION                1..120
                      note = Description of Artificial Sequence: Synthetic
                       polypeptide
source                1..120
                      mol_type = protein
                      organism = synthetic construct
SEQUENCE: 391
EVQLLESGGG SVQPGGSLRL SCAASGFTFS SYAMSWVRQA PGKGLEWVSG ISDNGNTYYA  60
DSVKGRFTIS RDNSKNTLYL QMNSLRAEDT AVYHCAKDLY SSGWLAFDIW GQGTMVTVSS  120

SEQ ID NO: 392        moltype = AA  length = 108
FEATURE               Location/Qualifiers
REGION                1..108
                      note = Description of Artificial Sequence: Synthetic
                       polypeptide
source                1..108
                      mol_type = protein
                      organism = synthetic construct
SEQUENCE: 392
DIQLTQSPSF LSASVGDRVT ITCRASQGIS TYLAWYQQKP GKAPKLLIYA ASTLQSGVPS  60
RFSGSGSGTE FTLTISSLQP EDFATYYCQQ LNSYPLYTFG QGTKVEIK              108

SEQ ID NO: 393        moltype = DNA  length = 446
FEATURE               Location/Qualifiers
misc_feature          1..446
                      note = Description of Artificial Sequence: Synthetic
                       polynucleotide
source                1..446
                      mol_type = other DNA
                      organism = synthetic construct
SEQUENCE: 393
atggagttgg ggctgtgctg gcttttctt gtggctattt taaaaggtgt ccagtgtgag  60
gtgcagttgt tggagtctgg gggaggctcg gtacagcctg gggggtccct gagactctcc  120
tgtgcagcct ctggattcac ctttagcagc tatgccatga gctgggtccg ccaggctcca  180
gggaagggc tggagtgggt ctcaggtatt agtgataatg gtaacacata ctacgcagac  240
tccgtgaagg gccggttcac catctccaga gacaattcca agaatacgct gtatctgcaa  300
atgaacagcc tgagagccga ggacacggcc gtatatcact gtgcgaaaga tctgtatagc  360
agtggctggt tggcttttga tatctggggc caagggacaa tggtcaccgt ctcctcagcc  420
tccaccaagg gcccatcggt cttccc                                      446

SEQ ID NO: 394        moltype = DNA  length = 399
FEATURE               Location/Qualifiers
misc_feature          1..399
                      note = Description of Artificial Sequence: Synthetic
                       polynucleotide
source                1..399
                      mol_type = other DNA
                      organism = synthetic construct
SEQUENCE: 394
atggacatga gggtcctcgc tcagctcctg gggctcctgc tgctctggct cccaggtgcc  60
agatgtgaca tccagttgac ccagtctcca tccttcctgt ctgcatctgt aggagacaga  120
gtcaccatca cttgccgggc cagtcagggc attagcactt atttagcctg gtatcagcaa  180
aaaccaggga aagcccctaa gctcctgatc tatgctgcat ccactttgca aagtggggtc  240
ccatcaaggt tcagcggcag tggatctggg acagaattca ctctcacaat cagcagcctg  300
cagcctgaag attttgcaac ttattactgt caacagctta atagttaccc tctgtacact  360
tttggccagg ggaccaaggt ggagatcaaa cgaactgtg                        399

SEQ ID NO: 395        moltype = AA  length = 10
```

-continued

```
FEATURE                Location/Qualifiers
REGION                 1..10
                       note = Description of Artificial Sequence: Synthetic peptide
source                 1..10
                       mol_type = protein
                       organism = synthetic construct
SEQUENCE: 395
GFTFSSYAMS                                                  10

SEQ ID NO: 396         moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 396
GISDNGNTYY ADSVKG                                           16

SEQ ID NO: 397         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 397
DLYSSGWLAF DI                                               12

SEQ ID NO: 398         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 398
RASQGISTYL A                                                11

SEQ ID NO: 399         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 399
AASTLQS                                                     7

SEQ ID NO: 400         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 400
QQLNSYPLYT                                                  10

SEQ ID NO: 401         moltype = AA  length = 6
FEATURE                Location/Qualifiers
REGION                 1..6
                       note = Description of Artificial Sequence: Synthetic 6xHis
                        tag
source                 1..6
                       mol_type = protein
                       organism = synthetic construct
SEQUENCE: 401
HHHHHH                                                      6

SEQ ID NO: 402         moltype = DNA  length = 348
FEATURE                Location/Qualifiers
misc_feature           1..348
                       note = Description of Artificial Sequence: Synthetic
                        polynucleotide
source                 1..348
                       mol_type = other DNA
                       organism = synthetic construct
SEQUENCE: 402
```

-continued

```
caggagcagc tggaggagtc cgggggagac ctggtcaagc ctggggcatc cctgacactc  60
acctgcaagt cctctggaat cgacttcagc agtgcctatt acatgtgctg ggtccgccag  120
gctcccggga aggggctgga gtggatcgca tgcatttata ctggtagcac ttactacgcg  180
aactgggcga aaggccgatt caccatctcc aaaacctcgt cgaccacggt gactctgcaa  240
atgaccagtc tgacagccgc ggacacggcc acttattttt gtgccagaga tcctattggt  300
tatatgtttg acttgtgggg cccaggcacc ctactcaccg tctcctca               348

SEQ ID NO: 403         moltype = AA  length = 116
FEATURE                Location/Qualifiers
REGION                 1..116
                       note = Description of Artificial Sequence: Synthetic
                        polypeptide
source                 1..116
                       mol_type = protein
                       organism = synthetic construct
SEQUENCE: 403
QEQLEESGGD LVKPGASLTL TCKSSGIDFS SAYYMCWVRQ APGKGLEWIA CIYTGSTYYA  60
NWAKGRFTIS KTSSTTVTLQ MTSLTAADTA TYFCARDPIG YMFDLWGPGT LLTVSS      116

SEQ ID NO: 404         moltype = DNA  length = 322
FEATURE                Location/Qualifiers
misc_feature           1..322
                       note = Description of Artificial Sequence: Synthetic
                        polynucleotide
source                 1..322
                       mol_type = other DNA
                       organism = synthetic construct
SEQUENCE: 404
gcattcgagt tgacccagac tccagcctcc gtggaggcag atgtgggagg cacagtcacc  60
atcaagtgcc aggccagtca gaacatttac agcaatttag cctggtatca acagaaacca  120
gggcagcctc ccaagctcct gatctatggt gcatccactc tggcatctgg ggtctcatcg  180
cggttcagag gcagtggatc tgggacagag ttcactctca ccatcagcga cctggagtgt  240
gccgatgctg ccacttacta ctgtcagggc ggtgatgatg atagttatgc tttcggcgga  300
gggaccgagg tggtggtcaa ag                                           322

SEQ ID NO: 405         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 405
AFELTQTPAS VEADVGGTVT IKCQASQNIY SNLAWYQQKP GQPPKLLIYG ASTLASGVSS  60
RFRGSGSGTE FTLTISDLEC ADAATYYCQG GDDDSYAFGG GTEVVVK                107

SEQ ID NO: 406         moltype = AA  length = 8
FEATURE                Location/Qualifiers
REGION                 1..8
                       note = Description of Artificial Sequence: Synthetic 8xHis
                        tag
source                 1..8
                       mol_type = protein
                       organism = synthetic construct
SEQUENCE: 406
HHHHHHHH                                                           8
```

The invention claimed is:

1. An antibody or antigen-binding fragment thereof that binds to CUB domain-containing protein 1 (CDCP1), wherein the antibody or antigen-binding fragment thereof comprises a heavy chain variable region comprising HCDR1, HCDR2, and HCDR3, and a light chain variable region comprising LCDR1, LCDR2, and LCDR3, wherein HCDR1, HCDR2, and HCDR3 comprise the amino acid sequences set forth in SEQ ID NOs: 85, 86, and 87 respectively, and LCDR1, LCDR2, and LCDR3 comprise the amino acid sequences set forth in SEQ ID NOs: 88, 89, and 90, respectively;

HCDR1, HCDR2, and HCDR3 comprise the amino acid sequences set forth in SEQ ID NOs: 125, 126, and 127 respectively, and LCDR1, LCDR2, and LCDR3 comprise the amino acid sequences set forth in SEQ ID NOs: 128, 129, and 130, respectively; or HCDR1, HCDR2, and HCDR3 comprise the amino acid sequences set forth in SEQ ID NOs: 35, 36, and 37 respectively, and LCDR1, LCDR2, and LCDR3 comprise the amino acid sequences set forth in SEQ ID NOs: 38, 39, and 40, respectively.

2. The antibody or antigen-binding fragment thereof of claim 1, wherein the antibody or antigen-binding fragment thereof comprises a heavy chain variable region (VH) and a light chain variable region (VL), wherein the VH comprises an amino acid sequence that is at least 90% identical to SEQ ID NO: 81, wherein the VH comprises HCDR1, HCDR2, and HCDR3 comprising the amino acid sequences set forth in SEQ ID NOs: 85, 86, and 87, respectively, and the VL sequence comprises an amino acid sequence that is at least 90% identical to SEQ ID NO: 82, wherein the VL comprises LCDR1, LCDR2, and LCDR3 comprising the amino acid sequences set forth in SEQ ID NOs: 88, 89, and 90, respectively;

the VH comprises an amino acid sequence that is at least 90% identical to SEQ ID NO: 121, wherein the VH comprises HCDR1, HCDR2, and HCDR3 comprising the amino acid sequences set forth in SEQ ID NOs: 125, 126, and 127, respectively, and the VL comprises an amino acid sequence that is at least 90% identical to SEQ ID NO: 122, wherein the VL comprises LCDR1, LCDR2, and LCDR3 comprising the amino acid sequences set forth in SEQ ID NOs: 128, 129, and 130, respectively; or the VH comprises an amino acid sequence that is at least 90% identical to SEQ ID NO: 31, wherein the VH comprises HCDR1, HCDR2, and HCDR3 comprising the amino acid sequences set forth in SEQ ID NOs: 35, 36, and 37 respectively, and the VL comprises an amino acid sequence that is at least 90% identical to SEQ ID NO: 32, wherein the VL comprises LCDR1, LCDR2, and LCDR3 comprising the amino acid sequences set forth in SEQ ID NOs: 38, 39, and 40, respectively.

3. The antibody or antigen-binding fragment thereof of claim 2, wherein the VH comprises the sequence of SEQ ID NO: 81 and the VL comprises the sequence of SEQ ID NO: 82;

the VH comprises the sequence of SEQ ID NO: 121 and the VL comprises the sequence of SEQ ID NO: 122; or the VH comprises the sequence of SEQ ID NO: 31 and the VL comprises the sequence of SEQ ID NO: 32.

4. A pharmaceutical composition comprising an antibody or antigen-binding fragment thereof of claim 1, and a pharmaceutically acceptable carrier.

5. An isolated nucleic acid encoding the antibody or antigen-binding fragment thereof of claim 1.

6. A vector comprising the nucleic acid of claim 5.

7. A host cell comprising the vector of claim 6.

8. A method of producing an antibody or antigen-binding fragment thereof, the method comprising: culturing the host cell of claim 7 under conditions wherein said antibody or antigen-binding fragment thereof is expressed; and recovering said antibody or antigen-binding fragment thereof.

9. A pharmaceutical composition comprising an antibody or antigen-binding fragment thereof of claim 2, and a pharmaceutically acceptable carrier.

10. An isolated nucleic acid encoding the antibody or antigen-binding fragment thereof of claim 2.

11. A vector comprising the nucleic acid of claim 10.

12. A host cell comprising the vector of claim 11.

13. A method of producing an antibody or antigen-binding fragment thereof, the method comprising: culturing the host cell of claim 12 under conditions wherein said antibody or antigen-binding fragment thereof is expressed; and recovering said antibody or antigen-binding fragment thereof.

14. The antibody or antigen-binding fragment thereof of claim 1, wherein the antibody or antigen-binding fragment thereof is an IgG1 isotype.

15. A method for treating a subject having a CDCP1 associated cancer, comprising administering to the subject an effective amount of an antibody or antigen-binding fragment thereof that binds to CUB domain-containing protein 1 (CDCP1), wherein:

the antibody or antigen-binding fragment thereof comprises a heavy chain variable region comprising HCDR1, HCDR2, and HCDR3, and a light chain variable region comprising LCDR1, LCDR2, and LCDR3, wherein HCDR1, HCDR2, and HCDR3 comprise the amino acid sequences set forth in SEQ ID NOs: 85, 86, and 87 respectively, and LCDR1, LCDR2, and LCDR3 comprise the amino acid sequences set forth in SEQ ID NOs: 88, 89, and 90, respectively;

HCDR1, HCDR2, and HCDR3 comprise the amino acid sequences set forth in SEQ ID NOs: 155, 156, and 157 respectively, and LCDR1, LCDR2, and LCDR3 comprise the amino acid sequences set forth in SEQ ID NOs: 158, 159, and 160, respectively;

HCDR1, HCDR2, and HCDR3 comprise the amino acid sequences set forth in SEQ ID NOs: 125, 126, and 127 respectively, and LCDR1, LCDR2, and LCDR3 comprise the amino acid sequences set forth in SEQ ID NOs: 128, 129, and 130, respectively; or HCDR1, HCDR2, and HCDR3 comprise the amino acid sequences set forth in SEQ ID NOs: 35, 36, and 37 respectively, and LCDR1, LCDR2, and LCDR3 comprise the amino acid sequences set forth in SEQ ID NOs: 38, 39, and 40, respectively thereby treating the subject having a CDCP1 associated cancer.

16. The method of claim 15, wherein the cancer is breast cancer, lung cancer, small cell lung cancer, liver cancer, pancreatic cancer, ovarian cancer, kidney cancer or colon cancer.

17. A method for inhibiting or decreasing solid tumor growth in a subject having a solid tumor, the method comprising administering to the subject an effective amount of an antibody or antigen-binding fragment thereof that binds to CUB domain-containing protein 1 (CDCP1), such that the solid tumor growth is inhibited or decreased, wherein:

the antibody or antigen-binding fragment thereof comprises a heavy chain variable region comprising HCDR1, HCDR2, and HCDR3, and a light chain variable region comprising LCDR1, LCDR2, and LCDR3, wherein HCDR1, HCDR2, and HCDR3 comprise the amino acid sequences set forth in SEQ ID NOs: 85, 86, and 87 respectively, and LCDR1, LCDR2, and LCDR3 comprise the amino acid sequences set forth in SEQ ID NOs: 88, 89, and 90, respectively;

HCDR1, HCDR2, and HCDR3 comprise the amino acid sequences set forth in SEQ ID NOs: 155, 156, and 157 respectively, and LCDR1, LCDR2, and LCDR3 comprise the amino acid sequences set forth in SEQ ID NOs: 158, 159, and 160, respectively;

HCDR1, HCDR2, and HCDR3 comprise the amino acid sequences set forth in SEQ ID NOs: 125, 126, and 127 respectively, and LCDR1, LCDR2, and LCDR3 comprise the amino acid sequences set forth in SEQ ID NOs: 128, 129, and 130, respectively; or HCDR1, HCDR2, and HCDR3 comprise the amino acid sequences set forth in SEQ ID NOs: 35, 36, and 37 respectively, and LCDR1, LCDR2, and LCDR3 comprise the amino acid sequences set forth in SEQ ID NOs: 38, 39, and 40, respectively.

18. The method of claim 17, wherein the antibody or antigen-binding fragment thereof is administered in combination with an additional agent or an additional therapy.

* * * * *